US007427623B2

(12) United States Patent
Adams et al.

(10) Patent No.: US 7,427,623 B2
(45) Date of Patent: Sep. 23, 2008

(54) 4-AMINO-2,3-DISUBSTITUTED THIENO[2,3-D]PYRIMIDINES AND PHARMACETICAL COMPOSITIONS THEREOF

(75) Inventors: Jerry Leroy Adams, King of Prussia, PA (US); Deborah Lynne Bryan, King of Prussia, PA (US); Yanhong Feng, Collegeville, PA (US); Shinichiro Matsunaga, Tsukuba (JP); Yutaka Maeda, Tsukuba (JP); Yasushi Miyazaki, Tsukuba (JP); Masato Nakano, Tsukuba (JP); Jean-Philippe Rocher, Vetraz-Mothoux (FR); Hideyuki Sato, Tsukuba (JP); Marcus Semones, Collegeville, PA (US); Domingos J. Silva, Collegeville, PA (US); Jun Tang, Tsukuba (JP)

(73) Assignee: SmithKline Beecham Corporation, Philadelphia, PA (US)

( * ) Notice: Subject to any disclaimer, the term of this patent is extended or adjusted under 35 U.S.C. 154(b) by 282 days.

(21) Appl. No.: 10/489,052

(22) PCT Filed: Sep. 10, 2002

(86) PCT No.: PCT/US02/28650

§ 371 (c)(1),
(2), (4) Date: Mar. 9, 2004

(87) PCT Pub. No.: WO03/022852

PCT Pub. Date: Mar. 20, 2003

(65) Prior Publication Data

US 2005/0004142 A1  Jan. 6, 2005

Related U.S. Application Data

(60) Provisional application No. 60/318,766, filed on Sep. 11, 2001.

(51) Int. Cl.
A61K 31/519 (2006.01)
C07D 495/04 (2006.01)
A61P 35/00 (2006.01)
A61P 9/00 (2006.01)

(52) U.S. Cl. .................... 514/260.1; 544/278
(58) Field of Classification Search ............. 544/278; 514/260.1
See application file for complete search history.

(56) References Cited

U.S. PATENT DOCUMENTS

| 3,577,420 A | 5/1971 | Cronin et al. | 544/250 |
| 3,830,813 A | 8/1974 | Reuter et al. | 544/278 |
| 4,196,207 A * | 4/1980 | Webber | 514/260.1 |
| 5,958,930 A | 9/1999 | Gangee | 514/265.1 |
| 6,001,839 A | 12/1999 | Rafferty et al. | 514/265.1 |
| 6,169,091 B1 | 1/2001 | Cockerill et al. | 514/228.2 |

FOREIGN PATENT DOCUMENTS

| DE | 287503 A5 | 2/1991 |
| EP | 0082023 A2 | 6/1983 |
| EP | 0447891 A1 * | 3/1991 |
| EP | 0447891 A1 | 9/1991 |
| JP | 5312888 A | 11/1993 |
| WO | 9841525 A1 | 9/1998 |
| WO | 0017202 A1 | 3/2000 |
| WO | 0119828 A2 | 3/2001 |

OTHER PUBLICATIONS

Dave, C.; Gould-Jacob type of reaction in the synthesis of thieno[3,2-e]pyrimidines: a comparison of classical heating vs solvent free microwave irradiation; Heterocycles; 1999 51(5), 1819-1826.*
Robba, M.; Thienopyrimidines;Bulletin de la Societe Chimique de France, 1976, 5-6, 761-764.*
Zhang, M., et al., "A concise synthetic entry to substituted 2-aminothieno '2,3-d!pyrimidines via a gewald precursor," Bioorganic & Medicinal Chemistry Letters, vol. 7, No. 13, Jul. 8, 1997, pp. 1629-1634.
Ali, M. et al., "Synthesis of furo(2,3-d) pyrimidines and furo(3,3-b) pyridines," Indian Journal of Heterocyclic Chemistry, 1995, vol. 4(3), pp. 191-194.
Bourguignon, J. et al., "Synthesis De Thienou2,2-Dpyrimidines Substitutes En 2 Et 4," Bulletin De La Societe Chimiwue De France, 1975, No. 3/4, pp. 815-819.
Khachatryan, V. et al., "Synthesis, Chemical and Sntitumor Properties of Some furo(2,3-d) pyrimidines," Khlmlcheskii Zhurnal Armenli, 199, vol. 52(1-2), pp. 95-101. (Abstract only).
McMahon, G., "VEGF Receptor Signaling in Tumor Angiogenesis," The Oncologist, 2000, vol. 5 (Suppl. 1), pp. 3-10.
Sakamoto, T. et al., "Condensed Heteraromatic Ring Systems. VII," Chemical and Pharmaceutical Bulletin, Pharmaceutical Society of Japan, 1986, vol. 34(7), pp. 2719-2724.
Sun, L. et al., "Design, Synthesis and Evaluations of Substituted 3-((3- or 4-carboxyethylpyrrol-2-yl)methylidenyl) indolin-2-ones as Inhibitors of VEGF, FGF and PDGF Receptor Tyrosine Kinases," J. Med. Chem., 199, vol. 42, pp. 5120-5130.
Ali ete al., "Synthesis of Furo[2,3-d]Pyrimidines and Furo [2,3-b]Pyridines," Indian Journal of Heterocyclic Chemistry, vol. 4, 1995, pp. 1919-194.

* cited by examiner

Primary Examiner—Brenda Coleman
Assistant Examiner—Susanna Moore
(74) Attorney, Agent, or Firm—John L. Lemanowicz

(57) ABSTRACT

Furo- and thienopyrimidine derivatives, which are useful as TIE-2 and/or VEGFR-2 inhibitors are described herein. The described invention also includes methods of making such furo- and thienopyrimidine derivatives as well as methods of using the same in the treatment of hyperproliferative diseases.

2 Claims, No Drawings

4-AMINO-2,3-DISUBSTITUTED THIENO[2,3-D]PYRIMIDINES AND PHARMACETICAL COMPOSITIONS THEREOF

This This application is filed pursuant to 35 U.S.C. § 371 as a United States National Phase Application of International Application No. PCT/US02/28650 filed Sep. 10, 2002, which claims priority from US 60/318,766 filed Sep. 11, 2001.

BACKGROUND OF THE INVENTION

The present invention relates to furo- and thienopyrimidine derivatives, compositions and medicaments containing the same, as well as processes for the preparation and use of such compounds, compositions and medicaments. Such furo- and thienopyrimidine derivatives are useful in the treatment of diseases associated with inappropriate angiogenesis.

The process of angiogenesis is the development of new blood vessels, generally capillaries, from pre-existing vasculature. Angiogenesis is defined as involving (i) activation of endothelial cells; (ii) increased vascular permeability; (iii) subsequent dissolution of the basement membrane and extravisation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vii) deposition of basement membrane and recruitment of perivascular cells to newly formed vessels. Normal angiogenesis is activated during tissue growth, from embryonic development through maturity, and then enters a period of relative quiescence during adulthood. Normal angiogensesis is also activated during wound healing, and at certain stages of the female reproductive cycle. Inappropriate angiogenesis has been associated with several disease states including various retinopathies; ischemic disease; atherosclerosis; chronic inflammatory disorders; and cancer. The role of angiogenesis in disease states is discussed, for instance, in Fan et al, Trends in Pharmacol Sci. 16:54–66; Shawver et al, DDT Vol. 2, No. 2 February 1997; Folkmann, 1995, Nature Medicine 1:27–31.

In cancer the growth of solid tumors has been shown to be angiogenesis dependent. (See Folkmann, J., J. Nat'l. Cancer Inst., 1990, 82, 4–6.) Consequently, the targeting of pro-angiogenic pathways is a strategy being widely pursued in order to provide new therapeutics in these areas of great, unmet medical need. The role of tyrosine kinases involved in angiogenesis and in the vascularization of solid tumors has drawn interest. Until recently most interest in this area has focused on growth factors such as vascular endothelial growth factor (VEGF) and its receptors termed vascular endothelial growth factor receptor(s) (VEGFR). VEGF, a polypeptide, is mitogenic for endothelial cells in vitro and stimulates angiogenic responses in vivo. VEGF has also been linked to inappropriate angiogenesis (Pinedo, H. M. et al The Oncologist, Vol. 5, No. 90001, 1–2, April 2000). VEGFR(s) are protein tyrosine kinases (PTKs). PTKs catalyze the phosphorylation of specific tyrosyl residues in proteins involved in the regulation of cell growth and differentiation. (A. F. Wilks, Progress in Growth Factor Research, 1990, 2, 97–111; S. A. Courtneidge, Dev. Supp.l, 1993, 57–64; J. A. Cooper, Semin. Cell Biol., 1994, 5(6), 377–387; R. F. Paulson, Semin. Immunol., 1995, 7(4), 267–277; A. C. Chan, Curr. Opin. Immunol., 1996, 8(3), 394–401).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. et al J. Cell Biol. 1995:129:895–898). Of particular interest is VEGFR-2, which is a transmembrane receptor PTK expressed primarily in endothelial cells. Activation of VEGFR-2 by VEGF is a critical step in the signal transduction pathway that initiates tumor angiogenesis. VEGF expression may be constitutive to tumor cells and can also be upregulated in response to certain stimuli. One such stimuli is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3–10, April 2000).

Angiopoieten 1 (Ang1), a ligand for the endothelium-specific receptor tyrosine kinase TIE-2 is a novel angiogenic factor (Davis et al, Cell, 1996, 87:1161–1169; Partanen et al, Mol. Cell Biol, 12:1698–1707 (1992); U.S. Pat. Nos. 5,521, 073; 5,879,672; 5,877,020; and 6,030,831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of an EGF-like domain and an immunoglobulin (IG) like domain, which consists of extracellular folding units, stabilized by intra-chain disulfide bonds (Partanen et al Curr. Topics Microbiol. Immunol., 1999, 237:159–172). Unlike VEGF, which functions during the early stages of vascular development, Ang1 and its receptor TIE-2 function in the later stages of vascular development, i.e., during vascular remodeling (remodeling refers to formation of a vascular lumen) and maturation (Yancopoulos et al, Cell, 1998, 93:661–664; Peters, K. G., Circ. Res., 1998, 83(3):342–3; Suri et al, Cell 87, 1171–1180 (1996)).

Consequently, inhibition of TIE-2 would be expected to serve to disrupt remodeling and maturation of new vasculature initiated by angiogenesis thereby disrupting the angiogenic process. Furthermore, inhibition at the kinase domain binding site of VEGFR-2 would block phosphorylation of tyrosine residues and serve to disrupt initiation of angiogenesis. Presumably then, inhibition of TIE-2 and/or VEGFR-2 should prevent tumor angiogenesis and serve to retard or eradicate tumor growth. Accordingly, a treatment for cancer or other disorder associated with inappropriate angiogenesis could be provided.

The present inventors have discovered novel furo- and thienopyrimidine compounds, which are inhibitors of TIE-2 and/or VEGFR-2 kinase activity. Such furo- and thienopyrimidine derivatives are useful in the treatment of disorders, including cancer, associated with inappropriate angiogenesis.

BRIEF SUMMARY OF THE INVENTION

In one aspect of the present invention, there is provided a compound of Formula (I):

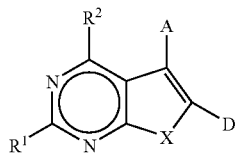

(I)

or a salt, solvate, or physiologically functional derivative thereof:

wherein:

X is O or S;

A is hydrogen, halo, $C_1$–$C_6$ alkyl, aryl, heteroaryl, aryl or heteroaryl substituted with at least one independently selected $R^3$ group, heterocyclyl, —$RR^3$, —C(O)$OR^4$, —C(O)$NR^5R^6$, or —C(O)$R^4$;

D is hydrogen, halo, $C_1$–$C_6$ alkyl, aryl, heteroaryl, aryl or heteroaryl substituted with at least one independently selected $R^3$ group, heterocyclyl, —$RR^3$, —C(O)O $R^4$, —C(O)$NR^5R^6$, or —C(O)$R^4$;

R is $C_1$–$C_6$ alkylene, $C_3$–$C_7$ cycloalkylene, $C_1$–$C_6$ alkenylene, or $C_1$–$C_6$ alkynylene;

$R^1$ is hydrogen, $C_1$–$C_6$ alkyl, $C_1$–$C_6$ alkoxy, —$SR^4$, —S(O)$_2R^4$, —$NR^7$, $R^7$, —NR'NR'''R'''', —N(H)$RR^3$, —C(O)$OR^7$, or —C(O)$NR^7R^7$;

$R^2$ is hydrogen, —OH, —$NR^7R^7$ or =NH;

$R^3$ is halo, $C_1$–$C_6$ alkyl, $C_1$–$C_6$ haloalkyl, $C_1$–$C_6$ alkoxy, $C_3$–$C_7$ cycloalkoxy, $C_1$–$C_6$ haloalkoxy, aryl, aralkyl, aryloxy, heteroaryl, heterocyclyl, —CN, —NHC(O)$R^4$, —N($R^8$)HC(O)$R^4$, —NHC(S)$R^4$, —$NR^5R^6$, —RN $R^5R^6$, —$SR^4$, —S(O)$_2R^4$, —RC(O)$OR^4$, —C(O)$OR^4$, —C(O)$R^4$, —C(O)$NR^5R^6$, —NHS(O)$_2R^4$, —N(S(O)$_2R^4$)S(O)$_2R^4$, —S(O)$_2NR^5R^6$, or —NHC(=NH)$R^4$;

$R^4$ is hydrogen, $C_1$–$C_6$ alkyl, aryl, heteroaryl, heterocyclyl, —$RR^3$, —NR'''R'''', or —NR'NR'''R'''';

$R^5$ is hydrogen, $C_1$–$C_6$ alkyl, $C_3$–$C_7$ cycloalkyl, cyanoalkyl, —R'R'', aryl, aralkyl, heteroaryl, —NHC(O)OR''', —R'NHC(O)OR''', —R'NHC(O)NR'''R'''', or —R'C(O)OR''';

$R^6$ is hydrogen, $C_1$–$C_6$ alkyl, $C_3$–$C_7$ cycloalkyl, cyanoalkyl, —R'R'', aryl, aralkyl, heteroaryl, —C(O)OR''', or —R'C(O)NR'''R''';

$R^7$ is hydrogen, $C_1$–$C_6$ alkyl, aryl, or —C(O)OR''';

$R^8$ is $C_1$–$C_3$ alkyl;

R' is $C_1$–$C_3$ alkylene;

R'' is heteroalkyl or NR'''R'''';

R''' is hydrogen, $C_1$–$C_6$ alkyl, aryl, aralkyl, heteroaryl, or $C_3$–$C_7$ cycloalkyl;

R'''' is hydrogen, $C_1$–$C_6$ alkyl, aryl, heteroaryl, or $C_3$–$C_7$ cycloalkyl.

In a second aspect of the present invention, there is provided a compound of Formula (II):

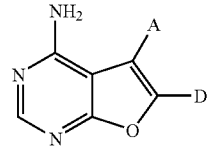

(II)

or a salt, solvate, or physiologically functional derivative thereof:

wherein:

A is hydrogen, halo, $C_1$–$C_6$ alkyl, aryl, heteroaryl, aryl or heteroaryl substituted with at least one independently selected $R^3$ group, heterocyclyl, —$RR^3$, —C(O)$OR^4$, —C(O)$NR^5R^6$, or —C(O)$R^4$;

D is hydrogen, halo, $C_1$–$C_6$ alkyl, aryl, heteroaryl, aryl or heteroaryl substituted with at least one independently selected $R^3$ group, heterocyclyl, —$RR^3$, —C(O)$OR^4$, —C(O)$NR^5R^6$, or —C(O)$R^4$;

R is $C_1$–$C_6$ alkylene, $C_3$–$C_7$ cycloalkylene, $C_1$–$C_6$ alkenylene, or $C_1$–$C_6$ alkynylene;

$R^3$ is halo, $C_1$–$C_6$ alkyl, $C_1$–$C_6$ haloalkyl, $C_1$–$C_6$ alkoxy, $C_3$–$C_7$ cycloalkoxy, $C_1$–$C_6$ haloalkoxy, aryl, aralkyl, aryloxy, heteroaryl, heterocyclyl, —CN, —NHC(O)$R^4$, —N($R^8$)HC(O)$R^4$, —NHC(S)$R^4$, —$NR^5R^6$, —RN $R^5R^6$, —$SR^4$, —S(O)$_2R^4$, —RC(O)$OR^4$, —C(O)$OR^4$, C(O)$R^4$, —C(O)$NR^5R^6$, —NHS(O)$_2R^4$, —N(S(O)$_2R^4$)S(O)$_2R^4$, —S(O)$_2NR^5R^6$, or —NHC(=NH)$R^4$;

$R^4$ is hydrogen, $C_1$–$C_6$ alkyl, aryl, heteroaryl, heterocyclyl, —$RR^3$, —NR'''R'''', or —NR'NR'''R'''';

$R^5$ is hydrogen, $C_1$–$C_6$ alkyl, $C_3$–$C_7$ cycloalkyl, cyanoalkyl, —R'R'', aryl, aralkyl, heteroaryl, —NHC(O)OR''', —R'NHC(O)OR''', —R'NHC(O)NR'''R'''', or —R'C(O)OR''';

$R^6$ is hydrogen, $C_1$–$C_6$ alkyl, $C_3$–$C_7$ cycloalkyl, cyanoalkyl, —R'R'', aryl, aralkyl, heteroaryl, —C(O)OR''', or —R'C(O)NR'''R''';

$R^8$ is $C_1$–$C_3$ alkyl;

R' is $C_1$–$C_3$ alkylene;

R'' is heteroalkyl or NR'''R'''';

R''' is hydrogen, $C_1$–$C_6$ alkyl, aryl, aralkyl, heteroaryl, or $C_3$–$C_7$ cycloalkyl;

R'''' is hydrogen, $C_1$–$C_6$ alkyl, aryl, heteroaryl, or $C_3$–$C_7$ cycloalkyl.

In a third aspect of the present invention, there is provided a compound of Formula (III):

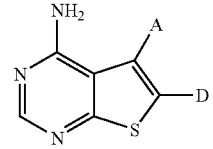

(III)

or a salt, solvate, or physiologically functional derivative thereof:

wherein:

A is hydrogen, halo, $C_1$–$C_6$ alkyl, aryl, heteroaryl, aryl or heteroaryl substituted with at least one independently selected $R^3$ group, heterocyclyl, —$RR^3$, —C(O)$OR^4$, —C(O)$NR^5R^6$, or —C(O)$R^4$;

D is hydrogen, halo, $C_1$–$C_6$ alkyl, aryl, heteroaryl, aryl or heteroaryl substituted with at least one independently selected $R^3$ group, heterocyclyl, —$RR^3$, —C(O)O$R^4$, —C(O)N$R^5R^6$, or —C(O)$R^4$;

R is $C_1$–$C_6$ alkylene, $C_3$–$C_7$ cycloalkylene, $C_1$–$C_6$ alkenylene, or $C_1$–$C_6$ alkynylene;

$R^3$ is halo, $C_1$–$C_6$ alkyl, $C_1$–$C_6$ haloalkyl, $C_1$–$C_6$ alkoxy, $C_3$–$C_7$ cycloalkoxy, $C_1$–$C_6$ haloalkoxy, aryl, aralkyl, aryloxy, heteroaryl, heterocyclyl, —CN, —NHC(O)$R^4$, —N($R^8$)HC(O)$R^4$, —NHC(S)$R^4$, —N $R^5R^6$, —RN $R^5R^6$, —S$R^4$, —S(O)$_2R^4$, —RC(O)O$R^4$, —C(O)O$R^4$, C(O)$R^4$, —C(O)N$R^5R^6$, —NHS(O)$_2R^4$, —N(S(O)$_2R^4$)S(O)$_2R^4$, —S(O)$_2$N$R^5R^6$, or —NHC(=NH)$R^4$;

$R^4$ is hydrogen, $C_1$–$C_6$ alkyl, aryl, heteroaryl, heterocyclyl, —$RR^3$, —NR'''R'''', or —NR'NR'''R'''';

$R^5$ is hydrogen, $C_1$–$C_6$ alkyl, $C_3$–$C_7$ cycloalkyl, cyanoalkyl, —R' R'', aryl, aralkyl, heteroaryl, —NHC(O)OR''', —R'NHC(O)OR''', —R'NHC(O)NR'''R'''', or —R'C(O)OR''';

$R^6$ is hydrogen, $C_1$–$C_6$ alkyl, $C_3$–$C_7$ cycloalkyl, cyanoalkyl, —R'R'', aryl, aralkyl, heteroaryl, —C(O)OR''', or —R'C(O)NR'''R''';

$R^8$ is $C_1$–$C_3$ alkyl;

R' is $C_1$–$C_3$ alkylene;

R'' is heteroalkyl or NR'''R'''';

R''' is hydrogen, $C_1$–$C_6$ alkyl, aryl, aralkyl, heteroaryl, or $C_3$–$C_7$ cycloalkyl;

R'''' is hydrogen, $C_1$–$C_6$ alkyl, aryl, heteroaryl, or $C_3$–$C_7$ cycloalkyl.

In a fourth aspect of the present invention, there is provided a compound of formula (II):

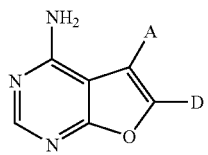

(II)

or a salt, solvate, or physiologically functional derivative thereof:

wherein:

A is halo, $C_1$–$C_6$ alkyl, aryl, heteroaryl, aryl or heteroaryl substituted with at least one independently selected $R^3$ group, heterocyclyl, —$RR^3$, —C(O)O$R^4$, —C(O)N$R^5R^6$, or —C(O)$R^4$;

D is halo, $C_1$–$C_6$ alkyl, aryl, heteroaryl, aryl or heteroaryl substituted with at least one independently selected $R^3$ group, heterocyclyl, —$RR^3$, —C(O)O$R^4$, —C(O)N$R^5R^6$, or —C(O)$R^4$;

R is $C_1$–$C_6$ alkylene, $C_1$–$C_6$ alkenylene, or $C_1$–$C_6$ alkynylene;

$R^3$ is halo, $C_1$–$C_6$ alkyl, $C_1$–$C_6$ haloalkyl, $C_1$–$C_6$ alkoxy, $C_3$–$C_7$ cycloalkoxy, $C_1$–$C_6$ haloalkoxy, aryl, aralkyl, aryloxy, heteroaryl, heterocyclyl, —CN, —NHC(O)$R^4$, —N($R^8$)HC(O)$R^4$, —NHC(S)$R^4$, —N $R^5R^6$, —RN $R^5R^6$, —S$R^4$, —S(O)$_2R^4$, —RC(O)O$R^4$, —C(O)O$R^4$, C(O)$R^4$, —C(O)N$R^5R^6$, —NHS(O)$_2R^4$, —N(S(O)$_2R^4$)S(O)$_2R^4$, —S(O)$_2$N$R^5R^6$, or —NHC(=NH)$R^4$;

$R^4$ is hydrogen, $C_1$–$C_6$ alkyl, aryl, heteroaryl, heterocyclyl, —$RR^3$, —NR'''R'''', or —NR'NR'''R'''';

$R^5$ is hydrogen, $C_1$–$C_6$ alkyl, $C_3$–$C_7$ cycloalkyl, cyanoalkyl, —R' R'', aryl, aralkyl, heteroaryl, —NHC(O)OR''', —R'NHC(O)OR''', —R'NHC(O)NR'''R'''', or —R'C(O)OR''';

$R^6$ is hydrogen, $C_1$–$C_6$ alkyl, $C_3$–$C_7$ cycloalkyl, cyanoalkyl, —R'R'', aryl, aralkyl, heteroaryl, —C(O)OR''', or —R'C(O)NR'''R''';

$R^8$ is $C_1$–$C_3$ alkyl;

R' is $C_1$–$C_3$ alkylene;

R'' is heteroalkyl or NR'''R'''';

R''' is hydrogen, $C_1$–$C_6$ alkyl, aryl, aralkyl, heteroaryl, or $C_3$–$C_7$ cycloalkyl;

R'''' is hydrogen, $C_1$–$C_6$ alkyl, aryl, heteroaryl, or $C_3$–$C_7$ cycloalkyl.

In a fifth aspect of the present invention, there is provided a compound of Formula (II):

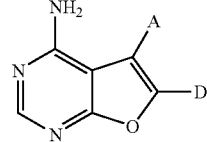

(II)

or a salt, solvate, or physiologically functional derivative thereof:

wherein:

A is halo, $C_1$–$C_6$ alkyl, aryl, heteroaryl, aryl or heteroaryl substituted with at least one independently selected $R^3$ group, heterocyclyl, —$RR^3$, —C(O)O$R^4$, —C(O)N$R^5R^6$, or —C(O)$R^4$;

D is hydrogen or halo;

R is $C_1$–$C_6$ alkylene, $C_3$–$C_7$ cycloalkylene, $C_1$–$C_6$ alkenylene, or $C_1$–$C_6$ alkynylene;

$R^3$ is halo, $C_1$–$C_6$ alkyl, $C_1$–$C_6$ haloalkyl, $C_1$–$C_6$ alkoxy, $C_3$–$C_7$ cycloalkoxy, $C_1$–$C_6$ haloalkoxy, aralkyl, aryloxy, heterocyclyl, —CN, —NHC(O)$R^4$, —N($R^8$)HC(O)$R^4$, —NHC(S)$R^4$, —N$R^5R^6$, —R N$R^5R^6$, —S$R^4$, —S(O)$_2R^4$, —RC(O)O$R^4$, —C(O)O$R^4$, C(O)$R^4$, —C(O)N$R^5R^6$, —NHS(O)$_2R^4$, —N(S(O)$_2R^4$)S(O)$_2R^4$, —S(O)$_2$N$R^5R^6$, or —NHC(=NH)$R^4$;

$R^4$ is hydrogen, $C_1$–$C_6$ alkyl, aryl, heteroaryl, heterocyclyl, —$RR^3$, —NR'''R'''', or —NR'NR'''R'''';

$R^5$ is hydrogen, $C_1$–$C_6$ alkyl, $C_3$–$C_7$ cycloalkyl, cyanoalkyl, —R' R'', aryl, aralkyl, heteroaryl, —NHC(O)OR''', —R'NHC(O)OR''', —R'NHC(O)NR'''R'''', or —R'C(O)OR''';

$R^6$ is hydrogen, $C_1$–$C_6$ alkyl, $C_3$–$C_7$ cycloalkyl, cyanoalkyl, —R'R'', aryl, aralkyl, heteroaryl, —C(O)OR''', or —R'C(O)NR'''R''';

$R^8$ is $C_1$–$C_3$ alkyl;

R' is $C_1$–$C_3$ alkylene;

R'' is heteroalkyl or NR'''R'''';

R''' is hydrogen, $C_1$–$C_6$ alkyl, aryl, aralkyl, heteroaryl, or $C_3$–$C_7$ cycloalkyl;

R'''' is hydrogen, $C_1$–$C_6$ alkyl, aryl, heteroaryl, or $C_3$–$C_7$ cycloalkyl.

In a sixth aspect of the present invention, there is provided a compound of Formula (III):

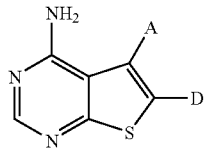

(III)

or a salt, solvate, or physiologically functional derivative thereof:

wherein:
A is halo, $C_1$–$C_6$ alkyl, aryl, heteroaryl, aryl or heteroaryl substituted with at least one independently selected $R^3$ group, heterocyclyl, —$RR^3$, —C(O)O$R^4$, —C(O)N$R^5R^6$, or —C(O)$R^4$;
D is hydrogen or halo;
R is $C_1$–$C_6$ alkylene, $C_3$–$C_7$ cycloalkylene, $C_1$–$C_6$ alkenylene, or $C_1$–$C_6$ alkynylene;
$R^3$ is halo, $C_1$–$C_6$ alkyl, $C_1$–$C_6$ haloalkyl, $C_1$–$C_6$ alkoxy, $C_3$–$C_7$ cycloalkoxy, $C_1$–$C_6$ haloalkoxy, aralkyl, aryloxy, heterocyclyl, —CN, —NHC(O)$R^4$, —N($R^8$)HC(O)$R^4$, —NHC(S)$R^4$, —N$R^5R^6$, —R N$R^5R^6$, —S$R^4$, —S(O)$_2R^4$, —RC(O)O$R^4$, —C(O)O$R^4$, C(O)$R^4$, —C(O)N$R^5R^6$, —NHS(O)$_2R^4$, —N(S(O)$_2R^4$)S(O)$_2R^4$, —S(O)$_2$N$R^5R^6$, or —NHC(=NH)$R^4$;
$R^4$ is hydrogen, $C_1$–$C_6$ alkyl, aryl, heteroaryl, heterocyclyl, —$RR^3$, —NR'''R'''', or —NR'NR'''R'''';
$R^5$ is hydrogen, $C_1$–$C_6$ alkyl, $C_3$–$C_7$ cycloalkyl, cyanoalkyl, —R' R'', aryl, aralkyl, heteroaryl, —NHC(O)OR''', —R'NHC(O)OR''', —R'NHC(O)NR'''R'''', or —R'C(O) OR''';
$R^6$ is hydrogen, $C_1$–$C_6$ alkyl, $C_3$–$C_7$ cycloalkyl, cyanoalkyl, —R'R'', aryl, aralkyl, heteroaryl, —C(O)OR''', or —R'C(O)NR'''R''';
$R^8$ is $C_1$–$C_3$ alkyl;
R' is $C_1$–$C_3$ alkylene;
R'' is heteroalkyl or NR'''R'''';
R''' is hydrogen, $C_1$–$C_6$ alkyl, aryl, aralkyl, heteroaryl, or $C_3$–$C_7$ cycloalkyl;
R'''' is hydrogen, $C_1$–$C_6$ alkyl, aryl, heteroaryl, or $C_3$–$C_7$ cycloalkyl.

In a seventh aspect of the present invention, there is provided a compound of Formula (IV):

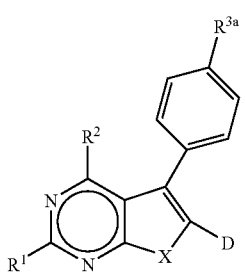

(IV)

or a salt, solvate, or physiologically functional derivative thereof:

wherein:
X is O or S;

D is hydrogen, halo, $C_1$–$C_6$ alkyl, aryl, heteroaryl, aryl or heteroaryl substituted with at least one independently selected $R^3$ group, heterocyclyl, —$RR^3$, —C(O)O $R^4$, —C(O)N$R^5R^6$, or —C(O)$R^4$;
R is $C_1$–$C_6$ alkylene, $C_3$–$C_7$ cycloalkylene, $C_1$–$C_6$ alkenylene, or $C_1$–$C_6$ alkynylene;
$R^1$ is hydrogen, $C_1$–$C_6$ alkyl, $C_1$–$C_6$ alkoxy, —S$R^4$, —S(O)$_2R^4$, —N$R^7R^7$, —NR'NR'''R'''', —N(H)R$R^3$, —C(O)O$R^7$, or —C(O)N$R^7R^7$;
$R^2$ is hydrogen, —OH, —N$R^7R^7$ or =NH;
$R^3$ is halo, $C_1$–$C_6$ alkyl, $C_1$–$C_6$ haloalkyl, $C_1$–$C_6$ alkoxy, $C_3$–$C_7$ cycloalkoxy, $C_1$–$C_6$ haloalkoxy, aryl, aralkyl, aryloxy, heteroaryl, heterocyclyl, —CN, —NHC(O)$R^4$, —N($R^8$)HC(O)$R^4$, —NHC(S)$R^4$, —N$R^5R^6$, —RN $R^5R^6$, —S$R^4$, —S(O)$_2R^4$, —RC(O)O$R^4$, —C(O)O$R^4$, —C(O)$R^4$, —C(O)N$R^5R^6$, —NHS(O)$_2R^4$, —N(S(O)$_2R^4$)S(O)$_2R^4$, —S(O)$_2$N$R^5R^6$, or —NHC(=NH)$R^4$;
$R^{3a}$ is —NHC(O) $R^4$, —N($R^8$)HC(O) $R^4$, —NHC(S) $R^4$, —N$R^5R^6$, —RN $R^5R^6$, —C(O)N$R^5R^6$, —NHS(O)$_2R^4$, —N(S(O)$_2R^4$)S(O)$_2R^4$, —S(O)$_2$N$R^5R^6$, or —NHC(=NH)$R^4$;
$R^4$ is hydrogen, $C_1$–$C_6$ alkyl, aryl, heteroaryl, heterocyclyl, —$RR^3$, —NR'''R'''', or —NR'NR'''R'''';
$R^5$ is hydrogen, $C_1$–$C_6$ alkyl, $C_3$–$C_7$ cycloalkyl, cyanoalkyl, —R'R'', aryl, aralkyl, heteroaryl, —NHC(O)OR''', —R'NHC(O)OR''', —R'NHC(O)NR'''R'''', or —R'C(O)OR''';
$R^6$ is hydrogen, $C_1$–$C_6$ alkyl, $C_3$–$C_7$ cycloalkyl, cyanoalkyl, —R'R'', aryl, aralkyl, heteroaryl, —C(O)OR''', or —R'C(O)NR'''R''';
$R^7$ is hydrogen, $C_1$–$C_6$ alkyl, aryl, or —C(O)OR''';
$R^8$ is $C_1$–$C_3$ alkyl;
R' is $C_1$–$C_3$ alkylene;
R'' is heteroalkyl or NR'''R'''';
R''' is hydrogen, $C_1$–$C_6$ alkyl, aryl, aralkyl, heteroaryl, or $C_3$–$C_7$ cycloalkyl;
R'''' is hydrogen, $C_1$–$C_6$ alkyl, aryl, heteroaryl, or $C_3$–$C_7$ cycloalkyl.

In an eighth aspect of the present invention, there is provided a pharmaceutical composition comprising a therapeutically effective amount of a compound of formula (I), or a salt, solvate, or a physiologically functional derivative thereof and one or more of pharmaceutically acceptable carriers, diluents and excipients.

In a ninth aspect of the present invention, there is provided a method of treating a disorder in a mammal, said disorder being mediated by at least one of inappropriate TIE-2 and VEGFR-2 activity, comprising: administering to said mammal a therapeutically effective amount of a compound of formula (I) or a salt, solvate or a physiologically functional derivative thereof.

In a tenth aspect of the present invention, there is provided a compound of formula (I), or a salt, solvate, or a physiologically functional derivative thereof for use in therapy.

In an eleventh aspect of the present invention, there is provided the use of a compound of formula (I), or a salt, solvate, or a physiologically functional derivative thereof in the preparation of a medicament for use in the treatment of a disorder mediated by at least one of inappropriate TIE-2 and VEGFR-2 activity.

In a twelvth aspect of the present invention, there is provided a method of treating a disorder in a mammal, said disorder being mediated by at least one of inappropriate TIE-2 and VEGFR-2 activity, comprising: administering to said mammal therapeutically effective amounts of (i) a compound of formula (I), or a salt, solvate or physiologically functional derivative thereof and (ii) an agent to inhibit growth factor receptor function.

In a thirteenth aspect of the present invention, there is provided a method of treating a disorder in a mammal, said disorder being characterized by inappropriate angiogenesis, comprising: administering to said mammal a therapeutically effective amount of a compound of formula (I), or a salt, solvate or physiologically functional derivative thereof.

DETAILED DESCRIPTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the numbering of the furo[2,3-d]pyrimidine scaffold in formula (I) is assigned as shown in the structure following.

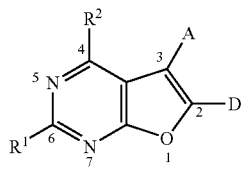

As used herein, the term "alkyl" refers to a straight or branched chain hydrocarbon radical having from one to twelve carbon atoms, optionally substituted with substituents selected from the group consisting of $C_1$–$C_6$ alkyl, $C_1$–$C_6$ hydroxyalkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, aryl, aryloxy, heteroaryl, aminosulfonyl optionally substituted by alkyl, nitro, cyano, halogen, or $C_1$–$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_1$–$C_6$ alkyl" refers to an alkyl group as defined above containing at least 1, and at most 6, carbon atoms. Examples of branched or straight chained "$C_1$–$C_6$ alkyl" groups useful in the present invention include, but are not limited to, methyl, ethyl, n-propyl, isopropyl, isobutyl, n-butyl, t-butyl, n-pentyl, and isopentyl.

As used herein, the term "alkylene" refers to a straight or branched chain divalent hydrocarbon radical having from one to ten carbon atoms, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and $C_1$–$C_6$ perfluoroalkyl, multiple degrees of substitution being allowed. Examples of "alkylene" as used herein include, but are not limited to, methylene, ethylene, n-propylene, n-butylene, and the like.

As used herein, the term "$C_1$–$C_3$ alkylene" refers to an alkylene group, as defined above, which contains at least 1, and at most 3, carbon atoms respectively. Examples of "$C_1$–$C_3$ alkylene" groups useful in the present invention include, but are not limited to, methylene, ethylene, and n-propylene.

As used herein, the term "alkenyl" refers to a hydrocarbon radical having from two to ten carbons and at least one carbon-carbon double bond, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and $C_1$–$C_6$ perfluoroalkyl, multiple degrees of substitution being allowed. Examples of "alkenyl" as used herein include, ethenyl, propenyl, 1-butenyl, 2-butenyl, and isobutenyl.

As used herein, the term "$C_1$–$C_6$ alkenyl" refers to an alkenyl group as defined above containing at least 1, and at most 6, carbon atoms. Examples of "$C_1$–$C_6$ alkyl" groups useful in the present invention include, but are not limited to, ethenyl, propenyl, 1-butenyl, 2-butenyl, and isobutenyl.

As used herein, the term "alkenylene" refers to an straight or branched chain divalent hydrocarbon radical having from two to ten carbon atoms and one or more carbon—carbon double bonds, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and $C_1$–$C_6$ perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "$C_1$–$C_3$ alkenylene" refers to an alkenylene group as defined above containing at least 1, and at most 3, carbon atoms. Examples of "$C_1$–$C_3$ alkenylene" groups useful in the present invention include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, aryl, hydroxy, mercapto, amino optionally substituted by alkyl, carboxy, carbamoyl optionally substituted by alkyl, aminosulfonyl optionally substituted by alkyl, nitro, cyano, halogen and $C_1$–$C_6$ perfluoroalkyl, multiple degrees of substitution being allowed. Examples of "alkynyl" as used herein, include but are not limited to acetylenyl, 1-propynyl, 1-butynyl, 2-butynyl, 1-pentynyl, and 1-hexynyl.

As used herein, the term "alkynylene" refers to a straight or branched chain divalent hydrocarbon radical having from two to ten carbon atoms and one or more carbon—carbon triple bonds, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and $C_1$–$C_6$ perfluoroalkyl, multiple degrees of substitution being allowed. Examples of "alkynylene" as used herein include, but are not limited to, ethyne-1,2-diyl, propyne-1,3-diyl, and the like.

As used herein, the terms "$C_1$–$C_3$ alkynylene" and "$C_1$–$C_6$ alkynylene" refer to an alkynylene group as defined above containing at least 1, and at most 3 or 6, carbon atoms. Examples of "$C_1$–$C_3$ alkynylene" and "$C_1$–$C_6$ alkynylene" groups useful in the present invention include, but are not limited to, ethyne-1,2-diyl, propyne-1,3-diyl, and the like.

As used herein, the term "halogen" refers to fluorine (F), chlorine (Cl), bromine (Br), or iodine (I) and the term "halo" refers to the halogen radicals fluoro (—F), chloro (—Cl), bromo (—Br), and iodo (—I).

As used herein, the term "$C_1$–$C_6$ haloalkyl" refers to an alkyl group as defined above containing at least 1, and at most 6, carbon atoms substituted with at least one halo group, halo being as defined herein. Examples of branched or straight chained "$C_1$–$C_6$ haloalkyl" groups useful in the present invention include, but are not limited to, methyl, ethyl, propyl, isopropyl, isobutyl and n-butyl substituted independently with one or more halos, e.g., fluoro, chloro, bromo and iodo.

As used herein, the term "$C_3$–$C_7$ cycloalkyl" refers to a non-aromatic cyclic hydrocarbon ring having from three to seven carbon atoms optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo, $C_1$–$C_6$ perfluoroalkyl, multiple degrees of substitution being allowed and which optionally includes a $C_1$–$C_6$ alkyl linker through which it may be attached. The $C_1$–$C_6$ alkyl group is as defined above. Exemplary "$C_3$–$C_7$ cycloalkyl" groups include, but are not limited to, cyclopropyl, cyclobutyl, cyclopentyl, cyclohexyl and cycloheptyl.

As used herein, the term "$C_3$–$C_7$ cycloalkylene" refers to a non-aromatic alicyclic divalent hydrocarbon radical having from three to seven carbon atoms, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo, $C_1$–$C_6$ perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a non-aromatic three to twelve-membered heterocyclic ring being saturated or having one or more degrees of unsaturation containing one or more heteroatomic substitutions selected from S, SO, $SO_2$, O, or N, optionally substituted with substituents selected from the group consisting of $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo, or $C_1$–$C_6$ perfluoroalkyl, multiple degrees of substitution being allowed and which optionally includes a $C_1$–$C_6$ alkyl linker through which it may be attached. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, piperidine, pyrrolidine, morpholine, tetrahydrothiopyran, tetrahydrothiophene, di-oxo tetrahydrothiophene, and the like.

As used herein, the term "heterocylylene" refers to a non-aromatic three to twelve-membered heterocyclic ring diradical being unsaturated or having one or more degrees of unsaturation containing-one or more heteroatoms selected from S, SO, $SO_2$, O, or N, optionally substituted with substituents selected from the group which includes $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo and $C_1$–$C_6$ perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein the term "heterocyclic spiro ring system" or "heterocyclyl spiro ring system" refers to a ring system having a three to twelve-membered non-aromatic heterocyclic ring, being saturated or having one or more degrees of unsaturation, containing one or more heteroatom substitutions selected from S, S(O), $S(O)_2$, O, or N, and a further ring being a heterocyclic, or aryl, or heteroaryl, or cycloalkyl ring, said rings of said ring system having one atom in common and being optionally substituted with substituents selected from the group consisting of $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo, aryl, aralkyl, heteroaryl, or $C_1$–$C_6$ perfluoroalkyl, multiple degrees of substitution being allowed. Examples of "heterocyclic spiro ring systems" moieties include, but are not limited to, 1,3-dioxo-2-aza-spiro[4.4]non-2-yl.

As used herein, the term "aryl" refers to an optionally substituted benzene ring or to an optionally substituted benzene ring system fused to one or more optionally substituted benzene rings or optionally substituted cycloalkyl rings to form, for example, anthracene, phenanthrene, napthalene, or indan ring systems. Exemplary optional substituents include $C_1$–$C_6$ alkyl, $C_1$–$C_6$ alkoxy, $C_1$–$C_6$ haloalkyl, $C_1$–$C_6$ haloalkoxy, $C_1$–$C_6$ alkylsulfanyl, $C_1$–$C_6$ alkylsulfenyl, $C_1$–$C_6$ alkylsulfonyl, $C_1$–$C_6$ alkylsulfonylamino, arylsulfonoamino, alkylcarboxy, alkylcarboxyamide, oxo, hydroxy, mercapto, amino optionally substituted by alkyl or acyl, carboxy, tetrazolyl, carbamoyl optionally substituted by alkyl, aryl, or heteroaryl, aminosulfonyl optionally substituted by alkyl, acyl, aroyl, aroylamino, heteroaroyl, acyloxy, aroyloxy, heteroaroyloxy, alkoxycarbonyl, nitro, cyano, halo, heteroaryl, heterocyclyl, heterocyclic spiro ring system, aryl optionally substituted with aryl, arylazo, halo, $C_1$–$C_6$ alkyl, $C_1$–$C_6$ haloalkyl, or $C_1$–$C_6$ alkylsulfonyl, ureido, arylurea, alkylurea, cycloalkylurea, alkylthiourea, aryloxy, heteroaryloxy, or aralkoxy, multiple degrees of substitution being allowed. Examples of "aryl" groups include, but are not limited to, phenyl, 2-naphthyl, 1-naphthyl, biphenyl, indan, as well as substituted derivatives thereof.

As used herein, the term "arylene" refers to a benzene ring diradical or to a benzene ring system diradical fused to one or more optionally substituted benzene rings, optionally substituted with substituents selected from the group which includes $C_1$–$C_6$ alkyl, $C_1$–$C_6$ alkoxy, aryloxy, heteroaryloxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halo, $C_1$–$C_6$ perfluoroalkyl, heterocyclyl, heterocyclic spiro ring system, heteroaryl and aryl, multiple degrees of substitution being allowed. Examples of "arylene" include, but are not limited to, benzene-1,4-diyl, naphthalene-1,8-diyl, anthracene-1,4-diyl, and the like.

As used herein, the term "aralkyl" refers to an aryl or heteroaryl group, as defined herein, attached through a $C_1$–$C_3$ alkylene linker, wherein the $C_1$–$C_3$ alkylene is as defined herein. Examples of "aralkyl" include, but are not limited to, benzyl, phenylpropyl, 2-pyridylmethyl, 3-isoxazolylmethyl, 5-methyl, 3-isoxazolylmethyl, and 2-imidazoyl ethyl.

As used herein, the term "heteroaryl" refers to a monocyclic five to seven membered aromatic ring, or to a fused bicyclic or tricyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, aroylamino, heteroaroyl, aryloxy, heteroaryloxy, acyloxy, aroyloxy, heteroaroyloxy, alkoxycarbonyl, nitro, cyano, halo, $C_1$–$C_6$ perfluoroalkyl, heterocyclyl, heterocyclic spiro ring system, heteroaryl, or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of: $C_1$–$C_6$ alkyl, $C_1$–$C_6$ alkoxy, aryloxy, heteroaryloxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halo, $C_1$–$C_6$ perfluoroalkyl, heterocyclyl, heterocyclic spiro ring system, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group $R_aO$—, where $R_a$ is alkyl as defined above and the term "$C_1$–$C_6$ alkoxy" refers to an alkoxy group as defined herein wherein the alkyl moiety contains at least 1, and at most 6, carbon atoms. Exemplary $C_1$–$C_6$ alkoxy groups useful in the present invention include, but are not limited to, methoxy, ethoxy, n-propoxy, isopropoxy, n-butoxy, and t-butoxy.

As used herein the term "aralkoxy" refers to the group $R_bR_aO$—, where $R_a$ is alkyl and $R_b$ is aryl as defined above.

As used herein the term "aryloxy" refers to the group $R_aO$—, where $R_a$ is aryl as defined above.

As used herein the term "heteroaryloxy" refers to the group $R_aO$—, where $R_a$ is heteroaryl as defined above.

As used herein the term "ureido" refers to the group —NHC(O)NH$_2$

As used herein, the term "arylurea" refers to the group —NHC(O)NHR$_a$ wherein R$_a$ is aryl as defined above.

As used herein, the term "arylthiourea" refers to the group —NHC(S)NHR$_a$ wherein R$_a$ is aryl as defined above.

As used herein, the term "alkylurea" refers to the group —NHC(O)NHR$_a$ wherein R$_a$ is alkyl as defined above.

As used herein, the term "cycloalkylurea" refers to the group —NHC(O)NHR$_a$ wherein R$_a$ is cycloalkyl as defined above.

As used herein, the term "$C_3$–$C_7$ cycloalkoxy" refers to the group R$_a$O—, where R$_a$ is $C_3$–$C_7$ cycloalkyl as defined above. Exemplary $C_3$–$C_7$ cycloalkoxy groups useful in the present invention include, but are not limited to, cyclobutoxy, and cyclopentoxy.

As used herein, the term "haloalkoxy" refers to the group R$_a$O—, where R$_a$ is haloalkyl as defined above and the term "$C_1$–$C_6$ haloalkoxy" refers to a haloalkoxy group as defined herein wherein the haloalkyl moiety contains at least 1, and at most 6, carbon atoms. Exemplary $C_1$–$C_6$ haloalkoxy groups useful in the present invention include, but is not limited to, trifluoromethoxy.

As used herein, the term "alkylsulfanyl" refers to the group R$_a$S—, where R$_a$ is alkyl as defined above and the term "$C_1$–$C_6$ alkylsulfanyl" refers to an alkylsulfanyl group as defined herein wherein the alkyl moiety contains at least 1, and at most 6, carbon atoms.

As used herein, the term "haloalkylsulfanyl" refers to the group R$_a$S—, where R$_a$ is haloalkyl as defined above and the term "$C_1$–$C_6$ haloalkylsulfanyl" refers to a haloalkylsulfanyl group as defined herein wherein the alkyl moiety contains at least 1, and at most 6, carbon atoms.

As used herein, the term "alkylsulfenyl" refers to the group R$_a$S(O)—, where R$_a$ is alkyl as defined above and the term "$C_1$–$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group R$_a$S(O)$_2$—, where R$_a$ is alkyl as defined above and the term "$C_1$–$C_6$ alkylsulfonyl" refers to an alkylsulfonyl group as defined herein wherein the alkyl moiety contains at least 1, and at most 6, carbon atoms.

As used herein, the term "alkylsulfonylamino" refers to the group —NHS(O)$_2$R$_a$ wherein R$_a$ is alkyl as defined above and the term "$C_1$–$C_6$ alkylsulfonylamino" refers to an alkylsulfonylamino group as defined herein wherein the alkyl moiety contains at least 1, and at most 6, carbon atoms.

As used herein, the term "arylsulfonylamino" refers to the group —NHS(O)$_2$R$_a$ wherein R$_a$ is aryl as defined above.

As used herein, the term "alkylcarboxyamide" refers to the group —NHC(O)R$_a$ wherein R$_a$ is alkyl, amino, or amino substituted with alkyl, aryl or heteroaryl as described above.

As used herein the term "alkylcarboxy" refers to the group —C(O)R$_a$ wherein R$_a$ is alkyl as described above.

As used herein the term "arylazo" refers to the group —N=NR$_a$ wherein R$_a$ is aryl as described above.

As used herein, the term "oxo" refers to the group =O.

As used herein, the term "mercapto" refers to the group —SH.

As used herein, the term "carboxyl" refers to the group —C(O)OH.

As used herein, the term "cyano" refers to the group —CN.

As used herein the term "cyanoalkyl" refers to the group —CNR$_a$, wherein R$_a$ is alkyl as defined above. Exemplary "cyanoalkyl" groups useful in the present invention include, but are not limited to, cyanomethyl, cyanoethyl, and cyanoisopropyl.

As used herein, the term "aminosulfonyl" refers to the group —S(O)$_2$NH$_2$.

As used herein, the term "carbamoyl" refers to the group —C(O)NH$_2$.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$—.

As used herein, the term "acyl" refers to the group R$_a$C(O)—, where R$_a$ is alkyl, cycloalkyl, or heterocyclyl as defined herein.

As used herein, the term "aroyl" refers to the group R$_a$C(O)—, where R$_a$ is aryl as defined herein.

As used herein, the term "aroylamino" refers to the group R$_a$C(O)NH—, which optionally includes a C$_1$–C$_6$ alkyl linker through which it may be attached, where R$_a$ is aryl as defined herein.

As used herein, the term "heteroaroyl" refers to the group R$_a$C(O)—, where R$_a$ is heteroaryl as defined herein.

As used herein, the term "alkoxycarbonyl" refers to the group R$_a$OC(O)—, where R$_a$ is alkyl as defined herein.

As used herein, the term "acyloxy" refers to the group R$_a$C(O)O—, where R$_a$ is alkyl, cycloalkyl, or heterocyclyl as defined herein.

As used herein, the term "aroyloxy" refers to the group R$_a$C(O)O—, where R$_a$ is aryl as defined herein.

As used herein, the term "heteroaroyloxy" refers to the group R$_a$C(O)O—, where R$_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or formula (II) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formulae (I) and (II) above as well as any wholly or partially equilibrated mixtures thereof. The present invention also covers the individual isomers of the compounds represented by the formulas above as mixtures with isomers thereof in which one or more chiral centers are inverted. Also, it is understood that all tautomers and mixtures of tautomers of the compounds of formulae (I) or (II) are included within the scope of the compounds of formulae (I) and (II).

It is to be understood that reference to compounds of formula (I), formula (II) and formula (III) above, following herein, refers to compounds within the scope of formula (I), formula (II), formula (III), and formulae (IV), (IVa), (IVb), and (IVc) as defined above with respect to X, A, D, R, R$^1$, R$^2$, R$^3$, R$^{3a}$, R$^4$, R$^5$, R$^6$, R$^7$, R$^8$, R', R'', R''', or R'''' unless specifically limited otherwise. It is also understood that the following embodiments, including uses and compositions, although recited with respect to formula (I) are also applicable to formula (II), formula (III), and formulae (IV), (IVa), (IVb), and (IVc).

In one embodiment, the compound of formula (I) is a compound of formula II):

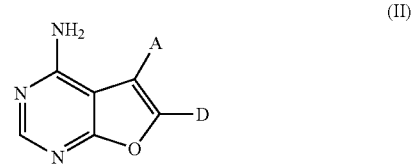

(II)

or salt, solvate, or physiologically functional derivative thereof, wherein A and D are as defined above in the first aspect of the invention.

In one embodiment, the compound of formula (I) is a compound of formula (III):

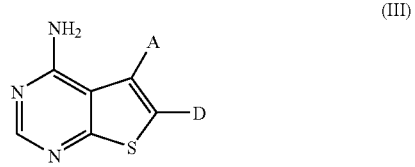

(III)

or salt, solvate, or physiologically functional derivative thereof, wherein A and D are as defined above in the first aspect of the invention.

In one embodiment, the compound of formula (I) is a compound of formula (IV):

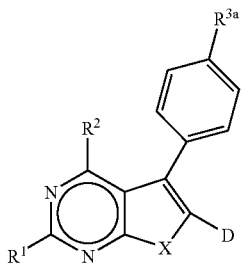

(IV)

or salt, solvate, or physiologically functional derivative thereof, wherein D, $R^1$, and $R^2$ are as defined above in the first aspect of the invention and $R^{3a}$ is as defined above in the seventh aspect of the invention.

In one embodiment, the compound of formula (I) is a compound of formula (IVa):

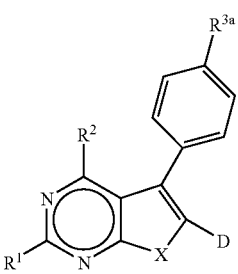

(IVa)

or salt, solvate, or physiologically functional derivative thereof, wherein D, $R^1$, $R^2$, and $R^3$ are as defined above in the first aspect of the invention.

In one embodiment, the compound of formula (I) is a compound of formula (IVb).

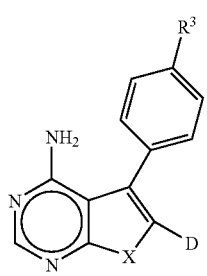

(IVb)

or salt, solvate, or physiologically functional derivative thereof, wherein D, $R^1$, $R^2$, and $R^3$ are as defined above in the first aspect of the invention.

In one embodiment, the compound of formula (I) is a compound of formula (IVc):

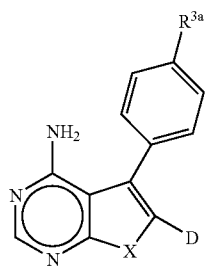

(IVc)

or salt, solvate, or physiologically functional derivative thereof, wherein D is as defined above in the first aspect of the invention and $R^{3a}$ is as defined above in the seventh aspect of the invention.

In one embodiment, X is O. In another embodiment, X is S.

In one embodiment, A is aryl, heteroaryl, or aryl or heteroaryl substituted with at least one independently selected $R^3$ group. In a preferred embodiment, A is aryl substituted with at least one independently selected $R^3$ group. In a more preferred embodiment, A is phenyl substituted with at least one independently selected $R^3$ group. In a most preferred embodiment, A is phenyl substituted with the group —NHC(O)$R^4$, wherein $R^4$ is the group NR'''R''''.

In one embodiment, D is hydrogen, halo, aryl, heteroaryl, or aryl or heteroaryl substituted with at least one independently selected $R^3$ group. In a preferred embodiment, D is hydrogen, halo, or aryl substituted with at least one independently selected $R^3$ group. In a more preferred embodiment, D is aryl substituted with at least one independently selected $R^3$ group. In another more preferred embodiment, D is hydrogen or halo.

In one embodiment, A is aryl, heteroaryl, or aryl or heteroaryl substituted with at least one independently selected $R^3$ group and D is hydrogen, halo, aryl, heteroaryl, or aryl or heteroaryl substituted with at least one independently selected $R^3$ group. In a preferred embodiment, A is aryl substituted with at least one independently selected $R^3$ group and D is hydrogen, halo, or aryl substituted with at least one independently selected $R^3$ group. In a more preferred embodiment, A is phenyl substituted with at least one independently selected $R^3$ group and D is hydrogen or halo. In another more preferred embodiment, A is phenyl substituted with at least one independently selected $R^3$ group and D is aryl substituted with at least one independently selected $R^3$ group.

In a most preferred embodiment, A is phenyl substituted with the group —NHC(O)$R^4$, wherein $R^4$ is the group NR'''R'''' and D is aryl substituted with at least one independently selected $R^3$ group. Alternatively, A is phenyl substituted with the group —NHC(O)$R^4$, wherein $R^4$ is the group NR'''R'''' and D is hydrogen or halo.

In one embodiment, $R^1$ is hydrogen, methyl, —C(O)NH$_2$, —NH$_2$, or —NHCH$_2$CH$_2$NR'''R''''. In a preferred embodiment, $R^1$ is hydrogen, methyl or —NH$_2$. In a more preferred embodiment $R^1$ is hydrogen.

In one embodiment, $R^2$ is $-NR^7R^7$. In a preferred embodiment, $R^2$ is $-NR^7R^7$ wherein the $R^7$ groups are selected from hydrogen or $C_1-C_6$ alkyl. In more preferred embodiment, $R^2$ is $-NH_2$.

In one embodiment, X is O, A is aryl, heteroaryl, or aryl or heteroaryl substituted with at least one independently selected $R^3$ group, D is hydrogen, halo, aryl, heteroaryl, or aryl or heteroaryl substituted with at least one independently selected $R^3$ group, $R^1$ is hydrogen, methyl, $-C(O)NH_2$, $-NH_2$, or $-NHCH_2CH_2NR'''R''''$, and $R^2$ is $-NR^7R^7$. In a preferred embodiment, X is O, A is aryl substituted with at least one independently selected $R^3$ group, D is hydrogen, halo, or aryl substituted with at least one independently selected $R^3$ group, $R^1$ is hydrogen, methyl, $-C(O)NH_2$, $-NH_2$, or $-NHCH_2CH_2NR'''R''''$, and $R^2$ is $-NR^7R^7$. In a more preferred embodiment, X is O, A is phenyl substituted with at least one independently selected $R^3$ group, D is hydrogen or halo, $R^1$ is hydrogen, methyl or $-NH_2$, and $R^2$ is $-NR^7R^7$ wherein the $R^7$ groups are selected from hydrogen or $C_1-C_6$ alkyl. In another more preferred embodiment, X is O, A is phenyl substituted with at least one independently selected $R^3$ group, D is aryl substituted with at least one independently selected $R^3$ group, $R^1$ is hydrogen or methyl, and $R^2$ is $-NR^7R^7$ wherein the $R^7$ groups are selected from hydrogen or $C_1-C_6$ alkyl.

In a most preferred embodiment, X is O, A is phenyl substituted with the group $-NHC(O)R^4$, wherein $R^4$ is the group $NR'''R''''$, D is aryl substituted with at least one independently selected $R^3$ group, $R^1$ is hydrogen, and $R^2$ is $-NH_2$. Alternatively, X is O, A is phenyl substituted with the group $-NHC(O)R^4$, wherein $R^4$ is the group $NR'''R''''$, D is hydrogen or halo, $R^1$ is hydrogen, and $R^2$ is $-NH_2$.

In one embodiment, X is S, A is aryl, heteroaryl, or aryl or heteroaryl substituted with at least one independently selected $R^3$ group, D is hydrogen, halo, aryl, heteroaryl, or aryl or heteroaryl substituted with at least one independently selected $R^3$ group, $R^1$ is hydrogen, methyl, $-C(O)NH_2$, $-NH_2$, or $-NHCH_2CH_2NR'''R''''$, and $R^2$ is $-NR^7R^7$. In a preferred embodiment, X is S, A is aryl substituted with at least one independently selected $R^3$ group, D is hydrogen, halo, or aryl substituted with at least one independently selected $R^3$ group, $R^1$ is hydrogen, methyl, $-C(O)NH_2$, $-NH_2$, or $-NHCH_2CH_2NR'''R''''$, and $R^2$ is $-NR^7R^7$. In a more preferred embodiment, X is S, A is phenyl substituted with at least one independently selected $R^3$ group, D is hydrogen or halo, $R^1$ is hydrogen, methyl or $-NH_2$, and $R^2$ is $-NR^7R^7$ wherein the $R^7$ groups are selected from hydrogen or $C_1-C_6$ alkyl. In another more preferred embodiment, X is S. A is phenyl substituted with at least one independently selected $R^3$ group, D is aryl substituted with at least one independently selected $R^3$ group $R^1$ is hydrogen, methyl or $-NH_2$, and $R^2$ is $-NR^7R^7$ wherein the $R^7$ groups are selected from hydrogen or $C_1-C_6$ alkyl.

In a most preferred embodiment, X is S, A is phenyl substituted with the group $-NHC(O)R^4$, wherein $R^4$ is the group $NR'''R''''$, D is aryl substituted with at least one independently selected $R^3$ group, $R^1$ is hydrogen, and $R^2$ is $-NH_2$. Alternatively, X is S, A is phenyl substituted with the group $-NHC(O)R^4$, wherein $R^4$ is the group $NR'''R''''$, D is hydrogen or halo, $R^1$ is hydrogen, and $R^2$ is $-NH_2$.

Specific examples of compounds of the present invention include the following:
4-Amino-3-(4-methoxyphenyl)-2-(3-(methylsulfonylamino)phenyl)furo[2,3-d]pyrimidine;
4-Amino-3-(4-(dimethylamino)phenyl)-2-(4-methoxyphenyl)-furo[2,3-d]pyrimidine;
4-Amino-3-(4-((3-chlorophenyl)sulfonylamino)phenyl)-2-(4-methoxyphenyl)furo[2,3-d]pyrimidine;
4-Amino-3-(4-((2-fluoro-5-(trifluoromethyl)phenyl)aminocarbonylamino)phenyl)-2-(4-methoxyphenyl)furo[2,3-d]pyrimidine;
4-Amino-3-(4-(2,3-difluorophenyl)phenyl)-2-(3-sulfamoylphenyl)-furo[2,3-d]pyrimidine;
4-Amino-3-(4-(3-biphenyl)phenyl)-2-(3-sulfamoylphenyl)furo[2,3-d]pyrimidine;
4-Amino-3-(4-((2-fluoro-5-(trifluoromethyl)phenyl)aminocarbonylamino)phenyl)thieno[2,3-d]pyrimidine;
4-Amino-3-(4-biphenyl)-2-(4-fluoro-3-(methylsulfonylamino)-phenyl)furo[2,3-d]pyrimidine; and
4-Amino-2-(3-cyanophenyl)-3-(4-((2-fluoro-5-(trifluoromethyl)-phenyl)amino carbonylamino)phenyl)furo[2,3-d]pyrimidine;

or a salt, solvate, or physiologically functional derivative thereof.

Further specific Examples of compounds of the present invention include:
4-Amino-2,3-diphenylfuro[2,3-d]pyrimidine;
4-Amino-2,3-bis(4-methoxyphenyl)furo[2,3-d]pyrimidine;
4-Amino-3-(methoxyphenyl)furo[2,3-d]pyrimidine;
4-Amino-2,3-bis(3,4-O-methylidenedioxyphenyl)furo[2,3-d]pyrimidine;
4-Amino-2,3-dibutylfuro[2,3-d]pyrimidine;
4-Amino-2-(4-methoxyphenyl)furo[2,3-d]pyrimidine;
4-Amino-2-(3-furanyl)-3-(2-furanyl)furo[2,3-d]pyrimidine;
4-Amino-2,3-bis(4-methyl phenyl)furo[2,3-d]pyrimidine;
4-Amino-2-(4-methylphenyl)-3-(4-trifluoromethylphenyl)furo[2,3-d]pyrimidine;
4-Amino-3-(4-methylphenyl)-2-(4-trifluoromethylphenyl)furo[2,3-d]pyrimidine;
4-Amino-2-(2-benzothienyl)-3-(4-methoxyphenyl)furo[2,3-d]pyrimidine;
4-Amino-2-(4-biphenyl)-3-(4-methoxyphenyl)furo[2,3-d]pyrimidine;
4-Amino-2-(2-chlorophenyl)-3-(4-methoxylphenyl)furo[2,3-d]pyrimidine;
4-Amino-2-(2-methoxylphenyl)-3-(4-methoxyl l)furo[2,3-d]pyrimidine;
4-Amino-3-(4-methoxyphenyl)-2-(1-naphthyl)furo[2,3-d]pyrimidine;
4-Amino-3-(4-methoxyphenyl)-2-(2-naphthyl)furo[2,3-d]pyrimidine;
4-Amino-3-(4-methoxyphenyl)-2-(4-trifluoromethyloxyphenyl)-furo[2,3-d]pyrimidine;
4-Amino-2-(3-methoxyphenyl)-3-(4-methoxyphenyl)furo[2,3-d]pyrimidine;
3-(3-Acetamidophenyl)-4-amino-2-(4-methoxyphenyl)furo[2,3-d]pyrimidine;
4-Amino-3-(3,4-dimethoxyphenyl)-2-(4-methoxyphenyl)furo[2,3-d]pyrimidine;
4-Amino-2-(4-methoxyphenyl)-3-(3,4,5-trimethoxyphenyl)furo[2,3-d]pyrimidine;
4-Amino-3-(4-isopropylphenyl)-2-(4-methoxyphenyl)furo[2,3-d]pyrimidine;
4-Amino-3-(4-butylphenyl)-2-(4-methoxyphenyl)furo[2,3-d]pyrimidine;
4-Amino-2-(4-methoxyphenyl)-3-(3-methoxyphenyl)furo[2,3-d]pyrimidine;
4-Amino-3-bromo-2-(4-methoxyphenyl)furo[2,3-d]pyrimidine;
4-Amino-3-(4-biphenyl)-2-(4-methoxyphenyl)furo[2,3-d]pyrimidine;

4-Amino-2-(4-methoxyphenyl)-3-(2-methoxyphenyl)furo[2,3-d]pyrimidine;
4-Amino-2-(4-methoxyphenyl)-3-((4-methylthio)phenyl)furo[2,3-d]pyrimidine;
4-Amino-2-(4-methoxyphenyl)-3-(1-naphthyl)furo[2,3-d]pyrimidine;
4-Amino-2-(4-methoxyphenyl)-3-(2-naphthyl)furo[2,3-d]pyrimidine;
4-Amino-2-(4-methoxyphenyl)-3-(4-(trifluoromethyloxy)phenyl)-furo[2,3-d]pyrimidine;
4-Amino-3-(2,5-dimethoxyphenyl)-2-(4-methoxyphenyl)furo[2,3-d]pyrimidine;
4-Amino-2-(4-methoxyphenyl)-3-(4-(methylsulfonyl)phenyl)-furo[2,3-d]pyrimidine;
4-Amino-2-(4-methoxyphenyl)-3-(4-(phenyloxy)phenyl)furo[2,3-d]pyrimidine;
4-Amino-2-(4-methoxyphenyl)-3-(3-pyridyl)furo[2,3-d]pyrimidine;
4-Amino-3-(4-cyanophenyl)-2-(4-methoxyphenyl)furo[2,3-d]pyrimidine;
4-Amino-2-(4-methoxyphenyl)-3-(4-tert-butylphenyl)furo[2,3-d]pyrimidine;
4-Amino-2-(4-methoxyphenyl)-3-((3-fluoro-4-phenyl)phenyl)-furo[2,3-d]pyrimidine;
4-Amino-3-((4-benzyloxy-3-fluoro)phenyl)-2-(4-methoxyphenyl)-furo[2,3-d]pyrimidine;
4-Amino-3-((4-ethylthio) phenyl)-2-(4-methoxyphenyl)furo[2,3-d]pyrimidine;
4-Amino-3-(3-chloro-4-fluorophenyl)-2-(4-methoxyphenyl)-furo[2,3-d]pyrimidine;
4-Amino-2-(3,4-dichlorophenyl)-3-(4-methoxyphenyl)furo[2,3-d]pyrimidine;
4-Amino-2-(4-methoxyphenyl)-3-(2-phenylethyn-1-yl)furo[2,3-d]pyrimidine;
4-Amino-3-(4-methoxyphenyl)-2-(2-methylphenyl)furo[2,3-d]pyrimidine;
4-Amino-2-(2-chlorophenyl)-3-(4-methoxyphenyl)furo[2,3-d]pyrimidine;
4-Amino-2-(2-fluorophenyl)-3-(4-methoxyphenyl)furo[2,3-d]pyrimidine;
4-Amino-2-(3-acetamidophenyl)-3-(4-methoxyphenyl)furo[2,3-d]pyrimidine;
4-Amino-3-(4-methoxyphenyl)-2-(3-pyridyl)furo[2,3-d]pyrimidine;
4-Amino-3-(2-butylethyn-1-yl)-2-(4-methoxyphenyl)furo[2,3-d]pyrimidine;
4-Amino-3-(2-(3-methylbutyl)ethyn-1-yl)-2-(4-methoxyphenyl)-furo[2,3-d]pyrimidine;
4-Amino-3-(2-(tert-butyl)ethyn-1-yl)-2-(4-methoxyphenyl)furo[2,3-d]pyrimidine;
4-Amino-3-(4-(hydroxymethyl)phenyl)-2-(4-methoxyphenyl)-furo[2,3-d]pyrimidine;
4-Amino-3-(4-biphenyl)-2-(2-methoxyphenyl)furo[2,3-d]pyrimidine;
4-Amino-2-(2-methoxyphenyl)-3-((4-methylthio)phenyl)furo[2,3-d]pyrimidine;
4-Amino-3-(4-methoxyphenyl)-2-(2-phenylethyn-1-yl)furo[2,3-d]pyrimidine;
4-Amino-2-(2-butylethyn-1-yl)-3-(4-methoxyphenyl)furo[2,3-d]pyrimidine;
4-Amino-2-(2-biphenyl)-3-(4-methoxyphenyl)furo[2,3-d]pyrimidine;
4-Amino-2-(3-biphenyl)-3-(4-methoxyphenyl)furo[2,3-d]pyrimidine;
4-Amino-2-(4-(2-carboxyethyl)phenyl)-3-(4-methoxyphenyl)furo[2,3-d]pyrimidine;

4-Amino-3-(4-methoxyphenyl)-2-(4-(methylsulfonyl)phenyl)-furo[2,3-d]pyrimidine;
4-Amino-2-(4-carboxyphenyl)-3-(4-methoxyphenyl)furo[2,3-d]pyrimidine;
4-Amino-3-(4-methoxyphenyl)-2-(1-(4-chlorophenyl)-1-hydroxy)methyl)furo[2,3-d]pyrimidine;
4-Amino-3-(4-isopropyl phenyl)-2-(2-methoxyphenyl)furo[2,3-d]pyrimidine;
4-Amino-3-(4-(cyclopentyloxy)phenyl)-2-(2-methoxyphenyl)furo[2,3-d]pyrimidine;
4-Amino-3-(4-(isopropyloxy)phenyl)-2-(2-methoxyphenyl)furo[2,3-d]pyrimidine;
4-Benzyloxycarbonylamino-3-(4-methoxyphenyl)furo[2,3-d]-pyrimidine;
4-Amino-3-(4-methoxyphenyl)-2-(2-phenylethen-1-yl)furo[2,3-d]pyrimidine;
4-Amino-3-(4-methoxyphenyl)-2-(2-phenylethyl)furo[2,3-d]pyrimidine;
4-Amino-3-(4-methoxyphenyl)-2-(4-(morpholinocarbonyl)phenyl)-furo[2,3-d]pyrimidine;
4-Amino-3-(4-methoxyphenyl)-2-(4-(N-methylcarbamoyl)phenyl)-furo[2,3-d]pyrimidine;
4-Amino-3-(4-methoxyphenyl)-2-(4-(N-(2-(4-imidazolyl)ethyl)carbamoyl)phenyl)furo[2,3-d]pyrimidine;
2,3-Bis(4-methoxyphenyl)-4,5-dihydro-4-imino-5-methyl-furo[2,3-d]pyrimidine;
3,4-Bis(4-methoxyphenyl)-4-methylaminofuro[2,3-d]pyrimidine;
4-Amino-3-(4-methoxyphenyl)-2-(4-(N-(2-dimethylaminoethyl)-carbamoyl)phenyl)furo[2,3-d]pyrimidine;
4-Amino-2-(1-hexen-1-yl)-3-(4-methoxyphenyl)furo[2,3-d]pyrimidine;
4-Amino-2-hexyl-3-(4-methoxyphenyl)furo[2,3-d]pyrimidine;
4-Amino-3-(2,4-dimethoxyphenyl)-2-(4-methoxyphenyl)furo[2,3-d]pyrimidine;
4-Amino-3-(4-methoxyphenyl)-2-(2-methoxypyridin-5-yl)furo[2,3-d]pyrimidine;
4-Amino-2-(4-(dimethylamino)phenyl)-3-(4-methoxyphenyl)furo[2,3-d]pyrimidine;
4-Amino-2-(2,4-dimethoxyphenyl)-3-(4-methoxyphenyl)furo[2,3-d]pyrimidine;
4-Amino-2-(4-methoxyphenyl)-3-(2-methoxypyridin-5-yl)furo[2,3-d]pyrimidine;
4-Amino-2-((3-chlorophenyl)oxymethyl)-3-(4-methoxyphenyl)-furo[2,3-d]pyrimidine;
4-Amino-2-((4-fluorophenyl)oxymethyl)-3-(4-methoxyphenyl)-furo[2,3-d]pyrimidine;
4-Amino-3-(4-methoxyphenyl)-2-((1-hydroxy-1-phenyl)methyl)-furo[2,3-d]pyrimidine;
4-Amino-2-(3-carbamoylphenyl)-3-(4-methoxyphenyl)furo[2,3-d]pyrimidine;
4-Amino-2-(3-(N-dimethylcarbamoyl)phenyl)-3-(4-methoxyphenyl) furo[2,3-d]pyrimidine;
4-Amino-2-(1-methylindol-5-yl)-3-(4-methoxyphenyl)furo[2,3-d]pyrimidine;
4-Amino-2-((2-hydroxymethyl)phenyl)-3-(4-methoxyphenyl)-furo[2,3-d]pyrimidine;
4-Amino-2-(3-aminophenyl)-3-(4-methoxyphenyl)furo[2,3-d]pyrimidine;
4-Amino-2-carboxy-3-(4-methoxyphenyl)furo[2,3-d]pyrimidine;
4-Amino-2-(2-carboxyphenyl)-3-(4-methoxyphenyl)furo[2,3-d]pyrimidine;
4-Amino-2-(3-methoxycarbonylphenyl)-3-(4-methoxyphenyl)-furo[2,3-d]pyrimidine;

4-Amino-2-(4-methoxyphenyl)-3-(1-methylindol-5-yl)furo[2,3-d]pyrimidine;
4-Amino-2-(3-carboxyphenyl)-3-(4-methoxyphenyl)furo[2,3-d]pyrimidine;
4-Amino-3-(4-methoxyphenyl)-2-(3-(N-(2-(4-imidazolyl)ethyl)carbamoyl)phenyl)furo[2,3-d]pyrimidine;
4-Amino-3-(4-methoxyphenyl)-2-(3-((4-methylpiperazin-1-yl)-carbonyl)phenyl)furo[2,3-d]pyrimidine;
4-Amino-3-(4-methoxyphenyl)-2-(3-(N-(2-dimethylaminoethyl)-carbamoyl)phenyl)furo[2,3-d]pyrimidine;
4-Amino-2-((2-cyanophenyl)oxymethyl)-3-(4-methoxyphenyl)-furo[2,3-d]pyrimidine;
4-Amino-2-((2-fluorophenyl)oxymethyl)-3-(4-methoxyphenyl)-furo[2,3-d]pyrimidine;
4-Amino-3-(4-methoxyphenyl)-2-(3-(N-(4-pyridyl)carbamoyl)-phenyl)furo[2,3-d]pyrimidine;
4-Amino-2-(2-carbamoylphenyl)-3-(4-methoxyphenyl)furo[2,3-d]pyrimidine;
4-Amino-2-(4-carboxy-2-methoxyphenyl)-3-(4-methoxyphenyl)-furo[2,3-d]pyrimidine;
4-Amino-3-(4-methoxyphenyl)-2-(3-(N-(3-pyridyl)carbamoyl)-phenyl)furo[2,3-d]pyrimidine;
2-((3-Acetamidophenyl)oxymethyl)-4-amino-3-(4-methoxyphenyl)-furo[2,3-d]pyrimidine;
4-Amino-2-((3-cyanophenyl)oxymethyl)-3-(4-methoxyphenyl)-furo[2,3-d]pyrimidine;
4-Amino-2-(3-methoxycarbonyl-4-(methylamino)phenyl)-3-(4-methoxyphenyl)furo[2,3-d]pyrimidine;
4-Amino-3-(4-methoxyphenyl)-2-(4-methylamino-3-carboxyphenyl)furo[2,3-d]pyrimidine hydrochloride;
4-Amino-2-(4-methoxyphenyl)-3-(4-(methylsulfonylamino)phenyl) furo[2,3-d]pyrimidine;
4-Amino-3-(4-methoxyphenyl)-2-(N-(3-methylindazol-5-yl)carbamoyl)furo[2,3-d]pyrimidine;
4-Amino-2-((1,2-bis(ethoxycarbonyl)hydradino)methyl)-3-(4-methoxyphenyl)furo[2,3-d]pyrimidine;
4-Amino-3-(4-(diethylamino)phenyl)-2-(4-methoxyphenyl)furo[2,3-d]pyrimidine;
4-Amino-3-(4-methoxyphenyl)-2-(N-phenylcarbamoyl)furo[2,3-d]pyrimidine;
4-Amino-2-(((5-amino-3-methyl)indazol-1-yl)carbonyl)-3-(4-methoxyphenyl)furo[2,3-d]pyrimidine;
4-Amino-3-(4-methoxyphenyl)-2-(1-pyrrolizinocarbonyl)furo[2,3-d]pyrimidine;
4-Amino-3-(4-methoxyphenyl)-2-((N,N-dicyclohexyl)carbamoyl)furo-[2,3-d]pyrimidine;
4-Amino-3-(4-methoxyphenyl)-2-(N-isopropylcarbamoyl)furo-[2,3-d]pyrimidine;
4-Amino-3-(4-methoxyphenyl)-2-(N-(2-dimethylaminoethyl)carbamoyl)furo[2,3-d]pyrimidine;
4-Amino-2-(4-methoxyphenyl)-3-(4-(1-pyrrolidino)phenyl)furo[2,3-d]pyrimidine;
4-Amino-2-(5-indolyl)-3-(4-methoxyphenyl)furo[2,3-d]pyrimidine;
4-Amino-3-(4-methoxyphenyl)-2-((2-(phenylamino)ethyl)oxycarbonyl)furo[2,3-d]pyrimidine;
4-Amino-2-((3-hydroxypiperizin-1-yl)carbonyl)-3-(4-methoxyphenyl)furo[2,3-d]pyrimidine;
4-Amino-3-(4-methoxyphenyl)-2-((N-(2-cyanoethyl)-N-phenyl)carbamoyl)furo[2,3-d]pyrimidine;
4-Amino-3-(4-biphenyl)-2-(3-carbamoylphenyl)furo[2,3-d]pyrimidine;
2-(3-Acetamidophenyl)-4-amino-3-(4-biphenyl)furo[2,3-d]pyrimidine;
4-Amino-3-(4-methoxyphenyl)-2-((N-(methoxycarbonylmethyl)-N-phenyl)carbamoyl)furo[2,3-d]pyrimidine;
4-Amino-2-(3-carbamoyl-4-chlorophenyl)-3-(4-methoxyphenyl)-furo[2,3-d]pyrimidine;
4-Amino-2-(3-aminophenyl)-3-(4-biphenyl)furo[2,3-d]pyrimidine;
4-Amino-2-(3-(aminomethyl)phenyl)-3-(4-biphenyl)furo[2,3-d]pyrimidine;
4-Amino-3-(4-biphenyl)-2-(4-(dimethylamino)phenyl)furo[2,3-d]pyrimidine;
4-Amino-2-((N-(2-(tert-butoxycarbonylamino)ethyl)-N-phenyl)carbamoyl)-3-(4-methoxyphenyl)furo[2,3-d]pyrimidine;
4-Amino-3-(4-methoxyphenyl)-2-((N-carboxymethyl-N-phenyl)carbamoyl)furo[2,3-d]pyrimidine;
4-Amino-2-carbamoyl-3-(4-methoxyphenyl)furo[2,3-d]pyrimidine;
4-Amino-3-(4-methoxyphenyl)-2-(3-((2-morpholinoethyl)sulfonylamino)phenyl)furo[2,3-d]pyrimidine;
4-Amino-3-(4-methoxyphenyl)-2-((2-methyl)benzothiazol-5-yl)furo[2,3-d]pyrimidine;
4-Amino-2-(6-indolyl)-3-(4-methoxyphenyl)furo[2,3-d]pyrimidine;
4-Amino-2-(3-carbamoyl-4-fluorophenyl)-3-(4-methoxyphenyl)furo[2,3-d]pyrimidine;
4-Amino-3-(4-biphenyl)-2-(3-carbamoyl-4-fluorophenyl)furo[2,3-d]pyrimidine;
4-Amino-2-((4-hydroxypiperizin-1-yl)carbonyl)-3-(4-methoxyphenyl)furo[2,3-d]pyrimidine;
4-Amino-2-(4-amino-3-(N-methylcarbamoyl)phenyl)-3-(4-methoxyphenyl)furo[2,3-d]pyrimidine;
4-Amino-2-((N-(carbamoylmethyl)-N-phenyl)carbamoyl)-3-(4-methoxyphenyl)furo[2,3-d]pyrimidine;
4-Amino-2-((N-(2-(aminocarbonylamino)ethyl)-N-phenyl)carbamoyl)-3-(4-methoxyphenyl)furo[2,3-d]pyrimidine;
4-Amino-2-(2-aminoxadiazol-5-yl)-3-(4-methoxyphenyl)furo[2,3-d]pyrimidine;
4-Amino-2-(4-(ethoxycarbonyl)thiazol-2-yl)-3-(4-methoxyphenyl)-furo[2,3-d]pyrimidine;
4-Amino-2-((4-(4-fluorophenyl)-5-methyl)thiazol-2-yl)-3-(4-methoxyphenyl)furo[2,3-d]pyrimidine;
4-Amino-2-(5-indolyl)-3-(4-(3-pyridyl)phenyl)furo[2,3-d]pyrimidine;
4-Amino-2-(2-imidazolin-2-yl)-3-(4-methoxyphenyl)furo[2,3-d]pyrimidine;
4-Amino-2-(2-(phenylamino)oxadiazol-5-yl)-3-(4-methoxyphenyl)-furo[2,3-d]pyrimidine;
4-Amino-2-(1H-indeno[3,2-d]thiazol-2-yl)-3-(4-methoxyphenyl)furo[2,3-d]pyrimidine;
4-Amino-3-(4-methoxyphenyl)-2-(4-methylthiazol-2-yl)furo[2,3-d]pyrimidine;
4-Amino-2-((3-(2-(dimethylamino)ethyl)aminocarbonylamino)phenyl)-3-(4-methoxyphenyl)furo[2,3-d]pyrimidine;
4-Amino-3-(4-biphenyl)-2-((3-(2-(dimethylamino)ethyl)-aminocarbonylamino)phenyl)furo[2,3-d]pyrimidine;
4-Amino-3-(4-biphenyl)-2-(3-(methylsulfonylamino)phenyl)furo[2,3-d]pyrimidine;
4-Amino-3-(4-methoxyphenyl)-2-(4-(N-methylcarbamoyl)thiazol-2-yl)furo[2,3-d]pyrimidine;
4-Amino-3-(4-(3-fluorophenyl)phenyl)-2-(3-(methylsulfonylamino)phenyl)furo[2,3-d]pyrimidine;
4-Amino-3-(4-methoxyphenyl)-2-(4-(N-phenylcarbamoyl)thiazol-2-yl)furo[2,3-d]pyrimidine;
4-Amino-2-(1-benzyl-4,5-dihydro-1H-imidazol-2-yl)-3-(4-methoxyphenyl)furo[2,3-d]pyrimidine;
4-Amino-3-(4-methoxyphenyl)-2-(3-sulfamoylphenyl)furo[2,3-d]pyrimidine;

4-Amino-3-(4-biphenyl)-2-(3-sulfamoylphenyl)furo[2,3-d]pyrimidine;
4-Amino-3-(4-methoxyphenyl)-2-(2-oxadiazolyl)furo[2,3-d]pyrimidine;
4-Amino-3-(4-methoxyphenyl)-2-(5,6,7,7a-tetrahydro-1H-pyrrolo[1,2–C]imidazol-3-yl)furo[2,3-d]pyrimidine;
4-Amino-2-(4-carboxythiazol-2-yl)-3-(4-methoxyphenyl)furo[2,3-d]pyrimidine;
4-Amino-2-(3-(methylsulfonylamino)phenyl)furo[2,3-d]pyrimidine;
4-Amino-3-(4-methoxyphenyl)-2-(N-(2-phenylethyl)carbamoyl)-furo[2,3-d]pyrimidine;
4-Amino-2-(N-(3-fluorophenyl)carbamoyl)-3-(4-methoxyphenyl)-furo[2,3-d]pyrimidine;
4-Amino-2-(N-(4-chlorophenyl)carbamoyl)-3-(4-methoxyphenyl)-furo[2,3-d]pyrimidine;
4-Amino-3-(4-methoxyphenyl)-2-(N-(4-methoxyphenyl)carbamoyl)-furo[2,3-d]pyrimidine;
4-Amino-2-(N-(2-benzoimidazolyl)carbamoyl)-3-(4-methoxyphenyl)furo[2,3-d]pyrimidine;
4-Amino-3-(4-(2,3-difluorophenyl)phenyl)-2-(4-fluoro-3-(methylsulfonylamino) phenyl)furo[2,3-d]pyrimidine;
4-Amino-2-(N-(2-hydroxyphenyl)carbamoyl)-3-(4-methoxyphenyl)furo[2,3-d]pyrimidine;
4-Amino-2-(4-fluoro-3-(methylsulfonylamino)phenyl)-3-(4-methoxyphenyl)furo[2,3-d]pyrimidine;
4-Amino-3-(4-biphenyl)-2-(4-fluoro-3-(methylsulfonylamino)phenyl)furo[2,3-d]pyrimidine;
4-Amino-2-((6,7-dimethoxy-1,2,3,4-tetrahydroisoquinolin-2-yl)carbonyl)-3-(4-methoxyphenyl)furo[2,3-d]pyrimidine;
4-Amino-2-(N-(2-carbamoylphenyl)carbamoyl)-3-(4-methoxyphenyl)furo[2,3-d]pyrimidine;
4-Amino-2-(4-fluoro-3-(methylsulfonylamino)phenyl)-3-(4-(3-thienyl) phenyl)furo[2,3-d]pyrimidine;
4-Amino-2-(3-(aminocarbonylamino)phenyl)-3-(4-methoxyphenyl)furo[2,3-d]pyrimidine;
4-Amino-2-(3-(aminocarbonylamino)phenyl)-3-(4-biphenyl)furo[2,3-d]pyrimidine;
4-Amino-2-(N-(3-cyanophenyl)carbamoyl)-3-(4-methoxyphenyl)furo[2,3-d]pyrimidine;
4-Amino-3-(4-methoxyphenyl)-2-(N-(3-pyridyl)carbamoyl)furo[2,3-d]pyrimidine;
4-Amino-2-(N-(α-cyanobenzyl)carbamoyl)-3-(4-methoxyphenyl)furo[2,3-d]pyrimidine;
4-Amino-2-(N-(3,5-dimethoxyphenyl)carbamoyl)-3-(4-methoxyphenyl)furo[2,3-d]pyrimidine;
4-Amino-3-(4-bi phenyl)-2-(4-methoxy-3-(methylsulfonylamino) phenyl)furo[2,3-d]pyrimidine;
4-Amino-3-(4-biphenyl)-2-(3-((2-fluoro-5-(trifluoromethyl)phenyl)amino carbonylamino)phenyl)furo[2,3-d]pyrimidine;
4-Amino-3-(4-biphenyl)-2-(4-(methylsulfonylamino)phenyl)furo[2,3-d]pyrimidine;
4-Amino-3-(4-biphenyl)-2-(4-(aminocarbonylamino)phenyl)furo[2,3-d]pyrimidine;
4-Amino-3-(4-bi phenyl)-2-(3-((4-pyridylcarbonyl)amino)phenyl)-furo[2,3-d]pyrimidine;
4-Amino-3-(4-methoxyphenyl)-2-(4-(methylsulfonylamino)-phenyl)furo[2,3-d]pyrimidine;
4-Amino-2-(4-(aminocarbonylamino)phenyl)-3-(4-methoxyphenyl)furo[2,3-d]pyrimidine;
4-Amino-2-(5-benzotriazolyl)-3-(4-biphenyl)furo[2,3-d]pyrimidine;
4-Amino-3-(4-biphenyl)-2-(3-(p-toluenesulfonylamino) phenyl)-furo[2,3-d]pyrimidine;
4-Amino-2-(5-benzimidazolyl)-3-(4-biphenyl)furo[2,3-d]pyrimidine;
4-Amino-3-(4-biphenyl)-2-(4-sulfamoylphenyl)furo[2,3-d]pyrimidine;
4-Amino-3-(4-biphenyl)-2-(3-(N-methylsulfonyl)phenyl)furo[2,3-d]pyrimidine;
4-Amino-2-(4-fluoro-3-(methylsulfonylamino)phenyl)-3-(4-(2-pyridyl)phenyl)furo[2,3-d]pyrimidine;
4-Amino-3-(4-biphenyl)-2-(4-((dimethylamino)sulfonylamino)-phenyl)furo[2,3-d]pyrimidine;
4-Amino-3-(4-biphenyl)-2-(4-((1-iminoethyl)amino)phenyl)furo[2,3-d]pyrimidine;
4-Amino-3-(4-(4-tert-butylphenyl)phenyl)-2-(3-sulfamoylphenyl)-furo[2,3-d]pyrimidine;
4-Amino-3-(4-biphenyl)-2-(3-((dimethylamino)sulfonylamino)-phenyl)furo[2,3-d]pyrimidine;
4-Amino-3-(4-(2-pyridyl)phenyl)-2-(3-sulfamoylphenyl)furo[2,3-d]pyrimidine;
4-Amino-3-(4-(3-pyridyl)phenyl)-2-(3-sulfamoylphenyl)furo[2,3-d]pyrimidine;
4-Amino-3-(4-biphenyl)-2-(4-cyanophenyl)furo[2,3-d]pyrimidine;
4-Amino-3-(4-biphenyl)-2-(4-(tetrazol-5-yl)phenyl)furo[2,3-d]pyrimidine;
4-Amino-3-(4-biphenyl)-2-(3-(tetrazol-5-yl)phenyl)furo[2,3-d]pyrimidine;
4-Amino-3-(4-(1-naphthyl)phenyl)-2-(3-sulfamoylphenyl)furo[2,3-d]pyrimidine;
4-Amino-3-(4-(4-(ethylsulfonyl)phenyl)phenyl)-2-(3-sulfamoylphenyl)furo[2,3-d]pyrimidine;
4-Amino-2,3-bis(4-methoxyphenyl)-6-(ethoxycarbonyl)furo[2,3-d]pyrimidine;
4-Amino-3-(4-(4,6-bis(trifluoromethyl)phenyl)phenyl)-2-(3-sulfamoyl phenyl)furo[2,3-d]pyrimidine;
4-Amino-3-(4-(2-fluorobiphen-4-yl)phenyl)-2-(3-sulfamoylphenyl)furo[2,3-d]pyrimidine;
4-Amino-2,3-bis(4-methoxyphenyl)-6-carbamoylfuro[2,3-d]pyrimidine;
4-Amino-3-(4-((4-chlorophenyl)aminocarbonylamino)phenyl)-2-(4-methoxyphenyl)furo[2,3-d]pyrimidine;
4-Amino-3-(4-methoxyphenyl)-2-(4-(tetrazol-5-yl)phenyl)furo[2,3-d]pyrimidine;
4-Amino-3-(4-methoxyphenyl)-2-(3-(tetrazol-5-yl)phenyl)furo[2,3-d]pyrimidine;
4-Amino-3-(4-((3-fluorobenzoyl)amino)phenyl)-2-(4-methoxyphenyl)furo[2,3-d]pyrimidine;
4-Amino-3-(4-((2-fluorobenzoyl)amino)phenyl)-2-(4-methoxyphenyl)furo[2,3-d]pyrimidine;
4-Amino-2,3-bis(4-methoxyphenyl)-6-methylfuro[2,3-d]pyrimidine;
4-Amino-3-(4-((2-fluoro-5-(trifluoromethyl)phenyl)-aminocarbonylamino)phenyl)-6-(methylamino)furo[2,3-d]pyrimidine;
4-Amino-3-(4-((2-naphthylsulfonyl)amino)phenyl)-2-(4-methoxyphenyl)furo[2,3-d]pyrimidine;
4-Amino-3-(4-(3-acetamidophenyl)phenyl)-2-(3-sulfamoylphenyl)-furo[2,3-d]pyrimidine;
4-Amino-3-(4-(aminocarbonylamino)phenyl)-2-(4-methoxyphenyl)-furo[2,3-d]pyrimidine;
4-Amino-2-(4-methoxyphenyl)-3-(4-(phenyl(aminocarbonylamino))-phenyl)furo[2,3-d]pyrimidine;
4-Amino-3-(4-(cyclohexyl(aminocarbonylamino))phenyl)-2-(4-methoxyphenyl)furo[2,3-d]pyrimidine;
4-Amino-3-(4-(butyl(aminocarbonylamino))phenyl)-2-(4-methoxyphenyl)furo[2,3-d]pyrimidine;

4-Amino-3-(4-(((2-fluoro-5-(trifluoromethyl)phenyl)-aminocarbonylamino)methyl)phenyl)-2-(4-methoxyphenyl)furo[2,3-d]pyrimidine;
4-Amino-3-(3-((2-fluoro-5-(trifluoromethyl)phenyl)-aminocarbonylamino)phenyl)-2-(4-methoxyphenyl)furo[2,3-d]pyrimidine;
4-Amino-3-(4-((2-fluoro-5-(trifluoromethyl)phenyl)-aminocarbonylamino)phenyl)furo[2,3-d]pyrimidine;
4-Amino-3-(4-(aminomethyl)phenyl)-2-(4-methoxyphenyl)furo[2,3-d]pyrimidine;
4-Amino-3-(3-aminophenyl)-2-(4-methoxyphenyl)furo[2,3-d]pyrimidine;
4-Amino-3-(4-((2-fluoro-5-(trifluoromethyl)phenyl)-aminocarbonylamino)phenyl)-2-(3-sulfamoylphenyl)furo[2,3-d]pyrimidine;
4-Amino-2-(4-cyanophenyl)-3-(4-((2-fluoro-5-(trifluoromethyl)-phenyl) aminocarbonylamino)phenyl)furo[2,3-d]pyrimidine;
4-Amino-3-(4-(phenyl(aminothiocarbonylamino))phenyl)furo[2,3-d]pyrimidine;
3-(4-nitrophenyl)-4-(phenylamino)furo[2,3-d]pyrimidine;
4-(methyllamino)-3-(4-nitrophenyl)-furo[2,3-d]pyrimidine;
3-(4-Aminophenyl)-4-(methylamino)furo[2,3-d]pyrimidine;
3-(4-Aminophenyl)-4-(phenylamino)furo[2,3-d]pyrimidine;
3-(4-Aminophenyl)-4-(dimethylamino)furo[2,3-d]pyrimidine;
4-(Dimethylamino)-3-(4-nitrophenyl)furo[2,3-d]pyrimidine;
3–4-((2-Fluoro-5-(trifluoromethyl)phenyl)aminocarbonylamino)-phenyl)-4-(methylamino)furo[2,3-d]pyrimidine;
3-(4-((2-Fluoro-5-(trifluoromethyl)phenyl)aminocarbonylamino)-phenyl)-4-(phenylamino)furo[2,3-d]pyrimidine;
4-(Dimethylamino)-3-(4-((2-Fluoro-5-(trifluoromethyl)phenyl)-aminocarbonylamino)phenyl)furo[2,3-d]pyrimidine;
4,5-Dihydro-3-(4-nitrophenyl)-4-oxofuro[2,3-d]pyrimidine;
3-(4-((2-Fluoro-5-(trifluoromethyl)phenyl)aminocarbonylamino)-phenyl)-6-(methylthio)furo[2,3-d]pyrimidine;
4-Amino-3-(4-((3-ethylphenyl)aminocarbonylamino)phenyl)furo[2,3-d]pyrimidine;
4-Amino-3-(4-((4-(dimethylamino)phenyl)aminocarbonylamino)-phenyl)furo[2,3-d]pyrimidine;
3-(4-((2-Fluoro-5-(trifluoromethyl)phenyl)aminocarbonylamino)-phenyl)-6-(methylsulfonyl)furo[2,3-d]pyrimidine;
4-Amino-3-(4-((4-methoxyphenyl)aminocarbonylamino)phenyl)-furo[2,3-d]pyrimidine;
4-Amino-3-(4-((2,2,4,4-tetrafluoro-1,3-benzodioxan-5-yl)-aminocarbonylamino)phenyl)furo[2,3-d]pyrimidine;
4-Amino-3-(4-((4-(phenyloxy)phenyl)aminocarbonylamino)phenyl)-furo[2,3-d]pyrimidine;
4-Amino-3-(4-((5-Indanyl)aminocarbonylamino)phenyl)furo[2,3-d]pyrimidine;
4-Amino-3-(4-((2,5-bis(trifluoromethyl)phenyl)aminocarbonylamino)-phenyl)furo[2,3-d]pyrimidine;
4-Amino-3-(4-((3-(phenyloxy)phenyl)aminocarbonylamino)phenyl)-furo[2,3-d]pyrimidine;
4-Amino-3-(4-((2,5-dimethoxyphenyl)aminocarbonylamino)phenyl)-furo[2,3-d]pyrimidine;
4-Amino-3-(4-((5-(trifluoromethyl)phenyl)aminocarbonylamino)-phenyl)furo[2,3-d]pyrimidine;
4-Amino-3-(4-((5-(trifluoromethylthio)phenyl)aminocarbonylamino)-phenyl)furo[2,3-d]pyrimidine;
4-Amino-3-(4-((3,4-(methylenedioxy)phenyl)aminocarbonylamino)-phenyl)furo[2,3-d]pyrimidine;
3-(4-((2-Fluoro-5-(trifluoromethyl)phenyl)aminocarbonylamino)-phenyl)-6-(methylamino)furo[2,3-d]pyrimidine;
6-((2-(Dimethylamino)ethyl)amino)-3-(4-((2-fluoro-5-(trifluoromethyl) phenyl)aminocarbonylamino)phenyl)furo[2,3-d]pyrimidine;
4-Amino-3-(4-((2-chlorophenyl)aminocarbonylamino)phenyl)furo[2,3-d]pyrimidine;
4-Amino-3-(4-((2-chloro-5-nitrophenyl)aminocarbonylamino)-phenyl)furo[2,3-d]pyrimidine;
4-Amino-3-(4-((3-chlorophenyl)aminocarbonylamino)phenyl)furo[2,3-d]pyrimidine;
4-Amino-3-(4-((2-chloro-5-(trifluoromethyl)phenyl)-aminocarbonylamino)phenyl)furo[2,3-d]pyrimidine;
4-Amino-3-(4-((2,5-dichlorophenyl)aminocarbonylamino)phenyl)-furo[2,3-d]pyrimidine;
3-(4-((2-Fluoro-5-(trifluoromethyl)phenyl)aminocarbonylamino)-phenyl)-6-(((2,4,6-trimethoxyphenyl)methyl)amino)furo[2,3-d]pyrimidine;
6-Amino-3-(4-((2-Fluoro-5-(trifluoromethyl)phenyl)-aminocarbonylamino)phenyl)furo[2,3-d]pyrimidine;
4-Amino-3-(4-aminophenyl)-6-(methylthio)furo[2,3-d]pyrimidine;
4-Amino-2-bromo-3-(4-((2-fluoro-5-(trifluoromethyl)phenyl)-aminocarbonylamino)phenyl)furo[2,3-d]pyrimidine;
4-Amino-3-(4-((4-tert-butylthiazol-2-yl)aminocarbonylamino)-phenyl)-2-(4-methoxyphenyl)furo[2,3-d]pyrimidine;
4-Amino-3-(4-((2-thienyl)aminocarbonylamino)phenyl)furo[2,3-d]pyrimidine; and
4-Amino-2-bromo-3-(4-((5-indanyl)aminocarbonylamino)phenyl)-furo[2,3-d]pyrimidine;

or a salt, solvate, or physiologically functional derivative thereof.

Further specific Examples of compounds of the present invention include:
4-Amino-3-(4-((2-fluoro-5-(trifluoromethyl)phenyl)aminocarbonyl-amino)phenyl)-6-(((2,4,6-trimethoxyphenyl)methyl)amino)furo[2,3-d]pyrimidine;
4-Amino-3-(4-((2-fluoro-5-(trifluoromethyl)phenyl)-aminocarbonylamino)phenyl)-2-(3-pyridyl)furo[2,3-d]pyrimidine;
4-Amino-3-(4-((2-fluoro-5-(trifluoromethyl)phenyl)-aminocarbonylamino)phenyl)-2-vinylfuro[2,3-d]pyrimidine;
4-Amino-2-(1,2-dihydroxyethyl)-3-(4-((2-fluoro-5-(trifluoromethyl)phenyl)aminocarbonylamino)phenyl)furo[2,3-d]pyrimidine;
4-Amino-2-carboxy-3-(4-((2-fluoro-5-(trifluoromethyl)phenyl)-aminocarbonylamino)phenyl)furo[2,3-d]pyrimidine;
4-Amino-3-(4-((2-fluoro-5-(trifluoromethyl)phenyl)-aminocarbonylamino)phenyl)-2-iodofuro[2,3-d]pyrimidine;
4-Amino-2-(4-carboxyphenyl)-3-(4-((2-fluoro-5-(trifluoromethyl)phenyl)aminocarbonylamino)phenyl)furo[2,3-d]pyrimidine;
4-Amino-2-carbamoyl-3-(4-((2-fluoro-5-(trifluoromethyl)phenyl)-aminocarbonylamino)phenyl)furo[2.3-d]pyrimidine;
4-Amino-2-(N-(carbamoylmethyl)carbamoyl)-3-(4-((2-fluoro-5-(trifluoromethyl)phenyl)aminocarbonylamino)phenyl)furo[2,3-d]pyrimidine;
4-Amino-6-dimethylamino-3-(4-((2-fluoro-5-(trifluoromethyl)-phenyl)aminocarbonylamino)phenyl)furo[2,3-d]pyrimidine;
4-Amino-6-((2-(dimethylamino)ethyl)amino)-3-(4-((2-fluoro-5-(trifluoromethyl)phenyl)aminocarbonylamino)phenyl)furo[2,3-d]pyrimidine;
4-Amino-3-(4-((2-fluoro-5-(trifluoromethyl)phenyl)aminocarbonyl-amino)phenyl)-6-((2-(methylsulfonylamino)ethyl)amino)furo[2,3-d]pyrimidine;

4-Amino-3-(4-((2-fluoro-5-(trifluoromethyl)phenyl)aminocarbonyl-amino)phenyl)-6-((3-(methylsulfinyl)propyl)amino)furo[2,3-d]pyrimidine;
4-Amino-3-(4-((2-fluoro-5-(trifluoromethyl)phenyl)aminocarbonyl-amino)phenyl)-6-((3-(methylthio)propyl)amino)furo[2,3-d]pyrimidine;
4-Amino-2-chloro-3-(4-((3-phenyl-1,2,4-thiadiazol-5-yl)aminocarbonylamino)phenyl)furo[2,3-d]pyrimidine;
4-Amino-3-(4-((5-tert-butylisoxazol-3-yl)aminocarbonyl-amino)phenyl)furo[2,3-d]pyrimidine;
4-Amino-3-(4-((3-fluorobenzoyl)amino)phenyl)-2-(3-pyridyl)furo[2,3-d]pyrimidine;
4-Amino-3-(4-((4-fluorobenzenesulfonyl)amino)phenyl)-2-(3-pyridyl)furo[2,3-d]pyrimidine;
4-Amino-2-(3-pyridyl)-3-(4-((2-thienylsulfonyl)amino)phenyl)-furo[2,3-d]pyrimidine;
4-Amino-3-(4-((2,3-dichlorobenzenesulfonyl)amino)phenyl)-2-(3-pyridyl)furo[2,3-d]pyrimidine;
4-Amino-2-(2-methoxypyridin-5-yl)-3-((4-(phenylsulfonyl)amino)phenyl)furo[2,3-d]pyrimidine;
4-Amino-2-(3-pyridyl)-3-((4-((1,2,3,4-tetrahydroisoquinolin-7-yl)sulfonyl)amino)phenyl)furo[2,3-d]pyrimidine;
4-Amino-3-(4-((2-fluoro-5-(trifluoromethyl)phenyl)-aminocarbonylamino)phenyl)furo[2,3-d]pyrimidine;
4-Amino-3-(4-((2-fluoro-5-methoxyphenyl)-aminocarbonylamino)phenyl)furo[2,3-d]pyrimidine;
4-Amino-3-(3-((4-chlorophenyl)aminocarbonylamino)-phenyl)furo[2,3-d]pyrimidine;
4-Amino-3-(3-((phenyl)aminocarbonylamino)phenyl)furo[2,3-d]pyrimidine;
4-Amino-3-(3-((cyclohexyl)aminocarbonylamino)phenyl)furo[2,3-d]pyrimidine;
4-Amino-3-(3-((butyl)aminocarbonylamino)phenyl)furo[2,3-d]pyrimidine;
4-Amino-3-(3-((tert-butyl)aminocarbonylamino)phenyl)furo[2,3-d]pyrimidine;
4-Amino-3-(3-(aminocarbonylamino)phenyl)furo[2,3-d]pyrimidine;
4-Amino-3-(3-((5-indanyl)aminocarbonylamino)phenyl)furo[2,3-d]pyrimidine;
4-Amino-3-(3-((5-tert-butylisoxazol-3-yl)aminocarbonylamino)-phenyl)furo[2,3-d]pyrimidine;
4-Amino-3-(4-((3-cyanophenyl)aminocarbonylamino)-phenyl)furo[2,3-d]pyrimidine;
4-Amino-3-(4-((3-acetylphenyl)aminocarbonylamino)phenyl)furo[2,3-d]pyrimidine;
4-Amino-3-(4-((3-(methoxycarbonyl)phenyl)-aminocarbonylamino)phenyl)furo[2,3-d]pyrimidine;
4-Amino-3-(4-((3-fluoro-5-(trifluoromethyl)phenyl)-aminocarbonylamino)phenyl)furo[2,3-d]pyrimidine;
4-Amino-3-(4-((3-fluorophenyl)aminocarbonylamino)phenyl)-furo[2,3-d]pyrimidine;
4-Amino-3-(4-((3-methoxyphenyl)aminocarbonylamino)phenyl)-furo[2,3-d]pyrimidine;
4-Amino-3-(4-((3-methoxyphenylacetyl)amino)phenyl)furo[2,3-d]pyrimidine;
4-Amino-3-(4-((2-thienylacetyl)amino)phenyl)furo[2,3-d]pyrimidine;
4-Amino-3-(4-(((5-methyl-2-phenyloxazol-4-yl)acetyl)amino)-phenyl)furo[2,3-d]pyrimidine;
4-Amino-3-(4-(((3,5-bis-(trifluoromethyl)phenyl)acetyl)amino)-phenyl)furo[2,3-d]pyrimidine;
4-Amino-3-(4-((benzenesulfonyl)amino)phenyl)furo[2,3-d]pyrimidine;
4-Amino-3-(4-((2,3-dichlorobenzenesulfonyl)amino)phenyl)furo[2,3-d]pyrimidine;
4-Amino-3-(4-((2,5-dichlorobenzenesulfonyl)amino)phenyl)furo[2,3-d]pyrimidine;
4-Amino-3-(4-(((5-chlorothiophene-2-sulfonyl)acetyl)amino)-phenyl)furo[2,3-d]pyrimidine;
4-Amino-3-(4-(((2,5-dichlorothiophene-3-sulfonyl)acetyl)amino)-phenyl)furo[2,3-d]pyrimidine;
4-Amino-3-(4-((3-fluorobenzenesulfonyl)amino)phenyl)furo[2,3-d]pyrimidine;
4-Amino-3-(4-((3,4-dichlorobenzenesulfonyl)amino)phenyl)furo[2,3-d]pyrimidine;
4-Amino-3-(4-((3-methoxybenzenesulfonyl)amino)phenyl)furo[2,3-d]pyrimidine;
4-Amino-3-(4-((7-chloro-benzo[1,2,5]oxadiazole-4-sulfonyl)amino)phenyl)furo[2,3-d]pyrimidine;
4-Amino-3-(4-((4-methoxybenzenesulfonyl)amino)phenyl)furo[2,3-d]pyrimidine;
4-Amino-3-(4-((5-chloro-1,3-dimethylpyrazole-4-sulfonyl)amino)phenyl)furo[2,3-d]pyrimidine;
4-Amino-3-(4-((4,5-dichlorothiophene-2-sulfonyl)amino)-phenyl)furo[2,3-d]pyrimidine;
4-Amino-3-(4-((2-phenylethenesulfonyl)amino)phenyl)furo[2,3-d]pyrimidine;
4-Amino-3-(4-((3,5-dichlorophenylsulfonyl)amino)phenyl)furo[2,3-d]pyrimidine;
4-Amino-3-(4-((2-(methoxycarbonyl)thiophene-3-sulfonyl)amino)-phenyl)furo[2,3-d]pyrimidine;
4-Amino-3-(4-((3-chlorobenzenesulfonyl)amino)phenyl)furo[2,3-d]pyrimidine;
4-Amino-3-(4-((1-methyl-1H-imidazole-4-sulfonyl)amino)phenyl)-furo[2,3-d]pyrimidine;
4-Amino-3-(4-((5-chlorobenzo[1,2,5]oxadiazole-4-sulfonyl)amino)-phenyl)furo[2,3-d]pyrimidine;
4-Amino-3-(4-((3,5-dimethoxybenzenesulfonyl)amino)-phenyl)furo[2,3-d]pyrimidine;
4-Amino-3-(4-((2,5-dimethoxybenzenesulfonyl)amino)-phenyl)furo[2,3-d]pyrimidine;
4-Amino-3-(4-((2-chloro-4-fluorobenzenesulfonyl)amino)-phenyl)furo[2,3-d]pyrimidine;
4-Amino-3-(4-((2-chloro-5-(trifluoromethyl)phenyl)-aminocarbonylamino)phenyl)furo[2,3-d]pyrimidine;
4-Amino-3-(4-((4-(methoxycarbonyl)-3-methoxythiophene-2-sulfonyl)amino)phenyl)furo[2,3-d]pyrimidine;
4-Amino-3-(4-((5-(1-methyl-5-(trifluoromethyl)pyrazol-3-yl)thiophene-2-sulfonyl)amino)phenyl)furo[2,3-d]pyrimidine;
4-Amino-3-(4-((5-bromo-6-chloropyridine-3-sulfonyl)amino)-phenyl)furo[2,3-d]pyrimidine;
4-Amino-3-(4-((2,3,4,5,6-pentafluorobenzenesulfonyl)amino)-phenyl)furo[2,3-d]pyrimidine;
4-Amino-3-(4-((4-(trifluoromethoxy)benzenesulfonyl)amino)-phenyl)furo[2,3-d]pyrimidine;
4-Amino-3-(4-((thiophene-2-sulfonyl)amino)phenyl)furo[2,3-d]pyrimidine;
4-Amino-3-(4-((4-isopropylbenzenesulfonyl)amino)phenyl)furo[2,3-d]pyrimidine;
4-Amino-3-(4-((quinoline-8-sulfonyl)amino)phenyl)furo[2,3-d]pyrimidine;
4-Amino-3-(4-((2-nitro-4-(trifluoromethyl)benzenesulfonyl)amino)-phenyl)furo[2,3-d]pyrimidine;
4-Amino-3-(4-((2,4,6-trimethylbenzenesulfonyl)amino)phenyl)-furo[2,3-d]pyrimidine;
4-Amino-3-(4-((5-bromo-2-methoxybenzenesulfonyl)amino)-phenyl)furo[2,3-d]pyrimidine;
4-Amino-3-(4-((4-propylbenzenesulfonyl)amino)phenyl)furo[2,3-d]pyrimidine;

4-Amino-3-(4-((4-bromo-2,5-difluorobenzenesulfonyl)amino)-phenyl)furo[2,3-d]pyrimidine;
4-Amino-3-(4-((2,6-dichloro-4-(trifluoromethyl)benzenesulfonyl)-amino)phenyl)furo[2,3-d]pyrimidine;
4-Amino-3-(4-((2-(trifluoromethoxy)benzenesulfonyl)-amino)phenyl)furo[2,3-d]pyrimidine;
4-Amino-3-(4-((3,5-dimethylisoxazole-4-sulfonyl)-amino)phenyl)furo[2,3-d]pyrimidine;
4-Amino-3-(4-((4-acetylbenzenesulfonyl)amino)phenyl)furo[2,3-d]pyrimidine;
4-Amino-3-(4-((2,4-dichlorobenzenesulfonyl)amino)phenyl)furo[2,3-d]pyrimidine;
4-Amino-3-(4-((3,5-bis-(trifluoromethyl)benzenesulfonyl)-amino)phenyl)furo[2,3-d]pyrimidine;
4-Amino-3-(4-((5-(N-(benzoyl)aminomethyl)thiophene-2-sulfonyl)-amino)phenyl)furo[2,3-d]pyrimidine;
4-Amino-3-(4-((2-(acetylamino)-4-methylthiazole-5-sulfonyl)-amino)phenyl)furo[2,3-d]pyrimidine;
4-Amino-3-(4-((3-chloro-4-fluorobenzenesulfonyl)amino)phenyl)-furo[2,3-d]pyrimidine;
4-Amino-3-(4-((4-ethylbenzenesulfonyl)amino)phenyl)furo[2,3-d]pyrimidine;
4-Amino-3-(4-((3,5-bis-(trifluoromethyl)phenylmethyl)sulfonyl)-amino)phenyl)furo[2,3-d]pyrimidine;
4-Amino-3-(4-((4-tert-butylbenzenesulfonyl)amino)phenyl)furo[2,3-d]pyrimidine;
4-Amino-3-(4-((2-nitrophenylmethyl)sulfonyl)amino)phenyl)furo[2,3-d]pyrimidine;
4-Amino-3-(4-((5-(isoxazol-3-yl)thiophene-2-sulfonyl)-amino)phenyl)furo[2,3-d]pyrimidine;
4-Amino-3-(4-((benzo[1,2,5]thiadiazole-4-sulfonyl)-amino)phenyl)furo[2,3-d]pyrimidine;
4-Amino-3-(4-((4-cyanobenzenesulfonyl)amino)phenyl)furo[2,3-d]pyrimidine;
4-Amino-3-(4-((benzo[1,4]dioxan-6-sulfonyl)amino)phenyl)-furo[2,3-d]pyrimidine;
4-Amino-3-(4-((5-(2-pyridyl)thiophene-2-sulfonyl)-amino)phenyl)furo[2,3-d]pyrimidine;
4-Amino-3-(4-((3-(trifluoromethyl)phenylmethyl)sulfonyl)-amino)phenyl)furo[2,3-d]pyrimidine;
4-Amino-3-(4-((3,5-dichlorophenylmethyl)sulfonyl)-amino)phenyl)furo[2,3-d]pyrimidine;
4-Amino-3-(4-((5-(N-(4-chlorobenzoyl)aminomethyl)thiophene-2-sulfonyl)amino)phenyl)furo[2,3-d]pyrimidine;
4-Amino-3-(4-((2,6-dichlorobenzenesulfonyl)amino)phenyl)-furo[2,3-d]pyrimidine;
4-Amino-3-(4-((4-(benzenesulfonyl)thiophene-2-sulfonyl)amino)-phenyl)furo[2,3-d]pyrimidine;
4-Amino-3-(4-((4-bromo-2-ethylbenzenesulfonyl)amino)phenyl)-furo[2,3-d]pyrimidine;
4-Amino-3-(4-((3-chloro-2-methylbenzenesulfonyl)amino)phenyl)-furo[2,3-d]pyrimidine;
4-Amino-3-(4-((5-bromothiophene-2-sulfonyl)amino)-phenyl)furo[2,3-d]pyrimidine;
4-Amino-3-(4-((4-fluorobenzenesulfonyl)amino)phenyl)furo[2,3-d]pyrimidine;
4-Amino-3-(4-((2-chlorobenzenesulfonyl)amino)phenyl)furo[2,3-d]pyrimidine;
4-Amino-3-(4-((5-(2-methylthio-pyrimidin-4-yl)thiophene-2-sulfonyl)amino)phenyl)furo[2,3-d]pyrimidine;
4-Amino-3-(4-((5-(5-(trifluoromethyl)pyridine-2-sulfonyl)thiophene-2-sulfonyl)amino)phenyl)furo[2,3-d]pyrimidine;
4-Amino-3-(4-((benzo[1,2,5]oxadiazole-4-sulfonyl)amino)phenyl)-furo[2,3-d]pyrimidine;
4-Amino-3-(4-((6-chloro-imidazo[2,1-b]thiazole-5-sulfonyl)amino)phenyl)-furo[2,3-d]pyrimidine;
4-Amino-3-(4-((2,5-dimethylbenzenesulfonyl)amino)phenyl)furo[2,3-d]pyrimidine;
4-Amino-3-(4-((5-(2-methylthiazol-4-yl)thiophene-2-sulfonyl)-amino)phenyl)furo[2,3-d]pyrimidine;
4-Amino-3-(4-((5-(5-trifluoromethyl-isoxazol-3-yl)thiophene-2-sulfonyl)-amino)phenyl)furo[2,3-d]pyrimidine;
4-Amino-3-(4-((2-methoxy-5-methylbenzenesulfonyl)amino)phenyl)-furo[2,3-d]pyrimidine;
4-Amino-3-(4-((5-chloro-3-methylbenzo[b]thiophene-2-sulfonyl)amino)phenyl)furo[2,3-d]pyrimidine;
4-Amino-3-(4-((2,4-dichloro-5-methylbenzenesulfonyl)amino)-phenyl)-furo[2,3-d]pyrimidine;
4-Amino-3-(4-((5-fluoro-2-methylbenzenesulfonyl)amino)phenyl)-furo[2,3-d]pyrimidine;
4-Amino-3-(4-((5-chloronaphthalenesulfonyl)amino)phenyl)-furo[2,3-d]pyrimidine;
4-Amino-3-(4-((4-(3,5-dichlorophenoxy)benzenesulfonyl)amino)-phenyl)furo[2,3-d]pyrimidine;
4-Amino-3-(4-((3-(4-chlorophenoxy)benzenesulfonyl)amino)-phenyl)furo[2,3-d]pyrimidine;
4-Amino-3-(4-(((4-pyridylmethyl)sulfonyl)amino)phenyl)furo[2,3-d]pyrimidine;
4-Amino-3-(4-((4-(2-pyridyloxy)benzenesulfonyl)amino)-phenyl)furo[2,3-d]pyrimidine;
4-Amino-3-(4-((5-([1,2,3]thiadiazol-4-yl)thiophene-2-sulfonyl)-amino)phenyl)furo[2,3-d]pyrimidine;
4-Amino-3-(4-((5-(4-cyano-1-methyl-5-methylthio-1H-pyrazol-3-yl)thiophene-2-sulfonyl)amino)phenyl)furo[2,3-d]pyrimidine;
4-Amino-3-(4-((3-(4-chlorophenyl)benzenesulfonyl)amino)-phenyl)furo[2,3-d]pyrimidine;
4-Amino-3-(4-((4-(4-pyridyloxy)benzenesulfonyl)amino)-phenyl)furo[2,3-d]pyrimidine;
4-Amino-3-(4-((4-butoxybenzenesulfonyl)amino)phenyl)-furo[2,3-d]pyrimidine;
4-Amino-3-(4-((4-acetamide-3-chlorobenzenesulfonyl)amino)-phenyl)furo[2,3-d]pyrimidine;
4-Amino-3-(4-((4-(trifluoromethyl)phenylmethyl)sulfonyl)-amino)phenyl)furo[2,3-d]pyrimidine;
4-Amino-3-(4-((4-chlorophenylmethyl)sulfonyl)amino)phenyl)-furo[2,3-d]pyrimidine;
4-Amino-3-(4-((3,4-dichlorophenylmethyl)sulfonyl)amino)phenyl)-furo[2,3-d]pyrimidine;
4-Amino-3-(4-((4-fluorophenylmethyl)sulfonyl)amino)phenyl)-furo[2,3-d]pyrimidine;
4-Amino-3-(4-((6-(dimethylamino)naphthalene-1-sulfonyl)amino)phenyl)furo[2,3-d]pyrimidine;
4-Amino-3-(4-((isoquinoline-5-sulfonyl)amino)phenyl)furo[2,3-d]pyrimidine;
4-Amino-3-(4-((1-naphthalenesulfonyl)amino)phenyl)furo[2,3-d]pyrimidine;
4-Amino-3-(4-((phenylmethyl)sulfonyl)amino)phenyl)furo[2,3-d]pyrimidine;
4-Amino-3-(4-(((2-fluoro-5-(trifluoromethyl)phenylmethyl)-sulfonyl)amino)phenyl)furo[2,3-d]pyrimidine;
4-Amino-3-(4-((4-(3,4-dichlorophenoxy)benzenesulfonyl)amino)-phenyl)furo[2,3-d]pyrimidine;
4-Amino-3-(4-((4-(2-chlorothiazol-5-ylmethoxy)benzenesulfonyl)-amino)phenyl)furo[2,3-d]pyrimidine;
4-Amino-3-(4-((4-(3,4-dichlorophenyl)benzenesulfonyl)amino)-phenyl)furo[2,3-d]pyrimidine;
4-Amino-3-(4-((4-(trifluoromethyl)benzenesulfonyl)amino)-phenyl)furo[2,3-d]pyrimidine;

4-Amino-3-(4-((1,1-dioxo-tetrahydro-1/-thiophene-3-sulfonyl)amino)phenyl)furo[2,3-d]pyrimidine;
4-Amino-3-(4-((4-(phenylazo)benzenesulfonyl)amino)-phenyl)furo[2,3-d]pyrimidine;
4-Amino-3-(4-((2,5-dibromo-3,6-difluorobenzenesulfonyl)amino)-phenyl)furo[2,3-d]pyrimidine;
4-Amino-3-(4-((4-bromo-2-(trifluoromethoxy)benzenesulfonyl)-amino)phenyl)furo[2,3-d]pyrimidine;
4-Amino-3-(4-((2-chloro-4-cyanobenzenesulfonyl)amino)-phenyl)furo[2,3-d]pyrimidine;
4-Amino-3-(4-((2,3,5,6-tetramethylbenzenesulfonyl)amino)-phenyl)furo[2,3-d]pyrimidine;
4-Amino-3-(4-((3,5-dichloro-2-hydroxybenzenesulfonyl)amino)-phenyl)furo[2,3-d]pyrimidine;
4-Amino-3-(4-((3-chloro-4-(1,3-dioxo-2-aza-spiro(4,4)non-2-yl)benzenesulfonyl)amino)phenyl)furo[2,3-d]pyrimidine;
4-Amino-3-(4-(((2-chloro-5-(trifluoromethyl)phenylmethyl)-sulfonyl)amino)phenyl)furo[2,3-d]pyrimidine;
4-Amino-3-(4-(((p-tolylmethyl)sulfonyl)amino)phenyl)furo[2,3-d]pyrimidine;
4-Amino-3-(4-(((1,2-dimethyl-1H-imidazol-4-yl)sulfonyl)amino)-phenyl)furo[2,3-d]pyrimidine;
4-Amino-3-(4-((5-((3-chloro-5-(trifluoromethyl)pyridin-2-yl)methyl)thiophene-2-sulfonyl)amino)phenyl)furo[2,3-d]pyrimidine;
4-Amino-3-(4-(((4-butylbenzenesulfonyl)amino)phenyl)furo[2,3-d]pyrimidine;
4-Amino-3-(4-((2-fluoro-5-(trifluoromethyl)phenyl)-aminocarbonylamino)phenyl)thieno[2,3-d]pyrimidine;
4-Amino-3-(4-((5-indanyl)aminocarbonylamino)phenyl)thieno[2,3-d]pyrimidine;
4-Amino-3-(4-((2-methylphenyl)aminocarbonylamino)phenyl)-thieno[2,3-d]pyrimidine;
4-Amino-3-(4-((3-methylphenyl)aminocarbonylamino)phenyl)-thieno[2,3-d]pyrimidine;
4-Amino-3-(4-((3-(trifluoromethyl)phenyl)aminocarbonylamino)-phenyl)thieno[2,3-d]pyrimidine;
4-Amino-3-(4-((2-chloro-5-(trifluoromethyl)phenyl)-aminocarbonylamino)phenyl)thieno[2,3-d]pyrimidine;
4-Amino-3-(4-(((2,5-difluorophenyl)acetyl)amino)phenyl)thieno[2,3-d]pyrimidine;
4-Amino-3-(4-((2-fluoro-5-(trifluoromethyl)benzoyl)amino)-phenyl)thieno[2,3-d]pyrimidine;
4-Amino-3-(4-(benzoylamino)phenyl)thieno[2,3-d]pyrimidine;
4-Amino-3-(4-((2,6-difluorobenzoyl)amino)phenyl)thieno[2,3-d]pyrimidine;
4-Amino-3-(4-(((S)-2-amino-2-phenylacetyl)amino)phenyl)-thieno[2,3-d]pyrimidine;
4-Amino-3-(4-(((1S,2S)-2-phenyl-cyclopropanecarbonyl)amino)-phenyl)thieno[2,3-d]pyrimidine;
4-Amino-3-(4-((2,5-difluorobenzoyl)amino)phenyl)thieno[2,3-d]pyrimidine;
4-Amino-3-(4-(((R)-2-amino-2-phenylacetyl)amino)phenyl)-thieno[2,3-d]pyrimidine;
4-Amino-3-(4-((1-phenyl-cyclopropanecarbonyl)amino)-phenyl)thieno[2,3-d]pyrimidine;
4-Amino-3-(4-(((2,6-difluorophenyl)acetyl)amino)phenyl)thieno[2,3-d]pyrimidine;
4-Amino-3-(4-((phenylacetyl)amino)phenyl)thieno[2,3-d]pyrimidine;
4-Amino-3-(4-(((3,5-bis-(trifluoromethyl)phenyl)acetyl)amino)-phenyl)thieno[2,3-d]pyrimidine;
4-Amino-3-(4-(((2,4-bis-(trifluoromethyl)phenyl)acetyl)amino)-phenyl)thieno[2,3-d]pyrimidine;
4-Amino-3-(4-(((3-(trifluoromethylthio)phenyl)acetyl)amino)-phenyl)thieno[2,3-d]pyrimidine;
4-Amino-3-(4-(((1R,2R)-2-phenyl-cyclopropanecarbonyl)amino)-phenyl)thieno[2,3-d]pyrimidine;
4-Amino-3-(4-(((E)-3-(2-chlorophenyl)acryloyl)amino)-phenyl)thieno[2,3-d]pyrimidine;
4-Amino-3-(4-(((E)-3-(3-chlorophenyl)acryloyl)amino)-phenyl)thieno[2,3-d]pyrimidine;
4-Amino-3-(4-(((E)-3-phenylacryloyl)amino)phenyl)thieno[2,3-d]pyrimidine;
4-Amino-3-(4-((1-phenylcyclopentanecarbonyl)amino)-phenyl)thieno[2,3-d]pyrimidine;
4-Amino-3-(4-((2-phenylisobutyryl)amino)phenyl)thieno[2,3-d]pyrimidine;
4-Amino-3-(4-(((2-fluoro-5-(trifluoromethyl)phenyl)acetyl)amino)-phenyl)thieno[2,3-d]pyrimidine;
4-Amino-3-(4-(((2,5-dichlorothiophene-3-yl)carbonyl)amino)-phenyl)thieno[2,3-d]pyrimidine;
4-Amino-3-(4-(((bicyclo[4.2.0]octa-1(6),2,4-trien-7-yl)carbonyl)-amino)phenyl)thieno[2,3-d]pyrimidine;
4-Amino-3-(4-((2-phenylbutyryl)amino)phenyl)thieno[2,3-d]pyrimidine;
4-Amino-3-(4-(((5-methyl-[1,3,4]thiadiazol-2-yl)carbonyl)amino)phenyl)thieno[2,3-d]pyrimidine;
4-Amino-3-(4-(((5-tert-butyl-2-methyl-2H-pyrazol-3-yl)carbonyl)amino)phenyl)thieno[2,3-d]pyrimidine;
4-Amino-3-(4-((4-(4-methyl-piperazin-1-yl-methyl)benzoyl)amino)phenyl)thieno[2,3-d]pyrimidine;
4-Amino-3-(4-((3-cyanobenzoyl)amino)phenyl)thieno[2,3-d]pyrimidine;
4-Amino-3-(4-((2-methoxybenzoyl)amino)phenyl)thieno[2,3-d]pyrimidine;
4-Amino-3-(4-((3-chlorobenzoyl)amino)phenyl)thieno[2,3-d]pyrimidine;
4-Amino-3-(4-((3-methoxybenzoyl)amino)phenyl)thieno[2,3-d]pyrimidine;
4-Amino-3-(4-((4-(trifluoromethoxy)benzoyl)amino)phenyl)-thieno[2,3-d]pyrimidine;
4-Amino-3-(4-((2-fluoro-5-(trifluoromethyl)phenyl)-aminocarbonyl(N-methylamino))phenyl)thieno[2,3-d]pyrimidine;
4-Amino-3-(4-((3-ethylphenyl)aminocarbonyl(N-methylamino))-phenyl)thieno[2,3-d]pyrimidine;
4-Amino-3-(4-((1-(3,4-dichlorophenyl)-cyclopropanecarbonyl)amino)phenyl)thieno[2,3-d]pyrimidine;
4-Amino-3-(4-((1-(2,5-difluorophenyl)-cyclopropanecarbonyl)amino)phenyl)thieno[2,3-d]pyrimidine;
4-Amino-3-(4-((1-(3,5-bis-(trifluoromethyl)phenyl)-cyclopropanecarbonyl)amino)phenyl)thieno[2,3-d]pyrimidine;
4-Amino-3-(4-((1-(3-chlorophenyl)cyclopropanecarbonyl)amino)-phenyl)thieno[2,3-d]pyrimidine;
4-Amino-3-(4-((1-(3-(trifluoromethyl)phenyl)-cyclopropanecarbonyl)amino)phenyl)thieno[2,3-d]pyrimidine;
4-Amino-3-(4-((1-(3,4-dichlorophenyl)-cyclopropanecarbonyl)amino)phenyl)furo[2,3-d]pyrimidine;
4-Amino-3-(4-((1-(2,5-difluorophenyl)-cyclopropanecarbonyl)amino)phenyl)furo[2,3-d]pyrimidine;
4-Amino-3-(4-((1-(3,5-bis-(trifluoromethyl)phenyl)-cyclopropanecarbonyl)amino)phenyl)furo[2,3-d]pyrimidine;
4-Amino-3-(4-((1-(3-chlorophenyl)cyclopropanecarbonyl)amino)-phenyl)furo[2,3-d]pyrimidine;
4-Amino-3-(4-((1-phenylcyclopropanecarbonyl)amino)-phenyl)furo[2,3-d]pyrimidine; and
4-Amino-3-(4-((1-(3-(trifluoromethyl)phenyl)-cyclopropanecarbonyl)amino)phenyl)furo[2,3-d]pyrimidine;
or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal. administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of formula (I) or a pharmaceutically acceptable salt or solvate thereof, or a physiologically functional derivative thereof, and the use of at least one other cancer treatment method. Preferably, combination therapies according to the present invention comprise the administration of at least one compound of formula (I) or a pharmaceutically acceptable salt or solvate thereof, or a physiologically functional derivative thereof, and at least one other pharmaceutically active agent, preferably an anti-neoplastic agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of the Formula (I) or salts, solvates, or physiologically functional derivatives thereof and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or salts, solvates, or physiologically functional derivatives thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts, solvates or physiologically functional derivatives thereof of formula I include the following:

(1) cell cycle specific anti-neoplastic agents include, but are not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine ; antimetabolites such as allopurinol, fludarabine, methotrexate, cladrabine, cytarabine, mercaptopurine and thioguanine; and camptothecins such as 9-amino camptothecin, irinotecan, topotecan, CPT-11 and the various optical forms of 7-(4-methyl piperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycin, epirubicin, idarubicin, mitomycin-C, dacttinomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestogens; urokinase plasminogen activator receptor function inhibitors; growth factor function inhibitors such as inhibitors of the functions of hepatocyte growth factor; erb-B2, erb-B4, epidermal growth factor receptor (EGFR), platelet derived growth factor receptor (PDGFR), vascular endothelial growth factor receptor (VEGFR, and TIE-2 (other than those VEGFR and TIE-2 inhibitors described in the present invention); and other tyrosine kinase inhibitors such as inhibitors of CDK2 and CDK4 inhibitors.

The compounds of formula (I) and salts, solvates and physiological functional derivatives thereof, are believed to have anticancer activity as a result of inhibition of the protein kinase TIE-2 and/or VEGFR-2 and its effect on selected cell lines whose growth is dependent on TIE-2 and/or VEGFR-2 protein kinase activity.

The present invention thus also provides compounds of formula (I) and pharmaceutically acceptable salts or solvates thereof, or physiologically functional derivatives thereof, for use in medical therapy, and particularly in the treatment of disorders mediated by at least one of inappropriate TIE-2 and VEGFR-2 activity.

The inappropriate TIE-2 and/or VEGFR-2 activity referred to herein is any TIE-2 and/or VEGFR-2 activity that deviates from the normal TIE-2 and/or VEGFR-2 activity expected in a particular mammalian subject Inappropriate TIE-2 and/or VEGFR-2 activity may take the form of, for instance, an abnormal increase in activity, or an aberration in the timing and or control of TIE-2 and/or VEGFR-2 activity. Such inappropriate activity may result then, for example, from overexpression or mutation of the protein kinase leading to inappropriate or uncontrolled activation. Furthermore, it is also understood that unwanted TIE-2 and/or VEGFR-2 activity may reside in an abnormal source, such as a malignancy. That is, the level of TIE-2 and/or VEGFR-2 activity does not have to be abnormal to be considered inappropriate, rather the activity derives from an abnormal source. In a like manner, the inappropriate angiogenesis referred to herein is any angiogenic activity that deviates from the normal angiogenic activity expected in a particular mammalian subject Inappropriate angiogenesis may take the form of, for instance, an abnormal increase in activity, or an aberration in the timing and or control of angiogenic activity. Such inappropriate activity may result then, for example, from overexpression or mutation of a protein kinase leading to inappropriate or uncontrolled activation. Furthermore, it is also understood that unwanted angiogenic activity may reside in an abnormal source, such as a malignancy. That is, the level of angiogenic activity does not have to be abnormal to be considered inappropriate, rather the activity derives from an abnormal source.

The present invention is directed to methods of regulating, modulating, or inhibiting TIE-2 and/or VEGFR-2 for the prevention and/or treatment of disorders related to unregulated TIE-2 and/or VEGFR-2 activity. In particular, the compounds of the present invention can also be used in the treatment of certain forms of cancer. Furthermore, the compounds of the present invention can be used to provide additive or synergistic effects with certain existing cancer chemotherapies, and/or be used to restore effectiveness of certain existing cancer chemotherapies and radiation.

The compounds of the present invention are also useful in the treatment of one or-more diseases afflicting mammals which are characterized by cellular proliferation in the area of disorders associated with neo-vascularization and/or vascular permeability including blood vessel proliferative disorders including arthritis and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, organ transplant rejection and glomerulopathies; and metabolic disorders include psoriasis, diabetes mellitus, chronic wound healing, inflammation and neurodegenerative diseases.

A further aspect of the invention provides a method of treatment of a mammal suffering from a disorder mediated by at least one of inappropriate TIE-2 and VEGFR-2 activity, including susceptible malignancies, which includes administering to said subject an effective amount of a compound of formula (I) or a pharmaceutically acceptable salt, solvate, or a physiologically functional derivative thereof. In a preferred embodiment, the disorder is cancer.

A further aspect of the invention provides a method of treatment of a mammal suffering from cancer which includes administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by at least one of inappropriate TIE-2 and VEGFR-2 activity. In a preferred embodiment, the disorder is cancer.

A further aspect of the present invention provides the use of a compound of formula (I), or a pharmaceutically acceptable salt or solvate thereof, or a physiologically functional derivative thereof, in the preparation of a medicament for the treatment of cancer and malignant tumors.

The mammal requiring treatment with a compound of the present invention is typicaltly a human being.

In another embodiment, therapeutically effective amounts of the compounds of formula (I) or salts, solvates or physiologically derived derivatives thereof and agents which inhibit growth factor receptor function may be administered in combination to a mammal for treatment of a disorder mediated by at least one of inappropriate TIE-2 and VEGFR-2 activity, for instance in the treatment of cancer. Such growth factor receptors include, for example, EGFR, PDGFR, erbB2, erbB4, VEGFR, and/or TIE-2. Growth factor receptors and agents that inhibit growth factor receptor function are described, for instance, in Kath, John C., Exp. Opin. Ther. Patents (2000) 10(6):803–818 and in Shawver et al DDT Vol 2, No. 2 February 1997.

The compounds of the formula (I) or salts, solvates, or physiologically functional derivatives thereof and the agent for inhibiting growth factor receptor function may be employed in combination concomitantly or sequentially in any therapeutically appropriate combination. The combination may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

In another aspect of the present invention, there is provided a method of treating a disorder in a mammal, said disorder being mediated by inappropriate angiogenesis, including: administering to said mammal a therapeutically effective amount of a compound of formula (I), or a salt, solvate or physiologically functional derivative thereof. In one embodiment, the inappropriate angiogenic activity is due to at least one of inappropriate VEGFR1, VEGFR2, VEGFR3, or TIE-2 activity. In another embodiment, the inappropriate angiogenesis is due to inappropriate VEGFR2 and TIE-2 activity. In a further embodiment, the method further includes administering a therapeutically effective amount of a VEGFR2 inhibitor along with the compounds of formula (I) or salts, solvates or physiologically functional derivatives thereof. Preferably the disorder is cancer.

In another aspect of the present invention, there is provided the use of a compound of formula (I), or a salt, solvate or physiologically functional derivative thereof in the preparation of a medicament for use in treating a disorder in a mammal, said disorder being characterized by inappropriate angiogenesis. In one embodiment, the inappropriate angiogenic activity is due to at least one of inappropriate VEGFR1, VEGFR2, VEGFR3 or TIE-2 activity. In another embodiment, the inappropriate angiogenesis is due to inappropriate VEGFR2 and TIE-2 activity. In a further embodiment, the use further includes use of a VEGFR2 inhibitor to prepare said medicament The combination of a compound of formula (I) or salts, solvates, or physiologically functional derivatives thereof with a VEGFR2 inhibitor may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art See, for example, *Stereochemistry of Organic Compounds* by E. L. Eliel, S. H. Wilen, and L. N. Mander (Wiley-Interscience, 1994).

Compounds of Formula (I) can be prepared according to the synthetic sequences illustrated in Schemes 1–4. Schemes 1–4 show general routes for the synthesis of the targeted furo[2,3-d]pyrimidines. Specific detail of synthetic routes according to Schemes 1–4 are shown in the Examples following wherein furo[2,3-d]pyrimidine compound examples having Tie2 and/or VEGFR-2 inhibitory activity were prepared.

The synthesis of the furo[2,3-d]pyrimidine scaffold having equivalent aryl groups at the C-2 and C-3 position is illustrated as shown in Scheme-1. This method is based on synthesis reported in the references: K. Gewald, Chem. Ber., 99, 1002 (1996); T. I. Temnikova, Yu. A. Sharanin, and V. S. Karaban, J. Org. Chem. USSR, 651–654 (1967) and ibd, 1938–1945 (1967); X. Feng, J.-C. Lancelot, H. Prunier, and S. Rault. J. Heterocyclic Chem., 33, 2007 (1996); J. Prousek, A. Jurascek, and J. Kovac, Collect. Czech. Chem. Commun., 45 (5), 1581–1588 (1980). This scheme can serve as a route to produce various derivatives starting from diaryl-α-hydroxyketones through 2-amino-3-cyano-4,5-diarylfurans.

Other effective synthetic routes were reported at: T. Matsuda, K. Yamagata, Y. Tomioka, M. Yamazaki, Chem. Pharm. Bull., 33 (3), 937–943 (1985) and are illustrated in Scheme-2 and Scheme-3. According to these methods, a variety of diaryl-furo[2,3-d]pyrimidines substituted at C-2 and C-3 can be synthesized. The effective syhthesis of 3-aryl furo[2,3-d]pyrimidine was achieved by the route as shown in Scheme-2. In this route, the cyclization to the desired scaffold proceeded smoothly and subsequent halogenations at C-2 were achieved successively.

Scheme-1

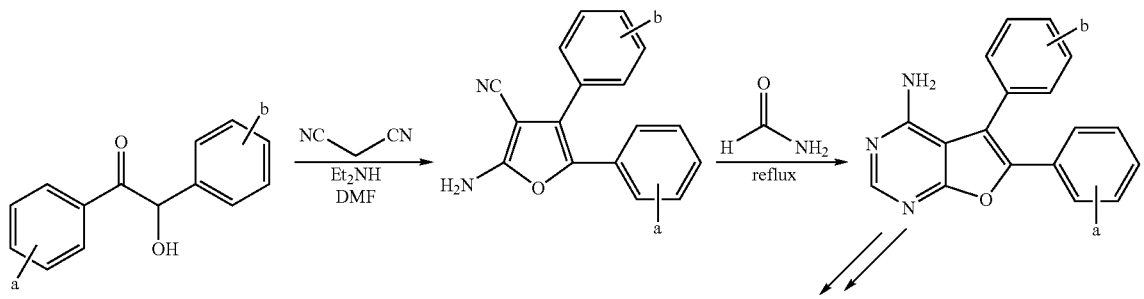

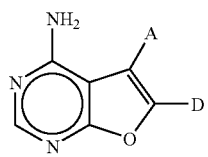

As indicated above Scheme 1 describes the synthesis of compounds of formula I wherein A and D are equivalent aryl groups (as indicated by the double arrows phenyl is utilized for A and D by way of Example) wherein the substituents -a, -b represent any substituents described herein within the scope of the definition of A and D as described above.

Scheme-2

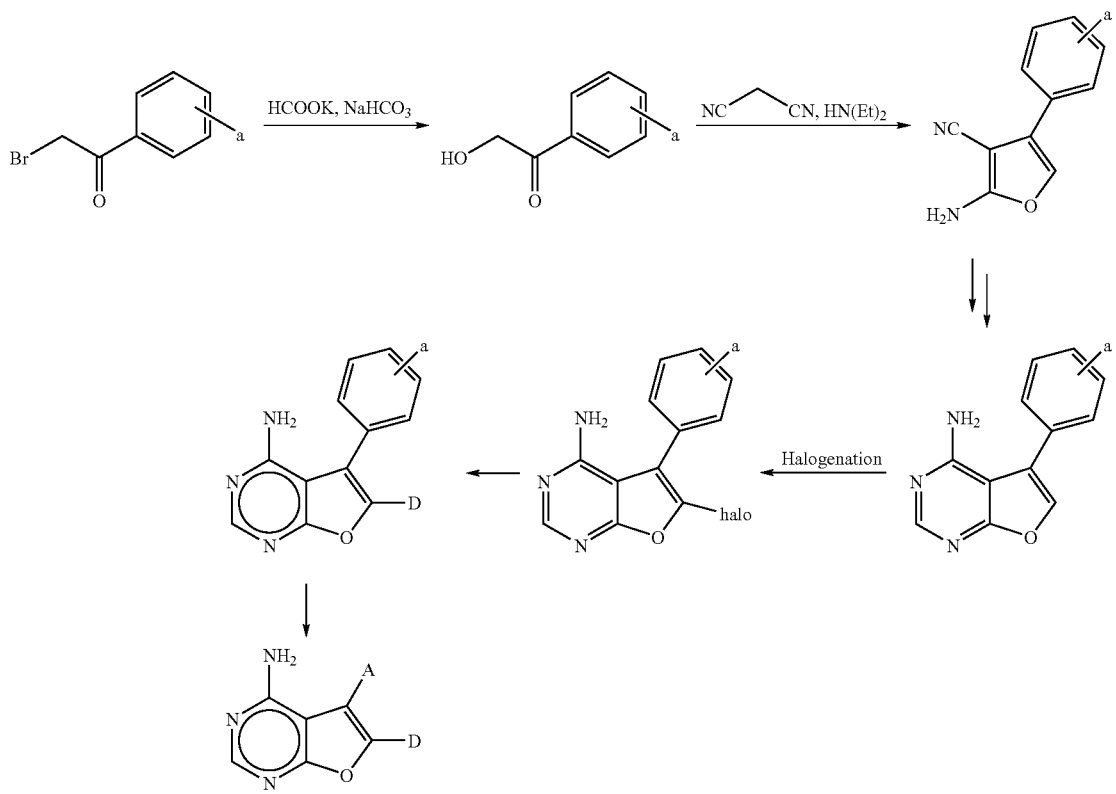

As indicated above Scheme 2 describes the synthesis of compounds of formula I wherein A is an aryl group (as indicated by the scheme phenyl is utilized for A by way of Example) wherein the substituent -a represents any substituents described herein within the scope of the definition of A as described above. As those skilled in the art will recognize, various D substituents are available by replacement of the halo group according to procedures known in the art.

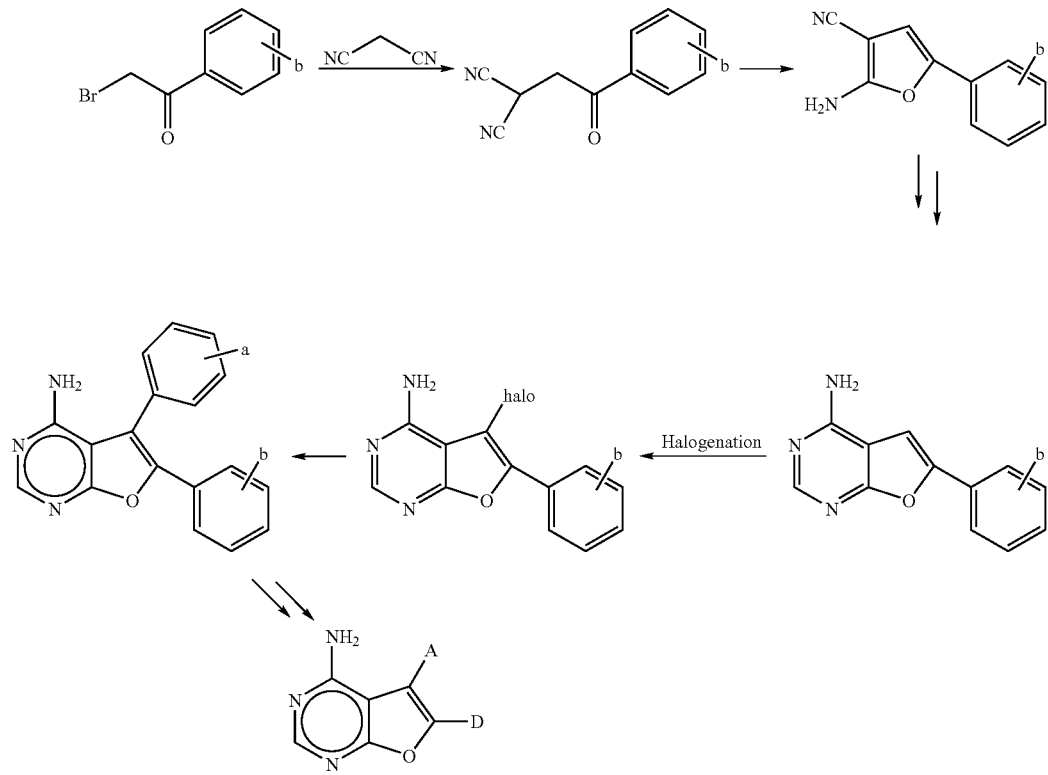

Scheme-3

The analogous route illustrated in Scheme-3 also afforded the desired 4-amino-2-arylfuro[2,3-d]pyrimidines as key intermediates for derivatizations at C-3.

Derivatization at C-4 and C-6 can be achieved by the convenient synthetic route shown in Scheme-4. This route was reported at: D. Dauzonne and A. Adam-Launay, Tetrahedron, 48 (15), 3069–3080 (1992).

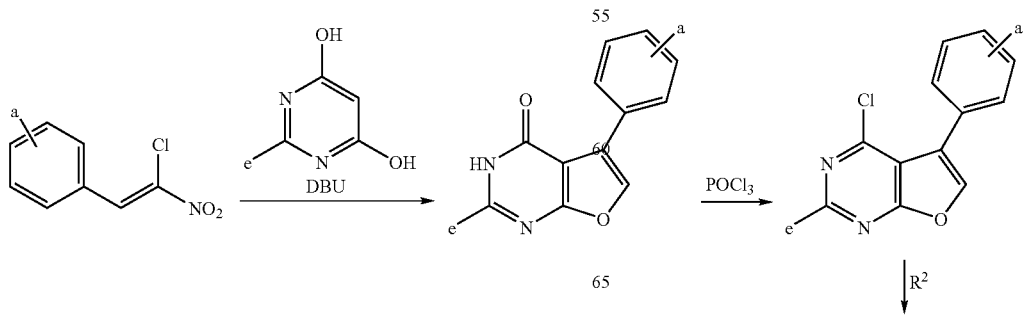

Scheme-4

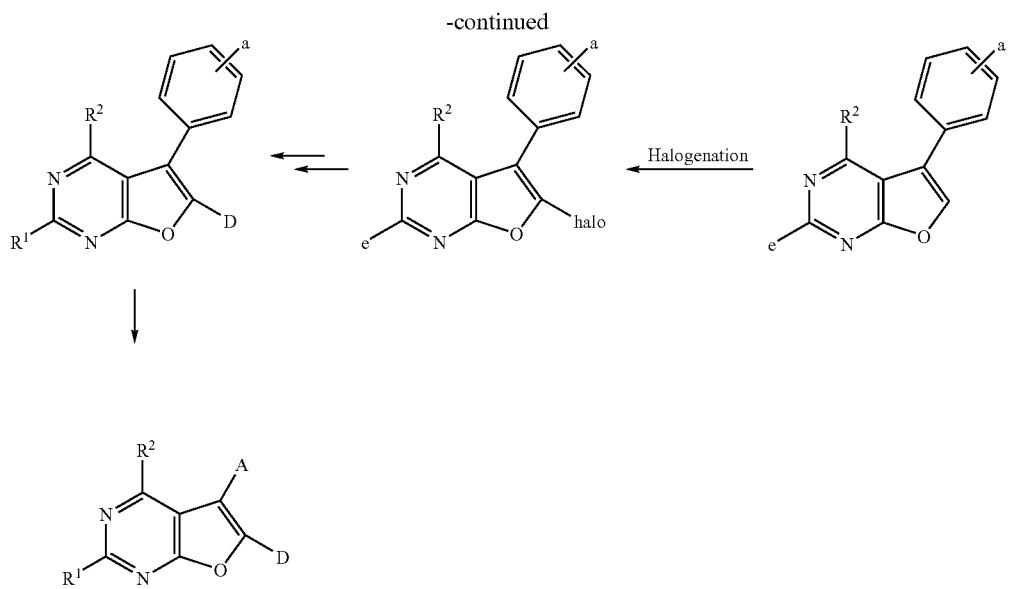

Wherein A, D, $R^1$, and $R^2$ are as described above for formula (I); and -a, and -e are any appropriate substituent within the scope of the invention.

The thieno[2,3-d]pyrimidines of the present invention may be prepared by the stepwise Gewald thiophene ring procedure described by Zhang and Harper (Bioorg. Med. Chem. *Lett.* (1997), 7, 1629–1634) and in Scheme 5. Knoevenagel condensation of malonodinitrile and a substituted acetophenone yielded the desired dicyanopropene. Upon heating with sulfur in DMF, the propene was converted to the substituted thiophene, which underwent condensation with formamide to generate the bicyclic thiophenopyrimidine. This system could then be derivatized using commonly known synthetic methods.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification.

Specifically, the following abbreviations may be used in the examples and throughout the specification:

Scheme 5

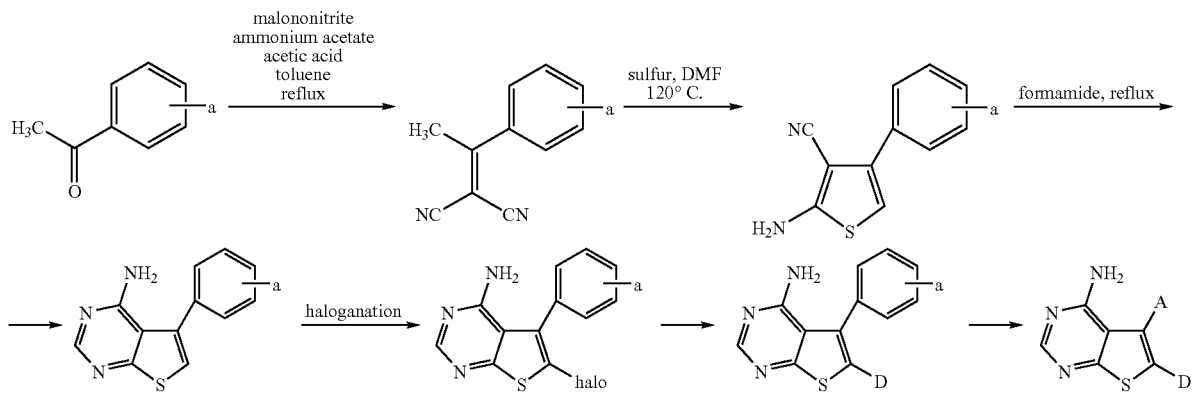

Certain embodiments of the present invention will now be illustrated by way of example only. The physical data given for the compounds exemplified is consistent with the assigned structure of those compounds.

g (grams); mg (milligrams);
L (liters); mL (milliliters);
μL (microliters); psi (pounds per square inch);
M (molar); mM (millimolar);
i. v. (intravenous); Hz (Hertz);
MHz (megahertz); mol (moles);
mmol (millimoles); rt (room temperature);
min (minutes); h (hours);
mp (melting point); TLC (thin layer chromatography);
$T_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); AcOEt (ethyl acetate);
DME (1,2-dimethoxyethane); DCM (dichloromethane);
DCE (dichloroethane); DMF (N,N-dimethylformamide);
DMPU (N,N'-dimethylpropyleneurea); (CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid; EDC (ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin)
ATP (adenosine triphosphate); HRP (horseradish peroxidase);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluronium hexafluorophosphate).
HEPES (4-(2-hydroxyethyl)-1-piperazine ethane sulfonic acid);
DPPA (diphenylphosphoryl azide);
fHNO₃ (fumed $HNO_3$); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

¹H NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

HPLC were recorded on a Gilson HPLC or Shimazu HPLC system by the following conditions. Column: 50×4.6 mm (id) stainless steel packed with 51 μm Phenomenex Luna C-18; Flow rate: 2.0 ml/min; Mobile phase: A phase=50 mM ammonium acetate (pH 7.4), B phase=acetonitrile, 0–0.5 min (A: 100%, B: 0%), 0.5–3.0 min (A: 100–0%, B: 0–100%), 3.0–3.5 min (A: 0%, B: 100%), 3.5–3.7 min (A: 0–100%, B: 100–0%), 3.7–4.5 min (A: 100%, B: 0%); Detection: UV 254 nm; Injection volume: 3 μL.

Low-resolution mass spectra (MS) were recorded on a JOEL JMS-AX505HA, JOEL SX-102, or a SCIEX-APIiii spectrometer; LC-MS were recorded on a micromass 2 MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230–400 mesh, Merck).

Example 1

4-Amino-3-(4-methoxyphenyl)-2-(3-(methylsulfonylamino)phenyl) furo[2,3-d]pyrimidine

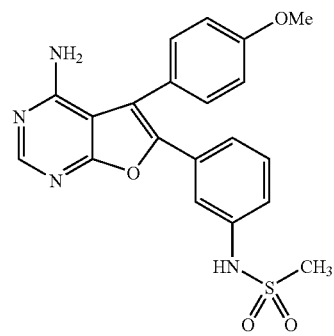

Example 1 was prepared according to procedures similar to those shown in Scheme 2.

1(A) 2-Amino-3-cyano-4-(4-methoxyphenyl)furan

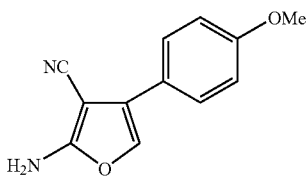

To a cooled solution of 2-hydroxy-4'-methoxyacetophenone (379 mg, 2.28 mmol) in DMF (0.75 ml) was added malononitrile (166 mg, 2.51 mmol) followed by diethylamine (0.1 ml, 0.97 mmol). The mixture was stirred at room temperature for 2 hours, and then poured into large amount of cold water. The precipitate was filtrated, washed with water, and dried under reduced pressure to give the intermediate of Example 1(A) (424 mg, 87%) as a brown solid. 1H NMR (400 MHz, CDCl3) ppm 3.83 (s, 3H), 4.73 (brs, 2H), 6.93 (m, 2H), 6.94 (s, 1H), 7.49 (m, 2H). LC/MS: m/z 215 (M+1)$^+$.

1(B) 4-Amino-3-(4-methoxyphenyl)furo[2,3-d]pyrimidine (Example 11)

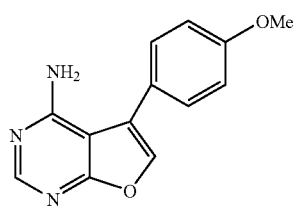

A solution of the intemediate of Example 1(A) (409 mg, 1.91 mmol) in formamide (12 ml) was refluxed (heated in an oil bath at around 200° C.) for 30 min. The mixture was cooled to room temperature, chilled in an ice bath, and then poured into cold water. The precipitate was filtrated, washed with water, and dried under reduced pressure to give the Intermediate of Example 1(B) (340 mg, 74%) as a brown solid. 1H NMR (400 MHz, CDCl3) ppm 3.89 (s, 3H), 5.17 (brs, 2H), 7.04 (m, 2H), 7.42 (m, 2H), 7.47 (s, 1H), 8.40 (s, 1H). LC/MS: m/z 242 (M+1)$^+$.

1(C) 4-Amino-2-bromo-3-(4-methoxyphenyl)furo[2,3-d]pyrimidine

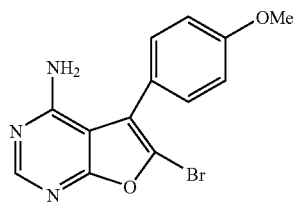

To a suspension of the Intermediate of Example 1(B) (833 mg, 3.45 mmol) in carbon tetrachloride (10 ml) was added NBS (685 mg, 3.85 mmol). After stirring at room temperature for 0.5 hour, the resultant suspension was concentrated in vacuo, and then the residue was triturated with a mixture of ethyl acetate and water. The insoluble material was filtered off, and then the filtrate was extracted with ethyl acetate. The organic phase was passed through a small silica gel pad and concentrated in vacuo. The residue was triturated with ethyl acetate/ether, filtrated, and dried under reduced pressure to give the Intermediate of Example 1(C) (550 mg). 1H NMR (400 MHz, CDCl3) ppm 3.87 (s, 3H), 5.15 (brs, 2H), 7.05 (m, 2H), 7.42 (m, 2H), 8.33 (s, 1H). LC/MS: m/z 320 (M)$^+$, 322 (M+2)$^+$.

1(D) 4-Amino-3-(4-methoxyphenyl)-2-(3-(methylsulfonylamino)phenyl) furo[2,3-d]pyrimidine

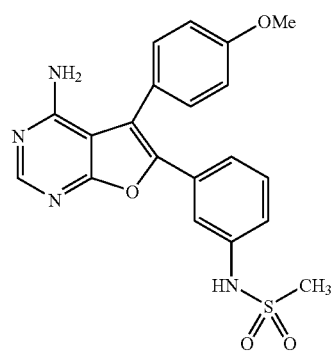

To a mixture of the Intermediate of Example 1(C) (51 mg, 0.16 mmol), 3-(methylsulfonyl-amino)phenylboronic acid, pinacol ester (55 mg, 0.19 mmol), and tetra-kis(triphenylphosphine)palladium(O) (10.5 mg, 0.01 mmol) was added DME (1.5 ml) and 2 M aqueous Na$_2$CO$_3$ (0.5 ml) under argon atmosphere. The mixture was heated at 85° C. for 12 hours. The mixture was diluted with dichloromethane and the insoluble material was filtered off. The filtrate was washed with water and purified by chromatography on a silical gel column using hexane/ethyl acetate as an eluant to afford the title compound of Example 1(32 mg) as a solid. 1H NMR (400 MHz, CDCl3) ppm 2.94 (s, 3H), 3.91 (s, 3H), 4.93 (brs, 2H), 6.26 (brs, 1H), 7.08 (m, 2H), 7.18 (m, 1H), 7.31 (m, 2H), 7.40 (m, 3H), 8.39 (s, 1H). LC/MS: m/z 411 (M+1)$^+$, 409 (M−1)$^−$.

Example 2

4-Amino-3-(4-(dimethylamino)phenyl)-2-(4-methoxyphenyl)-furo[2,3-d]pyrimidine

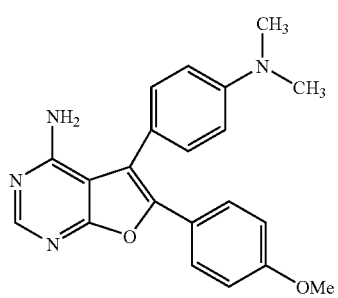

Example 2 was prepared according to procedures similar to those shown in Scheme 3.

2(A) 2-Amino-3-cyano-5-(4-methoxyphenyl)furan

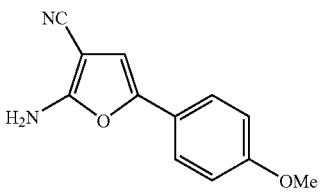

To a suspension of α-((4-methoxybenzoyl)methyl)malononitrile (9.66 g, 45.1 mmol) in acetic acid (50 ml) was added conc. hydrogen chloride (11,3 ml). The mixture was stirred at room temperature for 2 hours, and then poured into water. The resultant precipitation was filtrated, washed with water and ethanol, and dried under reduced pressure to give the Intermediate of Example 2(A) (5.54 g, 56%) as a solid. 1H NMR (400 MHz, CDCl3) ppm 3.83 (s, 3H), 4.74 (brs, 2H), 6.39 (s, 1H), 6.90 (m, 2H), 7.42 (m, 2H).

2(B) 4-Amino-2-(4-methoxyphenyl)furo[2,3-d]pyrimidine (Example 14)

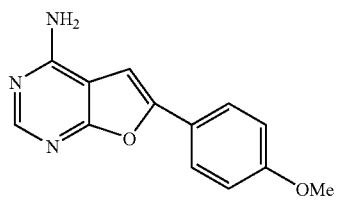

A solution of the Intermediate of Example 2(A) (5.54 g, 25.9 mmol) in formamide (100 ml) was heated at 200° C. for 1 hour. The mixture was cooled with an ice bath, and then poured into cold water. The precipitated material was filtrated, washed with water and ethanol, and dried under reduced pressure to give the Intermediate of Example 2(B) (5.61 g, 690%) as a solid. 1H NMR (400 MHz, CDCl3) ppm 3.87 (s, 3H), 5.14 (s, 2H), 6.72 (s, 1H), 6.99 (m, 1H), 7.78 (m, 2H), 8.38 (s, 1H). LC/MS: m/z 242 (M+1)$^+$;

2(C) 4-Amino-3-bromo-2-(4-methoxyphenyl)furo[2,3-d]pyrimidine (Example 33)

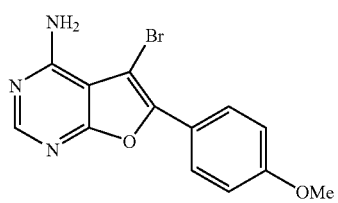

To a suspension of the Intermediate of Example 2(B) (4.02 g, 16.7 mmol) in carbon tetrachloride (100 ml), NBS (3.42 g, 19.2 mmol) was added. The mixture was refluxed for 4 hours, and then concentrated in vacuo. The residual material was suspended in ethanol, refluxed for 20 minutes, and cooled to 0° C. The precipitated material was filtrated, washed with ethanol, and dried under reduced pressure to afford the Intermediate of Example 2(C) (4.71 g, 88%). 1H NMR (400 MHz, DMSO-d6) ppm 3.84 (s, 3H), 7.13 (m, 2H), 7.95 (m, 2H), 8.24 (s, 1H). LC/MS: m/z 320 (M)$^+$, 322 (M+2)$^+$.

2(D) 4-Amino-3-(4-(dimethylamino)phenyl)-2-(4-methoxyphenyl)furo[2,3-d]pyrimidine

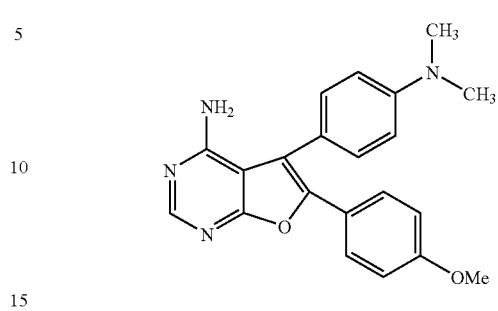

A mixture of the Intermediate of Example 2(C) (62.4 mg, 0.195 mmol), (4-dimethyl amino)phenyl-boronic acid (101 mg, 0.61 mmol), tetrakis(triphenyl phosphine)-palladium(O) (15.5 mg, 0.013 mmol) was suspended in the mixture of DME (2.0 ml), DMF (0.5 ml), and 2 M aqueousNa$_2$CO$_3$ (1.0 ml) under argon atmosphere. The mixture was refluxed over night, diluted with dichloromethane, and washed with aqueous Na$_2$CO$_3$. The organic phase was separated, concentrated in vacuo, and purified by chromatography on a silica gel column using hexane/ethyl acetate (3:1-1:1) as an eluant to afford the title compound of Example 2 (37 mg) as a solid. 1H NMR (400 MHz, CDCl3) ppm 3.05 (s, 6H), 3.80 (s, 3H), 4.94 (brs, 2H), 6.82 (m, 4H), 7.31 (m, 2H), 7.56 (m, 2H), 8.34 (s, 1H). LC/MS: m/z 361 (M+1)$^+$.

Example 3

4-Amino-3-(4-((3-chlorophenyl)sulfonylamino)phenyl)-2-(4-methoxyphenyl)furo[2,3-d]pyrimidine

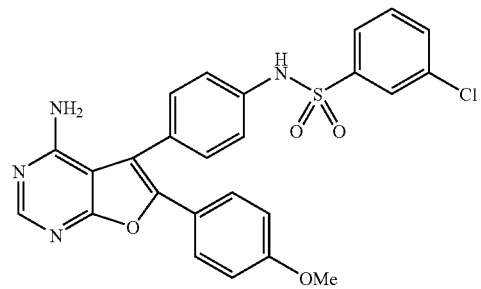

Example 3 was prepared according to procedures similar to those shown in Scheme 3.

3(A) 4-Amino-3-(4-aminophenyl)-2-(4-methoxyphenyl)furo[2,3-d]pyrimidine)

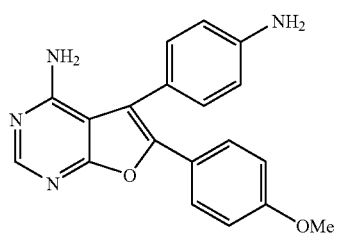

A mixture of the intermediate of Example 2(C) (628 mg), 4-(4,4,5,5-tetramethyl-1,3,2-dioxaborolan-2-yl)aniline(644 mg), tetrakis(triphenylphosphine)palla-dium(O) (226 mg) and 2 M Na$_2$CO$_3$ (4.9 ml) in DME (20 ml) was heated at 80° C. and stirred for 15 hours. The reaction mixture was poured into the mixture of ethyl acetate and sat NH$_4$Cl. The resultant insoluble material was collected by filtration, which was purified by a SCX column (Varian, 10 g) to give the Intermediate of Example 3(A) (200 mg). 1H-NMR (400 MHz, DMSO-d6) ppm 3.75 (s, 3H), 6.71 (d, J=8.3Hz, 2H), 6.94 (d, J=8.8 Hz, 2H), 7.11 (d, J=8.3 Hz, 2H), 7.45 (d, J=8.9 Hz, 2H), 8.21 (s, 1H). LC/MS: m/z 333 (M+1)$^+$.

3(B) 4-Amino-3-(4-((3-chlorophenyl)sulfonylamino)phenyl)-2-(4-methoxyphenyl)furo[2,3-d]pyrimidine

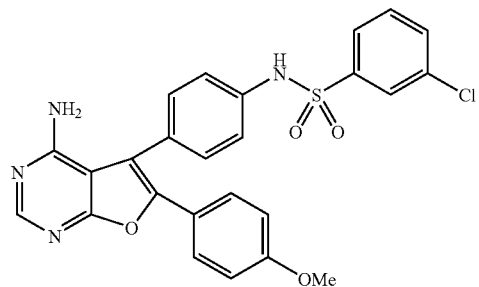

To a solution of the Intermediate of Example 3(A) (23.4 mg) in CH$_2$Cl$_2$(2 ml) and pyridine (0.5 ml) was added m-chlorobenzensulfonyl chloride (155 ul) at 0° C. The reaction mixture was stirred at ambient temperature a for 2 hours, and then poured into a mixture of AcOEt and 1N HCl. The organic layer was separated, dried over Na$_2$SO$_4$, and concentrated in vacuo. The residue was purified by chromatography on a silica gel column to give the title compound of Example 3 (28.5 mg). 1H NMR (400 MHz, DMSO-d6) ppm 3.76 (s, 3H), 6.86 (d, J=9.1 Hz, 2H), 7.24 (d, J=8.3 Hz, 2H), 7.25 (d, J=8.8 Hz, 2H), 7.37 (d, J=8.3 Hz, 2H), 7.63 (d, J=7.8 Hz, 1H), 7.73 (d, J=7.8 Hz, 1H), 7.76 (d, J=7.8 Hz, 1H), 7.78 (s, 1H), 8.22 (s, 1H). LC/MS: m/z 507 (M+1)$^+$, 509 (M+3)$^+$, 505 (M−1)$^-$, 507 (M+1)$^-$.

Example 4

4-Amino-3-(4-((2-fluoro-5-(trifluoromethyl)phenyl)amino-carbonylamino)phenyl)-2-(4-methoxyphenyl)furo[2,3-d]pyrimidine

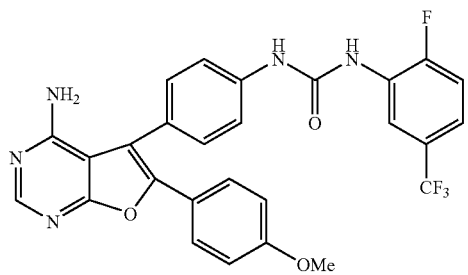

Example 4 was prepared according to procedures similar to those shown in Scheme 3.

To a solution of the Intermediate of Example 3(A) (28.8 mg) in DMF(2 ml) was added 2-fluoro-5-(trifluoromethyl)phenylisocyanate (13.8 ul). The reaction mixture was stirred for 2 hours at room temperature, and then concentrated under reduced pressure. The residue was purified by preparative TLC to give the title compound of Example 4 (27.7 mg). 1H NMR (400 MHz, DMSO-d6) ppm 3.75 (s, 3H), 6.95 (d, J=9.1 Hz, 2H), 7.41 (d, J=9.1 Hz, 2H), 7.43 (d, J=8.8 Hz, 2H), 7.53 (dd, J=8.8 Hz, 10.9 Hz, 1H), 7.66 (d, J=8.6 Hz, 2H), 8.64 (d, J=7.1 Hz, 1H), 9.04 (s, 1H), 9.46 (s, 1H). LC/MS: m/z 538 (M+1)$^+$, 536 (M−1)$^-$.

Example 5

4-Amino-3-(4-(2,3-difluorophenyl)phenyl)-2-(3-sulfamoylphenyl)-furo[2,3-d]pyrimidine

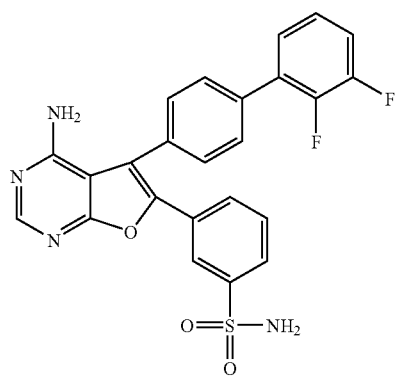

Example 5 was prepared according to procedures similar to those shown in Scheme 2.

5(A) 4-Amino-3-(4-bromophenyl)furo[2,3-d]pyrimidine

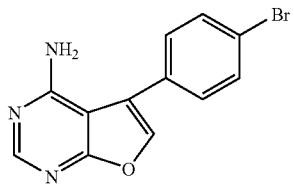

A suspension of 2-Amino-4-(4-bromophenyl)-3-cyanofuran in formamide was treated by the same method as in the procedure of Example 1(B) to afford the Intermediate of Example 5(A). 1H NMR (400 MHz, CDCl3) ppm 5.20 (brs, 2H), 7.38 (m, 2H), 7.53 (s, 1H), 7.65 (m, 2H), 8.42 (s, 1H). LC/MS: m/z 290 (M)$^+$, 292 (M+2)$^+$.

5(B) 4-Amino-3-(4-(2,3-difluorophenyl)phenyl)furo[2,3-d]pyrimidine

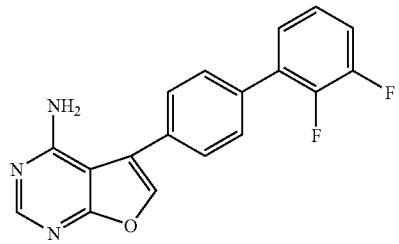

DME (5 ml) and 2 M Na$_2$CO$_3$ (1 ml) were added sequentially to a degassed mixture of the Intermediate of Example 5(A) (0.5 mmol, 145 mg), 2,3-difluoro phenylboronic acid (0.75 mmol, 118.5 mg), and tetrakis-(triphenyl phosphine) palladium(0) (0.05 mmol, 57.8 mg). The resultant suspension was heated at 80° C. under argon for 12 hours, and then cooled down to room temperature. The mixture was extracted with ethyl acetate 3 times (3×20 ml). The solvent was evaporated to dryness and the residual material was purified by chromatography on a SCX column using MeOH as an eluant to give the Intermediate of Example 5(B) (0.475 mmol, 153.5 mg), which was used in the next step without further purification.

1H-NMR(400 MHz, DMSO-d6) ppm 6.65 (br, 1H), 7.32–7.37 (m, 1H), 7.41–7.52 (m, 2H), 7.66 (d, 2H, J=8.3 Hz), 7.74 (dd, 2H, J=1.5, 8.3 Hz), 8.08 (s, 1H), 8.28 (s, 1H). LC/MS: m/z 324 (M+1)$^+$.

5(C) 4-Amino-2-bromo-3-(4-(2,3-difluorophenyl)phenyl)furo[2,3-d]-pyrimidine

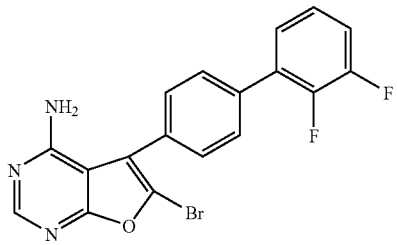

The Intermediate of Example 5(B) was brominated by a similar method as for the Intermediate of Example 1(C) except that THF was used as the solvent to afford the Intermediate of Example 5(C). 1H-NMR(400 MHz, DMSO-d6) ppm 7.35–7.38 (m, 1H), 7.45–7.51 (m, 2H), 7.65 (d, 2H, J=8.1 Hz), 7.78 (dd, 2H, J=1.3, 8.1 Hz), 8.27 (s, 1H). LC/MS: m/z 402 (M)$^+$, 404 (M+2)$^+$.

5(D) 4-Amino-3-(4-(2,3-difluorophenyl)phenyl)-2-(3-sulfamoyl-phenyl)furo[2,3-d]pyrimidine

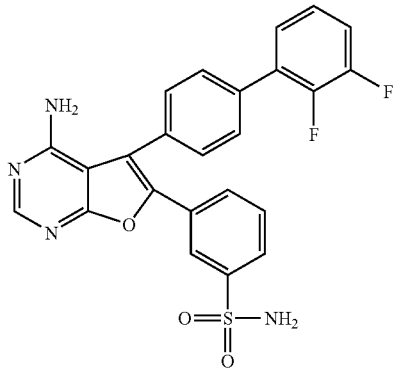

The Intermediate of Example 5(C) was reacted with 3-(4,4,5,5-tetramethyl-1,3,2-dioxa-borolan-2-yl)sulfamoylbenzen using the procedure of Example 5(B) to give the title compound of Example 5 (80% after purification). 1H-NMR (400 MHz, DMSO-d6) ppm 7.36–7.39 (m, 1H), 7.45–7.54 (m, 4H), 7.66 (d, 2H, J=8.3 Hz), 7.76 (dt, 1H, J=1.5, 7.6 Hz), 7.81(dd, 2H, J=1.3, 8.3 Hz), 8.10 (t, 1H, J=1.2 Hz), 8.33 (s, 1H). LC/MS: m/z 479 (M+1)$^+$.

Example 6

4-Amino-3-(4-(3-biphenyl)phenyl)-2-(3-sulfamoylphenyl)furo[2,3-d]pyrimidine

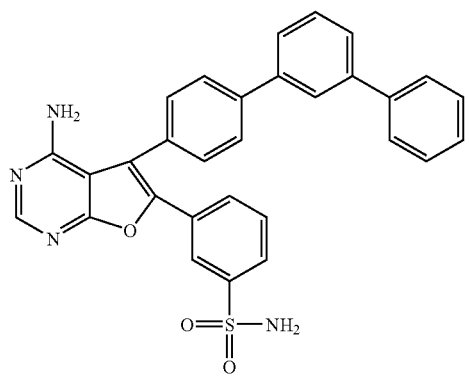

Example 6 was prepared according to procedures similar to those shown in Scheme 2.

6(A) 4-Amino-3-(4-(3-biphenyl)phenyl)furo[2,3-d]pyrimidine

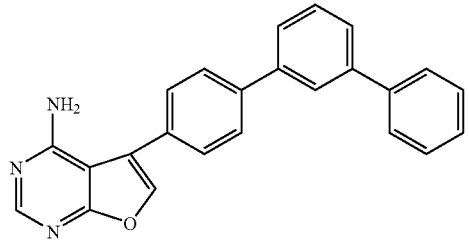

The Intermediate of Example 5(A) (174 mg), (3-biphenyl) boronic acid (178 mg), tetrakis-(triphenylphosphine)palladium(0) (69 mg), and K$_3$PO$_4$ (255 mg) was suspended in DMF (7 ml) and water (1.7 ml). The mixture was heated at 80° C. and stirred overnight. The reaction mixture was poured into a mixture of ethyl acetate and sat. NH$_4$Cl. The resultant insoluble material was filtered off and the filtrate was extracted with ethyl acetate. The organic layer was separated, dried over Na$_2$SO$_4$, and concentrated in vacuo. The residue was purified by chromatogphy on a silica gel column. The material was washed with ethanol and dried under reduced pressure to give the Intermediate of Example 6(A) (90 mg). 1H-NMR (400 MHz, DMSO-d6) ppm 7.41 (m, 1H), 7.51 (m, 2H), 7.60–7.66 (m, 3H), 7.69 (m, 1H), 7.75 (m, 1H), 7.79 (m, 2H), 7.95–7.99 (m, 3H), 8.07 (s, 1H), 8.28 (s, 1H).

6(B) 4-Amino-2-bromo-3-(4-(3-biphenyl)phenyl)furo[2,3-d]pyrimidine

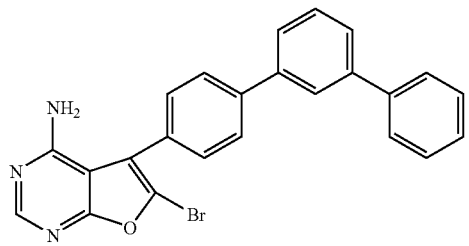

To a suspension of the Intermediate of Example 6(A) (72.4 mg) in a mixture of carbon tetrachloride (10 ml) and ethyl acetate (15 ml) was added NBS (40.8 mg). The mixture was stirred at room temperature for 3 hours. The reaction mixture was quenched by 10% $Na_2S_2O_4$ and extracted with ethyl acetate. The organic layer was dried over $Na_2SO_4$, filtered, and concentrated under reduced pressure. The residual solid was washed with AcOEt-hexane to give the Intermediate of Example 6(B) (73.8 mg). 1H NMR (400 MHz, DMSO-d6) ppm 7.39–7.43 (m, 1H), 7.49–7.53 (m, 2H), 7.59–7.64 (m, 3H), 7.7–7.72 (m, 1H), 7.76–7.82 (m, 3H), 8.01–7.97 (m, 3H), 8.27 (s, 1H), 8.31 (s, 1H). LC/MS: m/z 442 $(M)^+$, 444 $(M+2)^+$.

6(C) 4-Amino-3-(4-(3-biphenyl)phenyl)-2-(3-sulfamoyl phenyl)furo[2,3-d]pyrimidine

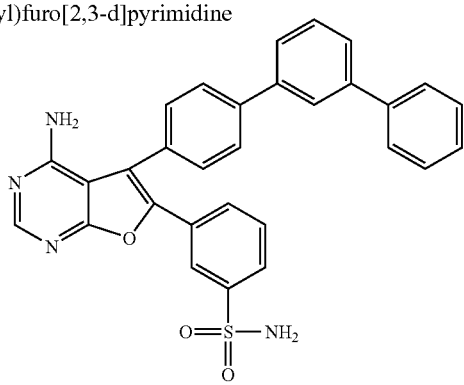

The mixture of the Intermediate of Example 6(B) (40 mg), 3-(4,4,5,5-tetramethyl-1,3,2-dioxaborolan-2-yl)sulfamoyl-benzene (38.2 mg), tetrakis (triphenylphosphine)-palladium (O) (10.4 mg) and 2 M $Na_2CO_3$ (0.23 ml) in DME (2.5 ml) was stirred at 80° C. for 15 hours. The reaction mixture was concentrated under reduced pressure. The residue was purified by chromatography on a silica gel column and sequentially purified by a SCX column (Varian, 1 g) to remove triphenylphosphineoxide to give the title compound of Example 6 (7.1 mg). 1H NMR (400 MHz, DMSO-d6) ppm 7.39–7.43 (m, 1H), 7.47–7.54 (m, 5H), 7.6–7.66 (m, 3H), 7.71–7.82 (m, 5H), 8.01–8.04 (m, 3H), 8.14 (s, 1H), 8.33 (s, 1H). LC/MS: m/z 519 $(M+1)^+$, 517 $(M-1)^-$.

Example 7

4-Amino-3-(4-biphenyl)-2-(4-fluoro-3-(methylsulfonylamino)-phenyl)furo[2,3-d]pyrimidine

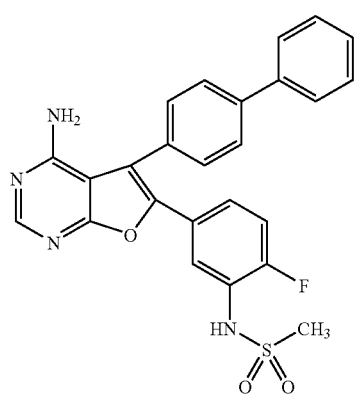

Example 7 was prepared according to procedures similar to those shown in Scheme 2.

7(A) 2-Amino-3-cyano-4-(4-biphenyl)furan

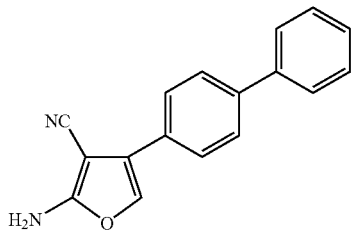

(2-hydroxy-4'-phenyl)acetophenone was reacted with malononitrile using the same procedure as in Example 1(A) to afford the Intermediate of Example 7(A). 1H NMR (400 MHz, CDCl3) ppm 4.81 (brs, 2H), 7.07 (s, 1H), 7.37 (m, 1H), 7.46 (m, 2H), 7.61–7.64 (m, 6H).

7(B) 4-Amino-3-(4-biphenyl)furo[2,3-d]pyrimidine

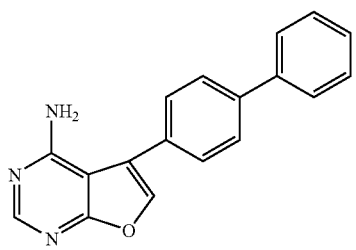

The Intermediate of Example 7(A) was treated with formamide using the same procedure method as in Example 1(B) to afford the Intermediate of Example 7(B). 1H NMR (400 MHz, CDCl3) ppm 5.25 (brs, 2H), 7.4–7.8 (m, 10H), 8.43 (s, 1H). LC/MS: m/z 288 $(M+1)^+$.

7(C) 4-Amino-3-(4-biphenyl)-2-bromofuro[2,3-d]pyrimidine

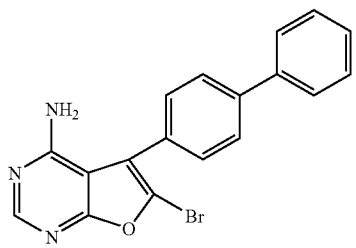

The Intermediate of Example 7B was brominated using the same procedure as in Example 1(C) except that a mixture of carbon tetrachloride and ethyl acetate was used as a solvent to afford the Intermediate of Example 7(C). 1H NMR (400 MHz, CDCl3) ppm 5.23 (brs, 2H), 7.42 (m, 1H), 7.50 (m, 2H), 7.59 (m, 2H), 7.65 (m, 2H), 7.77 (m, 2H), 8.38 (s, 1H). LC/MS: m/z 366 $(M)^+$, 368 $(M+2)^+$.

7(D) 4-Amino-3-(4-biphenyl)-2-(4-fluoro-3-(methylsulfonylamino)-phenyl)furo[2,3-d]pyrimidine

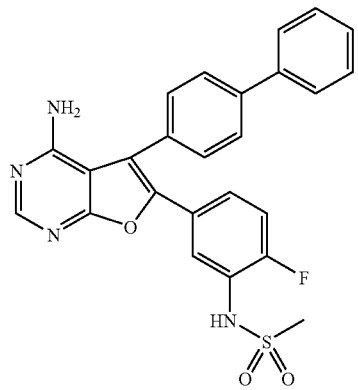

The Intermediate of Example 7(C) was reacted with 2-(methylsulfonylamino)-4-(4,4,5,5-tetramethyl-1,3,2-dioxaborolan-2-yl)fluorobenzen using the same method as in Example 1(D) to afford the title compound of Example 7. 1H NMR (400 MHz, CDCl3) ppm 2.84 (s, 3H), 4.98 (brs, 2H), 6.48 (brs, 1H), 7.12 (m, 1H), 7.41–7.53 (m, 4H), 7.58 (m, 2H), 7.66 (m, 3H), 7.79 (m, 2H), 8.42 (s, 1H). LC/MS: m/z 475 (M+1)+, 473 (M−1)−.

Example 8

4-Amino-2-(3-cyanophenyl)-3-(4-((2-fluoro-5-(trifluoromethyl)-phenyl)aminocarbonylamino)phenyl)furo[2,3-d]pyrimidine

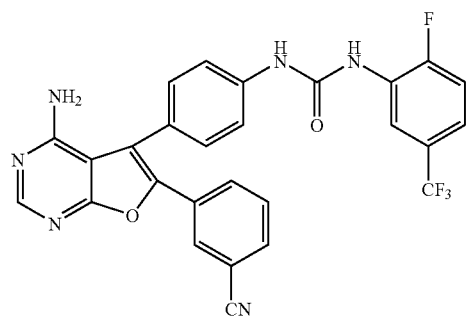

Example 8 was prepared according to procedures similar to those shown in Scheme 2.

8(A) 3-(4-Acetamidephenyl)-4-aminofuro[2,3-d]pyrimidine

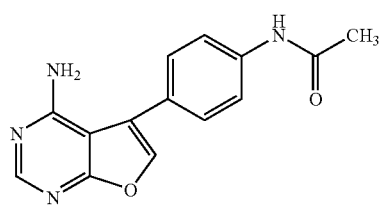

The title Intermediate of Example 8(A) was obtained using procedures similar to those of Example 1(B).

1H NMR (400 MHz, CDCl3) ppm 2.24 (s, 3H), 5.17 (brs, 2H), 7.46 (d, 2H, J=8.3 Hz), 7.50 (s, 1H), 7.66 (d, 2H, J=8.3 Hz), 8.41 (s, 1H). LC/MS: m/z 269 (M+1)+.

8(B) 4-Amino-3-(4-aminophenyl)furo[2,3-d]pyrimidine

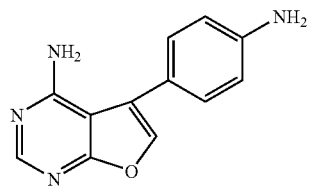

The Intermediate of Example 8(A) (242 mg, 0.90 mmol) was suspended in 2 M KOH in ethanol/H2O (4:1, 20 ml). The mixture was stirred at 60° C. overnight, and then concentrated in vacuo. The residual oil was triturated with water (6 ml). The precipitated material was filtrated, washed with water, and dried under reduced pressure to give the Intermediate of Example 8(B) (118 mg, 58%) as an orange powder. 1H NMR (400 MHz, CDCl3) ppm 3.85 (brs, 2H), 5.18 (brs, 2H), 6.79 (d, 2H, J=8.4 Hz), 7.28 (d, 2H, J=8.4 Hz), 7.44 (s, 1H), 8.39 (s, 1H). 1H NMR (400 MHz, DMSO-d6) ppm 5.35 (s, 2H), 6.68 (d, J=8.6 Hz, 2H), 7.16 (d, J=8.3 Hz, 2H), 7.78 (s, 1H), 8.22 (s, 1H). LC/MS: m/z 227 (M+1)+.

8(C) 4-Amino-3-(4-((2-fluoro-5-(trifluoromethyl)phenyl)-aminocarbonylamino) phenyl)furo[2,3-d]pyrimidine (Example 232)

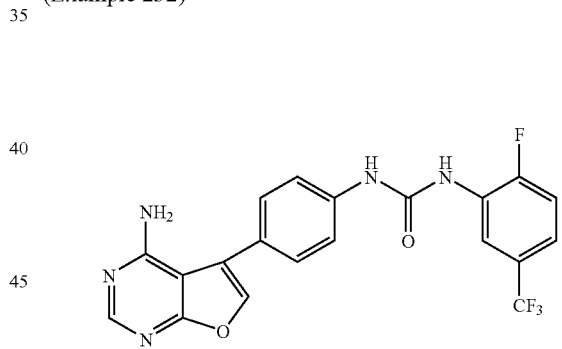

To a solution of the Intermediate of Example 8(B) (80 mg) in THF (10 ml) was added 2-fluoro-5-(trifluoromethyl)phenylisocyanate (53.8 ul) and the reaction mixture was stirred at 0° C. for 2 hours. The solvent was removed under reduced pressure and the residue was purified by chromatography on a silica gel column to afford the Intermediate of Example 8(C) (117 mg). 1H NMR (400 MHz, DMSO-d6) ppm 7.39–7.42 (m, 1H), 7.47 (d, J=8.6 Hz, 2H), 7.49–7.54 (m, 1H), 7.63 (d, J=8.8 Hz, 2H), 7.95 (s, 1H), 8.26 (s, 1H), 8.63 (d, J=7.1 Hz, 1H), 8.99 (s, 1H), 9.39 (s, 1H). LC/MS: m/z 432 (M+1)+, 430 (M−1)−.

8(D) 4-Amino-2-bromo-3-(4-((2-fluoro-5-(trifluoromethyl)phenyl)-aminocarbonylamino)phenyl)furo[2,3-d]pyrimidine (Example 272)

The Intermediate of Example 8(C) (218 mg) was brominated using the same procedure as in Example 1(C) except that a mixture of carbon tetrachloride (15 ml) and ethyl acetate (30 ml) was used as a solvent to afford the Intermediate of Example 8(D) (222 mg). 1H NMR (400 MHz, DMSO-d6) ppm 7.40–7.43 (m, 1H), 7.45 (d, J=8.6 Hz, 2H), 7.52 (dd, J=8.8 Hz, 10.9 Hz, 1H), 7.66 (d, J=8.6 Hz, 2H), 8.24 (s, 1H), 8.64 (d, J=7.1 Hz), 9.0 (s, 1H), 9.41 (s, 1H). LC/MS: m/z 510 (M)$^+$, 512 (M+2)$^+$.

8(E) 4-Amino-2-(3-cyanophenyl)-3-(4-((2-fluoro-5-(trifluoromethyl)-phenyl)aminocarbonylamino)phenyl)furo[2,3-d]pyrimidine The Intermediate of Example 8D (40 mg) was reacted with (3-cyanophenyl)boronic acid (34.4 mg) using the same procedure as in Example 1(D) to afford the title compound of Example 8 (40.5 mg). 1H NMR (400 MHz, DMSO-d6) ppm 7.4–7.44 (m, 1H), 7.47 (d, J=8.6 Hz, 2H), 7.50–7.61 (m, 2H), 7.69–7.73 (m, 3H), 7.80 (d, J=7.8 Hz, 2H), 7.83 (s, 1H), 8.30 (s, 1H), 8.63 (d, J=7.3 Hz, 1H), 9.06 (s, 1H), 9.51 (s, 1H). LC/MS: m/z 533 (M+1)$^+$, 531 (M−1)$^-$.

The following Examples 9–275 were prepared according according to procedures similar to those shown in similarly to Scheme 1, Scheme 2, Scheme 3, or Scheme 4 and obtained according to similar methods as recited in Examples 1–8.

Example 9

4-Amino-2,3-diphenylfuro[2,3-d]pyrimidine

Example 9 was prepared according to procedures similar to those shown in Scheme 1.
HPLC: RT 3.06 min, LC/MS: m/z 288 (M+1)$^+$.

Example 10

4-Amino-2,3-bis(4-methoxyphenyl)furo[2,3-d]pyrimidine

Example 10 was prepared according to procedures similar to those shown in Scheme 2.

1HNMR (400 MHz, CDCl3) ppm 3.80 (s, 3H), 3.90 (s, 3H), 4.89(brs, 2H), 6.82 (d, J=8.9 Hz, 2H), 7.05 (d, J=8.7 Hz, 2H), 7.41 (d, J=8.7 Hz, 2H), 7.50 (d, J=9.0 Hz, 2H), 8.36 (s, 1H); HPLC: RT 3.04 min, LC/MS: m/z 348 (M+1)$^+$.

Example 11 (Example 1(B))

4-Amino-3-(methoxyphenyl)furo[2,3-d]pyrimidine

1H NMR (400 MHz, CDCl3) ppm 3.89 (s, 3H), 5.17 (brs, 2H), 7.04 (m, 2H), 7.42 (m, 2H), 7.47 (s, 1H), 8.40 (s, 1H); HPLC: RT 2.60 min, LC/MS: m/z 242 (M+1)$^+$.

Example 12

4-Amino-2,3-bis(3,4-O-methylidenedioxyphenyl)furo[2,3-d]pyrimidine

Example 12 was prepared according to procedures similar to those shown in Scheme 1.
1H NMR (400 Hz, CDCl3) ppm 4.94 (s, 2H), 5.97 (s, 2H), 6.09 (s, 2H), 6.76 (d, J=8.2 Hz, 1H), 6.91–7.02 (m, 4H), 7.14 (dd, J=1.7, 8.2 Hz, 1H), 8.36 (s, 1H); HPLC: RT 2.93 min, LC/MS: m/z 376 (M+1)$^+$.

Example 13

4-Amino-2,3-dibutylfuro[2,3-d]pyrimidine

Example 13 was prepared according to procedures similar to those shown in Scheme 1.
HPLC: RT 3.23 min, LC/MS: m/z 248 (M+1)$^+$.

Example 14: (Example 2(8))

4-Amino-2-(4-methoxyphenyl)furo[2,3-d]pyrimidine

HPLC: RT 2.59 min, LC/MS: m/z 242 (M+1)$^+$.

Example 15

4-Amino-2-(3-furanyl)-3-(2-furanyl)furo[2,3-d]pyrimidine

Example 15 was prepared according to procedures similar to those shown in Scheme 1.
1H NMR (400 MHz, CDCl3) ppm 5.93 (brs, 2H), 6.57 (m, 1H), 6.63 (m, 1H), 6.97 (d, J=3.4 Hz, 1H), 7.00 (d, J=3.4 Hz, 1H), 7.54 (m, 1H), 7.62 (m, 1H), 8.38 (s, 1H); HPLC: RT min, LC/MS: m/z 268 (M+1)$^+$.

Example 16

4-Amino-2,3-bis(4-methylphenyl)furo[2,3-d]pyrimidine

Example 16 was prepared according to procedures similar to those shown in Scheme 1.
1H NMR (400 MHz, CDCl3) ppm 2.33 (s, 3H), 2.46 (s, 3H), 4.89 (brs, 2H), 7.10 (m, 2H), 7.32 (m, 2H), 7.38 (m, 2H), 7.45 (m, 2H), 8.37 (s, 1H); HPLC: RT min. LC/MS: m/z 316 (M+1)$^+$.

Example 17

4-Amino-2-(4-methyl phenyl)-3-(4-trifluoromethylphenyl)furo[2,3-d]pyrimidine

Example 17 was prepared according to procedures similar to those shown in Example 2.

1HNMR (400 MHz, CDCl3) ppm 3.81 (s, 3H), 4.84 (brs, 2H), 6.85 (d, J=8.9 Hz, 2H), 7.43 (d, J=9.0 Hz, 2H), 7.65 (d, J=7.9 Hz, 2H), 7.80 (d, J=8.1 Hz, 2H), 8.40 (s, 1H); HPLC: RT 3.27 min, LC/MS: m/z 386 (M+1)$^+$.

Example 18

4-Amino-3-(4-methyl phenyl)-2-(4-trifluoromethylphenyl)furo[2,3-d]pyrimidine

Example 18 was prepared according to procedures similar to those shown in Example 1.

1HNMR (400 MHz, CDCl3) ppm 3.90 (s, 3H), 4.96 (brs, 2H), 7.07 (d, J=8.7 Hz, 2H), 7.40 (d, J=8.6 Hz, 2H), 7.53 (d, J=8.4 Hz, 2H), 7.66 (d, J=8.4 Hz, 2H), 8.40 (s, 1H); HPLC: RT 3.34 min, LC/MS: m/z 386 (M+1)$^+$.

Example 19

4-Amino-2-(2-benzothienyl)-3-(4-methoxyphenyl)furo[2,3-d]pyrimidine

Example 19 was prepared according to procedures similar to those shown in Example 1.

1H NMR (400 Hz, CDCl3) ppm 3.94 (s, 3H), 4.95 (s, 2H), 7.12 (d, J=8.6 Hz, 2H), 7.29–7.33 (m, 2H), 7.49 (d, J=8.6 Hz, 2H), 7.64 (s, 1H), 7.70 (d, J=7.7 Hz, 1H), 7.74 (d, J=7.3 Hz, 1H), 8.40 (s, 1H); HPLC: RT 3.37 min, LC/MS: m/z 374 (M+1)$^+$.

Example 20

4-Amino-2-(4-biphenyl)-3-(4-methoxyphenyl)furo[2,3-d]pyrimidine

Example 20 was prepared according to procedures similar to those shown in Example 1.

1H NMR (400 MHz, CDCl3) ppm 3.92 (s, 3H), 4.92 (brs, 2H), 7.08 (m, 2H), 7.35 (m, 1H), 7.42–7.46 (m, 4H), 7.54 (m, 2H), 7.58 (m, 2H), 7.64 (m, 2H), 8.40 (s, 1H); HPLC: RT 3.57 min, LC/MS: m/z 394 (M+1)$^+$.

Example 21

4-Amino-2-(2-chlorophenyl)-3-(4-methoxylphenyl)furo[2,3-d]pyrimidine

Example 21 was prepared according to procedures similar to those shown in Example 1.

1H NMR (400 Hz, CDCl3) ppm 3.91 (s, 3H), 4.93 (s, 2H), 7.08 (d, J=8.6 Hz, 2H), 7.20–7.24 (m, 2H), 7.38–7.42 (m, 3H), 7.61 (s, 1H), 8.40 (s, 1H); HPLC: RT 3.28 min, LC/MS: m/z 352 (M+1)$^+$.

Example 22

4-Amino-2-(2-methoxylphenyl)-3-(4-methoxylphenyl)furo[2,3-d]pyrimidine

Example 22 was prepared according to procedures similar to those shown in Example 1.

1H NMR (400 MHz, CDCl3) ppm 3.46 (s, 3H), 3.83 (s, 3H), 5.07 (brs, 2H), 6.85 (m, 1H), 6.84–6.99 (m, 3H), 7.27–7.29 (m, 2H), 7.34 (m, 1H), 7.48 (m, 1H), 8.39 (s, 1H); HPLC: RT 2.92 min, LC/MS: m/z 348 (M+1)$^+$.

Example 23

4-Amino-3-(4-methoxyphenyl)-2-(1-naphthyl)furo[2,3-d]pyrimidine

Example 23 was prepared according to procedures similar to those shown in Example 1.

1H NMR (400 MHz, CDCl3) ppm 3.77 (s, 3H), 5.12 (brs, 2H), 6.85 (m, 2H), 7.24 (m, 2H), 7.35–7.51 (m, 4H), 7.87 (m, 2H), 8.00 (m, 1H), 8.45 (s, 1H); HPLC: RT 3.15 min, LC/MS: m/z 368 (M+1)$^+$.

Example 24

4-Amino-3-(4-methoxyphenyl)-2-(2-naphthyl)furo[2,3-d]pyrimidine

Example 24 was prepared according to procedures similar to those shown in Example 1.

1HNMR (400 MHz, CDCl3) ppm 3.91 (s, 3H), 4.93 (brs, 2H), 7.07 (d, J=8.7 Hz, 2H), 7.44–7.47 (m, 4H), 7.50–7.52 (m, 1H), 7.69 (d, J=8.9 Hz, 1H), 7.74–7.77 (m, 2H), 8.17 (s, 1H), 8.40 (s, 1H); HPLC: RT 2.60 min, LC/MS: m/z 368 (M+1)$^+$.

Example 25

4-Amino-3-(4-methoxyphenyl)-2-(4-trifluoromethyloxyphenyl)-furo[2,3-d]pyrimidine

Example 25 was prepared according to procedures similar to those shown in Example 1.

1H NMR (400 Hz, CDCl3) ppm 3.90 (s, 3H), 4.91 (s, 2H), 7.06 (d, J=8.6 Hz, 2H), 7.12 (d, J=8.9 Hz, 2H), 7.40 (d, J=8.6 Hz, 2H), 7.57 (d, J=8.9 Hz, 2H), 8.38 (s, 1H); HPLC: RT 3.42 min, LC/MS: m/z 402 (M+1)$^+$.

Example 26

4-Amino-2-(3-methoxyphenyl)-3-(4-methoxyphenyl)furo[2,3-d]pyrimidine

Example 26 was prepared according to procedures similar to those shown in Example 1.

1H NMR (400 MHz, CDCl3) ppm 3.69 (s, 3H), 3.88 (s, 3H), 4.89 (brs, 2H), 6.82 (m, 1H), 7.05 (m, 2H), 7.11 (m, 1H), 7.16 (m, 2H), 7.41 (m, 2H), 8.37 (s, 1H); HPLC: RT 3.03 min, LC/MS: m/z 348 (M+1)$^+$.

Example 27

3-(3-Acetamidophenyl)-4-amino-2-(4-methoxyphenyl)furo[2,3-d]pyrimidine

Example 27 was prepared according to procedures similar to those shown in Example 2.

1HNMR (400 MHz, CDCl3) ppm 2.20 (s, 3H), 3.81 (s, 3H), 6.83 (d, J=9.0 Hz, 2H), 7.22–7.26 (m, 2H), 7.45–7.50 (m, 3H), 7.57 (m, 1H), 7.65 (m, 1H), 8.37 (s, 1H); HPLC: RT 2.71 min, LC/MS: m/z 375 (M+1)$^+$.

Example 28

4-Amino-3-(3,4-dimethoxyphenyl)-2-(4-methoxyphenyl)furo[2,3-d]pyrimidine

Example 28 was prepared according to procedures similar to those shown in Example 2.

HPLC: RT 2.94 min, LC/MS: m/z 378 (M+1)$^+$.

Example 29

4-Amino-2-(4-methoxyphenyl)-3-(3,4,5-trimethoxyphenyl)furo[2,3-d]pyrimidine

Example 29 was prepared according to procedures similar to those shown in Example 2.

HPLC: RT 2.92 min, LC/MS: m/z 408 (M+1)$^+$.

Example 30

4-Amino-3-(4-isopropylphenyl)-2-(4-methoxyphenyl)furo[2,3-d]pyrimidine

Example 30 was prepared according to procedures similar to those shown in Example 2.

1H NMR (400 Hz, CDCl3) ppm 1.32 (d, J=7.0 Hz, 6H), 2.99 (m, 1H), 3.79 (s, 3H), 4.87 (s, 2H), 6.81 (d, J=8.9 Hz, 2H), 7.34–7.40 (m, 4H), 7.48 (d, J=8.9 Hz, 2H), 8.35 (s, 1H); HPLC: RT 3.48 min, LC/MS: m/z 360 (M+1)$^+$.

Example 31

4-Amino-3-(4-butylphenyl)-2-(4-methoxyphenyl)furo[2,3-d]pyrimidine

Example 31 was prepared according to procedures similar to those shown in Example 2.

HPLC: RT 3.72 min, LC/MS: m/z 374 (M+1)$^+$.

Example 32

4-Amino-2-(4-methoxyphenyl)-3-(3-methoxyphenyl)furo[2,3-d]pyrimidine

Example 32 was prepared according to procedures similar to those shown in Example 2.

1H NMR (400 MHz, CDCl3) ppm 3.81 (s, 3H), 3.83 (s, 3H), 4.91 (brs, 2H), 6.83 (m, 2H), 7.02 (m, 2H), 7.08 (m, 1H), 7.45 (m, 1H), 7.51 (m, 2H), 8.37 (s, 1H); HPLC: RT 3.07 min, LC/MS: m/z 348 (M+1)$^+$.

Example 33: (Example 2(c))

4-Amino-3-bromo-2-(4-methoxyphenyl)furo[2,3-d]pyrimidine

1H NMR (400 MHz, DMSO-d6) ppm 3.84 (s, 3H), 7.13 (m, 2H), 7.95 (m, 2H), 8.24 (s, 1H); HPLC: RT 2.87 min, LC/MS: m/z 320 (M)$^+$, 322 (M+2)$^+$.

Example 34

4-Amino-3-(4-biphenyl)-2-(4-methoxyphenyl)furo[2,3-d]pyrimidine

Example 34 was prepared according to procedures similar to those shown in Example 2.

1HNMR (400 MHz, CDCl3) ppm 3.80 (s, 3H), 4.94 (brs, 2H), 6.84 (d, J=9.1 Hz, 2H), 7.39–7.43 (m, 1H), 7.49–7.59 (m, 6H), 7.69 (d, J=8.6 Hz, 2H), 7.77 (d, J=8.3 Hz, 2H), 8.39 (s, 1H); HPLC: RT 3.55 min, LC/MS: m/z 394 (M+1)$^+$.

Example 35

4-Amino-2-(4-methoxyphenyl)-3-(2-methoxyphenyl)furo[2,3-d]pyrimidine

Example 35 was prepared according to procedures similar to those shown in Example 2.

HPLC: RT 3.01 min. LC/MS: m/z 348 (M+1)$^+$.

Example 36

4-Amino-2-(4-methoxyphenyl)-3-((4-methylthio)phenyl)furo[2,3-d]pyrimidine

Example 36 was prepared according to procedures similar to those shown in Example 2.

1H NMR (400 Hz, CDCl3) ppm 2.57 (s, 3H), 3.81 (s, 3H), 4.92 (s, 2H), 6.83 (d, J=9.1 Hz, 2H), 7.36–7.42 (m, 4H), 7.50 (d, J=8.8 Hz, 2H), 8.36 (s, 1H); HPLC: RT 3.22 min, LC/MS: m/z 364 (M+1)$^+$.

Example 37

4-Amino-2-(4-methoxyphenyl)-3-(1-naphthyl)furo[2,3-d]pyrimidine

Example 37 was prepared according to procedures similar to those shown in Example 2.

1H NMR (400 MHz, CDCl3) ppm 3.73 (s, 3H), 4.48 (brs, 2H), 6.71 (m, 2H), 7.36 (m, 2H), 7.47 (m, 1H), 7.56–7.62 (m, 3H), 7.77 (m, 1H), 8.00–8.04 (m, 2H), 8.39 (s, 1H); HPLC: RT 3.21 min, LC/MS: m/z 368 (M+1)$^+$.

Example 38

4-Amino-2-(4-methoxyphenyl)-3-(2-naphthyl)furo[2,3-d]pyrimidine

Example 38 was prepared according to procedures similar to those shown in Example 2.

HPLC: RT 3.36 min, LC/MS: m/z 368 (M+1)$^+$.

Example 39

4-Amino-2-(4-methoxyphenyl)-3-(4-(trifluoromethyloxy)phenyl)-furo[2,3-d]pyrimidine Example 39 was prepared according to procedures similar to those shown in Example 2.
1HNMR (400 MHz, CDCl3) ppm 3.81 (s, 3H), 4.87 (brs, 2H), 6.84 (d, J=8.8 Hz, 2H), 7.38 (d, J=7.8 Hz, 2H), 7.44 (d, J=8.8 Hz, 2H), 7.54 (d, J=8.6 Hz, 2H), 8.38 (s, 1H); HPLC: RT 3.32 min, LC/MS: m/z 402 (M+1)$^+$.

Example 40

4-Amino-3-(2,5-dimethoxyphenyl)-2-(4-methoxyphenyl)furo[2,3-d]pyrimidine

Example 40 was prepared according to procedures similar to those shown in Example 2.
HPLC: RT 2.97 min, LC/MS: m/z 378 (M+1)$^+$.

Example 41

4-Amino-2-(4-methoxyphenyl)-3-(4-(methylsulfonyl)phenyl)-furo[2,3-d]pyrimidine

Example 41 was prepared according to procedures similar to those shown in Example 2.
1H NMR (400 Hz, CDCl3) ppm 3.19 (s, 3H), 3.82 (s, 3H), 4.85 (s, 2H), 6.85 (d, J=8.8 Hz, 2H), 7.42 (d, J=8.8 Hz, 2H), 7.73 (d, J=8.3 Hz, 2H), 8.10 (d, J=8.3 Hz, 2H), 8.41 (s, 1H); HPLC: RT 2.77 min, LC/MS: m/z 396 (M+1)$^+$.

Example 42

4-Amino-2-(4-methoxyphenyl)-3-(4-(phenyloxy)phenyl)furo[2,3-d]pyrimidine

Example 42 was prepared according to procedures similar to those shown in Example 2.
1H NMR (400 MHz, CDCl3) ppm 3.82 (s, 3H), 4.91 (brs, 2H), 6.85 (m, 2H), 7.13 (m, 4H), 7.20 (m, 1H), 7.43 (m, 4H), 7.51 (m, 2H), 8.39 (brs, 1H); HPLC: RT 3.50 min, LC/MS: m/z 410 (M+1)$^+$.

Example 43

4-Amino-2-(4-methoxyphenyl)-3-(3-pyridyl)furo[2,3-d]pyrimidine

Example 43 was prepared according to procedures similar to those shown in Example 2.
1H NMR (400 MHz, CDCl3) ppm 3.81 (s, 3H), 4.81 (brs, 2H), 6.84 (m, 2H), 7.42–7.50 (m, 3H), 7.84 (m, 1H), 8.40 (s, 1H), 8.76 (m, 1H), 8.79 (m, 1H); HPLC: RT 2.72 min, LC/MS: m/z 319 (M+1)$^+$.

Example 44

4-Amino-3-(4-cyanophenyl)-2-(4-methoxyphenyl)furo[2,3-d]pyrimidine

Example 44 was prepared according to procedures similar to those shown in Example 2.
1HNMR (400 MHz, CDCl3) ppm 3.82 (s, 3H), 4.85 (brs, 2H), 6.85 (d, J=9.0 Hz, 2H), 7.40 (d, J=9.0 Hz, 2H), 7.64 (d, J=8.4 Hz, 2H), 7.83 (d, J=8.4 Hz, 2H), 8.40 (s, 1H); HPLC: RT 3.11 min, LC/MS: m/z 343 (M+1)$^+$.

Example 45

4-Amino-2-(4-methoxyphenyl)-3-(4-tert-butylphenyl)furo[2,3-d]pyrimidine

Example 45 was prepared according to procedures similar to those shown in Example 2.
HPLC: RT 3.75 min, LC/MS: m/z 374 (M+1)$^+$.

Example 46

4-Amino-2-(4-methoxyphenyl)-3-((3-fluoro-4-phenyl)phenyl)-furo[2,3-d]pyrimidine

Example 46 was prepared according to procedures similar to those shown in Example 2.
1H NMR (400 Hz, CDCl3) ppm 3.82 (s, 3H), 4.96 (s, 2H), 6.87 (d, J=8.8 Hz, 2H), 7.30–7.66 (m, 10H), 8.40 (s, 1H); HPLC: RT 3.63 min, LC/MS: m/z 412 (M+1)$^+$.

Example 47

4-Amino-3-((4-benzyloxy-3-fluoro)phenyl)-2-(4-methoxyphenyl)-furo[2,3-d]pyrimidine Example 47 was prepared according to procedures similar to those shown in Example 2.
1H NMR (400 MHz, CDCl3) ppm 3.82 (s, 3H), 4.86 (brs, 2H), 5.23 (s, 2H), 6.83 (m, 2H), 7.13–7.24(m, 3H), 7.37–7.52 (m, 7H), 8.37 (s, 1H); HPLC: RT 3.57 min, LC/MS: m/z 442 (M+1)$^+$.

Example 48

4-Amino-3-((4-ethylthio)phenyl)-2-(4-methoxyphenyl)furo[2,3-d]pyrimidine

Example 48 was prepared according to procedures similar to those shown in Example 2.
1H NMR (400 MHz, CDCl3) ppm 1.41 (t, 3H, J=7.3 Hz), 3.05 (q, 2H, J=7.3 Hz), 3.81 (s, 3H), 4.89 (brs, 2H), 6.83 (m, 2H), 7.41 (m, 4H), 7.49 (m, 2H), 7. (m, 2H), 8.37 (s, 1H); HPLC: RT 3.50 min, LC/MS: m/z 378 (M+1)$^+$.

Example 49

4-Amino-3-(3-chloro-4-fluorophenyl)-2-(4-methoxyphenyl)-furo[2,3-d]pyrimidine

Example 49 was prepared according to procedures similar to those shown in Example 1.
1HNMR (400 MHz, CDCl3) ppm 3.91 (s, 3H), 4.94 (brs, 2H), 7.04 (dd, J=8.7 Hz, 1H), 7.08 (d, J=8.8 Hz, 2H), 7.37 (ddd, J=2.3 Hz, 4.6 Hz, 8.7 Hz, 1H), 7.39 (dd, J=8.6 Hz, 2H), 7.66 (dd, J=2.3 Hz, 7.1 Hz), 8.39 (s, 1H); HPLC: RT 3.50 min, LC/MS: m/z 370 (M+1)$^+$, 372 (M+3)$^+$.

Example 50

4-Amino-2-(3,4-dichlorophenyl)-3-(4-methoxyphenyl)furo[2,3-d]pyrimidine

Example 50 was prepared according to procedures similar to those shown in Example 1.
HPLC: RT 3.71 min, LC/MS: m/z 386 (M)$^+$, 388(M+1)$^+$.

Example 51

4-Amino-2-(4-methoxyphenyl)-3-(2-phenylethyn-1-yl)furo[2,3-d]pyrimidine

Example 51 was prepared according to procedures similar to those shown in Example 2.
1HNMR (400 MHz, CDCl3) ppm 3.88 (s, 3H), 5.66 (brs, 2H), 7.02 (d, J=9.1 Hz, 2H), 7.42–7.45 (m, 3H), 7.57–7.60 (m, 2H), 8.21 (d, J=9.1 Hz, 2H), 8.37 (s, 1H); HPLC: RT 3.61 min, LC/MS: m/z 342 (M+1)$^+$.

Example 52

4-Amino-3-(4-methoxyphenyl)-2-(2-methylphenyl)furo[2,3-d]pyrimidine

Example 52 was prepared according to procedures similar to those shown in Example 1.
HPLC: RT 3.23 min, LC/MS: m/z 332 (M+1)$^+$.

Example 53

4-Amino-2-(2-chlorophenyl)-3-(4-methoxyphenyl)furo[2,3-d]pyrimidine

Example 53 was prepared according to procedures similar to those shown in Example 1.
1HNMR (400 MHz, CDCl3) ppm 3.82 (s, 3H), 5.14 (brs, 2H), 6.93 (d, J=8.8 Hz, 2H), 7.21–7.28 (m, 3H), 7.33 (ddd, J=1.6 Hz, 7.7 Hz, 1H), 7.37 (dd, J=1.6 Hz, 7.7 Hz, 1H), 7.42 (dd, J=1.1 Hz, 8.0 Hz), 8.43 (s, 1H); HPLC: RT 3.22 min, LC/MS: m/z 352 (M+1)$^+$, 354 (M+1)$^+$.

Example 54

4-Amino-2-(2-fluorophenyl)-3-(4-methoxyphenyl)furo[2,3-d]pyrimidine

Example 54 was prepared according to procedures similar to those shown in Example 1.
HPLC: RT 3.17 min, LC/MS: m/z 336 (M+1)$^+$.

Example 55

4-Amino-2-(3-acetamidophenyl)-3-(4-methoxyphenyl)furo[2,3-d]pyrimidine

Example 55 was prepared according to procedures similar to those shown in Example 1.
1HNMR (400 MHz, CDCl3) ppm 2.17 (s, 3H), 3.91 (s, 3H), 4.93 (brs, 2H), 7.07 (d, J=8.8 Hz, 2H), 7.17–7.23 (m, 2H), 7.41 (d, J=8.6 Hz, 2H), 7.54 (s, 1H), 7.70 (d, J=7.1 Hz, 1H), 8.38 (s, 1H); HPLC: RT 2.77 min, LC/MS: m/z 375 (M+1)$^+$.

Example 56

4-Amino-3-(4-methoxyphenyl)-2-(3-pyridyl)furo[2,3-d]pyrimidine

Example 56 was prepared according to procedures similar to those shown in Example 1.
1HNMR (400 MHz, CDCl3) ppm 3.90 (s, 3H), 4.99 (brs, 2H), 7.07 (d, J=8.8 Hz, 2H), 7.26 (dd, J=4.8 Hz, 8.3 Hz, 1H), 7.41 (d, J=8.6 Hz, 2H), 7.89 (ddd, J=1.8 Hz, 8.1 Hz, 2H), 8.40 (s, 1H), 8.49 (dd, J=1.8 Hz, 4.8 Hz, 1H), 8.75 (d, J=1.5 Hz, 1H); HPLC: RT 2.76 min, LC/MS: m/z 319 (M+1)$^+$.

Example 57

4-Amino-3-(2-butylethyn-1-yl)-2-(4-methoxyphenyl)furo[2,3-d]pyrimidine

Example 57 was prepared according to procedures similar to those shown in Example 2.
1HNMR (400 MHz, CDCl3) ppm 1.00 (t, J=7.2 Hz, 3H), 1.49–1.73 (m, 4H), 2.58 (t, J=7.1 Hz, 2H), 3.88 (s, 3H), 5.63 (brs, 2H), 6.99 (d, J=9.1 Hz, 2H), 8.15 (d, J=9.1 Hz, 2H), 8.34 (s, 1H); HPLC: RT 3.62 min, LC/MS: m/z 322 (M+1)$^+$.

Example 58

4-Amino-3-(2-(3-methylbutyl)ethyn-1-yl)-2-(4-methoxyphenyl)-furo[2,3-d]pyrimidine Example 58 was prepared according to procedures similar to those shown in Example 2.
HPLC: RT 3.74 min, LC/MS: m/z 336 (M+1)$^+$.

Example 59

4-Amino-3-(2-(tert-butyl)ethyn-1-yl)-2-(4-methoxyphenyl)furo[2,3-d]pyrimidine

Example 59 was prepared according to procedures similar to those shown in Example 2.
HPLC: RT 3.59 min, LC/MS: m/z 322 (M+1)$^+$.

Example 60

4-Amino-3-(4-(hydroxymethyl)phenyl)-2-(4-methoxyphenyl)-furo[2,3-d]pyrimidine

Example 60 was prepared according to procedures similar to those shown in Example 2.
1H NMR (400 Hz, CDCl3) ppm 1.84 (t, J=5.8 Hz, 1H), 3.80 (s, 3H), 4.83 (d, J=5.8 Hz, 2H), 4.85 (s, 2H), 6.82 (d, J=9.1 Hz, 2H), 7.46–7.55 (m, 6H), 8.37 (s, 1H); HPLC: RT 2.80 min, LC/MS: m/z 348 (M+1)$^+$.

Example 61

4-Amino-3-(4-biphenyl)-2-(2-methoxyphenyl)furo[2,3-d]pyrimidine

Example 61 was prepared according to procedures similar to those shown in Example 2.
1H NMR (400 MHz, CDCl3) ppm 3.40 (s, 3H), 5.15 (brs, 2H), 6.84 (m, 1H), 7.00 (m, 1H), 7.34–7.49 (m, 6H), 7.55 (m, 1H), 7.62–7.66 (m, 4H), 8.42 (s, 1H); HPLC: RT 3.56 min, LC/MS: m/z 394 (M+1)$^+$.

Example 62

4-Amino-2-(2-methoxyphenyl)-3-((4-methylthio)phenyl)furo[2,3-d]pyrimidine

Example 62 was prepared according to procedures similar to those shown in Example 2.
HPLC: RT 3.29 min, LC/MS: m/z 364 (M+1)$^+$.

Example 63

4-Amino-3-(4-methoxyphenyl)-2-(2-phenylethyn-1-yl)furo[2,3-d]pyrimidine

Example 63 was prepared according to procedures similar to those shown in Example 1.

1HNMR (400 MHz, CDCl3) ppm 3.90 (s, 3H), 5.25 (brs, 2H), 7.09 (d, J=8.8 Hz, 2H), 7.35–7.36 (m, 3H), 7.46–7.49 (m, 2H), 7.59 (d, J=8.6 Hz, 2H), 8.43 (s, 1H); HPLC: RT 3.43 min, LC/MS: m/z 342 (M+1)$^+$.

Example 64

4-Amino-2-(2-butylethyn-1-yl)-3-(4-methoxyphenyl)furo[2,3-d]pyrimidine

Example 64 was prepared according to procedures similar to those shown in Example 1.

HPLC: RT 3.46 min, LC/MS: m/z 322 (M+1)$^+$.

Example 65

4-Amino-2-(2-biphenyl)-3-(4-methoxyphenyl)furo[2,3-d]pyrimidine

Example 65 was prepared according to procedures similar to those shown in Example 1.

HPLC: RT 3.44 min, LC/MS: m/z 394 (M+1)$^+$.

Example 66

4-Amino-2-(3-biphenyl)-3-(4-methoxyphenyl)furo[2,3-d]pyrimidine

Example 66 was prepared according to procedures similar to those shown in Example 1.

HPLC: RT 3.70 min, LC/MS: m/z 394 (M+1)$^+$.

Example 67

4-Amino-2-(4-(2-carboxyethyl)phenyl)-3-(4-methoxyphenyl)furo[2,3-d]pyrimidine

Example 67 was prepared according to procedures similar to those shown in Example 1.

1HNMR (400 MHz, CDCl3-MeOH-d4) ppm 2.61 (t, J=7.8 Hz, 2H), 2.92 (t, J=7.8 Hz, 2H), 3.91 (s, 3H), 7.06 (d, J=8.6 Hz, 2H), 7.14 (d, J=8.1 Hz, 2H), 7.40 (d, J=8.1 Hz, 2H), 7.47 (d, J=8.3 Hz, 2H), 8.31 (s, 1H); HPLC: RT 2.36 min, LC/MS: m/z 390 (M+1)$^+$, 388 (M−1)$^−$.

Example 68

4-Amino-3-(4-methoxyphenyl)-2-(4-(methylsulfonyl)phenyl)-furo[2,3-d]pyrimidine

Example 68 was prepared according to procedures similar to those shown in Example 1.

1HNMR (400 MHz, CDCl3) ppm 3.05 (s, 3H), 3.92 (s, 3H), 5.01 (brs, 2H), 7.10 (d, J=8.8 Hz, 2H), 7.41 (d, J=8.6 Hz, 2H), 7.74 (d, J=8.6 Hz, 2H), 7.85 (d, J=8.8 Hz, 2H), 8.42 (s, 1H); HPLC: RT 2.84 min, LC/MS: m/z 396 (M+1)$^+$.

Example 69

4-Amino-2-(4-carboxyphenyl)-3-(4-methoxyphenyl)furo[2,3-d]pyrimidine

Example 69 was prepared according to procedures similar to those shown in Example 1.

HPLC: RT 2.26 min, LC/MS: m/z 362 (M+1)$^+$, 360 (M−1)$^−$.

Example 70

4-Amino-3-(4-methoxyphenyl)-2-(1-(4-chlorophenyl)-1-hydroxy)methyl)furo[2,3-d]pyrimidine Example 70 was prepared according to procedures similar to those shown in Example 1.

HPLC: RT 3.01 min, LC/MS: m/z 382 (M+1)$^+$, 384 (M+3)$^+$.

Example 71

4-Amino-3-(4-isopropylphenyl)-2-(2-methoxyphenyl)furo[2,3-d]pyrimidine

Example 71 was prepared according to procedures similar to those shown in Example 2.

HPLC: RT 3.56 min, LC/MS: m/z 360 (M+1)$^+$.

Example 72

4-Amino-3-(4-(cyclopentyloxy)phenyl)-2-(2-methoxyphenyl)furo[2,3-d]pyrimidine

Example 72 was prepared according to procedures similar to those shown in Example 2.

1H NMR (400 Hz, CDCl3) ppm 1.62–1.94 (m, 8H), 3.45 (s, 3H), 4.77 (m, 1H), 5.10 (s, 2H), 6.85 (d, J=8.3 Hz, 1H), 6.89 (d, J=8.6 Hz, 2H), 6.97 (dt, J=0.9 Hz, 7.5 Hz, 1H), 7.24 (d, J=8.8 Hz, 2H), 7.34 (ddd, J=1.5, 7.3, 8.5 Hz, 1H), 7.48 (dd, J=1.8, 7.6 Hz, 1H), 8.38 (s, 1H); HPLC: RT 3.64 min, LC/MS: m/z 402 (M+1)$^+$.

Example 73

4-Amino-3-(4-(isopropyloxy)phenyl)-2-(2-methoxyphenyl)furo[2,3-d]pyrimidine

Example 73 was prepared according to procedures similar to those shown in Example 2.

HPLC: RT 3.39 min, LC/MS: m/z 376 (M+1)$^+$.

Example 74

4-Benzyloxycarbonylamino-3-(4-methoxyphenyl)furo[2,3-d]-pyrimidine

Example 74 was prepared according to procedures similar to those shown in Example 1.

1H NMR (400 MHz, CDCl3) ppm 3.86 (s, 3H), 5.08 (s, 2H), 7.02 (m, 2H), 7.30–7.42 (m, 7H), 7.62 (s, 1H), 8.81 (s, 1H); HPLC: RT 3.20 min, LC/MS: m/z 376 (M+1)$^+$.

Example 75

4-Amino-3-(4-methoxyphenyl)-2-(2-phenylethen-1-yl)furo[2,3-d]pyrimidine

Example 75 was prepared according to procedures similar to those shown in Example 1.

1HNMR (400 MHz, CDCl3) ppm 3.91 (s, 3H), 5.07 (brs, 2H), 6.87 (d, J=16.2 Hz, 1H), 7.01 (d, J=8.6 Hz, 2H), 7.29–7.46 (m, 6H), 7.43 (d, J=8.8 Hz, 2H), 8.38 (s, 1H); HPLC: RT 3.52 min, LC/MS: m/z 344 (M+1)$^+$.

Example 76

4-Amino-3-(4-methoxyphenyl)-2-(2-phenylethyl)furo[2,3-d]pyrimidine

Example 76 was prepared according to procedures similar to those shown in Example 1.

1HNMR (400 MHz, CDCl3) ppm 2.96–3.08 (m, 4H), 3.85 (s, 3H), 4.88 (brs, 2H), 6.92 (d, J=8.8 Hz, 2H), 6.97 (d, J=8.6 Hz, 2H), 7.06–7.08 (m, 2H), 7.19–7.24 (m, 3H), 8.35 (s, 1H); HPLC: RT 3.34 min, LC/MS: m/z 346 (M+1)$^+$.

Example 77

4-Amino-3-(4-methoxyphenyl)-2-(4-(morpholinocarbonyl)phenyl)-furo[2,3-d]pyrimidine Example 77 was prepared according to procedures similar to those shown in Example 1.

HPLC: RT 2.74 min, LC/MS: m/z 431 (M+1)$^+$.

Example 78

4-Amino-3-(4-methoxyphenyl)-2-(4-(N-methylcarbamoyl)phenyl)-furo[2,3-d]pyrimidine Example 78 was prepared according to procedures similar to those shown in Example 1.

1HNMR (400 MHz, CDCl3) ppm 3.01 (d, 3H), 3.91 (s, 3H), 4.95 (brs, 2H), 6.07 (brs, 1H), 7.07 (d, J=8.6 Hz, 2H), 7.41 (d, J=8.8 Hz, 2H), 7.62 (d, J=8.8 Hz, 2H), 7.68 (d, J=8.6 Hz, 2H), 8.40 (s, 1H); HPLC: RT 2.66 min, LC/MS: m/z 375 (M+1)$^+$.

Example 79

4-Amino-3-(4-methoxyphenyl)-2-(4-(N-(2-(4-imidazolyl)ethyl) carbamoyl)phenyl)furo[2,3-d]pyrimidine Example 79 was prepared according to procedures similar to those shown in Example 1.

HPLC: RT 2.55 min, LC/MS: m/z 455 (M+1)$^+$.

Example 80

2,3-Bis(4-methoxyphenyl)-4,5-dihydro-4-imino-5-methylfuro[2,3-d]pyrimidine

Example 80 was prepared according to procedures similar to those shown in Scheme 1.

HPLC: RT 2.89 min, LC/MS: m/z.

Example 81

3,4-Bis(4-methoxyphenyl)-4-(methylamino)furo[2,3-d]pyrimidine

Example 81 was prepared according to procedures similar to those shown in Scheme 1.

HPLC: RT 3.43 min, LC/MS: m/z.

Example 82

4-Amino-3-(4-methoxyphenyl)-2-(4-(N-(2-dimethylaminoethyl)-carbamoyl)phenyl)furo[2,3-d]pyrimidine Example 82 was prepared according to procedures similar to those shown in Example 1.

HPLC: RT 2.45 min, LC/MS: m/Z 432 (M+1)$^+$.

Example 83

4-Amino-2-(1-hexen-1-yl)-3-(4-methoxyphenyl)furo[2,3-d]pyrimidine

Example 83 was prepared according to procedures similar to those shown in Example 1.

HPLC: RT 3.71 min, LC/MS: m/z 324 (M+1)$^+$.

Example 84

4-Amino-2-hexyl-3-(4-methoxyphenyl)furo[2,3-d]pyrimidine

Example 84 was prepared according to procedures similar to those shown in Example 1.

HPLC: RT 3.73 min, LC/MS: m/z 326 (M+1)$^+$.

Example 85

4-Amino-3-(2,4-dimethoxyphenyl)-2-(4-methoxyphenyl)furo[2,3-d]pyrimidine

Example 85 was prepared according to procedures similar to those shown in Example 2.

HPLC: RT 3.15 min, LC/MS: m/z 378 (M+1)$^+$.

Example 86

4-Amino-3-(4-methoxyphenyl)-2-(2-methoxypyridin-5-yl)furo[2,3-d]pyrimidine

Example 86 was prepared according to procedures similar to those shown in Example 1.

1H NMR (400 MHz, CDCl3) ppm 3.90 (s, 3H), 3.93 (s, 3H), 4.92 (brs, 2H), 6.70 (dd, 1H, J=0.8 Hz, 8.8 Hz), 7.06 (m, 2H), 7.40 (m, 2H), 7.76 (dd, 1H, J=2.5 Hz, 8.8 Hz), 8.35 (dd, 1H, J=0.8 Hz, 2.5 Hz), 8.38 (s, 1H); HPLC: RT 3.08 min, LC/MS: m/z 349 (M+1)$^+$.

Example 87

4-Amino-2-(4-(dimethylamino)phenyl)-3-(4-methoxyphenyl)furo[2,3-d]pyrimidine

Example 87 was prepared according to procedures similar to those shown in Example 1.

1H NMR (400 Hz, CDCl3) ppm 2.97 (s, 6H), 3.90 (s, 3H), 4.84 (s, 2H), 6.60 (d, J=9.1 Hz, 2H), 7.03 (d, J=8.8 Hz, 2H), 7.41 (d, J=8.8 Hz, 2H), 7.44 (d, J=9.1 Hz, 2H), 8.33 (s, 1H); HPLC: RT 3.34 min, LC/MS: m/z 361 (M+1)$^+$.

Example 88

4-Amino-2-(2,4-dimethoxyphenyl)-3-(4-methoxyphenyl)furo[2,3-d]pyrimidine

Example 88 was prepared according to procedures similar to those shown in Example 1.
HPLC: RT 3.09 min, LC/MS: m/z 378 (M+1)$^+$.

Example 89

4-Amino-2-(4-methoxyphenyl)-3-(2-methoxypyridin-5-yl)furo[2,3-d]pyrimidine

Example 89 was prepared according to procedures similar to those shown in Example 2.
1H NMR (400 MHz, CDCl3) ppm 3.81 (s, 3H), 4.03 (s, 3H), 4.87 (brs, 2H), 6.85 (m, 2H), 6.91 (dd, 1H, J=0.8 Hz, 8.6 Hz), 7.48 (m, 2H), 7.68 (dd, 1H, J=2.5 Hz, 8.6 Hz), 8.31 (dd, 1H, J=0.8 Hz, 2.5 Hz), 8.38 (s, 1H); HPLC: RT 3.02 min, LC/MS: m/z 349 (M+1)$^+$.

Example 90

4-Amino-2-((3-chlorophenyl)oxymethyl)-3-(4-methoxyphenyl)-furo[2,3-d]pyrimidine

Example 90 was prepared according to procedures similar to those shown in Example 1.
1HNMR (400 MHz, CDCl3) ppm 6.84 (d, J=8.6 Hz, 2H), 6.89 (s, 1H), 6.96 (d, J=8.6 2H), 7.05 (d, J=8.6 Hz, 2H), 7.19 (dd, J=8.1 Hz, 1H), 7.40 (d, J=8.6 Hz, 2H), 8.42 (s, 1H); HPLC: RT 3.37 min, LC/MS: m/z 382 (M+1)$^+$, 384 (M+3)$^+$.

Example 91

4-Amino-2-((4-fluorophenyl)oxymethyl)-3-(4-methoxyphenyl)-furo2,3-d]pyrimidine

Example 91 was prepared according to procedures similar to those shown in Example 1.
HPLC: RT 3.19 min, LC/MS: m/z 366 (M+1)$^+$.

Example 92

4-Amino-3-(4-methoxyphenyl)-2-((1-hydroxy-1-phenyl)methyl)-furo[2,3-d]pyrimidine Example 92 was prepared according to procedures similar to those shown in Example 1.
HPLC: RT 2.84 min, LC/MS: m/z 348 (M+1)$^+$.

Example 93

4-Amino-2-(3-carbamoylphenyl)-3-(4-methoxyphenyl)furo[2,3-d]pyrimidine

Example 93 was prepared according to procedures similar to those shown in Example 1.
1HNMR (400 MHz, CDCl3) ppm 3.91 (s, 3H), 4.97 (brs, 2H), 5.51 (brs, 1H), 5.88 (brs, 1H), 7.09 (d, J=8.6 Hz, 2H), 7.36 (t, J=7.7 Hz, 1H), 7.43 (d, J=8.8 Hz, 2H), 7.63 (d, J=8.1 Hz, 1H), 7.80 (d, J=7.8 Hz, 1H), 8.02 (s, 1H), 8.40 (s, 1H); HPLC: RT 2.58 min, LC/MS: m/z 361 (M+1)$^+$.

Example 94

4-Amino-2-(3-(N-dimethylcarbamoyl)phenyl)-3-(4-methoxyphenyl) furo[2,3-d]pyrimidine Example 94 was prepared according to procedures similar to those shown in Example 1.
HPLC: RT 2.68 min, LC/MS: m/z 389 (M+1)$^+$.

Example 95

4-Amino-2-(1-methylindol-5-yl)-3-(4-methoxyphenyl)furo[2,3-d]pyrimidine

Example 95 was prepared according to procedures similar to those shown in Example 1.
HPLC: RT 3.11 min, LC/MS: m/z 371 (M+1)$^+$.

Example 96

4-Amino-2-((2-hydroxymethyl)phenyl)-3-(4-methoxyphenyl)furo[2,3-d]pyrimidine

Example 96 was prepared according to procedures similar to those shown in Example 1.
HPLC: RT 2.72 min, LC/MS: m/z 348 (M+1)$^+$.

Example 97

4-Amino-2-(3-aminophenyl)-3-(4-methoxyphenyl) furo[2,3-d]pyrimidine

Example 97 was prepared according to procedures similar to those shown in Example 1.
1HNMR (400 MHz, CDCl3) ppm 3.65 (brs, 2H), 3.90 (s, 3H), 4.89 (brs, 2H), 6.60 (dd, J=7.8, 1.7 Hz, 1H), 6.89 (d, J=7.8, 1H), 6.97 (m, 1H), 7.04 (m, 1H), 7.05 (d, J=8.8 Hz, 2H), 7.41 (d, J=8.6 Hz, 2H), 8.37 (s, 1H); HPLC: RT 2.78 min, LC/MS: m/z 333 (M+1)$^+$.

Example 98

4-Amino-2-carboxy-3-(4-methoxyphenyl)furo[2,3-d]pyrimidine

Example 98 was prepared according to procedures similar to those shown in Example 1.
HPLC: RT 2.09 min, LC/MS: m/z 286 (M+1)$^+$.

Example 99

4-Amino-2-(2-carboxyphenyl)-3-(4-methoxyphenyl) furo[2,3-d]pyrimidine

Example 99 was prepared according to procedures similar to those shown in Example 1.
HPLC: RT 2.36 min, LC/MS: m/z 362 (M+1)$^+$.

Example 100

4-Amino-2-(3-methoxycarbonylphenyl)-3-(4-methoxyphenyl)-furo[2,3-d]pyrimidine

Example 100 was prepared according to procedures similar to those shown in Example 1.
HPLC: RT 3.07 min, LC/MS: m/z 376 (M+1)$^+$.

Example 101

4-Amino-2-(4-methoxyphenyl)-3-(1-methylindol-5-yl)furo[2,3-d]pyrimidine

Example 101 was prepared according to procedures similar to those shown in Example 2.
1H NMR (400 MHz, CDCl3) ppm 3.77 (s, 3H), 3.89 (s, 3H), 4.85 (brs, 2H), 6.54 (m, 1H), 6.77 (m, 2H), 7.18 (m, 1H), 7.29 (m, 1H), 7.46–7.53 (m, 3H), 7.74 (m, 1H), 8.36 (s, 1H); HPLC: RT 3.16 min, LC/MS: m/z 371 (M+1)$^+$.

Example 102

4-Amino-2-(3-carboxyphenyl)-3-(4-methoxyphenyl)furo[2,3-d]pyrimidine

Example 102 was prepared according to procedures similar to those shown in Example 1.
1HNMR (400 MHz, DMSO-d6) ppm 4.09 (s, 3H), 7.39 (d, J=7.6 Hz, 2H), 7.69–7.74 (m, 3H), 7.84 (d, J=7.8 Hz, 1H), 8.11 (d, J=7.8 Hz, 1H), 8.35 (s, 1H), 8.53 (s, 1H); HPLC: RT 2.33 min, LC/MS: m/z 362 (M+1)$^+$, 360 (M−1)$^-$.

Example 103

4-Amino-3-(4-methoxyphenyl)-2-(3-(N-(2-(4-imidazolyl)ethyl) carbamoyl)phenyl)furo[2,3-d]pyrimidine Example 103 was prepared according to procedures similar to those shown in Example 1.
HPLC: RT 2.51 min, LC/MS: m/z 455 (M+1)$^+$.

Example 104

4-Amino-3-(4-methoxyphenyl)-2-(3-((4-methylpiperazin-1-yl)-carbonyl)phenyl)furo[2,3-d]pyrimidine Example 104 was prepared according to procedures similar to those shown in Example 1.
HPLC: RT 2.58 min, LC/MS: m/z 444 (M+1)$^+$.

Example 105

4-Amino-3-(4-methoxyphenyl)-2-(3-(N-(2-dimethylaminoethyl)-carbamoyl)phenyl)furo[2,3-d]pyrimidine Example 105 was prepared according to procedures similar to those shown in Example 1.
1H NMR (400 MHz, CDCl3) ppm 2.29 (s, 6H), 2.53 (t, J=4.0 Hz, 2H), 3.49–3.54 (m, 2H), 3.90 (s, 3H), 4.98 (brs, 2H), 6.77 (brs, 1H), 7.07 (d, J=8.8 Hz, 2H), 7.33 (dd, J=7.8 Hz, 1H), 7.42 (d, J=8.6 Hz, 2H), 7.57 (m, 1H), 7.76 (m, 1H), 8.03 (brs, 1H), 8.40 (s, 1H) HPLC: RT 2.47 min, LC/MS: m/z 432 (M+1)$^+$.

Example 106

4-Amino-2-((2-cyanophenyl)oxymethyl)-3-(4-methoxyphenyl)-furo[2,3-d]pyrimidine

Example 106 was prepared according to procedures similar to those shown in Example 1.
HPLC: RT 2.93 min, LC/MS: m/z 374 (M+1)$^+$.

Example 107

4-Amino-2-((2-fluorophenyl)oxymethyl)-3-(4-methoxyphenyl)-furo[2,3-d]pyrimidine

Example 107 was prepared according to procedures similar to those shown in Example 1.
HPLC: RT 3.06 min, LC/MS: m/z 366 (M+1)$^+$.

Example 108

4-Amino-3-(4-methoxyphenyl)-2-(3-(N-(4-pyridyl)carbamoyl)-phenyl)furo[2,3-d]pyrimidine Example 108 was prepared according to procedures similar to those shown in Example 1.
HPLC: RT 2.75 min, LC/MS: m/z 438 (M+1)$^+$.

Example 109

4-Amino-2-(2-carbamoylphenyl)-3-(4-methoxyphenyl)furo[2,3-d]pyrimidine

Example 109 was prepared according to procedures similar to those shown in Example 1.
HPLC: RT 2.53 min, LC/MS: m/z 361 (M+1)$^+$.

Example 110

4-Amino-2-(4-carboxy-2-methoxyphenyl)-3-(4-methoxyphenyl)-furo[2,3-d]pyrimidine

Example 110 was prepared according to procedures similar to those shown in Example 1.
HPLC: RT 2.31 min, LC/MS: m/z 392 (M+1)$^+$, 390 (M−1)$^-$.

Example 111

4-Amino-3-(4-methoxyphenyl)-2-(3-(N-(3-pyridyl)carbamoyl)-phenyl)furo[2,3-d]pyrimidine Example 111 was prepared according to procedures similar to those shown in Example 1.
HPLC: RT 2.74 min, LC/MS: m/z 438 (M+1)$^+$.

Example 112

2-((3-Acetamidophenyl)oxymethyl)-4-amino-3-(4-methoxyphenyl)-furo[2,3-d]pyrimidine Example 112 was prepared according to procedures similar to those shown in Example 1.
HPLC: RT 2.75 min, LC/MS: m/z 405 (M+1)$^+$.

Example 113

4-Amino-2-((3-cyanophenyl)oxymethyl)-3-(4-methoxyphenyl)-furo[2,3-d]pyrimidine

Example 113 was prepared according to procedures similar to those shown in Example 1.
HPLC: RT 3.10 min, LC/MS: m/z 373 (M+1)$^+$.

Example 114

4-Amino-2-(3-methoxycarbonyl-4-(methylamino)phenyl)-3-(4-methoxyphenyl)furo[2,3-d]pyrimidine Example 114 was prepared according to procedures similar to those shown in Example 1.
1H NMR (400 MHz, CDCl3) ppm 2.90 (d, 3H, J=5.0 Hz), 3.48(d, 1H, J=5.0 Hz), 3.81 (s, 3H), 3.90 (s, 3H), 4.87 (brs, 2H), 6.54 (d, 1H, J=9.1 Hz), 7.06 (m, 2H), 7.42 (m, 2H), 7.84 (m, 1H), 8.29 (d, 1H, J=2.3 Hz), 8.35 (s, 1H); HPLC: RT 3.34 min, LC/MS: m/z 405 (M+1)$^+$.

Example 115

4-Amino-3-(4-methoxyphenyl)-2-(4-methylamino-3-carboxyphenyl)furo[2,3-d]pyrimidine hydrochloride Example 115 was prepared according to procedures similar to those shown in Example 1.
HPLC: RT 2.48 min, LC/MS: m/z 391 (M+1)$^+$, 389 (M−1)$^-$.

Example 116

4-Amino-2-(4-methoxyphenyl)-3-(4-(methylsulfonylamino)phenyl) furo[2,3-d]pyrimidine Example 116 was prepared according to procedures similar to those shown in Example 2.
1H NMR (400 Hz, CDCl3) ppm 3.17 (s, 3H), 3.81 (s, 3H), 4.90 (s, 2H), 6.62(s, 1H), 6.83 (d, J=9.1 Hz, 2H), 7.34 (d, J=8.6 Hz, 2H), 7.46 (d, J=9.1 Hz, 2H), 7.50 (d, J=8.6 Hz, 2H), 8.38 (s, 1H); HPLC: RT 2.85 min, LC/MS: m/z 411 (M+1)$^+$, 409 (M−1)$^-$.

Example 117

4-Amino-3-(4-methoxyphenyl)-2-(N-(3-methylindazol-5-yl)carbamoyl)furo[2,3-d]pyrimidine Example 117 was prepared according to procedures similar to those shown in Example 1.
1H NMR (400 MHz, DMSO-d6) ppm 2.60 (s, 3H), 4.00 (s, 3H), 7.24 (d, J=8.8 Hz, 2H), 7.52 (d, J=8.6 Hz, 1H), 7.66 (d, J=8.6 Hz, 2H), 7.76 (d, J=8.6 Hz, 1H), 8.20 (s, 1H), 8.55 (s, 1H); HPLC: RT 2.69 min, LC/MS: m/z 415 (M+1)$^+$.

Example 118

4-Amino-2-((1,2-bis(ethoxycarbonyl)hydradino)methyl)-3-(4-methoxyphenyl)furo[2,3-d]pyrimidine Example 118 was prepared according to procedures similar to those shown in Example 1.
HPLC: RT 2.77 min, LC/MS: m/z 430 (M+1)$^+$.

Example 119

4-Amino-3-(4-(diethylamino)phenyl)-2-(4-methoxyphenyl)furo[2,3-d]pyrimidine

Example 119 was prepared according to procedures similar to those shown in Example 2.
1H NMR (400 Hz, CDCl3) ppm 1.23 (t, J=7.3 Hz, 6H), 3.42 (q, J=7.3 Hz, 4H), 3.80 (s, 3H), 5.02 (s, 2H), 6.76 (d, J=8.6 Hz, 2H), 6.83 (d, J=8.8 Hz, 2H), 7.26 (d, J=8.6 Hz, 2H), 7.58 (d, J=8.8 Hz, 2H), 8.33 (s, 1H); HPLC: RT 3.70 min, LC/MS: m/z 389 (M+1)$^+$.

Example 120

4-Amino-3-(4-methoxyphenyl)-2-(N-phenylcarbamoyl)furo[2,3-d]pyrimidine

Example 120 was prepared according to procedures similar to those shown in Example 1.
HPLC: RT 2.98 min, LC/MS: m/z 361 (M+1)$^+$.

Example 121

4-Amino-2-(((5-amino-3-methyl)indazol-1-yl)carbonyl)-3-(4-methoxyphenyl)furo[2,3-d]pyrimidine Example 121 was prepared according to procedures similar to those shown in Example 1.
HPLC: RT 2.79 min, LC/MS: m/z 415 (M+1)$^+$.

Example 122

4-Amino-3-(4-methoxyphenyl)-2-(1-pyrrolizinocarbonyl)furo[2,3-d]pyrimidine

Example 122 was prepared according to procedures similar to those shown in Example 1.
HPLC: RT 2.55 min, LC/MS: m/z 339 (M+1)$^+$.

Example 123

4-Amino-3-(4-methoxyphenyl)-2-((N,N-dicyclohexyl)carbamoyl)furo-[2,3-d]pyrimidine Example 123 was prepared according to procedures similar to those shown in Example 1.
HPLC: RT 3.73 min, LC/MS: m/z 449 (M+1)$^+$.

Example 124

4-Amino-3-(4-methoxyphenyl)-2-(N-isopropylcarbamoyl)furo-[2,3-d]pyrimidine

Example 124 was prepared according to procedures similar to those shown in Example 1.
1H NMR (400 MHz, CDCl3) ppm 1.23 (d, J=6.6 Hz, 6H), 3.87 (s, 3H), 4.16–4.23 (m, 1H), 5.24 (brs, 2H), 6.45 (br, 1H), 7.04 (d, J=8.8 Hz, 2H), 7.50 (d, J=8.8 Hz, 2H), 8.44 (s, 1H); HPLC: RT 2.66 min, LC/MS: m/z 327 (M+1)$^+$.

Example 125

4-Amino-3-(4-methoxyphenyl)-2-(N-(2-dimethylaminoethyl)carbamoyl)furo[2,3-d]pyrimidine Example 125 was prepared according to procedures similar to those shown in Example 1.
HPLC: RT 2.24 min, LC/MS: m/z 356 (M+1)$^+$.

Example 126

4-Amino-2-(4-methoxyphenyl)-3-(4-(1-pyrrolidino)phenyl)furo[2,3-d]pyrimidine

Example 126 was prepared according to procedures similar to those shown in Example 2.
1H NMR (400 Hz, CDCl3) ppm 2.06–2.09 (m, 4H), 3.35–3.38 (m, 4H), 3.80 (s, 3H), 4.96 (s, 2H), 6.66 (d, J=8.6 Hz, 2H), 6.82 (d, J=8.8 Hz, 2H), 7.29 (d, J=8.6 Hz, 2H), 7.57 (d, J=8.8 Hz, 2H), 8.34 (s, 1H); HPLC: RT 3.69 min, LC/MS: m/z 387 (M+1)$^+$.

Example 127

4-Amino-2-(5-indolyl)-3-(4-methoxyphenyl)furo[2,3-d]pyrimidine

Example 127 was prepared according to procedures similar to those shown in Example 1.
1H NMR (400 MHz, DMSO-d6) ppm 3.85 (s, 3H), 6.42 (m, 1H), 7.11–7.17 (m, 3H), 7.32–7.38 (m, 2H), 7.43 (m, 2H), 7.74 (s, 1H), 8.23 (s, 1H), 11.26 (s, 1H); HPLC: RT 2.97 min, LC/MS: m/z 357 (M+1)$^+$.

Example 128

4-Amino-3-(4-methoxyphenyl)-2-((2-(phenylamino)ethyl)oxycarbonyl)furo[2,3-d]pyrimidine Example 128 was prepared according to procedures similar to those shown in Example 1.
HPLC: RT 3.12 min, LC/MS: m/z 405 (M+1)$^+$.

Example 129

4-Amino-2-((3-hydroxypiperizin-1-yl)carbonyl)-3-(4-methoxyphenyl)furo[2,3-d]pyrimidine Example 129 was prepared according to procedures similar to those shown in Example 1.
HPLC: RT 2.37 min, LC/MS: m/z 369 (M+1)$^+$.

Example 130

4-Amino-3-(4-methoxyphenyl)-2-((N-(2-cyanoethyl)-N-phenyl)carbamoyl)furo-[2,3-d]pyrimidine Example 130 was prepared according to procedures similar to those shown in Example 1.
HPLC: RT 2.78 min, LC/MS: m/z 414 (M+1)$^+$.

Example 131

4-Amino-3-(4-biphenyl)-2-(3-carbamoylphenyl)furo[2,3-d]pyrimidine

Example 131 was prepared according to procedures similar to those shown in Example 7.
1H NMR (400 MHz, CDCl3) ppm 5.03 (brs, 2H), 5.50 (br, 1H), 5.93 (br, 1H), 7.36–7.45 (m, 2H), 7.52 (m, 2H), 7.60 (m, 2H), 7.65–7.70 (m, 3H), 7.79–7.83 (m, 3H), 8.03 (m, 1H), 8.43 (s, 1H); HPLC: RT 2.92 min, LC/MS: m/z 407 (M+1)$^+$.

Example 132

2-(3-Acetamidophenyl)-4-amino-3-(4-biphenyl)furo[2,3-d]pyrimidine

Example 132 was prepared according to procedures similar to those shown in Example 7.
1H NMR (400 MHz, CDCl3) ppm 2.16 (s, 3H), 4.98 (brs, 2H), 7.08 (s, 1H), 7.23 (m, 2H), 7.42 (m, 1H), 7.51 (m, 2H), 7.58 (m, 3H), 7.70 (m, 3H), 7.79 (m, 2H), 8.41 (s, 1H); HPLC: RT 3.10 min, LC/MS: m/z 421 (M+1)$^+$.

Example 133

4-Amino-3-(4-methoxyphenyl)-2-((N-(methoxycarbonylmethyl)-N-phenyl)carbamoyl)furo-[2,3-d]pyrimidine Example 133 was prepared according to procedures similar to those shown in Example 1.
HPLC: RT 2.86 min, LC/MS: m/z 433 (M+1)$^+$.

Example 134

4-Amino-2-(3-carbamoyl-4-chlorophenyl)-3-(4-methoxyphenyl)-furo[2,3-d]pyrimidine Example 134 was prepared according to procedures similar to those shown in Example 1.
1H NMR (400 Hz, CDCl3) ppm 3.90 (s, 3H), 5.07 (s, 2H), 5.83 (s, 1H), 6.14 (s, 1H), 7.07 (d, J=8.6 Hz, 2H), 7.32 (d, J=8.6 Hz, 1H), 7.39 (d, J=8.6 Hz, 2H), 7.48 (dd, J=2.3, 8.6 Hz, 1H), 7.98 (d, J=2.3 Hz, 1H), 8.39 (s, 1H); HPLC: RT 2.69 min, LC/MS: m/z 395 (M+1)$^+$.

Example 135

4-Amino-2-(3-aminophenyl)-3-(4-biphenyl)furo[2,3-d]pyrimidine

Example 135 was prepared according to procedures similar to those shown in Example 7.
1H NMR (400 MHz, CDCl3) ppm 3.66 (brs, 2H), 4.95 (brs, 2H), 6.62 (m, 1H), 6.91 (m, 1H), 7.01 (m, 1H), 7.05 (t, 1H, J=8.1 Hz), 7.42 (m, 1H), 7.51 (m, 2H), 7.58 (m, 2H), 7.70 (m, 2H), 7.77 (m, 2H), 8.40 (s, 1H); HPLC: RT 3.22 min, LC/MS: m/z 379 (M+1)$^+$.

Example 136

4-Amino-2-(3-(aminomethyl)phenyl)-3-(4-biphenyl)furo[2,3-d]pyrimidine

Example 136 was prepared according to procedures similar to those shown in Example 7.
HPLC: RT 2.80 min, LC/MS: m/z 393 (M+1)$^+$.

Example 137

4-Amino-3-(4-biphenyl)-2-(4-(dimethylamino)phenyl)furo[2,3-d]pyrimidine

Example 137 was prepared according to procedures similar to those shown in Example 7.

1H NMR (400 MHz, CDCl3) ppm 2.97 (s, 6H), 4.90 (brs, 2H), 6.61 (m, 2H), 7.41 (m, 1H), 7.47–7.52 (m, 4H), 7.58 (m, 2H), 7.69 (m, 2H), 7.76 (m, 2H), 8.35 (s, 1H), HPLC: RT 3.86 min, LC/MS: m/z 407 (M+1)$^+$.

Example 138

4-Amino-2-((N-(2-(tert-butoxycarbonylamino)ethyl)-N-phenyl)carbamoyl)-3-(4-methoxyphenyl)furo-[2,3-d]pyrimidine Example 138 was prepared according to procedures similar to those shown in Example 1.

HPLC: RT 3.04 min, LC/MS: m/z 504 (M+1)$^+$.

Example 139

4-Amino-3-(4-methoxyphenyl)-2-((N-carboxymethyl-N-phenyl)carbamoyl)furo-[2,3-d]pyrimidine Example 139 was prepared according to procedures similar to those shown in Example 1.

HPLC: RT 2.26 min, LC/MS: m/z 419 (M+1)$^+$, 417 (M−1)$^-$.

Example 140

4-Amino-2-carbamoyl-3-(4-methoxyphenyl)furo-[2,3-d]pyrimidine

Example 140 was prepared according to procedures similar to those shown in Example 1.

1H NMR (400 MHz, CDCl3) ppm 3.88 (s, 3H), 5.22 (brs, 2H), 5.51 (brs, 1H), 6.48 (brs, 1H), 7.05 (d, J=8.6 Hz, 2H), 7.50 (d, J=8.6 Hz, 2H), 8.46 (s, 1H); HPLC: RT 2.27 min, LC/MS: m/z 285 (M+1)$^+$.

Example 141

4-Amino-3-(4-methoxyphenyl)-2-(3-((2-morpholinoethyl)-sulfonylamino)phenyl)furo[2,3-d]pyrimidine Example 141 was prepared according to procedures similar to those shown in Example 1.

1H NMR (400 MHz, CDCl3) ppm 2.46 (m, 4H), 2.86 (t, 2H, J=6.3 Hz), 3.19 (t, 2H, J=6.3 Hz), 3.66 (m, 4H), 3.90 (s, 3H), 4.93 (brs, 2H), 7.08 (m, 2H), 7.20–7.29 (m, 2H), 7.33 (m, 2H), 7.41 (m, 2H), 8.39 (s, 1H); HPLC: RT 2.76 min, LC/MS: m/z 510 (M+1)$^+$, 508 (M−1)$^-$.

Example 142

4-Amino-3-(4-methoxyphenyl)-2-((2-methyl)benzothiazol-5-yl) furo[2,3-d]pyrimidine Example 142 was prepared according to procedures similar to those shown in Example 1.

1H NMR (400 MHz, CDCl3) ppm 2.82 (s, 3H), 3.90 (s, 3H), 4.92 (brs, 2H), 7.06 (m, 2H), 7.44 (m, 2H), 7.65 (dd, 1H, J=1.5 Hz, 8.6 Hz), 7.76 (d, 1H, J=8.6 Hz), 8.10 (d, 1H, J=1.5 Hz), 8.40 (s, 1H); HPLC: RT 3.19 min, LC/MS: m/z 389 (M+1)$^+$.

Example 143

4-Amino-2-(6-indolyl)-3-(4-methoxyphenyl)furo[2,3-d]pyrimidine

Example 143 was prepared according to procedures similar to those shown in Example 1.

1H NMR (400 MHz, CDCl3) ppm 3.91 (s, 3H), 4.88 (brs, 2H), 6.52 (m, 1H), 7.06 (m, 2H), 7.44 (m, 2H), 7.51 (d, 1H, J=8.4 Hz), 7.71 (s, 1H), 8.19 (br, 1H), 8.37 (s, 1H); HPLC: RT 3.10 min, LC/MS: m/z 357 (M+1)$^+$.

Example 144

4-Amino-2-(3-carbamoyl-4-fluorophenyl)-3-(4-methoxyphenyl)furo-[2,3-d]pyrimidine Example 144 was prepared according to procedures similar to those shown in Example 1.

HPLC: RT 2.66 min, LC/MS: m/z 379 (M+1)$^+$.

Example 145

4-Amino-3-(4-biphenyl)-2-(3-carbamoyl-4-fluorophenyl)furo[2,3-d]pyrimidine

Example 145 was prepared according to procedures similar to those shown in Example 7.

1H NMR (400 MHz, CDCl3) ppm 5.01 (brs, 2H), 5.72 (br, 1H), 6.56 (br, 1H), 7.08 (dd, 1H, J=8.6 Hz, 11.4 Hz), 7.41 (m, 1H), 7.50 (m, 2H), 7.57 (m, 2H), 7.46–7.70 (m, 3H), 7.80 (m, 2H), 8.43 (m, 2H); HPLC: RT 2.98 min, LC/MS: m/z 425 (M+1)$^+$.

Example 146

4-Amino-2-((4-hydroxypiperizin-1-yl)carbonyl)-3-(4-methoxyphenyl)furo[2,3-d]pyrimidine Example 146 was prepared according to procedures similar to those shown in Example 1.

HPLC: RT 2.29 min, LC/MS: m/z 369 (M+1)$^+$.

Example 147

4-Amino-2-(4-amino-3-(N-methylcarbamoyl)phenyl)-3-(4-methoxyphenyl)furo[2,3-d]pyrimidine Example 147 was prepared according to procedures similar to those shown in Example 1.

HPLC: RT 2.66 min, LC/MS: m/z 390 (M+1)$^+$.

Example 148

4-Amino-2-((N-(carbamoylmethyl)-N-phenyl)carbamoyl)-3-(4-methoxyphenyl)furo-[2,3-d]pyrimidine Example 148 was prepared according to procedures similar to those shown in Example 1.

HPLC: RT 2.39 min, LC/MS: m/z 418 (M+1)$^+$.

Example 149

4-Amino-2-((N-(2-(aminocarbonylamino)ethyl)-N-phenyl)carbamoyl)-3-(4-methoxyphenyl)furo-[2,3-d]pyrimidine Example 149 was prepared according to procedures similar to those shown in Example 1.
HPLC: RT 2.42 min, LC/MS: m/z 447 (M+1)$^+$.

Example 150

4-Amino-2-(2-aminoxadiazol-5-yl)-3-(4-methoxyphenyl)furo[2,3-d]pyrimidine

Example 150 was prepared according to procedures similar to those shown in Example 1.
1H NMR (400 MHz, DMSO-d6) ppm 3.84 (s, 3H), 7.10 (d, J=8.8 Hz, 2H), 7.39 (s, 2H), 7.52 (d, J=8.6 Hz, 2H), 8.32 (s, 1H); HPLC: RT 2.33 min, LC/MS: m/z 325 (M+1)$^+$.

Example 151

4-Amino-2-(4-(ethoxycarbonyl)thiazol-2-yl)-3-(4-methoxyphenyl)-furo[2,3-d]pyrimidine Example 151 was prepared according to procedures similar to those shown in Example 1.
HPLC: RT 2.93 min, LC/MS: m/z 397 (M+1)$^+$.

Example 152

4-Amino-2-((4-(4-fluorophenyl)-5-methyl)thiazol-2-yl)-3-(4-methoxyphenyl)-furo[2,3-d]pyrimidine Example 152 was prepared according to procedures similar to those shown in Example 1.
HPLC: RT 3.55 min, LC/MS: m/z 433 (M+1)$^+$.

Example 153

4-Amino-2-(5-indolyl)-3-(4-(3-pyridyl)phenyl)furo[2,3-d]pyrimidine

Example 153 was prepared according to procedures similar to those shown in Example 5.
1H NMR (400 MHz, CDCl3) ppm 4.95 (brs, 2H), 6.52 (m, 1H), 7.22–7.49 (m, 5H), 7.67 (m, 2H), 7.77 (m, 2H), 7.94 (m, 1H), 7.98 (m, 1H), 8.26 (br, 1H), 8.39 (s, 1H), 8.66 (m, 1H), 8.97 (m, 1H); HPLC: RT 2.85 min, LC/MS: m/z 404 (M+1)$^+$.

Example 154

4-Amino-2-(2-imidazolin-2-yl)-3-(4-methoxyphenyl)furo[2,3-d]pyrimidine

Example 154 was prepared according to procedures similar to those shown in Example 1.
HPLC: RT 2.12 min, LC/MS: m/z 310 (M+1)$^+$.

Example 155

4-Amino-2-(2-(phenylamino)oxadiazol-5-yl)-3-(4-methoxyphenyl)furo[2,3-d]pyrimidine Example 155 was prepared according to procedures similar to those shown in Example 1.
HPLC: RT 2.86 min, LC/MS: m/z 401 (M+1)$^+$.

Example 156

4-Amino-2-(8H-indeno[1,2-d]thiazol-2-yl)-3-(4-methoxyphenyl)furo[2,3-d]pyrimidine Example 156 was prepared according to procedures similar to those shown in Example 1.
HPLC: RT 3.34 min, LC/MS: m/z 413 (M+1)$^+$.

Example 157

4-Amino-3-(4-methoxyphenyl)-2-(4-methylthiazol-2-yl)furo[2,3-d]pyrimidine

Example 157 was prepared according to procedures similar to those shown in Example 1.
1H NMR (400 MHz, CDCl3) ppm 2.46 (s, 3H), 3.91 (s, 3H), 5.05 (brs, 2H), 6.84 (s, 1H), 7.08 (d, J=8.8 Hz, 2H), 7.50 (d, J=8.6 Hz, 2H), 8.43 (s, 1H); HPLC: RT 2.81 min, LC/MS: m/z 339 (M+1)$^+$.

Example 158

4-Amino-2-((3-(2-(dimethylamino)ethyl)aminocarbonylamino)phenyl)-3-(4-methoxyphenyl)furo-[2,3-d]pyrimidine Example 158 was prepared according to procedures similar to those shown in Example 1.
1H NMR (400 MHz, CDCl3) ppm 2.29 (s, 6H), 2.50 (m, 2H), 3.30 (m, 2H), 3.90 (s, 3H), 4.94 (brs, 2H), 5.21 (br, 1H), 7.05 (m, 2H), 7.10 (m, 1H), 7.18 (t, 1H, J=8.0 Hz), 7.35 (m, 1H), 7.40 (m, 2H), 7.56 (m, 1H), 8.37 (s, 1H); HPLC: RT 2.49 min, LC/MS: m/z 447 (M+1)$^+$, 445 (M−1)$^−$.

Example 159

4-Amino-3-(4-biphenyl)-2-((3-(2-(dimethylamino)ethyl)-aminocarbonylamino)phenyl)furo-[2,3-d]pyrimidine Example 159 was prepared according to procedures similar to those shown in Example 7.
HPLC: RT 2.77 min, LC/MS: m/z 493 (M+1)$^+$, 491 (M−1)$^−$.

Example 160

4-Amino-3-(4-biphenyl)-2-(3-(methylsulfonylamino)phenyl)furo[2,3-d]pyrimidine

Example 160 was prepared according to procedures similar to those shown in Example 7.
1H NMR (400 MHz, CDCl3) ppm 2.89 (s, 3H), 5.01 (brs, 2H), 6.30 (m, 1H), 7.15 (m, 1H), 7.31 (t, 1H, J=7.9 Hz), 7.37 (m, 1H), 7.43 (m, 2H), 7.51 (m, 2H), 7.58 (m, 2H), 7.68 (m, 2H), 7.80 (m, 2H), 8.42 (s, 1H); HPLC: RT 3.17 min, LC/MS: m/z 452 (M+1)$^+$.

Example 161

4-Amino-3-(4-methoxyphenyl)-2-(4-(N-methylcarbamoyl)thiazol-2-yl)furo[2,3-d]pyrimidine Example 161 was prepared according to procedures similar to those shown in Example 1.

HPLC: RT 2.61 min, LC/MS: m/z 382 (M+1)$^+$.

Example 162

4-Amino-3-(4-(3-fluorophenyl)phenyl)-2-(3-(methylsulfonylamino)phenyl)furo[2,3-d]pyrimidine Example 162 was prepared according to procedures similar to those shown in Example 5.

1H NMR (400 Hz, DMSO-d6) ppm 2.88 (s, 3H), 7.13–7.15 (m, 2H), 7.23–7.33 (m, 2H), 7.44 (t, J=1.8 Hz, 1H), 7.53–7.67 (m, 5H), 7.92 (d, J=8.3 Hz, 2H), 8.30 (s, 1H), 9.90 (s, 1H); HPLC: RT 3.15 min, LC/MS: m/z 475 (M+1)$^+$, 473 (M–1)$^-$.

Example 163

4-Amino-3-(4-methoxyphenyl)-2-(4-(N-phenylcarbamoyl)thiazol-2-yl)furo[2,3-d]pyrimidine Example 163 was prepared according to procedures similar to those shown in Example 1.

HPLC: RT 3.24 min, LC/MS: m/z 444 (M+1)$^+$.

Example 164

4-Amino-2-(1-benzyl-4,5-dihydro-1H-imidazol-2-yl)-3-(4-methoxyphenyl)furo[2,3-d]pyrimidine Example 164 was prepared according to procedures similar to those shown in Example 1.

HPLC: RT 2.67 min, LC/MS: m/z 400 (M+1)$^+$.

Example 165

4-Amino-3-(4-methoxyphenyl)-2-(3-sulfamoylphenyl)furo[2,3-d]pyrimidine

Example 165 was prepared according to procedures similar to those shown in Example 1.

1H NMR (400 MHz, DMSO-d6) ppm 3.85 (s, 3H), 7.14 (m, 2H), 7.41–7.52 (m, 4H), 7.74 (m, 1H), 8.12 (m, 1H), 8.30 (s, 1H); HPLC: RT 2.73 min, LC/MS: m/z 397 (M+1)$^+$.

Example 166

4-Amino-3-(4-biphenyl)-2-(3-sulfamoylphenyl)furo[2,3-d]pyrimidine

Example 166 was prepared according to procedures similar to those shown in Example 7.

1H NMR (400 MHz, CDCl3) ppm 4.71 (s, 2H), 5.04 (brs, 2H), 7.43 (m, 2H), 7.51 (m, 2H), 7.58 (m, 2H), 7.69 (m, 3H), 7.82 (m, 3H), 8.23 (m, 1H), 8.44 (s, 1H); HPLC: RT 3.05 min, LC/MS: m/z 443 (M+1)$^+$.

Example 167

4-Amino-3-(4-methoxyphenyl)-2-(2-oxadiazolyl)furo[2,3-d]pyrimidine

Example 167 was prepared according to procedures similar to those shown in Example 1.

1H NMR (400 MHz, CDCl3) ppm 3.90 (s, 3H), 5.26 (brs, 2H), 7.09 (d, J=8.8 Hz, 2H), 7.54 (d, J=8.8 Hz, 2H), 8.43 (s, 1H), 8.49 (s, 1H); HPLC: RT 2.51 min, LC/MS: m/z 310 (M+1)$^+$.

Example 168

4-Amino-3-(4-methoxyphenyl)-2-(5,6,7,7a-tetrahydro-1H-pyrrolo[1,2–C]imidazol-3-yl)furo[2,3-d]pyrimidine Example 168 was prepared according to procedures similar to those shown in Example 1.

HPLC: RT 2.44 min, LC/MS: m/z 350 (M+1)$^+$.

Example 169

4-Amino-2-(4-carboxythiazol-2-yl)-3-(4-methoxyphenyl)furo[2,3-d]pyrimidine

Example 169 was prepared according to procedures similar to those shown in Example 1.

HPLC: RT 2.22 min, LC/MS: m/z 369 (M+1)$^+$, 367 (M–1)$^-$.

Example 170

4-Amino-2-(3-(methylsulfonylamino)phenyl)furo[2,3-d]pyrimidine

Example 170 was prepared according to procedures similar to those shown in Example 2(B).

HPLC: RT 2.48 min, LC/MS: m/z 305 (M+1)$^+$, 303 (M–1)$^-$.

Example 171

4-Amino-3-(4-methoxyphenyl)-2-(N-(2-phenylethyl)carbamoyl)-furo[2,3-d]pyrimidine Example 171 was prepared according to procedures similar to those shown in Example 1.

HPLC: RT 2.95 min, LC/MS: m/z 389 (M+1)$^+$.

Example 172

4-Amino-2-(N-(3-fluorophenyl)carbamoyl)-3-(4-methoxyphenyl)-furo[2,3-d]pyrimidine Example 172 was prepared according to procedures similar to those shown in Example 1.

HPLC: RT 3.04 min, LC/MS: m/z 379 (M+1)$^+$.

Example 173

4-Amino-2-(N-(4-chlorophenyl)carbamoyl)-3-(4-methoxyphenyl)-furo[2,3-d]pyrimidine Example 173 was prepared according to procedures similar to those shown in Example 1.

1H NMR (400 MHz, CDCl3) ppm 3.89 (s, 3H), 5.19 (brs, 2H), 7.07 (d, J=8.6 Hz, 2H), 7.30 (d, J=8.8 Hz, 2H), 7.53 (d, J=8.8 Hz, 2H), 7.59 (d, J=8.8 Hz, 2H), 8.37 (brs, 1H), 8.49 (s, 1H); HPLC: RT 3.19 min, LC/MS: m/z 395 (M+1)$^+$, 397 (M+3)$^+$.

Example 174

4-Amino-3-(4-methoxyphenyl)-2-(N-(4-methoxyphenyl)carbamoyl)-furo[2,3-d]pyrimidine Example 174 was prepared according to procedures similar to those shown in Example 1.

HPLC: RT 2.91 min, LC/MS: m/z 391 (M+1)$^+$.

Example 175

4-Amino-2-(N-(2-benzoimidazolyl)carbamoyl)-3-(4-methoxyphenyl)furo[2,3-d]pyrimidine Example 175 was prepared according to procedures similar to those shown in Example 1.

HPLC: RT 2.77 min, LC/MS: m/z 401 (M+1)$^+$.

Example 176

4-Amino-3-(4-(2,3-difluorophenyl)phenyl)-2-(4-fluoro-3-(methylsulfonylamino)phenyl)furo[2,3-d]pyrimidine Example 176 was prepared according to procedures similar to those shown in Example 5.

1H NMR (400 Hz, DMSO-d6) ppm 2.87 (s, 3H), 7.31–7.39 (m, 3H), 7.46–7.52 (m, 3H), 7.65 (d, J=8.3 Hz, 2H), 7.77 (d, J=8.3 Hz, 2H), 8.30 (s, 1H); HPLC: RT 3.14 min, LC/MS: m/z 511 (M+1)$^+$, 509 (M−1)$^-$.

Example 177

4-Amino-2-(N-(2-hydroxyphenyl)carbamoyl)-3-(4-methoxyphenyl)furo[2,3-d]pyrimidine Example 177 was prepared according to procedures similar to those shown in Example 1.

HPLC: RT 2.68 min, LC/MS: m/z 377 (M+1)$^+$, 375 (M−1)$^-$.

Example 178

4-Amino-2-(4-fluoro-3-(methylsulfonylamino)phenyl)-3-(4-methoxyphenyl)furo[2,3-d]pyrimidine Example 178 was prepared according to procedures similar to those shown in Example 1.

HPLC: RT 2.77 min, LC/MS: m/z 429 (M+1)$^+$.

Example 179

4-Amino-3-(4-biphenyl)-2-(4-fluoro-3-(methylsulfonylamino)phenyl)furo[2,3-d]pyrimidine Example 179 was prepared according to procedures similar to those shown in Example 7.

HPLC: RT 3.10 min, LC/MS: m/z 475 (M+1)$^+$.

Example 180

4-Amino-2-((6,7-dimethoxy-1,2,3,4-tetrahydroisoquinolin-2-yl)carbonyl)-3-(4-methoxyphenyl)furo[2,3-d]pyrimidine Example 180 was prepared according to procedures similar to those shown in Example 1.

HPLC: RT 2.69 min, LC/MS: m/z 461 (M+1)$^+$.

Example 181

4-Amino-2-(N-(2-carbamoylphenyl)carbamoyl)-3-(4-methoxyphenyl)furo[2,3-d]pyrimidine Example 181 was prepared according to procedures similar to those shown in Example 1.

HPLC: RT 2.81 min, LC/MS: m/z 404 (M+1)$^+$.

Example 182

4-Amino-2-(4-fluoro-3-(methylsulfonylamino)phenyl)-3-(4-(3-thienyl)phenyl)furo[2,3-d]pyrimidine Example 182 was prepared according to procedures similar to those shown in Example 5.

1H NMR (400 MHz, CDCl3) ppm 2.87 (s, 3H), 5.01 (brs, 2H), 6.59 (br, 1H), 7.09 (m, 1H), 7.42–7.73 (m, 7H), 7.78 (m, 2H), 8.40 (s, 1H); HPLC: RT 3.06 min, LC/MS: m/z 481 (M+1)$^+$.

Example 183

4-Amino-2-(3-(aminocarbonylamino)phenyl)-3-(4-methoxyphenyl)furo[2,3-d]pyrimidine Example 183 was prepared according to procedures similar to those shown in Example 1.

HPLC: RT 2.61 min, LC/MS: m/z 376 (M+1)$^+$, 374 (M−1)$^-$.

Example 184

4-Amino-2-(3-(aminocarbonylamino)phenyl)-3-(4-biphenyl)furo[2,3-d]pyrimidine

Example 184 was prepared according to procedures similar to those shown in Example 7.

1H NMR (400 MHz, DMSO-d6) ppm 5.88 (brs, 2H), 6.84 (m, 1H), 7.13 (t, 1H, J=8.0 Hz), 7.33 (m, 1H), 7.41 (m, 1H), 7.52 (m, 2H), 7.59 (m, 2H), 7.81 (m, 3H), 7.89 (m, 2H), 8.28 (s, 1H), 8.65 (s, 1H); HPLC: RT 2.90 min, LC/MS: m/z 422 (M+1)$^+$, 420 (M−1)$^-$.

Example 185

4-Amino-2-(N-(3-cyanophenyl)carbamoyl)-3-(4-methoxyphenyl)furo[2,3-d]pyrimidine

Example 185 was prepared according to procedures similar to those shown in Example 1.

HPLC: RT 2.95 min, LC/MS: m/z 386 (M+1)$^+$.

Example 186

4-Amino-3-(4-methoxyphenyl)-2-(N-(3-pyridyl)carbamoyl)furo[2,3-d]pyrimidine

Example 186 was prepared according to procedures similar to those shown in Example 1.
HPLC: RT 2.55 min, LC/MS: m/z 362 (M+1)$^+$.

Example 187

4-Amino-2-(N-(α-cyanobenzyl)carbamoyl)-3-(4-methoxyphenyl)furo[2,3-d]pyrimidine

Example 187 was prepared according to procedures similar to those shown in Example 1.
HPLC: RT 2.92 min, LC/MS: m/z 400 (M+1)$^+$.

Example 188

4-Amino-2-(N-(3,5-dimethoxyphenyl)carbamoyl)-3-(4-methoxyphenyl)furo[2,3-d]pyrimidine Example 188 was prepared according to procedures similar to those shown in Example 1.
HPLC: RT 3.02 min, LC/MS: m/z 421 (M+1)$^+$.

Example 189

4-Amino-3-(4-biphenyl)-2-(4-methoxy-3-(methylsulfonylamino)phenyl)furo[2,3-d]pyrimidine Example 189 was prepared according to procedures similar to those shown in Example 7.
HPLC: RT 3.17 min, LC/MS: m/z 487 (M+1)$^+$, 485 (M−1)$^-$.

Example 190

4-Amino-3-(4-biphenyl)-2-(3-((2-fluoro-5-(trifluoromethyl)phenyl)aminocarbonylamino)phenyl)furo[2,3-d]pyrimidine Example 190 was prepared according to procedures similar to those shown in Example 7.
1H NMR (400 MHz, CDCl3) ppm 5.00 (brs, 2H), 7.01 (br, 1H), 7.11–7.16 (m, 2H), 7.22–7.27 (m, 1H), 7.38–7.42 (m, 1H), 7.46–7.50 (m, 3H), 7.57 (m, 3H), 7.64 (m, 2H), 7.75 (d, J=8.1 Hz, 2H), 8.40 (s, 1H), 8.57–8.59 (m, 1H); HPLC: RT 3.96 min, LC/MS: m/z 584 (M+1)$^+$.

Example 191

4-Amino-3-(4-biphenyl)-2-(4-(methylsulfonylamino)phenyl)furo[2,3-d]pyrimidine

Example 191 was prepared according to procedures similar to those shown in Example 7.
HPLC: RT 3.14 min, LC/MS: m/z 457 (M+1)$^+$.

Example 192

4-Amino-3-(4-biphenyl)-2-(4-(aminocarbonylamino)phenyl)furo[2,3-d]pyrimidine

Example 192 was prepared according to procedures similar to those shown in Example 7.
HPLC: RT 2.86 min, LC/MS: m/z 422 (M+1)$^+$, 420 (M−1)$^-$.

Example 193

4-Amino-3-(4-biphenyl)-2-(3-((4-pyridylcarbonyl)amino)phenyl)-furo[2,3-d]pyrimidine Example 193 was prepared according to procedures similar to those shown in Example 7.
HPLC: RT 3.14 min, LC/MS: m/z 484 (M+1)$^+$.

Example 194

4-Amino-3-(4-methoxyphenyl)-2-(4-(methylsulfonylamino)-phenyl)furo[2,3-d]pyrimidine Example 194 was prepared according to procedures similar to those shown in Example 1.
1H NMR (400 MHz, CDCl3) ppm 3.03 (s, 3H), 3.91 (s, 3H), 4.91 (brs, 2H), 6.35 (s, 1H), 7.07 (m, 2H), 7.11 (m, 2H), 7.40 (m, 2H), 7.56 (m, 2H), 8.38 (s, 1H); HPLC: RT 2.76 min, LC/MS: m/z 411(M+1)$^+$.

Example 195

4-Amino-2-(4-(aminocarbonylamino)phenyl)-3-(4-methoxyphenyl)furo[2,3-d]pyrimidine Example 195 was prepared according to procedures similar to those shown in Example 1.
HPLC: RT 2.54 min, LC/MS: m/z 376 (M+1)$^+$, 374 (M−1)$^-$.

Example 196

4-Amino-2-(5-benzotriazolyl)-3-(4-biphenyl)furo[2,3-d]pyrimidine

Example 196 was prepared according to procedures similar to those shown in Example 7.
1H NMR (400 MHz, DMSO-d6) ppm 7.36–7.44 (m, 2H), 7.51–7.59 (m, 3H), 7.62 (d, J=8.3 Hz, 2H), 7.70 (s, 1H), 7.82 (d, J=8.6 Hz, 2H), 7.91 (d, J=8.3 Hz, 2H), 8.25 (s, 1H), 8.31 (s, 1H);
HPLC: RT 2.92 min, LC/MS: m/z 405 (M+1)$^+$.

Example 197

4-Amino-3-(4-biphenyl)-2-(3-(p-toluenesulfonylamino)phenyl)-furo[2,3-d]pyrimidine Example 197 was prepared according to procedures similar to those shown in Example 7.
HPLC: RT 3.50 min, LC/MS: m/z 533 (M+1)$^+$.

Example 198

4-Amino-2-(5-benzimidazolyl)-3-(4-biphenyl)furo[2,3-d]pyrimidine

Example 198 was prepared according to procedures similar to those shown in Example 7.
HPLC: RT 2.84 min, LC/MS: m/z 404 (M+1)$^+$.

Example 199

4-Amino-3-(4-biphenyl)-2-(4-sulfamoylphenyl)furo[2,3-d]pyrimidine

Example 199 was prepared according to procedures similar to those shown in Example 7.

1H NMR (400 Hz, DMSO-d6) ppm 7.42 (t, J=7.3 Hz, 1H), 7.52 (t, J=7.6 Hz, 2H), 7.61–7.64 (m, 4H), 7.78–7.83 (m, 4H), 7.91 (d, J=8.3 Hz, 2H), 8.32 (s, 1H); HPLC: RT 3.00 min, LC/MS: m/z 443 (M+1)$^+$, 441 (M−1)$^−$.

Example 200

4-Amino-3-(4-biphenyl)-2-(3-(N-methylsulfonyl)phenyl)furo[2,3-d]pyrimidine

Example 200 was prepared according to procedures similar to those shown in Example 7.

1H NMR (400 Hz, CDCl3) ppm 2.58 (d, J=5.6 Hz, 3H), 4.22(q, J=5.6 Hz, 1H), 5.04 (s, 2H), 7.41–7.59 (m, 6H), 7.67–7.81 (m, 6H), 8.10 (t, J=1.8 Hz, 1H), 8.44 (s, 1H); HPLC: RT 3.16 min, LC/MS: m/z 457 (M+1)$^+$, 455 (M−1)$^−$.

Example 201

4-Amino-2-(4-fluoro-3-(methylsulfonylamino)phenyl)-3-(4-(2-pyridyl)phenyl)furo[2,3-d]pyrimidine Example 201 was prepared according to procedures similar to those shown in Example 5.

1H NMR (400 MHz, CDCl3) ppm 2.89 (s, 3H), 5.00 (brs, 2H), 6.52 (s, 1H), 7.10 (m, 1H), 7.32 (m, 1H), 7.43 (m, 1H), 7.62 (m, 2H), 7.67 (m, 1H), 7.83 (m, 2H), 8.18 (m, 2H), 8.40 (s, 1H), 8.74 (m, 1H); HPLC: RT 2.78 min, LC/MS: m/z 476 (M+1)$^+$.

Example 202

4-Amino-3-(4-biphenyl)-2-(4-((dimethylamino)sulfonylamino)-phenyl)furo[2,3-d]pyrimidine Example 202 was prepared according to procedures similar to those shown in Example 7.
HPLC: RT 3.26 min, LC/MS: m/z 486 (M+1)$^+$.

Example 203

4-Amino-3-(4-biphenyl)-2-(4-((1-iminoethyl)amino)phenyl)furo[2,3-d]pyrimidine

Example 203 was prepared according to procedures similar to those shown in Example 7.
HPLC: RT 2.68 min, LC/MS: m/z 420 (M+1)$^+$;

Example 204

4-Amino-3-(4-(4-tert-butylphenyl)phenyl)-2-(3-sulfamoylphenyl)-furo[2,3-d]pyrimidine Example 204 was prepared according to procedures similar to those shown in Example 5.
HPLC: RT 3.50 min, LC/MS: m/z 499 (M+1)$^+$.

Example 205

4-Amino-3-(4-biphenyl)-2-(3-((dimethylamino)sulfonylamino)-phenyl)furo[2,3-d]pyrimidine Example 205 was prepared according to procedures similar to those shown in Example 7.

1H NMR (400 Hz, CDCl3) ppm 2.76 (s, 6H), 4.99 (s, 2H), 6.30 (s, 1H), 7.12–7.16 (m, 1H), 7.24–7.28 (m, 1H), 7.34–7.37 (m, 2H), 7.42 (t, J=7.3 Hz, 1H), 7.51 (t, J=7.8 Hz, 2H), 7.58 (d, J=8.3 Hz, 2H), 7.68–7.70 (m, 2H), 7.79 (d, J=8.3 Hz, 2H), 8.41 (s, 1H); HPLC: RT 3.27 min, LC/MS: m/z 486 (M+1)$^+$, 484 (M−1)$^−$.

Example 206

4-Amino-3-(4-(2-pyridyl)phenyl)-2-(3-sulfamoylphenyl)furo[2,3-d]pyrimidine

Example 206 was prepared according to procedures similar to those shown in Example 5.
HPLC: RT 2.71 min, LC/MS: m/z 444 (M+1)$^+$.

Example 207

4-Amino-3-(4-(3-pyridyl)phenyl)-2-(3-sulfamoylphenyl)furo[2,3-d]pyrimidine

Example 207 was prepared according to procedures similar to those shown in Example 5.

1H NMR (400 MHz, DMSO-d6) ppm 7.46–7.56 (m, 5H), 7.66 (d, J=8.3 Hz, 2H), 7.76 (ddd, J=1.6 Hz, 7.5 Hz, 1H), 7.80 (d, J=8.3 Hz, 2H), 8.11 (m, 1H), 8.21 (ddd, J=2.0 Hz, 8.3 Hz, 1H), 8.32 (s, 1H), 8.63 (dd, J=4.8 Hz, 1.5 Hz), 9.03 (m, 1H); HPLC: RT 2.61 min, LC/MS: m/z 444 (M+1)$^+$.

Example 208

4-Amino-3-(4-biphenyl)-2-(4-cyanophenyl)furo[2,3-d]pyrimidine

Example 208 was prepared according to procedures similar to those shown in Example 7.

1H NMR (400 Hz, CDCl3) ppm 5.04 (s, 2H), 7.42–7.59 (m, 7H), 7.68–7.71 (m, 4H), 7.82 (d, J=8.3 Hz, 2H), 8.44 (s, 1H); HPLC: RT 3.52 min, LC/MS: m/z 389 (M+1)$^+$.

Example 209

4-Amino-3-(4-biphenyl)-2-(4-(tetrazol-5-yl)phenyl)furo[2,3-d]pyrimidine hydrochloride Example 209 was prepared according to procedures similar to those shown in Example 7.

1H NMR (400 Hz, DMSO-d6) ppm 7.43 (t, J=7.3 Hz, 1H), 7.53 (t, J=7.3 Hz, 2H), 7.64 (d, J=8.4 Hz, 2H), 7.68 (d, J=8.6 Hz, 2H), 7.83 (d, J=8.6 Hz, 2H), 7.93 (d, J=8.4 Hz, 2H), 8.02 (d, J=8.6 Hz, 2H), 8.33 (s, 1H); HPLC: RT 2.60 min, LC/MS: m/z 432 (M+1)$^+$, 430 (M−1)$^−$.

Example 210

4-Amino-3-(4-biphenyl)-2-(3-(tetrazol-5-yl)phenyl)furo[2,3-d]pyrimidine

Example 210 was prepared according to procedures similar to those shown in Example 7.

1H NMR (400 Hz, DMSO-d6) ppm 7.33 (d, J=8.3 Hz, 1H), 7.39–7.44 (m, 2H), 7.52 (t, J=7.3 Hz, 2H), 7.64 (d, J=8.3 Hz, 2H), 7.81 (d, J=7.3 Hz, 2H), 7.90 (d, J=8.3 Hz, 2H), 7.96 (d, J=7.8 Hz, 1H), 8.33 (s, 1H), 8.38 (s, 1H); HPLC: RT 2.67 min, LC/MS: m/z 432 (M+1)$^+$, 430 (M–1)$^-$.

Example 211

4-Amino-3-(4-(1-naphthyl)phenyl)-2-(3-sulfamoylphenyl)furo[2,3-d]pyrimidine

Example 211 was prepared according to procedures similar to those shown in Example 5.
HPLC: RT 3.26 min, LC/MS: m/z 493 (M+1)$^+$.

Example 212

4-Amino-3-(4-(4-(ethylsulfonyl)phenyl)phenyl)-2-(3-sulfamoylphenyl)furo[2,3-d]pyrimidine Example 212 was prepared according to procedures similar to those shown in Example 5.
HPLC: RT 2.79 min, LC/MS: m/z 432 (M+1)$^+$.

Example 213

4-Amino-2,3-bis(4-methoxyphenyl)-6-(ethoxycarbonyl)furo[2,3-d]pyrimidine

Example 213 was prepared according to procedures similar to those shown in Scheme 1.
1H NMR (400 MHz, CDCl3) ppm 1.32 (t, J=7.2 Hz, 3H), 3.81 (s, 3H), 3.90 (s, 3H), 4.54 (q, J=7.2 Hz, 2H), 5.19 (brs, 2H), 6.83 (d, J=9.1 Hz, 2H), 7.06 (d, J=8.6 Hz, 2H), 7.41 (d, J=8.8 Hz, 2H), 7.51 (d, J=8.8 Hz, 2H); HPLC: RT 3.35 min, LC/MS: m/z 420 (M+1)$^+$.

Example 214

4-Amino-3-(4-(4,6-bis(trifluoromethyl)phenyl)phenyl)-2-(3-sulfamoylphenyl)furo[2,3-d]pyrimidine Example 214 was prepared according to procedures similar to those shown in Example 5.
HPLC: RT 3.43 min, LC/MS: m/z 579 (M+1)$^+$.

Example 215

4-Amino-3-(4-(2-fluorobiphen-4-yl)phenyl)-2-(3-sulfamoylphenyl)furo[2,3-d]pyrimidine Example 215 was prepared according to procedures similar to those shown in Example 6.
1H NMR (400 MHz, CDCl3) ppm 4.80 (brs, 2H), 5.06 (brs, 2H), 7.41–7.71 (m, 12H), 7.84 (m, 3H), 8.23 (m, 1H), 8.44 (s, 1H); HPLC: RT 3.41 min, LC/MS: m/z 537 (M+1)$^+$.

Example 216

4-Amino-2,3-bis(4-methoxyphenyl)-6-carbamoylfuro[2,3-d]pyrimidine

Example 216 was prepared according to procedures similar to those shown in Scheme 1.
1H NMR (400 MHz, DMSO-d6) ppm 3.76 (s, 3H), 3.85 (s, 3H), 6.69 (d, J=8.8 Hz, 2H), 7.13 (d, J=8.8 Hz, 2H), 7.40–7.44 (m, 4H), 7.62 (brs, 1H), 7.93 (brs, 1H); HPLC RT 2.98 min, LC/MS: m/z 391 (M+1)$^+$.

Example 217

4-Amino-3-(4-((4-chlorophenyl)aminocarbonylamino)phenyl)-2-(4-methoxyphenyl)furo[2,3-d]pyrimidine Example 217 was prepared according to procedures similar to those shown in Example 4.
1H NMR (400 MHz, DMSO-d6) ppm 3.75 (s, 3H), 6.94 (d, J=9.1 Hz, 2H), 7.35 (d, J=8.8 Hz, 2H), 7.40–7.42 (m, 4H), 7.52 (d, J=8.8 Hz, 2H), 7.65 (d, J=8.6 Hz, 2H), 8.24 (s, 1H), 8.97 (brs, 1H), 9.02 (brs, 1H); HPLC: RT 3.41 min, LC/MS: m/z 486 (M+1)$^+$, 488 (M+3)$^+$.

Example 218

4-Amino-3-(4-methoxyphenyl)-2-(4-(tetrazol-5-yl)phenyl)furo[2,3-d]pyrimidine hydrochloride Example 218 was prepared according to procedures similar to those shown in Example 1.
1H NMR (400 Hz, DMSO-d6) ppm 3.87 (s, 3H), 7.16 (d, J=8.8 Hz, 2H), 7.47 (d, J=8.6 Hz, 2H), 7.64 (d, J=8.8 Hz, 2H), 8.00 (d, J=8.6 Hz, 2H), 8.30 (s, 1H); HPLC: RT min, LC/MS: m/z 386 (M+1)$^+$, 384 (M–1)$^-$.

Example 219

4-Amino-3-(4-methoxyphenyl)-2-(3-(tetrazol-5-yl)phenyl)furo[2,3-d]pyrimidine hydrochloride Example 219 was prepared according to procedures similar to those shown in Example 1.
1H NMR (400 Hz, DMSO-d6) ppm 3.86 (s, 3H), 7.15 (d, J=8.8 Hz, 2H), 7.44–7.56 (m, 4H), 7.97 (d, J=7.8 Hz, 1H), 8.31 (s, 1H), 8.37 (s, 1H); HPLC: RT 2.39 min, LC/MS: m/z 386 (M+1)$^+$, 384 (M–1)$^-$.

Example 220

4-Amino-3-(4-((3-fluorobenzoyl)amino)phenyl)-2-(4-methoxyphenyl)furo[2,3-d]pyrimidine Example 220 was prepared according to procedures similar to those shown in Example 3.
1H NMR (400 MHz, DMSO-d6) ppm 3.76 (s, 3H), 6.95 (d, J=8.8 Hz, 2H), 7.41 (d, J=8.8 Hz, 2H), 7.46–7.51 (m, 3H), 7.60–7.65 (m, 1H), 7.78–7.85 (m, 2H), 8.00 (d, J=8.6 Hz, 2H), 8.25 (s, 1H); HPLC: RT 3.28 min, LC/MS: m/z 455 (M+1)$^+$, 453 (M–1)$^-$.

Example 221

4-Amino-3-(4-((2-fluorobenzoyl)amino)phenyl)-2-(4-methoxyphenyl)furo[2,3-d]pyrimidine Example 221 was prepared according to procedures similar to those shown in Example 3.
HPLC: RT 3.27 min, LC/MS: m/z 455 (M+1)$^+$, 453 (M–1)$^-$.

Example 222

4-Amino-2,3-bis(4-methoxyphenyl)-6-methylfuro[2,3-d]pyrimidine

Example 222 was prepared according to procedures similar to those shown in Scheme 1.

1H NMR (400 MHz, CDCl3) ppm 2.42–2.33 (br, 3H), 3.80 (s, 3H), 3.84 (s, 3H), 6.87 (d, J=9.0 Hz, 2H), 6.93 (d, J=8.8 Hz, 2H), 7.32–7.38 (m, 4H); HPLC: RT 3.30 min, LC/MS: m/z 362 $(M+1)^+$, 360 $(M-1)^-$. Example 223

4-Amino-3-(4-((2-fluoro-5-(trifluoromethyl)phenyl)-aminocarbonylamino)phenyl)-6-(methylamino)furo[2,3-d]pyrimidine Example 223 was prepared according to procedures similar to those shown in Scheme 4.

1H NMR (400 MHz, CDCl3) ppm 2.78 (d, J=4.8 Hz, 3H), 6.59 (m, 1H), 7.38–7.43 (m, 3H), 7.48 (s, 1H), 7.48–7.53 (m, 1H), 7.60 (d, J=8.6 Hz, 2H), 8.62 (dd, J=2.0 Hz, 7.3 Hz, 1H), 9.04 (brs, 1H), 9.42 (brs, 1H); LC/MS: m/z 461 $(M+1)^+$, 459 $(M-1)^-$.

Example 224

4-Amino-3-(4-((2-naphthylsulfonyl)amino)phenyl)-2-(4-methoxyphenyl)furo[2,3-d]pyrimidine Example 224 was prepared according to procedures similar to those shown in Example 3.

HPLC: RT 3.37 min, LC/MS: m/z 523 $(M+1)^+$, 521 $(M-1)^-$.

Example 225

4-Amino-3-(4-(3-acetamidophenyl)phenyl)-2-(3-sulfamoylphenyl)-furo[2,3-d]pyrimidine Example 225 was prepared according to procedures similar to those shown in Example 5.
HPLC: RT 2.68 min.

Example 226

4-Amino-3-(4-(aminocarbonylamino)phenyl)-2-(4-methoxyphenyl)-furo[2,3-d]pyrimidine Example 226 was prepared according to procedures similar to those shown in Example 4.

1H NMR (400 Hz, DMSO-d6) ppm 3.75 (s, 3H), 5.97 (s, 2H), 6.94 (d, J=9.1 Hz, 2H), 7.33 (d, J=8.6 Hz, 2H), 7.40 (d, J=8.8 Hz, 2H), 7.59 (d, J=8.6 Hz, 2H), 8.23 (s, 1H), 8.79 (s, 1H); HPLC: RT 2.65 min, LC/MS: m/z 376 $(M+1)^+$, 374 $(M-1)^-$.

Example 227

4-Amino-2-(4-methoxyphenyl)-3-(4-(phenyl(aminocarbonylamino))-phenyl)furo[2,3-d]pyrimidine Example 227 was prepared according to procedures similar to those shown in Example 4.

1H NMR (400 Hz, DMSO-d6) ppm 3.75 (s, 3H), 6.94–7.01 (m, 3H), 7.30 (t, J=7.6 Hz, 2H), 7.39–7.42 (m, 4H), 7.48 (d, J=7.6 Hz, 2H), 7.65 (d, J=8.6 Hz, 2H), 8.24 (s, 1H), 8.79 (s, 1H), 8.79 (s, 1H); HPLC: RT 3.21 min, LC/MS: m/z 452 $(M+1)^+$, 450 $(M-1)^-$.

Example 228

4-Amino-3-(4-(cyclohexyl(aminocarbonylamino))phenyl)-2-(4-methoxyphenyl)furo[2,3-d]pyrimidine Example 228 was prepared according to procedures similar to those shown in Example 4.
HPLC: RT 3.24 min.

Example 229

4-Amino-3-(4-(butyl(aminocarbonylamino))phenyl)-2-(4-methoxyphenyl)furo[2,3-d]pyrimidine Example 229 was prepared according to procedures similar to those shown in Example 4.
HPLC: RT 3.09 min.

Example 230

4-Amino-3-(4-(((2-fluoro-5-(trifluoromethyl)phenyl)-aminocarbonylamino)methyl)phenyl)-2-(4-methoxyphenyl)furo[2,3-d]pyrimidine Example 230 was prepared according to procedures similar to those shown in Example 4.

1H NMR (400 Hz, DMSO-d6) ppm 3.75 (s, 3H), 4.46 (s, 2H), 6.93 (d, J=9.1 Hz, 2H), 7.32–7.50 (m, 9H), 8.25 (s, 1H), 8.63–8.66 (m, 1H), 8.88 (s, 1H); HPLC: RT 3.48 min, LC/MS: m/z 552 $(M+1)^+$, 550 $(M-1)^-$.

Example 231

4-Amino-3-(3-((2-fluoro-5-(trifluoromethyl)phenyl)-aminocarbonylamino)phenyl)-2-(4-methoxyphenyl)furo[2,3-d]pyrimidine Example 231 was prepared according to procedures similar to those shown in Example 4.

1H NMR (400 Hz, DMSO-d6) ppm 3.75 (s, 3H), 6.95 (d, J=9.0 Hz, 2H), 7.13 (d, J=7.6 Hz, 1H), 7.40–7.58 (m, 6H), 7.65 (s, 1H), 8.25 (s, 1H), 8.56 (d, J=6.3 Hz, 1H), 9.00 (s, 1H), 9.44 (s, 1H); HPLC: RT 3.59 min, LC/MS: m/z 538 $(M+1)^+$, 536 $(M-1)^-$.

Example 232(a): (See Also Example 8(C) and Example 232(b))

4-Amino-3-(4-((2-fluoro-5-(trifluoromethyl)phenyl)-aminocarbonylamino)phenyl)furo[2,3-d]pyrimidine Example 232 was prepared according to procedures similar to those shown in Example 8.

1H NMR (400 MHz, DMSO-d6) ppm 7.39–7.42 (m, 1H), 7.47 (d, J=8.6 Hz, 2H), 7.49–7.54 (m, 1H), 7.63 (d, J=8.8 Hz, 2H), 7.95 (s, 1H), 8.26 (s, 1H), 8.63 (d, J=7.1 Hz, 1H), 8.99 (s, 1H), 9.39 (s, 1H); HPLC: RT 3.19 min, LC/MS: m/z 432 $(M+1)^+$, 430 $(M-1)^-$.

Example 233

4-Amino-3-(4-(aminomethyl)phenyl)-2-(4-methoxyphenyl)furo[2,3-d]pyrimidine

Example 233 was prepared according to procedures similar to those shown in Example 2.
HPLC: RT 2.47 min.

Example 234

4-Amino-3-(3-aminophenyl)-2-(4-methoxyphenyl)furo[2,3-d]pyrimidine

Example 234 was prepared according to procedures similar to those shown in Example 2.
HPLC: RT 2.88 min.

Example 235

4-Amino-3-(4-((2-fluoro-5-(trifluoromethyl)phenyl)-aminocarbonylamino)phenyl)-2-(3-sulfamoyl phenyl)furo[2,3-d]pyrimidine Example 235 was prepared according to procedures similar to those shown in Example 8.
HPLC: RT 3.11 min, LC/MS: m/z 587 (M+1)$^+$, 585 (M−1)$^−$.

Example 236

4-Amino-2-(4-cyanophenyl)-3-(4-((2-fluoro-5-(trifluoromethyl)-phenyl)aminocarbonylamino)phenyl)furo[2,3-d]pyrimidine Example 236 was prepared according to procedures similar to those shown in Example 8.
1H NMR (400 MHz, DMSO-d6) ppm 7.41–7.45 (m, 1H), 7.47 (d, J=8.6 Hz, 2H), 7.53 (dd, J=9.2 Hz, 10.5 Hz, 1H), 7.60 (d, J=8.8 Hz, 2H), 7.70 (d, J=8.6 Hz, 2H), 7.84 (d, J=8.6 Hz, 2H), 8.31 (s, 1H), 8.64 (dd, J=2.0 Hz, 7.3 Hz, 1H), 9.03 (brs, 1H), 9.48 (brs, 1H); HPLC: RT 3.52 min, LC/MS: m/z 533 (M+1)$^+$, 531 (M−1)$^−$.

Example 237

4-Amino-3-(4-(phenyl(aminothiocarbonylamino))phenyl)furo[2,3-d]pyrimidine

Example 237 was prepared according to procedures similar to those shown in Example 8.
HPLC: RT 2.78 min, LC/MS: m/z 362 (M+1)$^+$, 360 (M−1)$^−$.

Example 238

3-(4-nitrophenyl)-4-(phenylamino)furo[2,3-d]pyrimidine

Example 238 was prepared according to procedures similar to those shown in Scheme 4.
HPLC: RT 3.39 min, LC/MS: m/z 333 (M+1)$^+$, 331 (M−1)$^−$.

Example 239

4-(methyllamino)-3-(4-nitrophenyl)-furo[2,3-d]pyrimidine

Example 239 was prepared according to procedures similar to those shown in Scheme 4.
HPLC: RT 2.96 min, LC/MS: m/z 271 (M+1)$^+$.

Example 240

3-(4-Aminophenyl)-4-(methylamino)furo[2,3-d]pyrimidine

Example 240 was prepared according to procedures similar to those shown in Scheme 4.
HPLC: RT 2.60 min, LC/MS: m/z 241 (M+1)$^+$.

Example 241

3-(4-Aminophenyl)-4-(phenylamino)furo[2,3-d]pyrimidine

Example 241 was prepared according to procedures similar to those shown in Scheme 4.
HPLC: RT 3.21 min, LC/MS: m/z 303 (M+1)$^+$.

Example 242

3-(4-Aminophenyl)-4-(dimethylamino)furo[2,3-d]pyrimidine

Example 242 was prepared according to procedures similar to those shown in Scheme 4.
HPLC: RT 2.77 min, LC/MS: m/z (M+1)$^+$.

Example 243

4-(Dimethylamino)-3-(4-nitrophenyl)furo[2,3-d]pyrimidine

Example 243 was prepared according to procedures similar to those shown in Scheme 4.
HPLC: RT 3.14 min, LC/MS: m/z 285 (M+1)$^+$.

Example 244

3-(4-((2-Fluoro-5-(trifluoromethyl)phenyl)aminocarbonylamino)-phenyl)-4-(methylamino)furo[2,3-d]pyrimidine Example 244 was prepared according to procedures similar to those shown in Scheme 4.
1H NMR (400 MHz, DMSO-d6) ppm 2.94 (d, J=4.8 Hz, 3H), 5.99–6.01 (m, 1H), 7.39–7.45 (m, 3H), 7.52 (dd, J=8.8 Hz, 10.4 Hz, 1H), 7.63 (d, J=8.6 Hz, 2H), 7.92 (s, 1H), 8.34 (s, 1H), 8.64 (dd, J=2.3 Hz, 7.3 Hz, 1H), 8.98 (brs, 1H), 9.37 (brs, 1H); HPLC: RT 3.35 min, LC/MS: m/z 446 (M+1)$^+$.

Example 245

3-(4-((2-Fluoro-5-(trifluoromethyl)phenyl)aminocarbonylamino)-phenyl)-4-(phenylamino)furo[2,3-d]pyrimidine Example 245 was prepared according to procedures similar to those shown in Scheme 4.

1H NMR (400 MHz, DMSO-d6) ppm 7.07 (m, 1H), 7.33 (m, 2H), 7.40–7.43 (m, 1H), 7.52 (dd, J=9.4 Hz, 10.4 Hz, 1H), 7.56–7.60 (m, 4H), 7.66 (d, J=8.6 Hz, 2H), 7.91 (brs, 1H), 8.13 (s, 1H), 8.49 (s, 1H), 8.63 (dd, J=2.3 Hz, 7.3 Hz, 1H), 9.00 (brs, 1H), 9.40 (brs, 1H); HPLC: RT 3.72 min, LC/MS: m/z 508 (M+1)$^+$, 506 (M−1)$^-$.

Example 246

4-(Dimethylamino)-3-(4-((2-Fluoro-5-(trifluoromethyl)phenyl)-aminocarbonylamino)phenyl)furo[2,3-d]pyrimidine Example 246 was prepared according to procedures similar to those shown in Scheme 4.

1H NMR (400 MHz, DMSO-d6) ppm 2.82 (s, 6H), 7.39–7.43 (m, 3H), 7.52 (dd, J=9.1 Hz, 10.6 Hz, 1H), 7.59 (d, J=8.8 Hz, 2H), 7.99 (s, 1H), 8.36 (s, 1H), 8.63 (dd, J=2.3 Hz, 7.3 Hz, 1H), 8.99 (brs, 1H), 9.36 (brs, 1H); HPLC: RT 3.48 min, LC/MS: m/z 460 (M+1)$^+$, 458 (M−1)$^-$.

Example 247

4,5-Dihydro-3-(4-nitrophenyl)-4-oxofuro[2,3-d]pyrimidine

Example 247 was prepared according to procedures similar to those shown in Scheme 4.

HPLC: RT 2.77 min, LC/MS: m/z 256 (M−1)$^-$.

Example 248

3-(4-((2-Fluoro-5-(trifluoromethyl)phenyl)aminocarbonylamino)-phenyl)-6-(methylthio)furo[2,3-d]pyrimidine Example 248 was prepared according to procedures similar to those shown in Scheme 4.

1H NMR (400 MHz, DMSO-d6) ppm 2.61 (s, 3H), 7.39–7.42 (m, 1H), 7.52 (dd, J=9.4 Hz, 10.1 Hz, 1H), 7.61 (d, J=8.6 Hz, 2H), 7.79 (d, J=8.6 Hz, 2H), 8.48 (s, 1H), 8.62 (dd, J=2.3 Hz, 7.3 Hz, 1H), 8.97 (brs, 1H), 9.36 (s, 1H), 9.38 (brs, 1H); HPLC: RT 3.69 min, LC/MS: m/z 463 (M+1)$^+$, 461 (M−1)$^-$.

Example 249

4-Amino-3-(4-((3-ethylphenyl)aminocarbonylamino)phenyl)furo[2,3-d]pyrimidine

Example 249 was prepared according to procedures similar to those shown in Example 8(C).

HPLC: RT 3.08 min, LC/MS: m/z 374 (M+1)$^+$.

Example 250

4-Amino-3-(4-((4-(dimethylamino)phenyl)aminocarbonylamino)-phenyl)furo[2,3-d]pyrimidine Example 250 was prepared according to procedures similar to those shown in Example 8(C).

HPLC: RT 2.86 min, LC/MS: m/z 389 (M+1)$^+$, 387 (M−1)$^-$.

Example 251

3-(4-((2-Fluoro-5-(trifluoromethyl)phenyl)aminocarbonylamino)-phenyl)-6-(methylsulfonyl)furo[2,3-d]pyrimidine Example 251 was prepared according to procedures similar to those shown in Example 8(C).

1H NMR (400 MHz, DMSO-d6) ppm 3.48 (s, 3H), 7.41–7.44 (m, 1H), 7.52 (dd, J=9.5 Hz, 10.2 Hz, 1H), 7.66 (d, J=8.6 Hz, 2H), 7.87 (d, J=8.6 Hz, 2H), 8.63 (dd, J=2.2 Hz, 7.5 Hz, 1H), 8.91 (s, 1H), 8.99 (m, 1H), 9.43 (brs, 1H), 9.77 (s, 1H); HPLC: RT 3.32 min, LC/MS: m/z 495 (M+1)$^+$, 493 (M−1)$^-$.

Example 252

4-Amino-3-(4-((4-methoxyphenyl)aminocarbonylamino)phenyl)-furo[2,3-d]pyrimidine

Example 252 was prepared according to procedures similar to those shown in Example 8(C).

1H NMR (400 MHz, DMSO-d6) ppm 6.88 (d, J=9.1 Hz, 2H), 7.37 (d, J=9.1 Hz, 2H), 7.42 (d, J=8.6 Hz, 2H), 7.60 (d, J=8.8 Hz, 2H), 7.92 (s, 1H), 8.25 (s, 1H), 8.56 (brs, 1H), 8.81 (brs, 1H); HPLC: RT 2.82 min, LC/MS: m/z 376 (M+1)$^+$.

Example 253

4-Amino-3-(4-((2,2,4,4-tetrafluoro-1,3-benzodioxan-5-yl)-aminocarbonylamino)phenyl)furo[2,3-d]pyrimidine Example 253 was prepared according to procedures similar to those shown in Example 8(C).

HPLC: RT 3.28 min, LC/MS: m/z 476 (M+1)$^+$, 474 (M−1)$^-$.

Example 254

4-Amino-3-(4-((4-(phenyloxy)phenyl)aminocarbonylamino)phenyl)-furo[2,3-d]pyrimidine Example 254 was prepared according to procedures similar to those shown in Example 8(C).

HPLC: RT 3.20 min, LC/MS: m/z 438 (M+1)$^+$.

Example 255

4-Amino-3-(4-((5-Indanyl)aminocarbonylamino)phenyl)furo[2,3-d]pyrimidine

Example 255 was prepared according to procedures similar to those shown in Example 8(C).

1H NMR (400 MHz, DMSO-d6) ppm 1.97–2.04 (m, 2H), 2.78–2.85 (m, 4H), 7.11–7.17 (m, 2H), 7.40–7.43 (m, 3H), 7.60 (d, J=8.6 Hz, 2H), 7.92 (s, 1H), 8.25 (s, 1H), 8.61 (brs, 1H), 8.83 (brs, 1H); HPLC: RT 3.11 min, LC/MS: m/z 386 (M+1)$^+$.

Example 256

4-Amino-3-(4-((2,5-bis(trifluoromethyl)phenyl)aminocarbonylamino)-phenyl)furo[2,3-d]pyrimidine Example 256 was prepared according to procedures similar to those shown in Example 8(C).

HPLC: RT 3.38 min, LC/MS: m/z 482 (M+1)⁺, 480 (M−1)⁻.

Example 257

4-Amino-3-(4-((3-(phenyloxy)phenyl)aminocarbonylamino)phenyl)-furo[2,3-d]pyrimidine Example 257 was prepared according to procedures similar to those shown in Example 8(C).
HPLC RT 3.23 min, LC/MS: m/z 438 (M+1)⁺, 436 (M−1)⁻.

Example 258

4-Amino-3-(4-((2,5-dimethoxyphenyl)aminocarbonylamino)phenyl)-furo[2,3-d]pyrimidine Example 258 was prepared according to procedures similar to those shown in Example 8(C).
HPLC: RT 2.95 min, LC/MS: m/z 406 (M+1)⁺, 404 (M−1)⁻.

Example 259

4-Amino-3-(4-((5-(trifluoromethyl)phenyl)aminocarbonylamino)-phenyl)furo[2,3-d]pyrimidine Example 251 was prepared according to procedures similar to those shown in Example 8(C).
1H NMR (400 MHz, DMSO-d6) ppm 7.32 (d, J=7.6 Hz, 2H), 7.45 (d, J=8.4 Hz, 2H), 7.53 (dd, J=7.8 Hz, 1H), 7.59–7.64 (m, 3H), 7.94 (s, 1H), 8.04 (brs, 1H), 8.26 (s, 1H), 9.02 (brs, 1H), 9.13 (brs, 1H); HPLC: RT 3.13 min, LC/MS: m/z 414 (M+1)⁺, 412 (M−1)⁻.

Example 260

4-Amino-3-(4-((5-(trifluoromethylthio)phenyl)aminocarbonylamino)-phenyl)furo[2,3-d]pyrimidine Example 260 was prepared according to procedures similar to those shown in Example 8(C).
1H NMR (400 MHz, DMSO-d6) ppm 7.32 (d, J=7.8 Hz, 1H), 7.44–7.48 (m, 3H), 7.56–7.57 (m, 1H), 7.62 (d, J=8.6 Hz, 2H), 7.94 (s, 1H), 8.01 (brs, 1H), 8.25 (s, 1H), 8.98 (brs, 1H), 9.07 (brs, 1H); HPLC: RT 3.25 min, LC/MS: m/z 446 (M+1)⁺, 444 (M−1)⁻.

Example 261

4-Amino-3-(4-((3,4-(methylenedioxy)phenyl)aminocarbonylamino)-phenyl)furo[2,3-d]pyrimidine Example 261 was prepared according to procedures similar to those shown in Example 8(C).
HPLC: RT 2.81 min, LC/MS: m/z 390 (M+1)⁺.

Example 262

3-(4-((2-Fluoro-5-(trifluoromethyl)phenyl)aminocarbonylamino)-phenyl)-6-(methylamino)furo[2,3-d]pyrimidine Example 262 was prepared according to procedures similar to those shown in Scheme 4.

1H NMR (400 MHz, DMSO-d6) ppm 2.85–2.86 (br, 3H), 7.40–7.42 (m, 1H), 7.51 (dd, J=9.0 Hz, 10.5 Hz, 1H), 7.58 (d, J=8.8 Hz, 2H), 7.71 (d, J=8.8 Hz, 2H), 8.08 (s, 1H), 8.63 (dd, J=2.2 Hz, 7.2 Hz, 1H), 8.93 (brs, 1H), 8.98 (brs, 1H), 9.33 (brs, 1H); HPLC: RT 3.41 min, LC/MS: m/z 446 (M+1)⁺, 444 (M−1)⁻.

Example 263

6-((2-(Dimethylamino)ethyl)amino)-3-(4-((2-fluoro-5-(trifluoromethyl)phenyl)aminocarbonylamino)phenyl)furo[2,3-d]pyrimidine Example 263 was prepared according to procedures similar to those shown in Scheme 4.
HPLC: RT 3.16 min, LC/MS: m/z 503 (M+1)⁺.

Example 264

4-Amino-3-(4-((2-chlorophenyl)aminocarbonylamino)phenyl)furo[2,3-d]pyrimidine

Example 264 was prepared according to procedures similar to those shown in Example 8(C).
1H NMR (400 MHz, DMSO-d6) ppm 7.05 (m, 1H), 7.32 (m, 1H), 7.45–7.49 (m, 3H), 7.63 (d, J=8.6 Hz, 2H), 7.94 (s, 1H), 8.18 (dd, J=1.5 Hz, 8.3 Hz, 1H), 8.25 (s, 1H), 8.38 (brs, 1H), 9.59 (brs, 1H); HPLC: RT 3.03 min, LC/MS: m/z 380 (M+1)⁺, 382 (M+3)⁺, 378 (M−1)⁺, 380 (M+1)⁻.

Example 265

4-Amino-3-(4-((2-chloro-5-nitrophenyl)aminocarbonylamino)-phenyl)furo[2,3-d]pyrimidine Example 265 was prepared according to procedures similar to those shown in Example 8(C).
HPLC: RT 3.09 min, LC/MS: m/z 425 (M+1)⁺, 427 (M+3)⁺, 423 (M−1)⁻.

Example 266

4-Amino-3-(4-((3-chlorophenyl)aminocarbonylamino)phenyl)furo[2,3-d]pyrimidine

Example 266 was prepared according to procedures similar to those shown in Example 8(C).
HPLC: RT 3.05 min, LC/MS: m/z 380 (M+1)⁺, 382 (M+3)⁺, 378 (M−1)⁺, 380 (M+1)⁻.

Example 267

4-Amino-3-(4-((2-chloro-5-(trifluoromethyl)phenyl)-aminocarbonylamino)phenyl)furo[2,3-d]pyrimidine Example 267 was prepared according to procedures similar to those shown in Example 8(C).
1H NMR (400 MHz, DMSO-d6) ppm 7.40 (dd, J=1.8 Hz, 8.1 Hz, 1H), 7.48 (d, J=8.6 Hz, 2H), 7.64 (d, J=8.6 Hz, 2H), 7.74 (d, J=8.1 Hz, 1H), 7.95 (s, 1H), 8.26 (s, 1H), 8.66 (d, J=2.0 Hz, 2H), 8.68 (s, 1H), 9.75 (s, 1H); HPLC: RT 3.29 min. LC/MS: m/z 448 (M+1)⁺, 450 (M+3)⁺, 446 (M−1)⁺, 448 (M+1)⁻.

Example 268

4-Amino-3-(4-((2,5-dichlorophenyl)aminocarbonylamino)phenyl)-furo[2,3-d]pyrimidine Example 268 was prepared according to procedures similar to those shown in Example 8(C).

1H NMR (400 MHz, DMSO-d6) ppm 7.12 (dd, J=2.5 Hz, 8.6 Hz, 1H), 7.47 (d, J=8.6 Hz, 2H), 7.52 (d, J=8.6 Hz, 2H), 7.63 (d, J=8.6 Hz, 2H), 7.95 (s, 1H), 8.26 (s, 1H), 8.34 (d, J=2.5 Hz, 1H), 8.53 (s, 1H), 9.71(s, 1H); HPLC: RT 3.25 min, LC/MS: m/z 414 (M)$^+$, 416(M+2)$^+$, 412 (M−2)$^+$, 414 (M)$^-$.

Example 269

3-(4-((2-Fluoro-5-(trifluoromethyl)phenyl)aminocarbonylamino)-phenyl)-6-(((2,4,6-trimethoxyphenyl)methyl)amino)furo[2,3-d]pyrimidine Example 269 was prepared according to procedures similar to those shown in Scheme 4.

HPLC: RT 3.72 min, LC/MS: m/z 612 (M+1)$^+$.

Example 270

6-Amino-3-(4-((2-Fluoro-5-(trifluoromethyl)phenyl)-aminocarbonylamino)phenyl)furo[2,3-d]pyrimidine Example 270 was prepared according to procedures similar to those shown in Scheme 4.

1H NMR (400 MHz, DMSO-d6) ppm 6.88 (s, 2H), 7.39–7.43 (m, 1H), 7.51 (dd, J=9.0 Hz, 10.5 Hz, 1H), 7.58 (d, J=8.8 Hz, 2H), 7.71 (d, J=8.6 Hz, 2H), 8.08 (s, 1H), 8.63 (dd, J=2.3 Hz, 7.3 Hz, 1H), 8.94 (s, 1H), 8.96 (brs, 1H), 9.35 (brs, 1H); HPLC: RT 3.23 min, LC/MS: m/z 432 (M+1)$^+$.

Example 271

4-Amino-3-(4-aminophenyl)-6-(methylthio)furo[2,3-d]pyrimidine

Example 271 was prepared according to procedures similar to those shown in Scheme 4.

1H NMR (400 MHz, DMSO-d6) ppm 2.47 (s, 3H), 5.34 (s, 2H), 6.67 (d, J=8.6 Hz, 2H), 7.14 (d, J=8.4 Hz, 2H), 7.66 (s, 1H); HPLC: RT 2.91 min. LC/MS: m/z 273 (M+1)$^+$.

Example 272: (Example 8(D))

4-Amino-2-bromo-3-(4-((2-fluoro-5-(trifluoromethyl)phenyl)-aminocarbonylamino)phenyl)furo[2,3-d]pyrimidine Example 272 was prepared according to procedures similar to those shown in Example 8.

1H NMR (400 MHz, DMSO-d6) ppm 7.40–7.43 (m, 1H), 7.45 (d, J=8.6 Hz, 2H), 7.52 (dd, J=8.8 Hz, 10.9 Hz, 1H), 7.66 (d, J=8.6 Hz, 2H), 8.24 (s, 1H), 8.64 (d, J=7.1 Hz, 1H), 9.00 (s, 1H), 9.41 (s, 1H); LC/MS: m/z 510 (M)$^+$, 512 (M+2)$^+$.

Example 273

4-Amino-3-(4-((4-tert-butylthiazol-2-yl)aminocarbonylamino)-phenyl)-2-(4-methoxyphenyl)furo[2,3-d]pyrimidine Example 273 was prepared according to procedures similar to those shown in Example 8(C).

1H NMR (400 MHz, DMSO-d6) ppm 1.27 (s, 9H), 3.75 (s, 3H), 6.67 (s, 1H), 6.95 (m, 2H), 7.42 (m, 4H), 7.65 (m, 2H), 8.24 (s, 1H), 9.10 (br, 1H), 10.72 (br, 1H); LC/MS: m/z 515 (M+1)$^+$.

Example 274

4-Amino-3-(4-((2-thienyl)aminocarbonylamino)phenyl)furo[2,3-d]pyrimidine

Example 274 was prepared according to procedures similar to those shown in Example 8(C).

1H NMR (400 MHz, DMSO-d6) ppm 6.58 (m, 1H), 6.82 (m, 1H), 6.89 (m, 1H), 7.44 (m, 2H), 7.62 (m, 2H), 7.93 (s, 1H), 8.25 (s, 1H), 8.97 (br, 1H), 9.74 (br, 1H); LC/MS: m/z 352 (M+1)$^+$,

Example 275

4-Amino-2-bromo-3-(4-((5-indanyl)aminocarbonylamino)phenyl)-furo[2,3-d]pyrimidine Example 275 was prepared according to procedures similar to those shown in Example 8(C).

1H NMR (400 MHz, DMSO-d6) ppm 2.01 (m, 2H), 2.82 (m, 4H), 7.15 (m, 2H), 7.41 (m, 3H), 7.64 (m, 2H), 8.24 (s, 1H), 8.72 (br, 1H), 8.97(br, 1H); LC/MS: m/z 464 (M) +, 466 (M+2)$^+$.

Example 276

4-Amino-3-(4-((2-fluoro-5-(trifluoromethyl)phenyl)aminocarbonylamino)phenyl)thieno[2,3-d]pyrimidine;

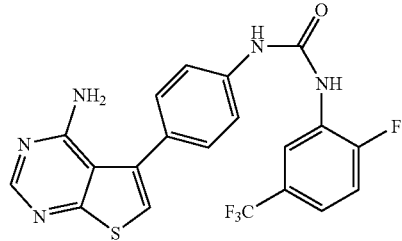

276(A): 1,1-dicyano-2-(4-nitro-phenyl)-propene

4Nitro acetophenone (2.0 g, 12.1 mmoles, 1 eq) and malonodinitrile (2.4 g, 36.3 mmoles, 3 eq) were dissolved in 20 mL of anhydrous toluene. To the solution were added glacial acetic acid (0.40 mL, 7.0 mmoles, 0.19 eq) and ammonium acetate (0.26 g, 3.3 mmoles, 0.09 eq). The system was heated to reflux using a Dean-Stark trap and a condenser. After 1 hour, the reaction mixture was cooled to room temperature and poured into brine (50 mL) and ethyl acetate (100 mL). The aqueous layer was washed with 3×10 mL ethyl acetate. The combined organic layers were washed with 50 mL brine, dried over anhydrous sodium sulfate and concentrated to dryness. The dark residue was partially purified using a silica plug (40% ethyl acetate-hexane) affording crude 1,1-dicyano-2-(4-nitrophenyl)-propene. The product was used as such in the next step. TLC (40% ethyl acetate-hexane)=0.61. LC-MS (m/e)=214.2 (MH+).

276(B): 1-amino-2-cyano-3-(4-nitro-phenyl) thiophene 1,1-Dicyano-2-(4-nitrophenyl)-propene (0.97 g crude, 4.55 mmoles assumed, 1 eq) was dissolved in 12 mL DMF, treated with sulfur (0.44 g, 13.8 mmoles, 3 eq) and heated to 120° C. for 10 minutes. The system was cooled to room temperature and poured into brine (20 mL) and methylene chloride (50 mL). The aqueous layer was washed with methylene chloride (2×10 mL). The organic layers were combined, dried over anhydrous sodium sulfate and concentrated to dryness. The residue was agitated in 20 mL methylene chloride; excess sulfur separated and was removed by filtration. The resulting solution was concentrated to dryness and purified by column chromatography (40% ethyl acetate-hexane) to afford 1-amino-2-cyano-3-(4-nitro-phenyl) thiophene. $^1$H-NMR (CDCl3): δ 5.0 (2H, br), 6.6 (1H, s), 8.1 (2H, d, J=8.8 Hz), 8.3 (2H, d, J=8.8 Hz). LC-MS (m/e)=246.0 (MH+). TLC (40% ethyl acetate-hexane)=0.44.

276(C): 5-(4-nitro-phenyl)-thieno[2,3-d]pyrimidin-4-ylamine

1-Amino-2-cyano-3-(4-nitro-phenyl) thiophene (250 mg, 1.02 mmoles) was heated to reflux in 5 mL formamide. The system was cooled to room temperature and poured into 20 mL methylene chloride and 20 mL brine. The organic layer was washed with 10 mL brine. The aqueous layers were combined and extracted with 3×10 mL methylene chloride. The organic layers were combined, dried over anhydrous sodium sulfate, and concentrated to dryness under vacuum, yielding a yellow solid residue. This solid was dissolved in methanol, treated with 1.5 g silica gel and concentrated to dryness under vacuum. The resulting solid was loaded onto a silica gel column pre-equilibrated with 80% ethyl acetate-hexane and eluted with 80% ethyl acetate-hexane, to afford 5-(4-nitro-phenyl)-thieno[2,3-d]pyrimidin-4-ylamine. $^1$H-NMR (CDCl$_3$): δ 4.9 (2H, br), 6.9 (1H, s), 7.2 (1H, s), 7.6 (2H, d, J=8.8 Hz), 8.4 (2H, d, J=8.8 Hz). LC-MS (m/e)=273.0 (MH+). TLC (100% ethyl acetate)=0.63.

276 (D): 5-(4-amino-phenyl)-thieno[2,3-d]pyrimidin-4-ylamine 5-(4-Nitro-phenyl)-thieno[2,3-d]pyrimidin-4-ylamine (50 mg, 0.18 mmoles, 1 eq) was suspended in 5 mL aqueous HCl 6N and treated with tin (100 mg, 0.90 mmoles, 5 eq). TLC (100% ethyl acetate) indicated that the reaction was complete after 30 minutes. The system was basified with NH$_4$OH (conc) to pH 10 and treated with 20 mL brine and 20 mL CH$_2$Cl$_2$. The aqueous layer was back-extrated with 3×10 mL CH$_2$Cl$_2$. All organic layers were combined, washed with 30 mL brine, dried over anhydrous sodium sulfate and concentrated to dryness. The residue was dissolved in minimal amount of methylene chloride, filtered and concentrated to dryness. The resulting 5-(4-amino-phenyl)-thieno[2,3-d]pyrimidin-4-ylamine was used as such in the next step. TLC (100% ethyl acetate)=0.58. LC-MS (m/e)=243.0 (MH+).

276 (E): 1-[4-(4-Amino-thieno[2,3-d]pyrimidin-5-yl)-phenyl]-3-(2-fluoro-5-trifluoromethyl-phenyl)-urea 5-(4-Amino-phenyl)-thieno[2,3-d]pyrimidin-4-ylamine (0.18 mmoles) was dissolved in 6 mL anhydrous THF and treated with 510 µL of a 0.35 M THF solution of 2-fluoro-5-trifluoromethyl-phenyl isocyanate (0.18 mmoles, 1 eq). After 30 minutes, the solution was treated with 2 mL methanol and 1 mL triethylamine, stirred for 30 minutes and concentrated to dryness under vacuum. The residue was purified by preparative HPLC to afford the title compound: 1-[4-(4-aminothieno[2,3-d]pyrimidin-5-yl)-phenyl]-3-(2-fluoro-5-trifluoromethyl-phenyl)-urea. $^1$H-NMR (DMSO-d6): δ 7.2 (2H, d, J=8.8 Hz), 7.3 (1H, s), 7.4 (2H, d, J=8.8 Hz), 8.2 (1H, br), 8.4 (1H, br), 8.8 (1H, s), 9.2 (1H, br). TLC (80% ethyl acetate-hexane)=0.48. LC-MS (m/e)=448.2.0 (MH+).

Example 277

4-Amino-3-(4-((2-fluoro-5-(trifluoromethyl)phenyl) aminocarbonyl-amino)phenyl)-6-(((2,4,6-trimethoxyphenyl)methyl)amino)furo[2,3-d]pyrimidine Example 277 was prepared according to procedures similar to those shown in Scheme 4.

1H NMR (400 MHz, DMSO-d6) ppm 3.78 (s, 3H), 3.78 (s, 6H), 4.38 (d, J=5.1 Hz, sH), 5.78 (m, 1H), 6.00 (br, 2H), 6.25 (s, 2H), 7.39–7.42 (m, 1H), 7.43 (d, J=7.34 Hz, 2H), 7.49–7.54 (m, 1H), 7.50 (s, 1H), 7.60 (d, J=8.59 Hz), 8.63 (dd, J=2.0 Hz, 7.33 Hz), 8.97 (brs, 1H), 9.35 (brs, 1H);

LC/MS: m/z 627 (M+1)$^+$, 625 (M−1)$^-$.

Example 278

4-Amino-3-(4-((2-fluoro-5-(trifluoromethyl)phenyl)-aminocarbonylamino)phenyl)-2-(3-pyridyl)furo[2,3-d]pyrimidine Example 278 was prepared according to procedures similar to those shown in Example 8.

1H NMR (400 MHz, DMSO-d6) ppm 7.40–7.45 (m, 2H), 7.46 (d, J=8.6 Hz, 2H), 7.52 (dd, J=9.3 Hz, 10.4 Hz, 1H), 7.69 (d, J=8.6 Hz, 2H), 7.84 (ddd, J=1.9 Hz, 1.9 Hz, 8.3 Hz, 1H), 8.30 (s, 1H), 8.51 (dd, J=1.5 Hz, 4.8 Hz, 1H), 8.60 (d, J=2.3 Hz, 1H), 8.63 (dd, J=2.1 Hz, 7.2 Hz, 1H), 9.07 (brs, 1H), 9.50 (brs, 1H);

LC/MS: m/z 509 (M+1)$^+$, 507 (M−1)$^-$.

Example 279

4-Amino-3-(4-((2-fluoro-5-(trifluoromethyl)phenyl)-aminocarbonylamino)phenyl)-2-vinylfuro[2,3-d] pyrimidine Example 279 was prepared according to procedures similar to those shown in Example 8.

1H NMR (400 MHz, DMSO-d6) ppm 5.44 (d, J=12.6 Hz, 1H), 5.88 (d, J=17.3 Hz, 1H), 6.57 (dd, J=11.4 Hz, 17.2 Hz, 1H), 7.40–7.42 (m, 1H), 7.41 (d, J=8.6 Hz, 2H), 7.52 (dd, J=9.1 Hz, 10.4 Hz, 1H), 7.67 (d, J=8.59, 2H), 8.27 (s, 1H), 8.65 (dd, J=2.1 Hz, 7.20 Hz, 1H), 8.99 (brs, 1H), 9.42 (brs, 1H);

LC/MS: m/z 458 (M+1)$^+$, 456 (M−1)$^-$.

Example 280

4-Amino-2-(1,2-dihydroxyethyl)-3-(4-((2-fluoro-5-(trifluoromethyl)phenyl)aminocarbonylamino)phenyl)furo[2,3-d]pyrimidine Example 280 was prepared according to procedures similar to those shown in Example 8.

1H NMR (400 MHz, DMSO-d6) ppm 3.67–3.70 (m, 2H), 4.54 (m, 1H), 7.93 (m, 1H), 5.58 (m, 1H), 7.39–7.44 (m, 1H), 7.46 (d, J=8.6 Hz, 2H), 7.49–7.54 (m, 1H), 7.64 (d, J=8.6 Hz, 2H), 8.24 (s, 1H), 8.63 (m, 1H), 9.02 (brs, 1H), 9.41 (brs, 1H); LC/MS: m/z 492 (M+1)$^+$, 490 (M−1)$^-$.

Example 281

4-Amino-2-carboxy-3-(4-((2-fluoro-5-(trifluoromethyl)phenyl)-aminocarbonylamino)phenyl)furo[2,3-d]pyrimidine Example 281 was prepared according to procedures similar to those shown in Example 8.
1H NMR (400 MHz, DMSO-d6) ppm 7.40–7.43 (m, 1H), 7.46 (d, J=8.6 Hz, 2H), 7.50–7.54 (m, 1H), 7.61 (d, J=8.6 Hz, 2H), 8.35 (s, 1H), 8.64 (dd, J=2.0 Hz, 7.3 Hz, 1H), 9.00 (brs, 1H), 9.40(brs, 1H);

Example 282

4-Amino-3-(4-((2-fluoro-5-(trifluoromethyl)phenyl)-aminocarbonylamino)phenyl)-2-iodofuro[2,3-d]pyrimidine Example 282 was prepared according to procedures similar to those shown in Example 8.
1H NMR (400 MHz, DMSO-d6) ppm 7.41 (d, J=8.6 Hz, 2H), 7.52 (dd, J=9.5 Hz, 9.7 Hz, 1H), 7.66 (d, J=8.6 Hz, 2H), 7.95 (s, 1H), 8.18 (s, 1H), 8.62 (d, J=6.8 Hz, 1H), 9.18 (brs, 1H), 7.59 (brs, 1H); LC/MS: m/z 492 (M+1)$^+$, 490 (M−1)$^-$.

Example 283

4-Amino-2-(4-carboxyphenyl)-3-(4-((2-fluoro-5-(trifluoromethyl)phenyl)aminocarbonylamino)phenyl)furo[2,3-d]pyrimidine Example 283 was prepared according to procedures similar to those shown in Example 8.
1H NMR (400 MHz, DMSO-d6) ppm 7.40–7.44 (m, 1H), 7.46 (d, J=8.6 Hz, 2H), 7.49–7.55 (m, 1H), 7.55 (d, J=8.3 Hz, 2H), 7.69 (d, J=8.6 Hz, 2H), 7.89 (d, J=8.3 Hz, 2H), 8.29 (s, 1H), 8.62 (dd, J=2.1 Hz, 7.2 Hz, 1H), 9.07 (brs, 1H), 9.51 (brs, 1H); LC/MS: m/z 552 (M+1)$^+$, 550 (M−1)$^-$.

Example 284

4-Amino-2-carbamoyl-3-(4-((2-fluoro-5-(trifluoromethyl)phenyl)-aminocarbonylamino)phenyl)furo[2,3-d]pyrimidine Example 284 was prepared according to procedures similar to those shown in Example 8.
1H NMR (400 MHz, DMSO-d6) ppm 7.39–7.43 (m, 1H), 7.44 (d, J=8.8 Hz, 2H), 7.49–7.54 (m, 1H), 7.59 (d, J=8.6 Hz, 2H), 7.90 (brs, 1H), 7.59 (brs, 1H), 8.34 (s, 1H), 8.64 (dd, J=2.1 Hz, 7.2 Hz, 1H), 9.04 (brs, 1H), 9.43 (brs, 1H);
LC/MS: m/z 475 (M+1)$^+$, 473 (M−1)$^-$.

Example 285

4-Amino-2-(N-(carbamoylmethyl)carbamoyl)-3-(4-((2-fluoro-5-(trifluoromethyl)phenyl)aminocarbonylamino)phenyl)furo[2,3-d]pyrimidine Example 285 was prepared according to procedures similar to those shown in Example 8.
1H NMR (400 MHz, DMSO-d6) ppm 3.74 (d, J=5.8 Hz, 2H), 7.04 (brs, 1H), 7.40–7.54 (m, 5H), 7.59 (d, J=8.6 Hz, 2H), 8.34 (s, 1H), 8.57 (t, J=5.8 Hz, 1H), 8.64 (dd, J=2.0 Hz, 7.3 Hz, 1H), 9.00 (brs, 1H), 9.43 (brs, 1H); LC/MS: m/z 532 (M+1)$^+$.

Example 286

4-Amino-6-dimethylamino-3-(4-((2-fluoro-5-(trifluoromethyl)-phenyl)aminocarbonylamino)phenyl)furo[2,3-d]pyrimidine Example 286 was prepared according to procedures similar to those shown in Scheme 4.
1H NMR (400 MHz, DMSO-d6) ppm 3.09 (s, 6H), 6.06 (brs, 2H), 7.39–7.44 (m, 3H), 7.52 (s, 1H), 7.49–7.54 (m, 1H), 7.60 (d, J=8.6 Hz, 2H), 8.63 (dd, J=2.1 Hz, 7.2 Hz), 9.00 (brs, 1H), 9.37 (brs, 1H); LC/MS: m/z 475 (M+1)$^+$, 473 (M−1)$^-$.

Example 287

4-Amino-6-((2-(dimethylamino)ethyl)amino)-3-(4-((2-fluoro-5-(trifluoromethyl)phenyl)aminocarbonylamino)phenyl)furo[2,3-d]pyrimidine Example 287 was prepared according to procedures similar to those shown in Scheme 4.
1H NMR (400 MHz, DMSO-d6) ppm 2.20 (s, 6H), 2.42 (t, J=6.7 Hz, 2H), 2.46–2.53 (m, 2H), 6.43 (m, 1H), 7.38–7.44 (m, 1H), 7.41 (d, J=8.6 Hz, 2H), 7.49 (s, 1H), 7.50–7.54 (m, 1H), 7.60 (d, J=8.6 Hz, 2H), 8.22 (s, 1H), 8.63 (dd, J=2.0 Hz, 7.1 Hz, 1H), 9.03 (brs, 1H), 9.41 (brs, 1H);

Example 288

4-Amino-3-(4-((2-fluoro-5-(trifluoromethyl)phenyl)aminocarbonyl-amino)phenyl)-6-((2-(methylsulfonylamino)ethyl)amino)furo[2,3-d]pyrimidine Example 288 was prepared according to procedures similar to those shown in Scheme 4.
1H NMR (400 MHz, DMSO-d6) ppm 2.91 (s, 3H), 3.10–3.15 (m, 2H), 6.01 (brs, 2H), 6.68 (m, 1H), 7.07 (m, 1H), 7.38–7.41 (m, 1H), 7.42 (d, J=8.6 Hz, 2H), 7.51 (s, 1H), 7.48–7.53 (m, 1H), 7.60 (d, J=8.6 Hz, 2H), 8.62 (dd, J=2.3 Hz, 7.1 Hz, 1H), 9.01 (brs, 1H), 9.38 (brs, 1H); LC/MS: m/z 568 (M+1)$^+$, 566 (M−1)$^-$.

Example 289

4-Amino-3-(4-((2-fluoro-5-(trifluoromethyl)phenyl)aminocarbonyl-amino)phenyl)-6-((3-(methylsulfinyl)propyl)amino)furo[2,3-d]pyrimidine Example 289 was prepared according to procedures similar to those shown in Scheme 4.
1H NMR (400 MHz, DMSO-d6) ppm 1.85–1.93 (m, 2H), 2.53 (s, 3H), 2.66–2.73 (m, 1H), 2.79–2.86 (m, 1H), 5.98 (brs, 2H), 6.81 (m, 1H), 7.39–7.42 (m, 1H), 7.42 (d, J=8.6 Hz, 2H), 7.48–7.54 (m, 1H), 7.49 (s, 1H), 7.60 (d, J=8.8 Hz, 2H), 8.62 (dd, J=2.3 Hz, 7.1 Hz, 1H), 9.05 (brs, 1H), 9.43 (brs, 1H); LC/MS: m/z 551 (M+1)$^+$, 549 (M−1)$^-$.

Example 290

4-Amino-3-(4-((2-fluoro-5-(trifluoromethyl)phenyl)aminocarbonyl-amino)phenyl)-6-((3-(methylthio)propyl)amino)furo[2,3-d]pyrimidine Example 290 was prepared according to procedures similar to those shown in Scheme 4.
1H NMR (400 MHz, DMSO-d6) ppm 1.75–7.82 (m, 2H), 2.05 (s, 3H), 6.77 (brs, 1H), 7.39–7.41 (m, 1H), 7.42 (d, J=8.6

Hz, 2H), 7.50 (s, 1H), 7.48–7.54 (m, 1H), 7.59 (d, J=8.6 Hz, 2H), 8.64 (dd, J=2.4 Hz, 7.2 Hz, 1H), 9.00 (brs, 1H), 9.33 (brs, 1H); LC/MS: m/z 535 (M+1)+, 533 (M−1)−.

Example 291

4-Amino-2-chloro-3-(4-((3-phenyl-1,2,4-thiadiazol-5-yl)aminocarbonylamino)phenyl)furo[2,3-d]pyrimidine Example 291 was prepared according to procedures similar to those shown in Example 8(D).
1H NMR (400 MHz, DMSO-d6) ppm 7.49–7.53 (m, 6H), 7.71–7.73 (m, 2H), 7.97 (s, 1H), 8.16–8.19 (m, 3H), 8.28 (s, 1H), 9.46 (s, 1H), 11.64 (s, 1H); HPLC: RT min, LC/MS: m/z 464 (M+1)+, 466 (M+3)+, 462 (M−2)−, 464 (M+1)−.

Example 292

4-Amino-3-(4-((5-tert-butylisoxazol-3-yl)aminocarbonyl-amino)phenyl)furo[2,3-d]pyrimidine Example 292 was prepared according to procedures similar to those shown in Example 8(C).
1H NMR (400 MHz, DMSO-d6) ppm 1.30 (s, 9H), 6.52 (s, 1H), 7.44–7.46 (m, 2H), 7.59–7.62 (m, 2H), 7.94 (s, 1H), 8.25 (s, 1H), 9.00 (s, 1H), 9.58 (s, 1H); HPLC: RT min, LC/MS: m/z 393 (M+1)+, 391 (M−1)−.

Example 293

4-Amino-3-(4-((3-fluorobenzoyl)amino)phenyl)-2-(3-pyridyl)furo[2,3-d]pyrimidine

Example 293 was prepared according to procedures similar to those shown in Example 3.
1H NMR (400 MHz, DMSO-d6) ppm 7.42–7.53 (m, 4H), 7.53–7.65 (m, 1H), 7.77–7.87 (m, 3H), 8.00–8.03 (m, 2H), 8.30 (s, 1H), 8.50–8.52 (m, 1H), 8.59–8.60 (m, 1H), 10.57 (s, 1H); HPLC: RT min, LC/MS: m/z 426 (M+1)+, 427 (M+2)+, 424 (M−1)−,b, 425 (M)−.

Example 294

4-Amino-3-(4-((4-fluorobenzenesulfonyl)amino)phenyl)-2-(3-pyridyl)furo[2,3-d]pyrimidine Example 294 was prepared according to procedures similar to those shown in Example 3.
1H NMR (400 MHz, DMSO-d6) ppm 7.20–7.22 (m, 3H), 7.37–7.44 (m, 6H), 7.72–7.80 (m, 1H), 7.81–7.83 (m, 2H), 8.27 (s, 1H), 8.45–8.51 (m, 2H), 10.52 (s, 1H); HPLC: RT min, LC/MS: m/z 462 (M+1)+, 460 (M−1)−, 461 (M)−.

Example 295

4-Amino-2-(3-pyridyl)-3-(4-((2-thienylsulfonyl)amino)phenyl)-furo[2,3-d]pyrimidine Example 295 was prepared according to procedures similar to those shown in Example 3.
1H NMR (400 MHz, DMSO-d6) ppm 7.16–7.19 (m, 1H), 7.29–7.31 (m, 2H), 7.38–7.45 (m, 3H), 7.57–7.59 (m, 1H), 7.70–7.74 (m, 1H), 7.93–7.95 (m, 1H), 8.29 (s, 1H), 8.50–8.52 (m, 2H), 10.63 (s, 1H); HPLC: RT min, LC/MS: m/z 450 (M+1)+, 451 (M+2)+, 448 (M−1)−, 449 (M)−, 450 (M+1)−.

Example 296

4-Amino-3-(4-((2,3-dichlorobenzenesulfonyl)amino)phenyl)-2-(3-pyridyl)furo[2,3-d]pyrimidine Example 296 was prepared according to procedures similar to those shown in Example 3.
1H NMR (400 MHz, DMSO-d6) ppm 7.24–7.26 (m, 2H), 7.32–7.35 (m, 3H), 7.38–7.41 (m, 2H), 7.56–7.60 (m, 1H), 7.62–7.66 (m, 1H), 7.96–7.99 (m, 1H), 8.07–8.09 (m, 1H), 8.27 (s, 1H), 8.46–8.51 (m, 2H), 11.09 (s, 1H); HPLC: RT min, LC/MS: m/z 512 (M)+, 514 (M+2)+, 515 (M+3)+, 510 (M−2)−, 512 (M)−, 514 (M+3)−.

Example 297

4-Amino-2-(2-methoxypyridin-5-yl)-3-((4-(phenylsulfonyl)amino)phenyl)furo[2,3-d]pyrimidine Example 297 was prepared according to procedures similar to those shown in Example 3.
1H NMR (400 MHz, DMSO-d6) ppm 3.86 (s, 1H), 6.78–6.81 (m, 1H), 7.21–7.24 (m, 2H), 7.35–7.38 (m, 2H), 7.57–7.68 (m, 4H), 7.75–7.79 (m, 2H), 8.08 (br, 1H), 8.25 (s, 1H), 10.49 (s, 1H); HPLC: RT min, LC/MS: m/z 474 (M+1)+, 476 (M+3)+, 472 (M−1)−, 473 (M)−, 474 (M+2)−.

Example 298

4-Amino-2-(3-pyridyl)-3-((4-((1,2,3,4-tetrahydroisoquinolin-7-yl)sulfonyl)amino)phenyl)furo[2,3-d]pyrimidine Example 298 was prepared according to procedures similar to those shown in Example 3.
1H NMR (400 MHz, DMSO-d6) ppm 2.68 (t, J=5.7 Hz, 2H), 2.92 (t, J=5.7 Hz, 2H), 3.17 (d, J=4.3 Hz, 1H), 3.83 (s, 2H), 7.02–7.04 (m, 2H), 7.11–7.18 (m, 3H), 7.36–7.40 (m, 2H), 7.43–7.46 (m, 1H), 7.78–7.82 (m, 1H), 8.26 (s, 1H), 8.47–8.49 (m, 1H), 8.57–8.58 (m, 1H); HPLC: RT min, LC/MS: m/z 499 (M+1)+, 500 (M+2)+, 501 (M+3)+, 497 (M−1)−, 498 (M)−, 499 (M+2)−.

Example 232(b) and Examples 299–479 are made according to the procedures of Schemes 6–12 and Intermediate Examples 1–13.

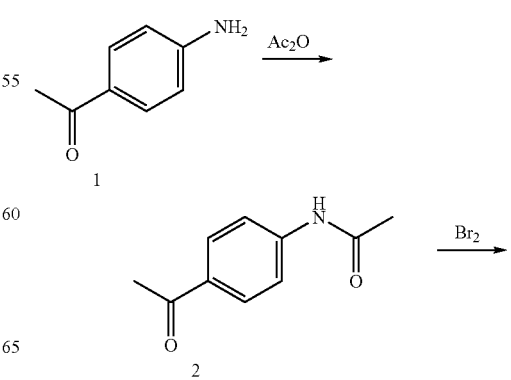

Scheme 6

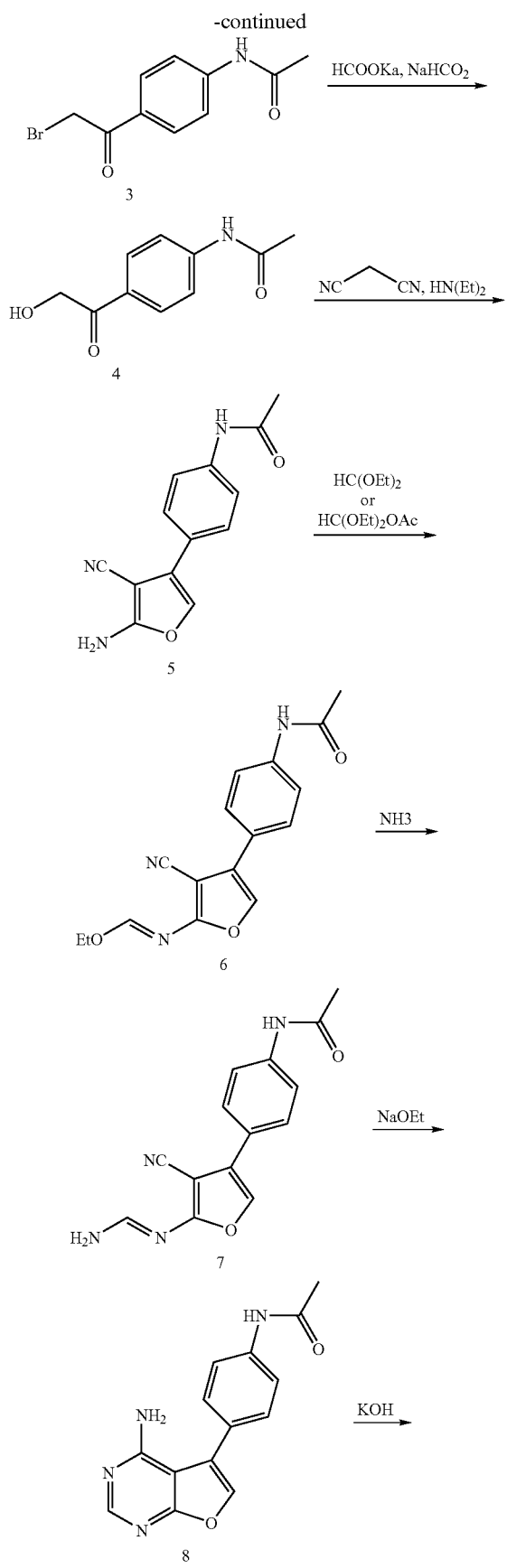

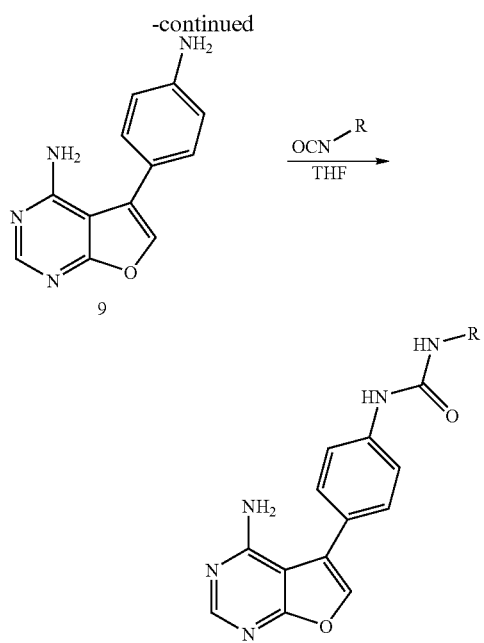

The numerals 1 through 9 in the following examples refer to Scheme 6.

Intermediate Example 1

4'-Acetamido-acetophenone (2)

To a suspension of 4-aminoacetophenone 1 (74 g, 547 mmol) in toluene (700 mL), acetic anhydride (56 mL 593 mmol) was added dropwise at room temperature. Soon after added all of acetic anhydride, the reaction mixture became a clear solution and then rapidly began to make a white precipitation. The precipitation were filtrated and washed with a small amount of toluene then dried under reduced pressure to afford 2 as a white solid (93 g, 960% yield): MS(ES) m/e 178 [M+H].

Intermediate Example 2

4'-Acetamido-2-bromoacetophenone (3)

To a suspension of 4'-acetamido-acetophenone 2 (21.84 g, 123 mmol) in acetic acid (184 mL), bromine (6.5 mL, 127 mmol) was added. The mixture was heated (inner temp: 52° C., oil bath temp: 60~65° C.) with vigorous stirring until the suspension make a clear solution. The heating bath was rapidly removed, and the mixture was stirred at room temperature for 15 min and then stirred in an ice-water bath for 2 h(inner temp. 50° C.~20° C.). The precipitation was filtrated, washed with 30% EtOH in water, and dried under reduced pressure to give 3 as a pale brown solid (24.0 g, 75% yield): MS(ES) m/e 257 [M+H].

Intermediate Example 3

4'-Acetamido-2-hydroxyacetophenone (4)

To a suspension of 4'-acetamido-2-bromoacetophenone 3 (10.0 g, 39 mmol) in EtOH (800 mL), aqueous potassium formate (35.4 g in 200 mL) was added then followed by sodium bicarbonate (3.68 g). The mixture was stirred at 38° C. (inner temp.) for 22 h. The mixture was evaporated in vacuo until the total volume reached to ca. 300 mL The mixture was diluted with ethyl acetate (1200 mL), washed with water (200 mL), then brine (2×400 mL). Aqueous layers were extracted with ethyl acetate (800 mL then 400 mL). Combined organic layer was dried over anhydrous sodium sulfate and then evaporated in vacuo to give crude 4 as a solid (7.17 g, 95%) which was used to the next step without any purification. MS(ES) m/e 194 [M+H].

Intermediate Example 4

4-(4-Acetamidophenyl)-2-amino-3-cyanofurane (5)

To a solution of 4'-acetamido-2-hydroxyacetophenone 4 (7.17 g, 39 mmol) in DMF (65 mL), malononitrile (2.84 g, 43 mmol) was added. With cooling in an ice-water bath, diethylamine (6.05 mL 59 mmol) was gradually added within 20 min. The mixture was stirred at room temperature for 2 h and then diluted with ethyl acetate (400 mL). The mixture was washed with brine (3×200 mL), dried over sodium sulfate, and then evaporated in vacuo. Residual material was treated with dichloromethane and n-hexane, concentrated in vacuo, and precipiated in the concentrated mixture. The precipitated material was filtrated and washed with n-hexane to give 5 (7.64 g) as a brown solid. MS(ES) m/e 242 [M+H].

Intermediate Example 5

4-(4-Acetamidophenyl)-3-cyano-2-[(ethoxymethylidene)amino]furane (6)

Method A (by Means of Triethyl Orthoformate)

To a suspension of 4-(4-acetamidophenyl)-2-amino-3-cyanofurane 5 (7.64 g, 39 mmol) in triethyl orthoformate (306 mL), acetic anhydride (15 mL) was added at room temperature. The mixture was heated (inner temp: 100° C.) in an oil bath for 1 h. The black material was precipitated in the mixture and then filtrated. The filtrated material was purified on a silica gel column (eluted by n-hexane-EtOAc 1:3) to afford 473 mg of 6 as a yellow solid. The filtered solution was concentrated in vacuo to afford 6 (7.44 g) as a dark orange solid.

Method B (by Means of Diethoxymethyl Acetate)

At room temperature, to the mixture of 4-(4-acetamidophenyl)-2-amino-3-cyanofurane 5 (6.0 g, 25 mmol) in acetic acid (60 mL), diethoxymethyl acetate (41 mL, 25 mmol) was added dropwise. The mixture was stirred at room temperature for 30 min and then concentrated (below 40° C. in water bath). The residual paste was dried up with a pump. The dried solid material was triturated with ether then filtrated to afford 6 (3.93 g) as a solid. MS(ES) m/e 298 [M+H].

Intermediate Example 6

4-(4-Acetamidophenyl)-2-[(aminomethylidene)amino]-3-cyanofurane (7)

A suspension of 4-(4-acetamidophenyl)-3-cyano-2-[(ethoxymethylidene) amino]furane 6 (1.12 g, 3.76 mmol) in a mixture of EtOH (40 mL) and THF (40 mL) was chilled in an ice-water bath. Into the mixture with vigorous stirring, NH3 gas was bubbled for 25 min. The suspension was once dissolved and then it began to make a precipitation. The mixture in a tightly closed flask was stirred at room temperature for 3 h. The mixture was evaporated in vacuo to give 7 (1.1 g) as a brown solid which was used for the next step without any purification. MS(ES) m/e 269 [M+H].

Intermediated Example 7

3-(4-Acetamidophenyl)-4-aminofuro[2,3-d]pyrimidine (8)

The crude 4-(4-Acetamidophenyl)-2-[(aminomethylidene)amino]-3-cyanofurane 7 obtained from the last step was suspended in the mixture of EtOH(30 mL) and THF (30 mL). To the suspension was added dropwise 5 mL (0.8N, 4 mmol) of sodium ethoxide (freshly prepared ethanol solution) within 5 min. The suspended material was gradually dissolved with stirring at room temperature. After stirred for 4 h, the mixture was concentrated in vacuo to obtain ca. 15 mL of a residual solution. The solution was diluted with ethyl acetate (200 mL), washed with brine (×2), and dried over anhydrous sodium sulfate. The mixture was concentrated and dried under reduced pressure to give 8 (0.92 g) as a brown solid. MS(ES) m/e 269 [M+H].

Intermediate Example 8

4-Amino-3-(4-aminophenyl)furo[2,3-d]pyrimidine (9)

Compound 3-(4-acetamidophenyl)-4-aminofuro[2,3-d] pyrimidine 8 (242 mg) was dissolved in 2 M potassium hydroxide in the mixture of EtOH (16 mL) and water (4 mL). The mixture was heated (60° C.) for 24 h then concentrated in vacuo. Residual oil was triturated with cold water (6 mL) to give precipitation, which was filtrated, washed with water, and dried under the reduced pressure. The compound 9 (118 mg) as pale orange colored was obtained. MS(ES) m/e 227M+H].

Example 232(b)

4-Amino-3-(4-((2-fluoro-5-(trifluoromethyl)phenyl)-aminocarbonylamino)phenyl)furo[2,3-d]pyrimidine To compound 4-Amino-3-(4-aminophenyl)furo[2,3-d]pyrimidine (9) (1 g 4.42 mmol) in THF (50 mL), 2-fuoro-5-(trifluoromethyl)-phenyl isocyanate (0.7 mL, 4.86 mmol) was added in one portion. After the mixture was stirred at room temperature for 2 h, the solvent was evaporated. The residue was purified by column. (1:1 EtOAc/hexane–9:1 EtOAc/hexane) to afford the desired product. MS(ES) m/e 432 [M+H].

Example 299

4-Amino-3-(4-((2-fluoro-5-methoxyphenyl)-aminocarbonylamino)phenyl)furo[2,3-d]pyrimidine The compound was prepared following the procedure described in Example 232(b), using 2-fluoro-5-methoxyphenyl isocyanate as the isocyanate of choice, and 4-Amino-3-(3-aminophenyl)furo[2,3-d]pyrimidine (10) as the diamine of choice. MS(ES) m/e 394 [M+H]+.

Scheme 7

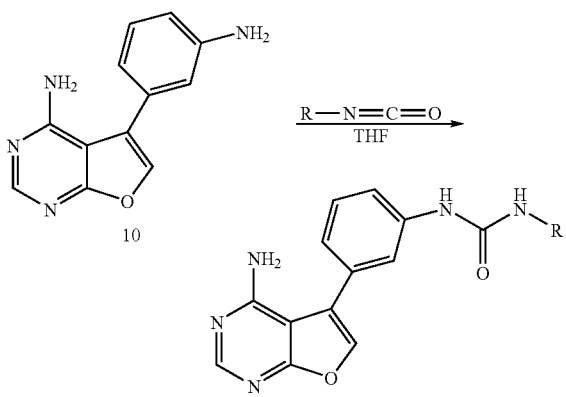

Example 300
Example 301
Example 302
Example 303
Example 304
Example 305
Example 306
Example 307

Intermediate Example 9

4-Amino-3-(3-aminophenyl)furo[2,3-d]pyrimidine (10)

The compound was prepared following the procedures described in making 4-Amino-3-(4-aminophenyl)furo[2,3-d]pyrimidine (9), using 3-aminoacetophenone instead of 4-aminoacetophenone as starting material. MS(ES) m/e 227 [M+H]$^+$.

Example 300

4-Amino-3-(3-((4-chlorophenyl)aminocarbonylamino)-phenyl)furo[2,3-d]pyrimidine The compound was prepared following the procedure described Example 232(b), using 4-chlorophenyl isocyanate as the isocyanate of choice and 4-Amino-3-(3-aminophenyl)furo[2,3-d]pyrimidine (10) as the diamine of choice. MS(ES) m/e 380 [M+H]$^+$.

Example 301

4-Amino-3-(3-((phenyl)aminocarbonylamino)phenyl)furo[2,3-d]pyrimidine

The compound was prepared following the procedure described in Example 232(b), using phenyl isocyanate as the isocyanate of choice, and 4-Amino-3-(3-aminophenyl)furo[2,3-d]pyrimidine (10) as the diamine of choice. MS(ES) m/e 346 [M+H]$^+$.

Example 302

4-Amino-3-(3-((cyclohexyl)aminocarbonylamino)phenyl)furo[2,3-d]pyrimidine

The compound was prepared following the procedure described in Example 232(b), using cyclohexyl isocyanate as the isocyanate of choice, and 4-Amino-3-(3-aminophenyl)furo[2,3-d]pyrimidine (10) as the diamine of choice. MS(ES) m/e 352 [M+H]$^+$.

Example 303

4-Amino-3-(3-((butyl)aminocarbonylamino)phenyl)furo[2,3-d]pyrimidine

The compound was prepared following the procedure described in Example 232(b), using butyl isocyanate as the isocyanate of choice, and 4-Amino-3-(3-aminophenyl)furo[2,3-d]pyrimidine (10) as the diamine of choice. MS(ES) m/e 326 [M+H]$^+$.

Example 304

4-Amino-3-(3-((tert-butyl)aminocarbonylamino)phenyl)furo[2,3-d]pyrimidine

The compound was prepared following the procedure described in Example 232(b), using t-butyl isocyanate as the isocyanate of choice, and 4-Amino-3-(3-aminophenyl)furo[2,3-d]pyrimidine (10) as the diamine of choice. MS(ES) m/e 326 [M+H]$^+$.

Example 305

4-Amino-3-(3-(aminocarbonylamino)phenyl)furo[2,3-d]pyrimidine

The compound was prepared following the procedure described in Example 232(b), using chlorosulfonyl isocyanate as the isocyanate of choice, and 4-Amino-3-(3-aminophenyl)furo[2,3-d]pyrimidine (10) as the diamine of choice. MS(ES) m/e 270 [M+H]$^+$.

Example 306

4-Amino-3-(3-((5-indanyl)aminocarbonylamino)phenyl)furo[2,3-d]pyrimidine

The compound was prepared following the procedure described in Example 232(b), using 5-indanyl isocyanate as the isocyanate of choice, and 4-Amino-3-(3-aminophenyl)furo[2,3-d]pyrimidine (10) as the diamine of choice. MS(ES) m/e 386 [M+H]$^+$.

Example 307

4-Amino-3-(3-((5-tert-butylisoxazol-3-yl)aminocarbonylamino)-phenyl)furo[2,3-d]pyrimidine The compound was prepared following the procedure described in Example 232(b), using (5-t-butyl-isoxazol-3-yl)-carbamic acid phenyl ester as the isocyanate of choice, and 4-Amino-3-(3-aminophenyl)furo[2,3-d]pyrimidine (10) as the diamine of choice. MS(ES) m/e 393 [M+H]$^+$.

Example 308

4-Amino-3-(4-((3-cyanophenyl)aminocarbonylamino)-phenyl)furo[2,3-d]pyrimidine The compound was prepared following the procedure described in Example 232(b), using 3-cyano-phenyl isocyanate as the isocyanate of choice. MS(ES) m/e 371 [M+H]$^+$.

Example 309

4-Amino-3-(4-((3-acetylphenyl)aminocarbony-lamino)phenyl)furo[2,3-d]pyrimidine

The compound was prepared following the procedure described in Example 232(b), using 3-acetyl-phenyl isocyanate as the isocyanate of choice. MS(ES) m/e 388 [M+H]$^+$.

Example 310

4-Amino-3-(4-((3-(methoxycarbonyl)phenyl)-aminocarbonylamino)phenyl)furo[2,3-d]pyrimidine

The compound was prepared following the procedure described in Example 232(b), using 3-isocyanato-benzoic acid methyl ester as the isocyanate of choice. MS(ES) m/e 404 [M+H]$^+$.

Example 311

4-Amino-3-(4-((3-fluoro-5-(trifluoromethyl)phenyl)-aminocarbonylamino)phenyl)furo[2,3-d]pyrimidine

The compound was prepared following the procedure described in Example 232(b), using 3-fluoro-5-trifluromethyl-phenyl isocyanate as the isocyanate of choice. MS(ES) m/e 432 [M+H]$^+$.

Example 312

4-Amino-3-(4-((3-fluorophenyl)aminocarbony-lamino)phenyl)-furo[2,3-d]pyrimidine

The compound was prepared following the procedure described in Example 232(b), using 3-fluoro-phenyl isocyanate as the isocyanate of choice. MS(ES) m/e 364 [M+H]$^+$.

Example 313

4-Amino-3-(4-((3-methoxyphenyl)aminocarbony-lamino)phenyl)-furo[2,3-d]pyrimidine

The compound was prepared following the procedure described in Example 232(b), using 3-methoxy-phenyl isocyanate as the isocyanate of choice. MS(ES) m/e 376 [M+H]$^+$.

Scheme 8

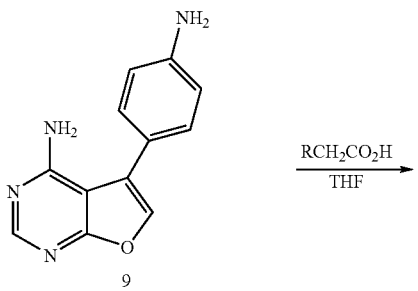

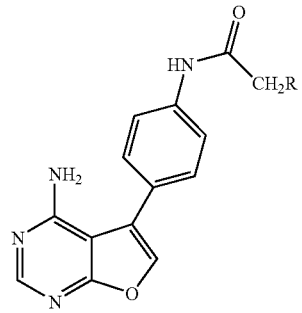

Example 314
Example 315
Example 316
Example 317

Example 314

4-Amino-3-(4-((3-methoxyphenylacetyl)amino)phenyl)furo[2,3-d]pyrimidine

The carboxylic acid of choice (3-methoxyphenyl acetic acid, 0.055 mmol) and 0.055 mmol of HBTU were dissolved in 0.5 mL amine-free DMF. To this solution was added dropwise a solution of 4-Amino-3-(4-aminophenyl)furo[2,3-d]pyrimidine (9) in 0.5 mL DMF. The resulting solution was treated with 0.024 mL of N,N-diisopropylethylamine. The system was stirred at room temperature overnight and then was concentrated to dryness in a Speedvac system, reconstituted in 1 mL DMSO and purified by prep HPLC to give the title compound. MS(ES) m/e 375 [M+H]$^+$.

Example 315

4-Amino-3-(4-((2-thienylacetyl)amino)phenyl)furo[2,3-d]pyrimidine

The compound was prepared following the procedure described Example 314, using 2-thienylacetic acid as the carboxylic acid of choice. MS(ES) m/e 351 [M+H]$^+$.

Example 316

4-Amino-3-(4-(((5-methyl-2-phenyloxazol-4-yl)acetyl)amino)-phenyl)furo[2,3-d]pyrimidine

The compound was prepared following the procedure described in Example 314, using 5-methyl-2-phenyloxazol-4-ylacetic acid as the carboxylic acid of choice. MS(ES) m/e 426 [M+H]$^+$.

Example 317

4-Amino-3-(4-(((3,5-bis-(trifluoromethyl)phenyl)acetyl)amino)-phenyl)furo[2,3-d]pyrimidine

The compound was prepared following the procedure described in Example 314, using 3,5-bis(trifluoromethyl)phenylacetic acid as the carboxylic acid of choice. MS(ES) m/e 481 [M+H]$^+$.

123

Scheme 9

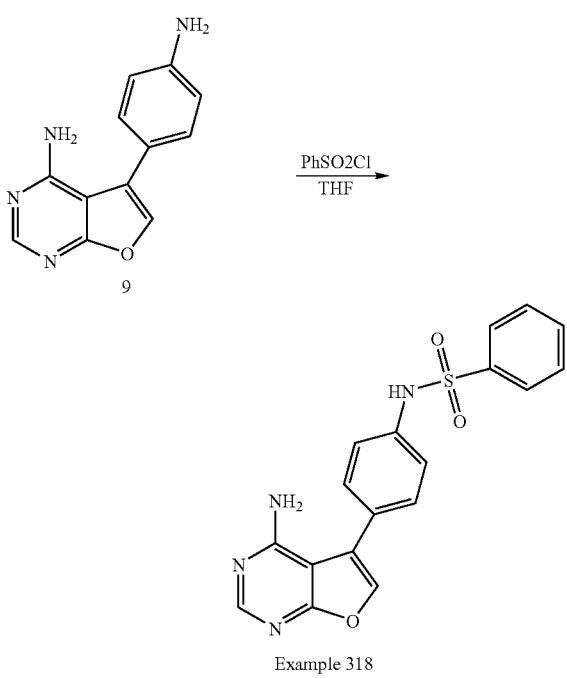

Example 318

4-Amino-3-(4-((benzenesulfonyl)amino)phenyl)furo[2,3-d]pyrimidine

To compound 4-Amino-3-(4-aminophenyl)furo[2,3-d]pyrimidine (9) (24 mg, 0.044 mmol) in THF (1 mL), benzenesulfonyl chloride (6.8 uL, 0.053 mmol), and N,N-diisopropylethylamine (9 uL, 0.053 mmol) were added. After the mixture was stirred at room temperature for 6 h, water was added to quench the reaction. The solution was extracted with EtOAc. The organic layer was separated, dried (MgSO4), and filtered. The solvent was evaporated. The residue was purified by gilson to afford the desired product MS(ES) m/e 367 $[M+H]^+$.

Example 319

4-Amino-3-(4-((2,3-dichlorobenzenesulfonyl)amino)phenyl)furo[2,3-d]pyrimidine

The compound was prepared following the procedure described in Example 318, using 2,3-dichloro-benzenesulfonyl chloride as the sulfonyl chloride of choice. MS(ES) m/e 435 $[M+H]^+$.

Example 320

4-Amino-3-(4-((2,5-dichlorobenzenesulfonyl)amino)phenyl)furo[2,3-d]pyrimidine

The compound was prepared following the procedure described in Example 318, using 2,5-dichloro-benzenesulfonyl chloride as the sulfonyl chloride of choice. MS(ES) m/e 435 $[M+H]^+$.

124

Example 321

4-Amino-3-(4-(((5-chlorothiophene-2-sulfonyl)acetyl)amino)-phenyl)furo[2,3-d]pyrimidine The compound was prepared following the procedure described in Example 318, using 5-chlorothiophene-2-sulfonyl chloride as the sulfonyl chloride of choice. MS(ES) m/e 407 $[M+H]^+$.

Example 322

4-Amino-3-(4-(((2,5-dichlorothiophene-3-sulfonyl)acetyl)amino)-phenyl)furo[2,3-d]pyrimidine The compound was prepared following the procedure described in Example 318, using 2,5-dichlorothiophene-3-sulfonyl chloride as the sulfonyl chloride of choice. MS(ES) m/e 441 $[M+H]^+$.

Example 323

4-Amino-3-(4-((3-fluorobenzenesulfonyl)amino)phenyl)furo[2,3-d]pyrimidine

The compound was prepared following the procedure described in Example 318, using 3-fluorobenzenesulfonyl chloride as the sulfonyl chloride of choice. MS(ES) m/e 385 $[M+H]^+$.

Example 324

4-Amino-3-(4-((3,4-dichlorobenzenesulfonyl)amino)phenyl)furo[2,3-d]pyrimidine

The compound was prepared following the procedure described in Example 318, using 3,4-dichlorobenzenesulfonyl chloride as the sulfonyl chloride of choice. MS(ES) m/e 436 $[M+H]^+$.

Example 325

4-Amino-3-(4-((3-methoxybenzenesulfonyl)amino)phenyl)furo[2,3-d]pyrimidine

The compound was prepared following the procedure described in Example 318, using 3-methoxy-benzenesulfonyl chloride as the sulfonyl chloride of choice. MS(ES) m/e 397 $[M+H]^+$. Example 326

4-Amino-3-(4-((7-chloro-benzo[1,2,5]oxadiazole-4-sulfonyl)amino)phenyl)furo[2,3-d]pyrimidine The compound was prepared following the procedure described in Example 318, using 7-chloro-benzo(1,2,5)oxadiazole-4-sulfonyl chloride as the sulfonyl chloride of choice. MS(ES) m/e 443 $[M+H]^+$.

Example 327

4-Amino-3-(4-((4-methoxybenzenesulfonyl)amino)phenyl)furo[2,3-d]pyrimidine

The compound was prepared following the procedure described in Example 318, using 4-methoxy-benzenesulfonyl chloride as the sulfonyl chloride of choice. MS(ES) m/e 397 $[M+H]^+$.

Example 328

4-Amino-3-(4-((5-chloro-1,3-dimethyl pyrazole-4-sulfonyl)amino)phenyl)furo[2,3-d]pyrimidine The compound was prepared following the procedure described in Example 318, using 5-chloro-1,3-dimethyl-1-pyrazole-4-sulfonyl chloride as the sulfonyl chloride of choice. MS(ES) m/e 419 [M+H]$^+$.

Example 329

4-Amino-3-(4-((4,5-dichlorothiophene-2-sulfonyl)amino)-phenyl)furo[2,3-d]pyrimidine The compound was prepared following the procedure described in Example 318, using 4,5-dichloro-thiophene-2-sulfonyl chloride as the sulfonyl chloride of choice. MS(ES) m/e 441 [M+H]$^+$.

Example 330

4-Amino-3-(4-((2-phenylethenesulfonyl)amino)phenyl)furo[2,3-d]pyrimidine

The compound was prepared following the procedure described in Example 318, using (E)-2-Phenyl-ethenesulfonyl chloride as the sulfonyl chloride of choice. MS(ES) m/e 392 [M+H]$^+$.

Example 331

4-Amino-3-(4-((3,5-dichlorophenylsulfonyl)amino)phenyl)furo[2,3-d]pyrimidine

The compound was prepared following the procedure described in Example 318, using 3,5-dichloro-benzenesulfonyl chloride as the sulfonyl chloride of choice. MS(ES) m/e 435 [M+H]$^+$.

Example 332

4-Amino-3-(4-((2-(methoxycarbonyl)thiophene-3-sulfonyl)amino)-phenyl)furo[2,3-d]pyrimidine The compound was prepared following the procedure described in Example 318, using 3-chlorosulfonyl-thiophene-2-carboxylic acid methyl ester as the sulfonyl chloride of choice. MS(ES) m/e 429 [M+H]$^+$.

Example 333

4-Amino-3-(4-((3-chlorobenzenesulfonyl)amino)phenyl)furo[2,3-d]pyrimidine

The compound was prepared following the procedure described in Example 318, using 3-chloro-benzenesulfonyl chloride as the sulfonyl chloride of choice. MS(ES) m/e 401 [M+H]$^+$.

Example 334

4-Amino-3-(4-((1-methyl-1H-imidazole-4-sulfonyl)amino)phenyl)-furo[2,3-d]pyrimidine The compound was prepared following the procedure described in Example 318, using 1-methyl-1H-imidazole-4-sulfonyl chloride as the sulfonyl chloride of choice. MS(ES) m/e 370 [M+H]$^+$.

Example 335

4-Amino-3-(4-((5-chlorobenzo[1,2,5]oxadiazole-4-sulfonyl)amino)-phenyl)furo[2,3-d]pyrimidine The compound was prepared following the procedure described in Example 318, using 5-chloro-benzo(1,2,5)oxadiazole-4-sulfonyl chloride as the sulfonyl chloride of choice. MS(ES) m/e 443 [M+H]$^+$.

Example 336

4-Amino-3-(4-((3,5-dimethoxybenzenesulfonyl)amino)-phenyl)furo[2,3-d]pyrimidine

The compound was prepared following the procedure described in Example 318, using 3,5-dimethoxy-benzenesulfonyl chloride as the sulfonyl chloride of choice. MS(ES) m/e 427 [M+H]$^+$.

Example 337

4-Amino-3-(4-((2,5-dimethoxybenzenesulfonyl)amino)-phenyl)furo[2,3-d]pyrimidine

The compound was prepared following the procedure described in Example 318, using 2,5-dimethoxy-benzenesulfonyl chloride as the sulfonyl chloride of choice. MS(ES) m/e 427 [M+H]$^+$.

Example 338

4-Amino-3-(4-((2-chloro-4-fluorobenzenesulfonyl)amino)-phenyl)furo[2,3-d]pyrimidine The compound was prepared following the procedure described in Example 318, using 2-chloro-4-fluoro-benzenesulfonyl chloride as the sulfonyl chloride of choice. MS(ES) m/e 419 [M+H]$^+$.

Example 339

4-Amino-3-(4-((2-chloro-5-(trifluoromethyl)phenyl)-aminocarbonylamino)phenyl)furo[2,3-d]pyrimidine The compound was prepared following the procedure described in Example 318, using 2-chloro-5-trifluoromethyl-benzenesulfonyl chloride as the sulfonyl chloride of choice. MS(ES) m/e 470 [M+H]$^+$.

Example 340

4-Amino-3-(4-((4-(methoxycarbonyl)-3-methoxythiophene-2-sulfonyl)amino)phenyl)furo[2,3-d]pyrimidine The compound was prepared following the procedure described in Example 318, using 3-chlorosulfonyl-thiophene-2-carboxylic acid methyl ester as the the sulfonyl chloride of choice. MS(ES) m/e 461 [M+H]$^+$.

Example 341

4-Amino-3-(4-((5-(1-methyl-5-(trifluoromethyl) pyrazol-3-yl)thiophene-2-sulfonyl)amino)phenyl) furo[2,3-d]pyrimidine The compound was prepared following the procedure described in Example 318, 5-(methyl-trifluromethyl-1H-pyrazol-3-yl)-thiophene-2-sulfonyl chloride as the sulfonyl chloride of choice. MS(ES) m/e 521 [M+H]$^+$.

Example 342

4-Amino-3-(4-((5-bromo-6-chloropyridine-3-sulfonyl)amino)-phenyl)furo[2,3-d]pyrimidine The compound was prepared following the procedure described in Example 318, 5-bromo-6-chloro-pyridine-3-sulfonyl chloride as the sulfonyl chloride of choice. MS(ES) m/e 481 [M+H]$^+$.

Example 343

4-Amino-3-(4-((2,3,4,5,6-pentafluorobenzenesulfonyl)amino)-phenyl)furo[2,3-d]pyrimidine The compound was prepared following the procedure described in Example 318, using 2,3,4,5,6-pentafluoro-benzenesulfonyl chloride as the sulfonyl chloride of choice. MS(ES) m/e 457 [M+H]$^+$.

Example 344

4-Amino-3-(4-((4-(trifluoromethoxy)benzenesulfonyl)amino)-phenyl)furo[2,3-d]pyrimidine The compound was prepared following the procedure described in Example 318, using 4-trifluoromethoxy-benzenesulfonyl chloride as the sulfonyl chloride of choice. MS(ES) m/e 451 [M+H]$^+$.

Example 345

4-Amino-3-(4-((thiophene-2-sulfonyl)amino)phenyl) furo[2,3-d]pyrimidine

The compound was prepared following the procedure described in Example 318, thiophene-2-sulfonyl chloride as the sulfonyl chloride of choice. MS(ES) m/e 373 [M+H]$^+$.

Example 346

4-Amino-3-(4-((4-isopropylbenzenesulfonyl)amino) phenyl)furo[2,3-d]pyrimidine

The compound was prepared following the procedure described in Example 318, using 4-isopropyl-benzenesulfonyl chloride as the sulfonyl chloride of choice. MS(ES) m/e 409 [M+H]$^+$.

Example 347

4-Amino-3-(4-((quinoline-8-sulfonyl)amino)phenyl) furo[2,3-d]pyrimidine

The compound was prepared following the procedure described in Example 318, quinoline-8-sulfonyl chloride as the sulfonyl chloride of choice. MS(ES) m/e 417 [M+H]$^+$.

Example 348

4-Amino-3-(4-((2-nitro-4-(trifluoromethyl)benzenesulfonyl)amino)-phenyl)furo[2,3-d]pyrimidine The compound was prepared following the procedure described in Example 318, using 2-nitro-4-trifluoromethyl-benzenesulfonyl chloride as the sulfonyl chloride of choice. MS(ES) m/e 480 [M+H]$^+$.

Example 349

4-Amino-3-(4-((2,4,6-trimethylbenzenesulfonyl) amino)phenyl)-furo[2,3-d]pyrimidine The compound was prepared following the procedure described in making Example 318, using 2,4,6-trimethyl-benzenesulfonyl chloride as the sulfonyl chloride of choice. MS(ES) m/e 408 [M+H]$^+$.

Example 350

4-Amino-3-(4-((5-bromo-2-methoxybenzenesulfonyl)amino)-phenyl)furo[2,3-d]pyrimidine The compound was prepared following the procedure described in Example 318, using 5-bromo-2-methoxy-benzenesulfonyl chloride as the sulfonyl chloride of choice. MS(ES) m/e 476 [M+H]$^+$.

Example 351

4-Amino-3-(4-((4-propylbenzenesulfonyl)amino) phenyl)furo[2,3-d]pyrimidine

The compound was prepared following the procedure described in Example 318, using 4-propyl-benzenesulfonyl chloride as the sulfonyl chloride of choice. MS(ES) m/e 409 [M+H]$^+$.

Example 352

4-Amino-3-(4-((4-bromo-2,5-difluorobenzenesulfonyl)amino)-phenyl)furo[2,3-d]pyrimidine The compound was prepared following the procedure described in Example 318, using 4-bromo-2,5-difluoro-benzenesulfonyl chloride as the sulfonyl chloride of choice. MS(ES) m/e 482 [M+H]$^+$.

Example 353

4-Amino-3-(4-((2,6-dichloro-4-(trifluoromethyl) benzenesulfonyl)-amino)phenyl)furo[2,3-d]pyrimidine The compound was prepared following the procedure described in Example 318, using 2,6-dichloro-4-trifluoromethyl-benzenesulfonyl chloride as the sulfonyl chloride of choice. MS(ES) m/e 504 [M+H]$^+$.

Example 354

4-Amino-3-(4-((2-(trifluoromethoxy)benzenesulfonyl)-amino)phenyl)furo[2,3-d]pyrimidine The compound was prepared following the procedure described in Example 318, using 2-trifluoromethoxy-benzenesulfonyl chloride as the sulfonyl chloride of choice. MS(ES) m/e 451 [M+H]$^+$.

Example 355

4-Amino-3-(4-((3,5-dimethylisoxazole-4-sulfonyl)-amino)phenyl)furo[2,3-d]pyrimidine The compound was prepared following the procedure described in Example 318, using 3,5-Dimethyl-isoxazole-4-sulfonyl chloride as the sulfonyl chloride of choice. MS(ES) m/e 386 [M+H]$^+$.

Example 356

4-Amino-3-(4-((4-acetylbenzenesulfonyl)amino)phenyl)furo[2,3-d]pyrimidine

The compound was prepared following the procedure described in Example 318, using 4-acetyl-benzenesulfonyl chloride as the sulfonyl chloride of choice. MS(ES) m/e 408 [M+H]$^+$.

Example 357

4-Amino-3-(4-((2,4-dichlorobenzenesulfonyl)amino)phenyl)furo[2,3-d]pyrimidine

The compound was prepared following the procedure described in Example 318, using 2,4-dichloro-benzenesulfonyl chloride as the sulfonyl chloride of choice. MS(ES) m/e 435 [M+H]$^+$.

Example 358

4-Amino-3-(4-((3,5-bis-(trifluoromethyl)benzenesulfonyl)-amino)phenyl)furo[2,3-d]pyrimidine The compound was prepared following the procedure described in Example 318, using 3,5-bis-trifluoromethyl-benzenesulfonyl chloride as the sulfonyl chloride of choice. MS(ES) m/e 503 [M+H]$^+$.

Example 359

4-Amino-3-(4-((5-(N-(benzoyl)aminomethyl)thiophene-2-sulfonyl)-amino)phenyl)furo[2,3-d]pyrimidine The compound was prepared following the procedure described in Example 318, using 5-(N-(benzoyl)aminomethyl)thiophene-2-sulfonyl chloride as the the sulfonyl chloride of choice. MS(ES) m/e 506 [M+H]$^+$.

Example 360

4-Amino-3-(4-((2-(acetylamino)-4-methylthiazole-5-sulfonyl)-amino)phenyl)furo[2,3-d]pyrimidine The compound was prepared following the procedure described in Example 318, using 2-acetylamino-4-metylthiazole-5-sulfonyl chloride as the the sulfonyl chloride of choice. MS(ES) m/e 445 [M+H]$^+$.

Example 361

4-Amino-3-(4-((3-chloro-4-fluorobenzenesulfonyl)amino)phenyl)-furo[2,3-d]pyrimidine The compound was prepared following the procedure described in Example 318, using 3-chloro-4-fluoro-benzenesulfonyl chloride as the sulfonyl chloride of choice. MS(ES) m/e 420 [M+H]$^+$.

Example 362

4-Amino-3-(4-((4-ethyl benzenesulfonyl)amino)phenyl)furo[2,3-d]pyrimidine

The compound was prepared following the procedure described in Example 318, using 4-ethyl-benzenesulfonyl chloride as the sulfonyl chloride of choice. MS(ES) m/e 395 [M+H]$^+$.

Example 363

4-Amino-3-(4-((3,5-bis-(trifluoromethyl)phenylmethyl)sulfonyl)-amino)phenyl)furo[2,3-d]pyrimidine The compound was prepared following the procedure described in Example 318, using (3,5-bis-trifluoromethylphenyl)-methanesulfonyl chloride as the sulfonyl chloride of choice. MS(ES) m/e 517 [M+H]$^+$.

Example 364

4-Amino-3-(4-((4-tert-butylbenzenesulfonyl)amino)phenyl)furo[2,3-d]pyrimidine

The compound was prepared following the procedure described in Example 318, using 4-tert-butyl-benzenesulfonyl chloride as the sulfonyl chloride of choice. MS(ES) m/e 423 [M+H]$^+$.

Example 365

4-Amino-3-(4-((2-nitrophenylmethyl)sulfonyl)amino)phenyl)furo[2,3-d]pyrimidine

The compound was prepared following the procedure described in Example 318, using (2-nitro-phenyl)-methanesulfonyl chloride as the sulfonyl chloride of choice. MS(ES) m/e 426 [M+H]$^+$.

Example 366

4-Amino-3-(4-((5-(isoxazol-3-yl)thiophene-2-sulfonyl)-amino)phenyl)furo[2,3-d]pyrimidine The compound was prepared following the procedure described in Example 318, using 5-isoxazol-3-yl-thiophene-2-sulfonyl chloride as the sulfonyl chloride of choice. MS(ES) m/e 440 [M+H]$^+$.

Example 367

4-Amino-3-(4-((benzo[1,2,5]thiadiazole-4-sulfonyl)-amino)phenyl)furo[2,3-d]pyrimidine The compound was prepared following the procedure described in Example 318, using benzo(1,2,5)thiadiazole-4-sulfonyl chloride as the sulfonyl chloride of choice. MS(ES) m/e 425 [M+H]$^+$.

Example 368

4-Amino-3-(4-((4-cyanobenzenesulfonyl)amino)phenyl)furo[2,3-d]pyrimidine

The compound was prepared following the procedure described in Example 318, using 4-cyano-benzenesulfonyl chloride as the sulfonyl chloride of choice. MS(ES) m/e 392 [M+H]$^+$.

Example 369

4-Amino-3-(4-((benzo[1,4]dioxan-6-sulfonyl)amino)phenyl)-furo[2,3-d]pyrimidine

The compound was prepared following the procedure described in Example 318, using 2,3-dihydro-benzo(1,4)dioxine-6-sulfonyl chloride as the sulfonyl chloride of choice. MS(ES) m/e 425 [M+H]$^+$.

Example 370

4-Amino-3-(4-((5-(2-pyridyl)thiophene-2-sulfonyl)-amino)phenyl)furo[2,3-d]pyrimidine The compound was prepared following the procedure described in Example 318, using 5-pyridin-2-yl-thiophene-2-sulfonyl chloride as the sulfonyl chloride of choice. MS(ES) m/e 450 [M+H]$^+$.

Example 371

4-Amino-3-(4-((3-(trifluoromethyl)phenylmethyl)sulfonyl)-amino)phenyl)furo[2,3-d]pyrimidine The compound was prepared following the procedure described in Example 318, using (3-trifluoromethyl-phenyl)-methanesulfonyl chloride as the sulfonyl chloride of choice. MS(ES) m/e 449 [M+H]$^+$.

Example 372

4-Amino-3-(4-((3,5-dichlorophenylmethyl)sulfonyl)-amino)phenyl)furo[2,3-d]pyrimidine The compound was prepared following the procedure described in Example 318, using (3,5-dichloro-phenyl)-methanesulfonyl chloride as the sulfonyl chloride of choice. MS(ES) m/e 450 [M+H]$^+$.

Example 373

4-Amino-3-(4-((5-(N-(4-chlorobenzoyl)aminomethyl)thiophene-2-sulfonyl)amino)phenyl)furo[2,3-d]pyrimidine The compound was prepared following the procedure described in Example 318, using 5-(N-(4-chlorobenzoyl)aminomethyl)-thiophene-2-sulfonyl chloride as the the sulfonyl chloride of choice. MS(ES) m/e 541 [M+H]$^+$.

Example 374

4-Amino-3-(4-((2,6-dichlorobenzenesulfonyl)amino)phenyl)-furo[2,3-d]pyrimidine

The compound was prepared following the procedure described in Example 318, using 2,6-dichloro-benzenesulfonyl chloride as the sulfonyl chloride of choice. MS(ES) m/e 436 [M+H]$^+$.

Example 375

4-Amino-3-(4-((4-(benzenesulfonyl)thiophene-2-sulfonyl)amino)-phenyl)furo[2,3-d]pyrimidine The compound was prepared following the procedure described in Example 318, using 4-benzenesulfonyl-thiophene-2-sulfonyl chloride as the sulfonyl chloride of choice. MS(ES) m/e 513 [M+H]$^+$.

Example 376

4-Amino-3-(4-((4-bromo-2-ethylbenzenesulfonyl)amino)phenyl)-furo[2,3-d]pyrimidine The compound was prepared following the procedure described in Example 318, using 4-bromo-2-ethyl-benzenesulfonyl chloride as the sulfonyl chloride of choice. MS(ES) m/e 474 [M+H]$^+$.

Example 377

4-Amino-3-(4-((3-chloro-2-methylbenzenesulfonyl)amino)phenyl)-furo[2,3-d]pyrimidine The compound was prepared following the procedure described in Example 318, using 3-chloro-2-methyl-benzenesulfonyl chloride as the sulfonyl chloride of choice. MS(ES) m/e 416 [M+H]$^+$.

Example 378

4-Amino-3-(4-((5-bromothiophene-2-sulfonyl)amino)-phenyl)furo[2,3-d]pyrimidine

The compound was prepared following the procedure described in Example 318, using 5-bromo-thiophene-2-sulfonyl chloride as the sulfonyl chloride of choice. MS(ES) m/e 452 [M+H]$^+$.

Example 379

4-Amino-3-(4-((4-fluorobenzenesulfonyl)amino)
phenyl)furo[2,3-d]pyrimidine

The compound was prepared following the procedure described in Example 318, using 4-fluoro-benzenesulfonyl chloride as the sulfonyl chloride of choice. MS(ES) m/e 385 [M+H]$^+$.

Example 380

4-Amino-3-(4-((2-chlorobenzenesulfonyl)amino)
phenyl)furo[2,3-d]pyrimidine

The compound was prepared following the procedure described in Example 318, using 2-chloro-benzenesulfonyl chloride as the sulfonyl chloride of choice. MS(ES) m/e 402 [M+H]$^+$.

Example 381

4-Amino-3-(4-((5-(2-methylthio-pyrimidin-4-yl)
thiophene-2-sulfonyl)amino)phenyl)furo[2,3-d]pyrimidine The compound was prepared following the procedure described in Example 318, using 5-(2-methylsulfanyl-pyrimidin-4-yl)-thiophene-2-sulfonyl chloride as the sulfonyl chloride of choice. MS(ES) m/e 497 [M+H]$^+$.

Example 382

4-Amino-3-(4-((5-(5-(trifluoromethyl)pyridine-2-sulfonyl)thiophene-2-sulfonyl)amino)phenyl)furo[2,3-d]pyrimidine The compound was prepared following the procedure described in Example 318, using 5-(5-trifluoromethyl-pyridine-2-sulfonyl)-thiophene-2-sulfonyl chloride as the sulfonyl chloride of choice. MS(ES) m/e 582 [M+H]$^+$.

Example 383

4-Amino-3-(4-((benzo[1,2,5]oxadiazole-4-sulfonyl)
amino)phenyl)-furo[2,3-d]pyrimidine The compound was prepared following the procedure described in Example 318, using benzo(1,2,5)oxadiazole-4-sulfonyl chloride as the sulfonyl chloride of choice. MS(ES) m/e 409 [M+H]$^+$.

Example 384

4-Amino-3-(4-((6-chloro-imidazo[2,1-b]thiazole-5-sulfonyl)amino)phenyl)-furo[2,3-d]pyrimidine The compound was prepared following the procedure described in Example 318, using 6-chloro-imidazo(2,1b)thiazole-5-sulfonyl chloride as the sulfonyl chloride of choice. MS(ES) m/e 448 [M+H]$^+$.

Example 385

4-Amino-3-(4-((2,5-dimethylbenzenesulfonyl)
amino)phenyl)furo[2,3-d]pyrimidine

The compound was prepared following the procedure described in Example 318, using 2,5-dimethyl-benzenesulfonyl chloride as the sulfonyl chloride of choice. MS(ES) m/e 395 [M+H]$^+$.

Example 386

4-Amino-3-(4-((5-(2-methylthiazol-4-yl)thiophene-2-sulfonyl)-amino)phenyl)furo[2,3-d]pyrimidine The compound was prepared following the procedure described in Example 318, using 5-(2-methyl-thiazol-4-yl)-thiophene-2-sulfonyl chloride as the sulfonyl chloride of choice. MS(ES) m/e 470 [M+H]$^+$.

Example 387

4-Amino-3-(4-((5-(5-trifluoromethyl-isoxazol-3-yl)
thiophene-2-sulfonyl)-amino)phenyl)furo[2,3-d]pyrimidine The compound was prepared following the procedure described in Example 318, using 5-(5-trifluoromethyl-isoxazole-3-yl)-thiophene-2-sulfonyl chloride as the sulfonyl chloride of choice. MS(ES) m/e 508 [M+H]$^+$.

Example 388

4-Amino-3-(4-((2-methoxy-5-methylbenzenesulfonyl)amino)phenyl)-furo[2,3-d]pyrimidine The compound was prepared following the procedure described in Example 318, using 2-methoxy-5-methyl-benzenesulfonyl chloride as the sulfonyl chloride of choice. MS(ES) m/e 411 [M+H]$^+$.

Example 389

4-Amino-3-(4-((5-chloro-3-methylbenzo[b]
thiophene-2-sulfonyl)amino)phenyl)furo[2,3-d]pyrimidine The compound was prepared following the procedure described in Example 318, using 5-chloro-3-methyl-benzo(b)-thiophene-2-sulfonyl chloride as the sulfonyl chloride of choice. MS(ES) m/e 472 [M+H]$^+$.

Example 390

4-Amino-3-(4-((2,4-dichloro-5-methylbenzenesulfonyl)amino)-phenyl)furo[2,3-d]pyrimidine The compound was prepared following the procedure described in Example 318, using 2,4-dichloro-5-methyl-benzenesulfonyl chloride as the sulfonyl chloride of choice. MS(ES) m/e 450 [M+H]$^+$.

Example 391

4-Amino-3-(4-((5-fluoro-2-methylbenzenesulfonyl)amino)phenyl)-furo[2,3-d]pyrimidine The compound was prepared following the procedure described in Example 318, using 2-methyl-5-fluoro-benzenesulfonyl chloride as the sulfonyl chloride of choice. MS(ES) m/e 399 [M+H]$^+$.

Example 392

4-Amino-3-(4-((5-chloronaphthalenesulfonyl)amino)phenyl)-furo[2,3-d]pyrimidine

The compound was prepared following the procedure described in Example 318, using 5-chloro-naphthalene-1-sulfonyl chloride as the sulfonyl chloride of choice. MS(ES) m/e 452 [M+H]$^+$.

Example 393

4-Amino-3-(4-((4-(3,5-dichlorophenoxy)benzenesulfonyl)amino)-phenyl)furo[2,3-d]pyrimidine The compound was prepared following the procedure described in Example 318, using 4-(3,5-dichloro-phenoxy)-benzenesulfonyl chloride as the sulfonyl chloride of choice. MS(ES) m/e 528 [M+H]$^+$.

Example 394

4-Amino-3-(4-((3-(4-chlorophenoxy)benzenesulfonyl)amino)-phenyl)furo[2,3-d]pyrimidine The compound was prepared following the procedure described in Example 318, using 3-(4-chloro-phenoxy)-benzenesulfonyl chloride as the sulfonyl chloride of choice. MS(ES) m/e 494 [M+H]$^+$.

Example 395

4-Amino-3-(4-(((4-pyridylmethyl)sulfonyl)amino)phenyl)furo[2,3-d]pyrimidine

The compound was prepared following the procedure described in Example 318, using pyridin-4-yl-methanesulfonyl chloride as the sulfonyl chloride of choice. MS(ES) m/e 382 [M+H]$^+$.

Example 396

4-Amino-3-(4-((4-(2-pyridyloxy)benzenesulfonyl)amino)-phenyl)furo[2,3-d]pyrimidine The compound was prepared following the procedure described in Example 318, using 4-(pyridin-2-yloxy)-benzenesulfonyl chloride as the sulfonyl chloride of choice. MS(ES) m/e 461 [M+H]$^+$.

Example 397

4-Amino-3-(4-((5-([1,2,3]thiadiazol-4-yl)thiophene-2-sulfonyl)-amino)phenyl)furo[2,3-d]pyrimidine The compound was prepared following the procedure described in Example 318, 5-(1,2,3)thiadiazol-4-yl-thiophene-2-sulfonyl chloride as the sulfonyl chloride of choice. MS(ES) m/e 457 [M+H]$^+$.

Example 398

4-Amino-3-(4-((5-(4-cyano-1-methyl-5-methylthio-1H-pyrazol-3-yl)thiophene-2-sulfonyl)amino)phenyl)furo[2,3-d]pyrimidine The compound was prepared following the procedure described in Example 318, 5-(4-cyano-1-methyl-5-methylsulfanyl-1 H-pyrazol-3-yl)-thiophene-2-sulfonyl chloride as the sulfonyl chloride of choice. MS(ES) m/e 524 [M+H]$^+$.

Example 399

4-Amino-3-(4-((3-(4-chlorophenyl)benzenesulfonyl)amino)-phenyl)furo[2,3-d]pyrimidine The compound was prepared following the procedure described in Example 318, 4-chloro-biphenyl-3-sulfonyl chloride as the sulfonyl chloride of choice. MS(ES) m/e 478 [M+H]$^+$.

Example 400

4-Amino-3-(4-((4-(4-pyridyloxy)benzenesulfonyl)amino)-phenyl)furo[2,3-d]pyrimidine The compound was prepared following the procedure described in Example 318, using 4-(pyridin-4-yloxy)-benzenesulfonyl chloride as the sulfonyl chloride of choice. MS(ES) m/e 461 [M+H]$^+$.

Example 401

4-Amino-3-(4-((4-butoxybenzenesulfonyl)amino)phenyl)furo[2,3-d]pyrimidine

The compound was prepared following the procedure described in Example 318, using 4-butoxy-benzenesulfonyl chloride as the sulfonyl chloride of choice. MS(ES) m/e 439 [M+H]$^+$.

Example 402

4-Amino-3-(4-((4-acetamide-3-chlorobenzenesulfonyl)amino)-phenyl)furo[2,3-d]pyrimidine The compound was prepared following the procedure described in Example 318, using 4-acetylamino-3-chloro-benzenesulfonyl chloride as the sulfonyl chloride of choice. MS(ES) m/e 459 [M+H]$^+$.

Example 403

4-Amino-3-(4-((4-(trifluoromethyl)phenylmethyl)sulfonyl)-amino)phenyl)furo[2,3-d]pyrimidine The compound was prepared following the procedure described in Example 318, using (4-trifluoromethyl-phenyl)-methanesulfonyl chloride as the sulfonyl chloride of choice. MS(ES) m/e 449 [M+H]$^+$.

Example 404

4-Amino-3-(4-((4-chlorophenylmethyl)sulfonyl)amino)phenyl)-furo[2,3-d]pyrimidine The compound was prepared following the procedure described in Example 318, using (4-chloro-phenyl)-methanesulfonyl chloride as the sulfonyl chloride of choice. MS(ES) m/e 416 [M+H]$^+$.

Example 405

4-Amino-3-(4-((3,4-dichlorophenylmethyl)sulfonyl)amino)phenyl)-furo[2,3-d]pyrimidine The compound was prepared following the procedure described in Example 318, using (3,4-dichloro-phenyl)-methanesulfonyl chloride as the sulfonyl chloride of choice. MS(ES) m/e 450 [M+H]$^+$.

Example 406

4-Amino-3-(4-((4-fluorophenylmethyl)sulfonyl)amino)phenyl)-furo[2,3-d]pyrimidine The compound was prepared following the procedure described in Example 318, using (4-fluoro-phenyl)-methanesulfonyl chloride as the sulfonyl chloride of choice. MS(ES) m/e 399 [M+H]$^+$.

Example 407

4-Amino-3-(4-((6-(dimethylamino)naphthalene-1-sulfonyl)amino)phenyl)furo[2,3-d]pyrimidine The compound was prepared following the procedure described in Example 318, using 6-dimethylamino-naphthalene-1-sulfonyl chloride as the sulfonyl chloride of choice. MS(ES) m/e 460 [M+H]$^+$.

Example 408

4-Amino-3-(4-((isoquinoline-5-sulfonyl)amino)phenyl)furo[2,3-d]pyrimidine

The compound was prepared following the procedure described in Example 318, using isoquinoline-5-sulfonyl chloride as the sulfonyl chloride of choice. MS(ES) m/e 418 [M+H]$^+$.

Example 409

4-Amino-3-(4-((1-naphthalenesulfonyl)amino)phenyl)furo[2,3-d]pyrimidine

The compound was prepared following the procedure described in Example 318, using naphthalene-1-sulfonyl chloride as the sulfonyl chloride of choice. MS(ES) m/e 417 [M+H]$^+$.

Example 410

4-Amino-3-(4-((phenylmethyl)sulfonyl)amino)phenyl)furo[2,3-d]pyrimidine

The compound was prepared following the procedure described in Example 318, using phenyl-methanesulfonyl chloride as the sulfonyl chloride of choice. MS(ES) m/e 381 [M+H]$^+$.

Example 411

4-Amino-3-(4-(((2-fluoro-5-(trifluoromethyl)phenylmethyl)-sulfonyl)amino)phenyl)furo[2,3-d]pyrimidine The compound was prepared following the procedure described in Example 318, using (2-fluoro-5-trifluoromethyl-phenyl)-methanesulfonyl chloride as the sulfonyl chloride of choice. MS(ES) m/e 467 [M+H]$^+$.

Example 412

4-Amino-3-(4-((4-(3,4-dichlorophenoxy)benzenesulfonyl)amino)-phenyl)furo[2,3-d]pyrimidine The compound was prepared following the procedure described in Example 318, using (3,4-dichloro-phenoxy)-benzenesulfonyl chloride as the sulfonyl chloride of choice. MS(ES) m/e 528 [M+H]$^+$.

Example 413

4-Amino-3-(4-((4-(2-chlorothiazol-5-ylmethoxy)benzenesulfonyl)-amino)phenyl)furo[2,3-d]pyrimidine The compound was prepared following the procedure described in Example 318, using (2-chloro-thiazol-5-yl-methoxy)-benzenesulfonyl chloride as the sulfonyl chloride of choice. MS(ES) m/e 515 [M+H]$^+$.

Example 414

4-Amino-3-(4-((4-(3,4-dichlorophenyl)benzenesulfonyl)amino)-phenyl)furo[2,3-d]pyrimidine The compound was prepared following the procedure described in Example 318, using 3',4'-dichloro-biphenyl-4-sulfonyl chloride as the sulfonyl chloride of choice. MS(ES) m/e 512 [M+H]$^+$.

Example 415

4-Amino-3-(4-((4-(trifluoromethyl)benzenesulfonyl)amino)-phenyl)furo[2,3-d]pyrimidine The compound was prepared following the procedure described in Example 318, using trifluoromethyl-benzenesulfonyl chloride as the sulfonyl chloride of choice. MS(ES) m/e 435 [M+H]$^+$.

Example 416

4-Amino-3-(4-((1,1-dioxo-tetrahydro-1/-thiophene-3-sulfonyl)amino)phenyl)furo[2,3-d]pyrimidine The compound was prepared following the procedure described in Example 318, using 1,1-dioxo-tetrahydro-1/-thiophene-3-sulfonyl chloride as the sulfonyl chloride of choice. MS(ES) m/e 409 [M+H]$^+$.

Example 417

4-Amino-3-(4-((4-(phenylazo)benzenesulfonyl)amino)-phenyl)furo[2,3-d]pyrimidine

The compound was prepared following the procedure described in Example 318, using 4-phenylazo-benzenesulfonyl chloride as the sulfonyl chloride of choice. MS(ES) m/e 471 [M+H]$^+$.

Example 418

4-Amino-3-(4-((2,5-dibromo-3,6-difluorobenzenesulfonyl)amino)-phenyl)furo[2,3-d]pyrimidine The compound was prepared following the procedure described in Example 318, using 2,5-dibromo-3,6-difluorobenzenesulfonyl chloride as the sulfonyl chloride of choice. MS(ES) m/e 561 [M+H]$^+$.

Example 419

4-Amino-3-(4-((4-bromo-2-(trifluoromethoxy)benzenesulfonyl)-amino)phenyl)furo[2,3-d]pyrimidine The compound was prepared following the procedure described in Example 318, using 4-bromo-2-trifluoromethoxy-benzenesulfonyl chloride as the sulfonyl chloride of choice. MS(ES) m/e 530 [M+H]$^+$.

Example 420

4-Amino-3-(4-((2-chloro-4-cyanobenzenesulfonyl)amino)-phenyl)furo[2,3-d]pyrimidine The compound was prepared following the procedure described in Example 318, using 2-chloro-4-cyano-benzenesulfonyl chloride as the sulfonyl chloride of choice. MS(ES) m/e 427 [M+H]$^+$.

Example 421

4-Amino-3-(4-((2,3,5,6-tetramethylbenzenesulfonyl)amino)-phenyl)furo[2,3-d]pyrimidine The compound was prepared following the procedure described in Example 318, using 2,3,5,6-tetramethyl-benzenesulfonyl chloride as the sulfonyl chloride of choice. MS(ES) m/e 423 [M+H]$^+$.

Example 422

4-Amino-3-(4-((3,5-dichloro-2-hydroxybenzenesulfonyl)amino)-phenyl)furo[2,3-d]pyrimidine The compound was prepared following the procedure described in Example 318, using 3,5-dichloro-2-hydroxy)-benzenesulfonyl chloride as the sulfonyl chloride of choice. MS(ES) m/e 452 [M+H]$^+$.

Example 423

4-Amino-3-(4-((3-chloro-4-(1,3-dioxo-2-aza-spiro(4,4)non-2-yl)benzenesulfonyl)amino)phenyl)furo[2,3-d]pyrimidine The compound was prepared following the procedure described in Example 318, using 3-chloro-4-[1,3-dioxo-2-aza-spiro(4,4)non-2-yl]-benzenesulfonyl chloride as the sulfonyl chloride of choice. MS(ES) m/e 553 [M+H]$^+$.

Example 424

4-Amino-3-(4-(((2-chloro-5-(trifluoromethyl)phenylmethyl)-sulfonyl)amino)phenyl)furo[2,3-d]pyrimidine The compound was prepared following the procedure described in Example 318, using (2-chloro-5-trifluoromethyl-phenyl)-methanesulfonyl chloride as the sulfonyl chloride of choice. MS(ES) m/e 483 [M+H]$^+$.

Example 425

4-Amino-3-(4-(((p-tolylmethyl)sulfonyl)amino)phenyl)furo[2,3-d]pyrimidine

The compound was prepared following the procedure described in Example 318, using p-tolyl-methanesulfonyl chloride as the sulfonyl chloride of choice. MS(ES) m/e 395 [M+H]$^+$.

Example 426

4-Amino-3-(4-(((1,2-dimethyl-1H-imidazol-4-yl)sulfonyl)amino)-phenyl)furo[2,3-d]pyrimidine The compound was prepared following the procedure described in Example 318, using 1,2-dimethyl-1H-imidazole-4-sulfonyl chloride as the sulfonyl chloride of choice. MS(ES) m/e 385 [M+H]$^+$.

Example 427

4-Amino-3-(4-((5-((3-chloro-5-(trifluoromethyl)pyridin-2-yl)methyl)thiophene-2-sulfonyl)amino)phenyl)furo[2,3-d]pyrimidine The compound was prepared following the procedure described in Example 318, using 5-(chloro-trifluoromethyl-pyridin-2-ylmethyl)-thiophene-2-sulfonyl chloride as the sulfonyl chloride of choice. MS(ES) m/e 567 [M+H]$^+$.

Example 428

4-Amino-3-(4-((4-butylbenzenesulfonyl)amino)phenyl)furo[2,3-d]pyrimidine

The compound was prepared following the procedure described in Example 318, using 4-butyl-benzenesulfonyl chloride as the sulfonyl chloride of choice. MS(ES) m/e 423 [M+H]$^+$.

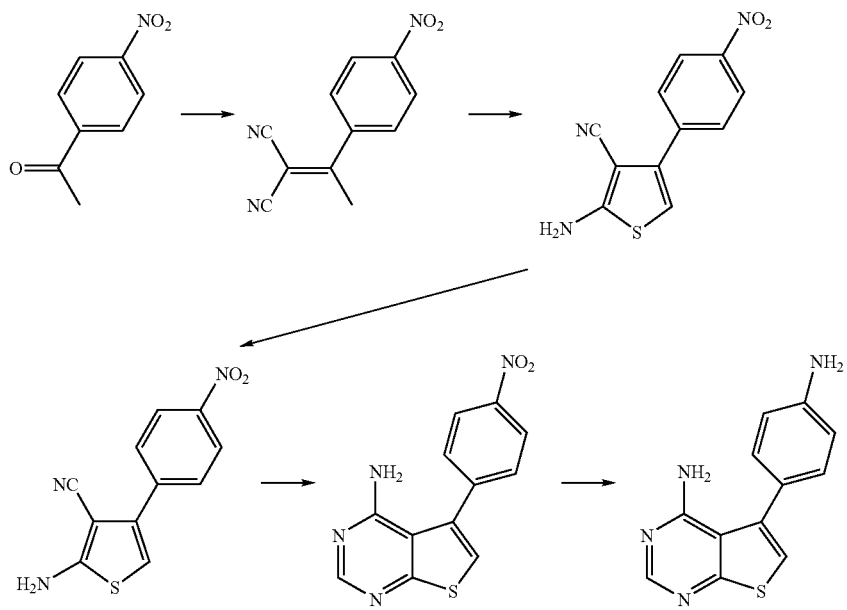

Scheme 10

Preparation of Intermediates 10–13 following are depicted in Scheme 10.

Intermediate Example 10

2-[1-(4-Nitrophenyl)-ethylidene]-malononitrile p-Nitro-acetophenone (165 g/mole; 4.0 g; 24 mmoles), ammonium acetate (0.50 g) and glacial acetic acid (0.80 mL) were added to a round-bottom flask containing 20 mL toluene, and heated to reflux using a Dean-Stark trap and a reflux condenser. Separately, malononitrile (66 g/mole; 2.0 g; 30.3 mmoles) was dissolved in 5 mL dioxane and 20 mL toluene, transferred to an addition funnel and added dropwise to the heated solution of ketone. Upon completion of the addition, the system was heated for 2 hours and then cooled to room temperature. The reaction mixture was poured into 150 mL brine and 100 mL ethyl acetate. The aqueous layer was separated and washed with 50 mL ethyl acetate. The organic layers were combined and dried over anhydrous sodium sulfate. The solvent was removed in vacuo and the crude product 2-[1-(4-nitrophenyl)-ethylidene]-malononitrile (213 g/mole) was used as such in Intermediate Example 11.

Intermediate Example 11

2-Amino-4-(4-nitro-phenyl)-thiophene-3-carbonitrile

Crude 2-[1-(4-nitrophenyl)-ethylidene]-malononitrile (24 mmoles assumed) was treated with sulfur (2 g) and 50 mL DMF. The system was heated to 120° C. in an oil bath. When the reaction was judged complete by TLC (product has Rf=0.44 in 40% ethyl acetate-hexane), the mixture was cooled to room temperature and poured into 50 mL brine and 100 mL ethyl acetate. The yellow solid that separated (mostly sulfur) was removed by filtration. The organic layer was washed with 3×50 mL brine, and the combined aqueous layers were back-extracted with 50 mL ethyl acetate. The combined organic layers were dried over anhydrous sodium sulfate, filtered and concentrated to dryness. The residue was treated with 100 mL methylene chloride, warmed to reflux, cooled to 15° C. and filtered. The resulting yellow precipitate was mostly desired product 2-amino-4-(4-nitro-phenyl)-thiophene-3-carbonitrile (245 g/mole; ~50% yield from p-nitro-acetophenone; MP 193–195° C. (dec)).

Intermediate Example 12

4-Amino-3-(4-nitrophenyl)thieno[2,3-d]pyrimidine

2-Amino-4-(4-nitrophenyl)-thiophene-3-carbonitrile (17.5 g; 245 g/mole; 71.5 moles) was heated in 250 mL formamide at 200° C. for 15 minutes and cooled to room temperature. The dark solution was poured into 1 L methylene chloride and 500 mL brine. A dark precipitate (A) formed and was collected by filtration. The filtrate (B) was reserved. Precipitate (A) was washed with 3×500 mL hot ethyl acetate. The washings were reserved, while the solid constituted crude product (Rf=0.76 in 100% ethyl acetate). Filtrate (B) was decanted and the organic layer was reserved. The aqueous layer was washed with 2×100 mL ethyl acetate, and the resulting stripped aqueous layer was discarded. All organic layers, including washings, were combined and concentrated to dryness. The resulting solid residue was submitted to washings with hot ethyl acetate. The resulting washed solid was combined with the previous crop of crude product, in a total ~36% yield of 4-Amino-3-(4-nitrophenyl)-thieno[2,3-d]pyrimidine in 3 steps.

Intermediate Example 13

4-Amino-3-(4-aminophenyl)thieno[2,3-d]pyrimidine

4-Amino-3-(4-nitrophenyl)thieno[2,3-d]pyrimidine (11.6 g; 272 g/mole; 42.6 mmoles) was treated with 500 mL HCl 6N and 15 g elemental tin at room temperature. After 15 minutes the reaction was complete by TLC (product has Rf=0.50 in 100% ethyl acetate). The system was placed in an ice bath and treated with concentrated ammonium hydroxide to pH 10 (~300 mL). At this point, extensive precipitation was observed. Precipitate (A) was collected by filtration and reserved, and the clear solution was treated with 1 L methylene chloride. The aqueous layer was then back-extracted with 3×200 mL methylene chloride. The organic layers were combined, dried over anhydrous sodium sulfate, and filtered. Precipitate (A), consisting of a mixture of tin salts and product, was extracted with boiling methanol until washings showed no more product by TLC. The resulting solution was combined with the previously reserved organic layers, filtered, concentrated to dryness and dried overnight, generating desired product 4-Amino-3-(4-aminophenyl)thieno[2,3-d]pyrimidine (242 g/mole; nearly quantitative yield), which was recrystallized from methanol.

Example 429

4-Amino-3-(4-((2-fluoro-5-(trifluoromethyl)phenyl)-aminocarbonylamino)phenyl)thieno[2,3-d]pyrimidine 4-Amino-3-(4-aminophenyl)thieno[2,3-d]pyrimidine (0.2 mmoles) was dissolved in 1 mL amine-free DMF and treated with 0.3 mmoles of the isocyanate of choice (2-fluoro-5-trifluoromethyl-phenyl isocyanate) and 0.6 mmoles of diisopropylethylamine for 2 hours at room temperature. The reaction mixture was treated with 0.5 mL 1:1 methanol-triethylamine for half an hour and concentrated to dryness in a Speedvac system, reconstituted in 1 mL DMSO and purified by prep HPLC. The fraction containing the desired product was collected and concentrated to dryness. MH+=448.

Example 430

4-Amino-3-(4-((5-indanyl)aminocarbonylamino)phenyl)thieno[2,3-d]pyrimidine

The compound was prepared following the procedure described in Example 429, using 3-indan-5-yl isocyanate as the isocyanate of choice. MH+=402.

Example 431

4-Amino-3-(4-((2-methylphenyl)aminocarbonylamino)phenyl)-thieno[2,3-d]pyrimidine The compound was prepared following the procedure described in Example 429, using o-tolyl isocyanate as the isocyanate of choice. MH+=376.

Example 432

4-Amino-3-(4-((3-methylphenyl)aminocarbonylamino)phenyl)-thieno[2,3-d]pyrimidine The compound was prepared following the procedure described in Example 429, using m-tolyl isocyanate as the isocyanate of choice. MH+=376.

Example 433

4-Amino-3-(4-((3-(trifluoromethyl)phenyl)aminocarbonylamino)-phenyl)thieno[2,3-d]pyrimidine The compound was prepared following the procedure described in Example 429, using m-trifluoromethylphenyl isocyanate as the isocyanate of choice. MH+=430.

Example 434

4-Amino-3-(4-((2-chloro-5-(trifluoromethyl)phenyl)-aminocarbonylamino)phenyl)thieno[2,3-d]pyrimidine The compound was prepared following the procedure described in Example 429, using 2-chloro-5-trifluoromethyl-phenyl isocyanate as the isocyanate of choice. MH+=464.

Example 435

4-Amino-3-(4-(((2,5-difluorophenyl)acetyl)amino)phenyl)thieno[2,3-d]pyrimidine 0.25 mmoles of the carboxylic acid of choice (2,5-difluorophenyl-acetic acid; 0.25 mmoles) and 0.25 mmoles of HBTU were dissolved in 1 mL amine-free DMF. To this solution was added dropwise a solution of 4-Amino-3-(4-aminophenyl)thieno[2,3-d]-pyrimidine in 1 mL DMF. The resulting solution was treated with 0.3 mL of Hunig's base. The system was stirred at room temperature overnight and then treated with 0.5 mL of 1:1 MeOH-diethylamine. The system was concentrated to dryness in a Speedvac system, reconstituted in 1 mL DMSO and purified by prep HPLC. MH+=397.

Example 436

4-Amino-3-(4-((2-fluoro-5-(trifluoromethyl)benzoyl)amino)-phenyl)thieno[2,3-d]pyrimidine The compound was prepared following the procedure described in Example 435, using 2-fluoro-5-trifluoromethyl-benzoic acid as the carboxylic acid of choice. MH+=433.

Example 437

4-Amino-3-(4-(benzoylamino)phenyl)thieno[2,3-d]pyrimidine

The compound was prepared following the procedure described in Example 435, using benzoic acid as the carboxylic acid of choice. MH+=347.

Example 438

4-Amino-3-(4-((2,6-difluorobenzoyl)amino)phenyl)thieno[2,3-d]pyrimidine

The compound was prepared following the procedure described in Example 435, using 2,6-difluorobenzoic acid as the carboxylic acid of choice. MH+=383.

Example 439

4-Amino-3-(4-(((S)-2-amino-2-phenylacetyl)amino)
phenyl)-thieno[2,3-d]pyrimidine The compound was prepared following the procedure described in Example 435, using (S)-N-Boc-2-amino-phenylacetic acid as the carboxylic acid of choice. After amide coupling and HPLC purification, the Boc-containing product was stirred with 20% trifluoroacetic acid-methylene chloride for 5 minutes, concentrated to dryness and purified by HPLC to afford the desired product MH+=376.

Example 440

4-Amino-3-(4-(((1S,2S)-2-phenyl-cyclopropanecarbonyl)amino)-phenyl)thieno[2,3-d]pyrimidine The compound was prepared following the procedure described in Example 435, using (1S,2S)-2-phenyl-cyclopropanecarboxylic acid as the carboxylic acid of choice. MH+=387.

Example 441

4-Amino-3-(4-((2,5-difluorobenzoyl)amino)phenyl)
thieno[2,3-d]pyrimidine

The compound was prepared following the procedure described in Example 435, using 2,5-difluorophenylacetic acid as the carboxylic acid of choice. MH+=383.

Example 442

4-Amino-3-(4-(((R)-2-amino-2-phenylacetyl)amino)
phenyl)-thieno[2,3-d]pyrimidine The compound was prepared following the procedure described in Example 435, using (R)-N-Boc-2-amino-phenylacetic acid as the carboxylic acid of choice. After amide coupling and HPLC purification, the Boc-containing product was stirred with 20% trifluoroacetic acid-methylene chloride for 5 minutes, concentrated to dryness and purified by HPLC to afford the desired product MH+=376.

Example 443

4-Amino-3-(4-((1-phenyl-cyclopropanecarbonyl)
amino)-phenyl)thieno[2,3-d]pyrimidine The compound was prepared following the procedure described in Example 435, using 1-phenyl-cyclopropanecarboxylic acid as the carboxylic acid of choice. MH+=387.

Example 444

4-Amino-3-(4-(((2,6-difluorophenyl)acetyl)amino)
phenyl)thieno[2,3-d]pyrimidine

The compound was prepared following the procedure described in Example 435, using 2,6-difluorophenylacetic acid as the carboxylic acid of choice. MH+=397.

Example 445

4-Amino-3-(4-((phenylacetyl)amino)phenyl)thieno
[2,3-d]pyrimidine

The compound was prepared following the procedure described in Example 435, using phenylacetic acid as the carboxylic acid of choice. MH+=361.

Example 446

4-Amino-3-(4-(((3,5-bis-(trifluoromethyl)phenyl)
acetyl)amino)-phenyl)thieno[2,3-d]pyrimidine The compound was prepared following the procedure described in Example 435, using 3,5-bis-trifluoromethyl-phenylacetic acid as the carboxylic acid of choice. MH+=497.

Example 447

4-Amino-3-(4-(((2,4-bis-(trifluoromethyl)phenyl)
acetyl)amino)-phenyl)thieno[2,3-d]pyrimidine The compound was prepared following the procedure described in Example 435, using 2,4-bis-trifluoromethyl-phenylacetic acid as the carboxylic acid of choice. MH+=497.

Example 448

4-Amino-3-(4-(((3-(trifluoromethylthio)phenyl)
acetyl)amino)-phenyl)thieno[2,3-d]pyrimidine The compound was prepared following the procedure described in Example 435, using 3-trifluoromethylthio-phenylacetic acid as the carboxylic acid of choice. MH+=461.

Example 449

4-Amino-3-(4-(((1R,2R)-2-phenyl-cyclopropanecarbonyl)amino)-phenyl)thieno[2,3-d]pyrimidine The compound was prepared following the procedure described in Example 435, using (1R,2R)-2-phenyl-cyclopropanecarboxylic acid as the carboxylic acid of choice. MH+=387.

Example 450

4-Amino-3-(4-(((E)-3-(2-chlorophenyl)acryloyl)
amino)-phenyl)thieno[2,3-d]pyrimidine The compound was prepared following the procedure described in Example 435, using (E)-3-(2-chlorophenyl)-acrylic acid as the carboxylic acid of choice. MH+=407.

Example 451

4-Amino-3-(4-(((E)-3-(3-chlorophenyl)acryloyl)
amino)-phenyl)thieno[2,3-d]pyrimidine The compound was prepared following the procedure described in Example 435, using (E)-3-(3-chlorophenyl)-acrylic acid as the carboxylic acid of choice. MH+=407.

Example 452

4-Amino-3-(4-(((E)-3-phenylacryloyl)amino)phenyl)thieno[2,3-d]pyrimidine

The compound was prepared following the procedure described in Example 435, using (E)-3-phenyl-acrylic acid as the carboxylic acid of choice. MH+=373.

Example 453

4-Amino-3-(4-((1-phenylcyclopentanecarbonyl)amino)-phenyl)thieno[2,3-d]pyrimidine The compound was prepared following the procedure described in Example 435, using phenylcyclopentanecarboxylic acid as the carboxylic acid of choice. MH+=415.

Example 454

4-Amino-3-(4-((2-phenylisobutyryl)amino)phenyl)thieno[2,3-d]pyrimidine

The compound was prepared following the procedure described in Example 435, using 2-methyl-2-phenylpropionic acid as the carboxylic acid of choice. MH+=389.

Example 455

4-Amino-3-(4-(((2-fluoro-5-(trifluoromethyl)phenyl)acetyl)amino)-phenyl)thieno[2,3-d]pyrimidine The compound was prepared following the procedure described in Example 435, using 2-fluoro-5-trifluoromethylphenyl)-acetic acid as the carboxylic acid of choice. MH+=447.

Example 456

4-Amino-3-(4-(((2,5-dichlorothiophene-3-yl)carbonyl)amino)-phenyl)thieno[2,3-d]pyrimidine The compound was prepared following the procedure described in Example 435, using 2,5-dichloro-thiophene-3-carboxylic acid as the carboxylic acid of choice. MH+=422.

Example 457

4-Amino-3-(4-(((bicyclo[4.2.0]octa-1(6),2,4-trien-7-yl)carbonyl)-amino)phenyl)thieno[2,3-d]pyrimidine The compound was prepared following the procedure described in Example 435, using bicyclo[4.2.0]octa-1(6),2,4-triene-7-carboxylic acid as the carboxylic acid of choice. MH+=373.

Example 458

4-Amino-3-(4-((2-phenylbutyryl)amino)phenyl)thieno[2,3-d]pyrimidine

The compound was prepared following the procedure described in Example 435, using 2-phenyl-butyric acid as the carboxylic acid of choice. MH+=389.

Example 459

4-Amino-3-(4-(((5-methyl-[1,3,4]thiadiazol-2-yl)carbonyl)amino)phenyl)thieno[2,3-d]pyrimidine The compound was prepared following the procedure described in Example 435, using 5-methyl-[1,3,4]thiadiazole-2-carboxylic acid as the carboxylic acid of choice. MH+=369.

Example 460

4-Amino-3-(4-(((5-tert-butyl-2-methyl-2H-pyrazol-3-yl)carbonyl)amino)phenyl)thieno[2,3-d]pyrimidine The compound was prepared following the procedure described in Example 435, using 5-tert-butyl-2-methyl-2H-pyrazole-3-carboxylic acid as the carboxylic acid of choice. MH+=407.

Example 461

4-Amino-3-(4-((4-(4-methyl-piperazin-1-yl-methyl)benzoyl)amino)phenyl)thieno[2,3-d]pyrimidine The compound was prepared following the procedure described in Example 435, using 4-(4-methyl-piperazin-1-ylmethyl)-benzoic acid as the carboxylic acid of choice. MH+=459.

Example 462

4-Amino-3-(4-((3-cyanobenzoyl)amino)phenyl)thieno[2,3-d]pyrimidine

The compound was prepared following the procedure described in Example 435, using 3-cyano-benzoic acid as the carboxylic acid of choice. MH+=372.

Example 463

4-Amino-3-(4-((2-methoxybenzoyl)amino)phenyl)thieno[2,3-d]pyrimidine

The compound was prepared following the procedure described in Example 435, using 2-methoxy-benzoic acid as the carboxylic acid of choice. MH+=377.

Example 464

4-Amino-3-(4-((3-chlorobenzoyl)amino)phenyl)thieno[2,3-d]pyrimidine

The compound was prepared following the procedure described in Example 435, using 3-chloro-benzoic acid as the carboxylic acid of choice. MH+=381

Example 465

4-Amino-3-(4-((3-methoxybenzoyl)amino)phenyl)thieno[2,3-d]pyrimidine

The compound was prepared following the procedure described in Example 435, using 3-methoxy-benzoic acid as the carboxylic acid of choice. MH+=377.

Example 466

4-Amino-3-(4-((4-(trifluoromethoxy)benzoyl)amino)phenyl)-thieno[2,3-d]pyrimidine The compound was prepared following the procedure described in Example 435, using 4-trifluoromethoxy-benzoic acid as the carboxylic acid of choice. MH+=431.

Example 467

4-Amino-3-(4-((2-fluoro-5-(trifluoromethyl)phenyl)-aminocarbonyl(N-methylamino))phenyl)thieno[2,3-d]pyrimidine The compound was prepared following the procedure described in Example 429, substituting 4-amino-3-(4-(methylamino)phenyl)-thieno[2,3-d]pyrimidine as the amine and using 2-fluoro-5-trifluoromethyl-phenyl isocyanate as the isocyanate of choice. MH+=462.

Example 468

4-Amino-3-(4-((3-ethylphenyl)aminocarbonyl(N-methylamino))-phenyl)thieno[2,3-d]pyrimidine The compound was prepared following the procedure described in Example 429, substituting 4-amino-3-(4-(methylamino)phenyl)-thieno[2,3-d]pyrimidine as the amine and using 2-ethyl-phenyl isocyanate as the isocyanate of choice. MH+=404.

Schemes 11–13 depict the preparation of Examples 469–479.

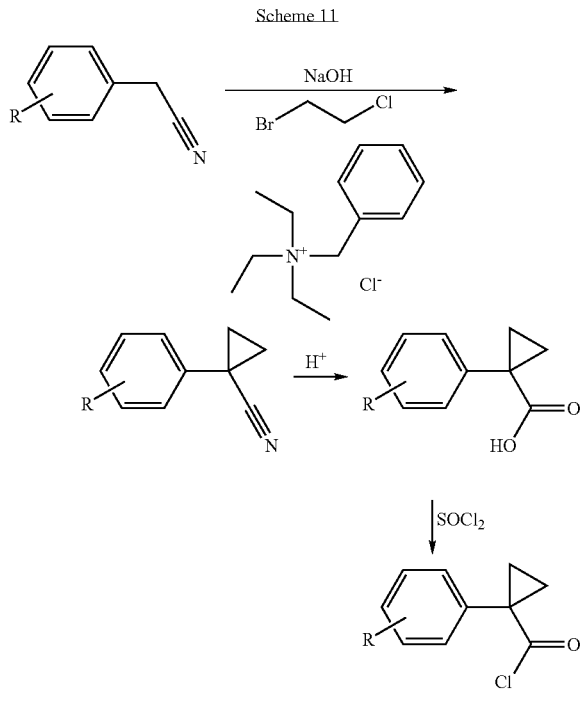

Scheme 11

Example 469

4-Amino-3-(4-((1-(3,4-dichlorophenyl)-cyclopropanecarbonyl)amino)phenyl)thieno[2,3-d]pyrimidine a) 1-(3,4-Dichloro-phenyl)-cyclopropanecarbonitrile To a stirred mixture of 3,4-Dichloro-phenylacetonitrile (4.65 g, 25 mmol) triethylbenzylammonium chloride (0.2 g) and 1-bromochoroethane (4.2 ml, 50 mmol), 50% sodium hydroxide (16 ml, 200 mmol) was added dropwise at 50° then the reaction was stirred at 50° for 10 hrs. After cooling to rt, the reaction mixture was diluted with water and extracted with EtOAc (×3). The layers were separated, washed with water (×3) and brine, then dried over $MgSO_4$. Evaporation of the solvent under reduced pressure afforded the title compound (5.43 g) which was then recrystallized from $Et_2O$/hexanes as a pale pink solid (4.49 g, 85%). Lc/MS(ES) m/e 212 [M+H]+.

b) 1-(3,4-Dichloro-phenyl)-cyclopropanecarboxylic acid 1-(3,4-Dichloro-phenyl)-cyclopropanecarbonitrile (2 g, 9.48 mmol) was heated at 100° overnight in a sealed vessel in conc. HCl (10 ml). The reaction was poured into ice water and extracted with tBuOMe (×2), washed with water (×2) and brine, then dried over $MgSO_4$ and evaporated under reduced pressure to give the title compound which was recrystallized from $Et_2O$/hexane as a white solid. (2.26 g, quant.) Lc/MS (ES) m/e 231[M+H]+.

c) 1-(3,4-Dichloro-phenyl)-cyclopropanecarbonyl chloride 1-(3,4-Dichloro-phenyl)-cyclopropanecarboxylic acid (1 g, 4.35 mmol) was stirred in thionyl chloride (2 ml) at 37° for 72 h then the thionyl chloride was removed under reduced pressure. The residue was rotovapped from benzene (×3) affording the title compound as a yellow oil. (1.1 g, quant) $^1$H NMR(400 MHz, CDCl3) δ 7.46 (dd, J=8.3 Hz, 4.4 Hz, 2H), 7.23 (d, J=8.3, 1H), 2.00 (dd, J=4.6, Hz, 7.6 Hz, 2H), 1.485 (dd, J=4.6, Hz, 7.6 Hz, 2H).

d) 4-Amino-3-(4-((1-(3,4-dichlorophenyl)-cyclopropanecarbonyl)amino)phenyl)thieno[2,3-d]pyrimidine To a solution of 4-Amino-3-(4-aminophenyl)thieno[2,3-d]pyrimidine (0.3 mL of a 0.324 M solution, 0.1 mmol) 1-(3,4-Dichloro-phenyl)-cyclopropanecarbonyl chloride (0.2 mL of a 1 M solution in pyridine, 0.2 mmol) was added in one portion. After the mixture was stirred at room temperature for 3 d, the reaction was purified by hplc to afford the title compound as a beige solid. MS(ES) m/e 455 [M+H].

Example 470

4-Amino-3-(4-((1-(2,5-difluorophenyl)-cyclopropanecarbonyl)amino)phenyl)thieno[2,3-d]pyrimidine a) 1-(2,5-Difluoro-phenyl)-cyclopropanecarbonyl chloride Utilizing the procedure of Example 469(a)–(c), except substituting 2,5-Difluoro-phenylacetonitrile for 3,4-Dichloro-phenylacetonitrile, the title compound was prepared (1.17, 92%). $^1$H NMR(400 MHz, CDCl3) δ 7.13–6.98 (m, 3H), 2.03(dd, J=4.6, Hz, 7.8 Hz, 2H), 1.50(dd, J=4.6, Hz, 7.8 Hz, 2H).

b) 4-Amino-3-(4-((1-(2,5-difluorophenyl)-cyclopropanecarbonyl)amino)phenyl)thieno[2,3-d]pyrimidine The compound was prepared following the procedure described in Example 469, using 1-(2,5-Difluoro-phenyl)-cyclopropanecarbonyl chloride as the acid chloride of choice, and 4-Amino-3-(4-aminophenyl)thieno[2,3-d]pyrimidine as the diamine of choice. MS(ES) m/e 423 [M+H]+.

Example 471

4-Amino-3-(4-((1-(3,5-bis-(trifluoromethyl)phenyl)-cyclopropanecarbonyl)amino)phenyl)thieno[2,3-d]pyrimidine a) 1-(Bis-3,5-trifluoromethyl-phenyl)-cyclopropanecarbonyl chloride

Following the procedure of Example 469(a)–(c), except substituting (Bis-3,5-trifluoromethyl-phenyl)-acetonitrile for 3,4-Dichloro-phenylacetonitrile, the title compound was prepared (1.07, 97[1]H NMR(400 MHz, CDCl3) δ 7.88 (s, 1H), 7.84 (s, 2H), 2.11 (dd, J=4.6, Hz, 7.6 Hz, 2H), 1.58 (dd, J=4.8, Hz, 7.6 Hz, 2H).

b) 4-Amino-3-(4-((1-(3,5-bis-(trifluoromethyl)phenyl)-cyclopropanecarbonyl)amino)phenyl)thieno[2,3-d]pyrimidine The compound was prepared following the procedure described in Example 469, using 1-(Bis-3,5-trifluoromethyl-phenyl)-cyclopropanecarbonyl chloride as the acid chloride of choice, and 4-Amino-3-(4-aminophenyl)thieno[2,3-d]pyrimidine as the diamine of choice. MS(ES) m/e 523 [M+H]$^+$.

Example 472

4-Amino-3-(4-((1-(3-chlorophenyl)cyclopropanecarbonyl)amino)-phenyl)thieno[2,3-d]pyrimidine a) 1-(3-chloro-phenyl)-cyclopropanecarbonyl chloride

Following the procedure of Example 469(b)–(c), except substituting 1-(3-chloro-phenyl)-cyclopropanecarbonitrile for 1-(3,4-Dichloro-phenyl)-cyclopropanecarbonitrile, the title compound was prepared (0.230, 75%). Characterized by dissolving in MeOH, MS(ES) m/e 210 [M+H]$^+$(methyl ester).

b) 4-Amino-3-(4-((1-(3-chlorophenyl)cyclopropanecarbonyl)-amino)phenyl)thieno[2,3-d]pyrimidine The compound was prepared following the procedure described in Example 469, using 1-(3-chloro-phenyl)-cyclopropanecarbonyl chloride as the acid chloride of choice, and 4-Amino-3-(4-aminophenyl)thieno[2,3-d]pyrimidine as the diamine of choice. MS(ES) m/e 421 [M+H]$^+$.

Example 473

4-Amino-3-(4-((1-(3-(trifluoromethyl)phenyl)-cyclopropanecarbonyl)amino)phenyl)thieno[2,3-d]pyrimidine a) 1-(3-Trifluoromethyl-phenyl)-cyclopropanecarbonyl chloride

Following the procedure of Example 469 (a)–(c), except substituting 3-Trifluoromethyl-phenylacetonitrile for 3,4-Dichloro-phenylacetonitrile with prolonged heating for the hydrolysis (8 days at 120°, the title compound was prepared. $^1$H NMR(400 MHz, CDCl3) δ 7.63–749 (m, 4H), 2.05 (dd, J=4.6, Hz, 7.6 Hz, 2H), 1.53 (dd, J=4.6, Hz, 7.6 Hz, 2H).

b) 4-Amino-3-(4-((1-(3-(trifluoromethyl)phenyl)-cyclopropanecarbonyl)amino)phenyl)thieno[2,3-d]pyrimidine The compound was prepared following the procedure described in Example 469, using 1-(3-Trifluoromethyl-phenyl)-cyclopropanecarbonyl chloride as the acid chloride of choice, and 4-Amino-3-(4-aminophenyl)thieno[2,3-d]pyrimidine as the diamine of choice. MS(ES) m/e 455 [M+H]$^+$.

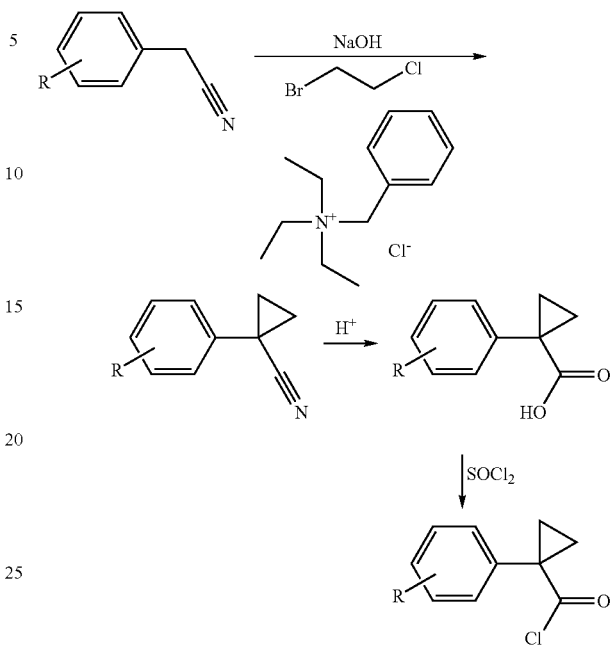

Scheme 12

Example 474

4-Amino-3-(4-((1-(3,4-dichlorophenyl)-cyclopropanecarbonyl)amino)phenyl)furo[2,3-d]pyrimidine a) 1-(3,4-Dichloro-phenyl)-cyclopropanecarbonitrile

To a stirred mixture of 3,4-Dichloro-phenylacetonitrile (4.65 g. 25 mmol) triethylbenzylammonium chloride (0.2 g) and 1-bromochoroethane (4.2 ml, 50 mmol), 50% sodium hydroxide (16 ml, 200 mmol) was added dropwise at 50° then the reaction was stirred at 50° for 10 hrs. After cooling to rt, the reaction mixture was diluted with water and extracted with EtOAc (×3). The layers were separated, washed with water (×3) and brine, then dried over MgSO$_4$. Evaporation of the solvent under reduced pressure afforded the title compound (5.43 g) which was then recrystallized from Et$_2$O/hexanes as a pale pink solid (4.49 g, 85%). Lc/MS(ES) m/e 212 [M+H]$^+$.

b) Preparation of 1-(3,4-Dichloro-phenyl)-cyclopropanecarboxylic acid 1-(3,4-Dichloro-phenyl)-cyclopropanecarbonitrile (2 g, 9.48 mmol) was heated at 100° overnight in a sealed vessel in conc. HCl (10 ml). The reaction was poured into ice water and extracted with tBuOMe (×2), washed with water (×2) and brine, then dried over MgSO$_4$ and evaporated under reduced pressure to give the title compound which was recrystallized from Et$_2$O/hexane as a white solid. (2.26 g, quant.) Lc/MS (ES) m/e 231 [M+H]$^+$.

c) Preparation of 1-(3,4-Dichloro-phenyl)-cyclopropanecarbonyl chloride 1-(3,4-Dichloro-phenyl)-cyclopropanecarboxylic acid (1 g, 4.35 mmol) was stirred in thionyl chloride (2 ml) at 37° for 72 h then the thionyl chloride was removed under reduced pressure the residue was rotovapped from benzene (×3) affording the title compound as a yellow oil. (1.1 g, quant) $^1$H NMR(400 MHz, CDCl3) δ 7.46 (dd, J=8.3 Hz, 4.4 Hz, 2H), 7.23 (d, J=8.3, 1H), 2.00 (dd, J=4.6, Hz, 7.6 Hz, 2H), 1.485 (dd, J=4.6, Hz, 7.6 Hz, 2H).

d) 4-Amino-3-(4-((1-(3,4-dichlorophenyl)-cyclopropanecarbonyl)amino)phenyl)furo[2,3-d]pyrimidine To compound 4-Amino-3-(4-aminophenyl)furo[2,3-d]pyrimidine (9) (0.3 mL of a 0.324 M solution in pyridine 0.1 mmol) 1-(3,4-Dichloro-phenyl)-cyclopropanecarbonyl chloride (0.2 mL of a 1 M solution in pyridine, 0.2 mmol) was added in one portion. After the mixture was stirred at room temperature for 3 d, the reaction was purified by hplc to afford the title compound. MS(ES) m/e 439 [M+H].

Scheme 13

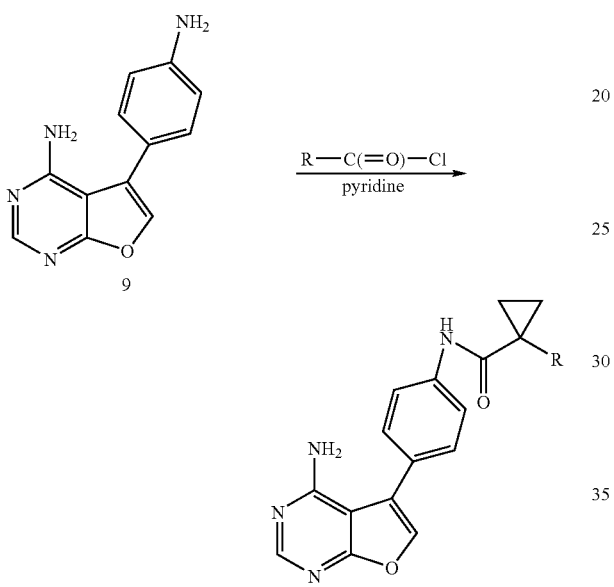

Example 474
Example 475
Example 476
Example 477
Example 478
Example 479

Example 475

4-Amino-3-(4-((1-(2,5-difluorophenyl)-cyclopropanecarbonyl)amino)phenyl)furo[2,3-d]pyrimidine a) 1-(2,5-Difluoro-phenyl)-cyclopropanecarbonyl chloride Following the procedure of Example 474 (a)–(c), except substituting 2,5-Difluoro-phenylacetonitrile for 3,4-Dichloro-phenylacetonitrile, the title compound was prepared (1.17, 92%). $^1$H NMR(400 MHz, CDCl3)δ 7.13–6.98 (m, 3H), 2.03(dd, J=4.6, Hz, 7.8 Hz, 2H), 1.50(dd, J=4.6, Hz, 7.8 Hz, 2H).

b) 4-Amino-3-(4-((1-(2,5-difluorophenyl)-cyclopropanecarbonyl)amino)phenyl)furo[2,3-d]pyrimidine The compound was prepared following the procedure described in Example 474, using 1-(2,5-Difluoro-phenyl)-cyclopropanecarbonyl chloride as the acid chloride of choice, and 4-Amino-3-(4-aminophenyl)furo[2,3-d]pyrimidine (9) as the diamine of choice. MS(ES) m/e 407 [M+H]$^+$.

Example 476

4-Amino-3-(4-((1-(3,5-bis-(trifluoromethyl)phenyl)-cyclopropanecarbonyl)amino)phenyl)furo[2,3-d]pyrimidine a) 1-(Bis-3,5-trifluoromethyl-phenyl)-cyclopropanecarbonyl chloride Following the procedure of Example 474 (a)–(c), except substituting (Bis-3,5-trifluoromethyl-phenyl)-acetonitrile for 3,4-Dichloro-phenylacetonitrile, the title compound was prepared (1.07, 97$^1$H NMR(400 MHz, CDCl3) δ 7.88 (s, 1H), 7.84 (s, 2H), 2.11 (dd, J=4.6, Hz, 7.6 Hz, 2H), 1.58 (dd, J=4.8, Hz, 7.6 Hz, 2H).

b) 4-Amino-3-(4-((1-(3,5-bis-(trifluoromethyl)phenyl)-cyclopropanecarbonyl)amino)phenyl)furo[2,3-d]pyrimidine The compound was prepared following the procedure described in Example 474, using 1-(Bis-3,5-trifluoromethyl-phenyl)-cyclopropanecarbonyl chloride as the acid chloride of choice, and 4-Amino-3-(4-aminophenyl)furo[2,3-d]pyrimidine (9) as the diamine of choice. MS(ES) m/e 507 [M+H]$^+$.

Example 477

4-Amino-3-(4-((1-(3-chlorophenyl)cyclopropanecarbonyl)amino)-phenyl)furo[2,3-d]pyrimidine a) 1-(3-chloro-phenyl)-cyclopropanecarbonyl chloride Following the procedure of Example 474 (b)–(c), except substituting 1-(3-chloro-phenyl)-cyclopropanecarbonitrile for 1-(3,4-Dichloro-phenyl)-cyclopropanecarbonitrile, the title compound was prepared (0.230, 75%). Characterized by dissolving in MeOH, MS(ES) m/e 210 [M+H]$^+$(methyl ester).

b) 4-Amino-3-(4-((1-(3-chlorophenyl)cyclopropanecarbonyl)-amino)phenyl)furo[2,3-d]pyrimidine The compound was prepared following the procedure described in Example 474, using 1-(3-chloro-phenyl)-cyclopropanecarbonyl chloride as the acid chloride of choice, and 4-Amino-3-(4-aminophenyl)furo[2,3-d]pyrimidine (9) as the diamine of choice. MS(ES) m/e 405 [M+H]$^+$.

Example 478

4-Amino-3-(4-((1-phenylcyclopropanecarbonyl)amino)-phenyl)furo[2,3-d]pyrimidine a) 1-(Phenyl)-cyclopropanecarbonyl chloride Following the procedure of Example 474 (c), except substituting 1-(Phenyl)-cyclopropanecarboxylic acid for 1-(3,4-Dichloro-phenyl)-cyclopropanecarboxylic acid, the title compound was prepared (3.0, quant.). $^1$H NMR(400 MHz, CDCl3) 7.3 (m, 5H), 2.02 (dd, 2H), 1.56 (dd, 2H).

b) 4-Amino-3-(4-((1-phenylcyclopropanecarbonyl)amino)-phenyl)furo[2,3-d]pyrimidine The compound was prepared following the procedure described in Example 474, using 1-Phenyl-cyclopropanecarbonyl chloride as the acid chloride of choice, and 4-Amino-3-(4-aminophenyl)furo[2,3-d]pyrimidine (9) as the diamine of choice. MS(ES) m/e 371 [M+H]$^+$.

Example 479

4-Amino-3-(4-((1-(3-(trifluoromethyl)phenyl)-cyclopropanecarbonyl)amino)phenyl)furo[2,3-d]pyrimidine a) 1-(3-Trifluoromethyl-phenyl)-cyclopropanecarbonyl chloride Following the procedure of Example 474 (a)–(c), except substituting 3-Trifluoromethyl-phenylacetonitrile for 3,4-Dichloro-phenylacetonitrile with prolonged heating for the hydrolysis (8 days at 120°, the title compound was prepared. $^1$H NMR(400 MHz, CDCl3) δ 7.63–749 (m, 4H), 2.05 (dd, J=4.6, Hz, 7.6 Hz, 2H), 1.53 (dd, J=4.6, Hz, 7.6 Hz, 2H).

b) 4-Amino-3-(4-((1-(3-(trifluoromethyl)phenyl)-cyclopropanecarbonyl)amino)phenyl)furo[2,3-d]pyrimidine The compound was prepared following the procedure described in making Example 474, using 1-(3-Trifluoromethyl-phenyl)-cyclopropanecarbonyl chloride as the acid chloride of choice, and 4-Amino-3-(4-aminophenyl)furo[2,3-d]pyrimidine (9) as the diamine of choice. MS(ES) m/e 436 [M+H]$^+$.

Biological Data

TIE-2 Enzyme assay (TIE2-E)

The TIE-2 enzyme assay used the LANCE method (Wallac) and GST-TIE2, baculovirus expressed recombinant constructs of the intracellular domains of human TIE2 (amino acids 762-1104, GenBank Accession #L06139) tagged by GST). The method measured the ability of the purified enzymes to catalyse the transfer of the γ-phosphate from ATP onto tyrosine residues in a biotinylated synthetic peptide, D1–15 (biotin-C6-LEARLVAYEGWVAGKKKamide). This peptide phosphorylation was detected using the following procedure: for enzyme preactivation, GST-TIE2 was incubated for 30 mins at room temperature with 2 mM ATP, 5 mM MgCl2 and 12.5 mM DTT in 22.5 mM HEPES buffer (pH 7.4). Preactivated GST-TIE2 was incubated for 30 mins at room temperature in 96 well plates with 1 uM D1–15 peptide, 80 uM ATP, 10 mM MgCl2, 0.1 mg/ml BSA and the test compound (diluted from a 10 mM stock in DMSO, final DMSO concentration was 2.4%) in 1 mM HEPES (pH 7.4). The reaction was stopped by the addition of EDTA (final concentration 45 mM). Streptavidin linked-APC (allophycocyanin, Molecular Probe) and Europium-labeled anti-phosphorylated tyrosine antibody (Wallac) were then added at the final concentration of 17 ug/well and 2.1 ug/well, respectively. The APC signal was measured using an ARVO multilabel counter. (Wallac Berthold Japan). The percent inhibition of activity was calculated relative to blank control wells. The concentration of test compound that inhibits 50% of activity (IC$_{50}$) was interpolated using nonlinear regression (Levernberg-Marquardt) and the equation, y=Vmax (1–x/(K+x))+Y2, where "K" was equal to the IC$_{50}$. The IC$_{50}$ values were converted to pIC$_{50}$ values, i.e., –log IC$_{50}$ in Molar concentration. The results are represented in Table 1 below.

TIE-2 Autophosphorylation Assay (TIE2-C)

The TIE-2 autophosphorylation assay used an ELISA method and a TIE2 intracellular domain/c-fms extracellular domain (TIE2/c-fms) chimeric protein expressing mouse 3T3 cells. This assay measured the autophosphorylation level of TIE2 protein expressed in cells. The cells were cultured in high glucose DMEM (Sigma) containing 10% serum at 37° C. in a humidified 10% CO2, 90% air incubator. The test compound (diluted from a 10 mM stock in DMSO, final DMSO concentration was 0.1%) was incubated with TIE2/c-fms expressing cells for 1 hr in serum free DMEM in 96 well plates followed by the activation of TIE2/c-fms receptor using c-fms ligand, MCSF (macrophage colony stimulating factor). The culture media was removed by aspiration and the cells incubated for at least 30 mins on ice with lysis buffer containing 137 mM NaCl, 2 mM EDTA, 10% glycerol, 0.09 ml sodium ortho vanadate and complete protease inhibitor cocktail (Roche) in 20 mM Tris-HCl (pH 8.0). The cell extracts were transferred into Rat anti-c-fms antibody coated 96 well plates and incubated for 12 hrs at 4 degrees. The extracts were removed by aspiration and the plate was incubated with biotinylated anti-phosphotyrosine antibody, PT66 (Sigma) and then with HRP (Horseradish Peroxidase)-labeled streptavidin (PIERCE). The optical density at 450 nm derived from HRP catalyzed TMB was measured with an ARVO multilabel counter. (Wallac Berthold Japan). The percent inhibition of activity was calculated relative to blank control wells. The concentration of test compound that inhibits 50% of activity (IC$_{50}$) was interpolated using nonlinear regression (Levernberg-Marquardt) and the equation, y=Vmax (1–x/(K+x))+Y2, where "K" was equal to the IC$_{50}$. The IC$_{50}$ values were converted to pIC$_{50}$ values, i.e., –log IC$_{50}$ in Molar concentration. The results are represented in Table 1 below.

Tie2 Fluorescence Polarization Kinase Activity Assay: (TIE2-FP)

Activation of Recombinant Tie2 Activation:

Recombinant GST-Tie2 was activated by incubating the enzyme in 20 mM Tris-HCl, pH 7.5, 12 mM MgCl$_2$, 100 mM NaCl, 20 μM sodium vanidate, 1 mM DTT and 300 μM ATP at room temperature for 2 hours. The activation mixture was then passed through a NAP-25 desalting column (Pharmacia Biotech cat no. 17-0852-02) to remove the free ATP. The activated enzyme was stored as aliquots at –80° C. in 20 mM Tris-HCl, pH 7.5 and 11 mM NaCl.

Assay Conditions:

The final assay conditions were 50 mM HEPES, pH 7.5, 5% DMSO (when screening compounds), 200 μM ATP, 5 mM MgCl$_2$, 1 mM DTT, 50 μM sodium vanidate, 1 nM activated enzyme, and 200 μM peptide. IC$_{50}$'s of compounds were measured under subsaturating ATP (200 μM) and varing concentrations of activated Tie2 and peptide substrate (RF-WKYEFWR-OH; MW 1873 Da, TFA salt). Panvera Anti-phosphotyrosine antibody (Cat#P2840) and PTK Green Tracer (Cat#P2842) were used to detect the phosphorylated peptide. Polarization was measured on a TECAN Polarion in 138-second cycles for 30 minutes at room temperature. IC$_{50}$'s were then determined from the % polarization using normal calculation methods. Results are indicated below.

VEGF-R2 Enzyme Assay (VEGF-E)

The VEGF enzyme assay used the LANCE method (Wallac) and GST-VEGFR2, baculovirus expressed recombinant constructs of the intracellular domains of human TIE2 tagged by GST. The method measured the ability of the purified enzymes to catalyse the transfer of the γ-phosphate from ATP onto tyrosine residues in a biotinylated synthetic peptide, (biotin-aminohexyl-EEEEYFELVAKKKK-NH2). This peptide phosphorylation was detected using the following procedure: GST-VEGFR2 was incubated for 40–60 mins at room temperature with 75 uM ATP, 5 mM MgCl2, 0.1 mM DTT, 0.1 mg/mL BSA and the test compound (diluted from a 10 mM stock in DMSO for desired concentration) in 100 mM HEPES buffer. The reaction was stopped by the addition of EDTA (final concentration 50 mM). Streptavidin linked-APC (allophycocyanin, Molecular Probe) and Europium-labeled anti-phosphorylated tyrosine antibody (Wallac) were then added at the final concentration of 15 nM and 1 nM, respectively. The APC signal was measured using an ARVO multilabel counter (Wallac Berthold, Japan). The percent inhibition of activity was calculated relative to blank control wells. The concentration of test compound that inhibits 50% of activity ($IC_{50}$) was interpolated using nonlinear regression (Levernberg-Marquardt) and the equation, y=Vmax (1−x/(K+x))+Y2, where "K" was equal to the $IC_{50}$. The $IC_{50}$ values were converted to $pIC_{50}$ values, i.e., −log $IC_{50}$ in Molar concentration. The results are represented in Table 1 below.

VEGF-Driven Cellular Proliferation Assay. BrdU Incorporation Assay (VEGF-C)

Human umbilical cord endothelial cells (HUVEC, Clonetics, CC2519) were passaged in Type I collagen-coated 100-mm petridishes in EGM-MV medium (Clonetics, CC3125) at 37 C in a humidified 5% $CO_2$, 95% air incubator. (HUVEC passaged more than 6 times in vitro were discarded and not subjected to assaying.) The cells were harvested using trypsin/EDTA, counted using a haemocytometer and plated at 5000 cells/well in a Type I-collagen coated 96-well plate (Becton Dickinson, 354407) in M199 medium (Gibco BRL 12340-030) containing 5% FBS (Hyclone, A 1115-L) and gentamicin (at 50 ug/ml, Gibco BRL). After incubation overnight at 37° C., the media were replaced with 100 ul of M199 serum-free medium containing compounds at various concentrations with 0.6% DMSO and gentamicin. The compounds were diluted in serum-free M199 medium from 10 mM stock solutions prepared in 100% DMS0. After a 30 min incubation at 37° C., the cells were fed with 100 ul of serum-free M199 medium containing gentamicin, 0.2% culture-grade bovine serum albumin (BSA, Sigma A1993) and 20 ng/ml of VEGF (R&tD systems, 293-VE) or 0.6 ng/ml of basic FGF (R&tD systems, 233-FB), and cultured at 37° C. for another 24 h. The cells were pulsed with bromodeoxyuridine (BrdU at 10 uM in serum-free M199) at 37° C. for an additional 24 h. The incorporation of BrdU into the proliferating HUVEC were analyzed using BrdU Cell Proliferation ELISA (Roche Molecular Biochemicals, 1647229) according to the manufacturer's protocols. The optical density at 450 nm was measured with a multilabel counter (ARVO SX, Wallac). The percent inhibition of cell growth was calculated relative to blank control wells. The concentration of test compound that inhibits 50% of cell growth ($IC_{50}$) was interpolated using nonlinear regression (Levernberg-Marquardt) and the equation, y=Vmax (1−x/(K+x))+Y2, where "K" was equal to the $IC_{50}$. The $IC_{50}$ values were converted to $pIC_{50}$ values, i.e., −log $IC_{50}$ in Molar concentration. The results are represented in Table 1 below.

TABLE I

| Ex. No | TIE2-E | TIE2-C | VEGF-E | VEGF-C |
|---|---|---|---|---|
| 1 | ++ | +++ | +++ | − |
| 2 | ++ | ++ | ++ | |
| 3 | ++ | | | |
| 4 | +++ | +++ | +++ | +++ |
| 5 | ++ | ++ | +++ | + |
| 6 | ++ | ++ | | |
| 8 | +++ | +++ | +++ | +++ |
| 10 | ++ | ++ | ++ | − |
| 15 | + | + | ++ | + |
| 16 | + | + | ++ | + |
| 19 | ++ | + | ++ | − |
| 32 | + | + | ++ | − |
| 34 | ++ | − | + | |
| 36 | ++ | + | ++ | |
| 42 | + | + | ++ | |

TABLE I-continued

| Ex. No | TIE2-E | TIE2-C | VEGF-E | VEGF-C |
|---|---|---|---|---|
| 43 | − | − | ++ | |
| 55 | ++ | ++ | ++ | − |
| 57 | − | | +++ | − |
| 72 | ++ | ++ | | |
| 93 | ++ | ++ | ++ | − |
| 95 | ++ | ++ | ++ | − |
| 105 | + | ++ | + | + |
| 108 | ++ | ++ | | + |
| 131 | ++ | ++ | ++ | + |
| 132 | + | ++ | ++ | + |
| 135 | ++ | ++ | +++ | − |
| 144 | + | ++ | +++ | − |
| 145 | ++ | ++ | +++ | − |
| 147 | + | ++ | ++ | + |
| 153 | ++ | ++ | | + |
| 159 | ++ | ++ | ++ | ++ |
| 160 | ++ | ++ | +++ | − |
| 162 | ++ | ++ | ++ | − |
| 165 | ++ | ++ | +++ | + |
| 166 | ++ | ++ | +++ | + |
| 176 | ++ | ++ | ++ | − |
| 178 | + | ++ | ++ | + |
| 179 | ++ | ++ | | − |
| 182 | ++ | ++ | +++ | − |
| 184 | ++ | ++ | +++ | + |
| 189 | ++ | ++ | +++ | + |
| 191 | ++ | ++ | ++ | − |
| 192 | ++ | ++ | +++ | + |
| 194 | ++ | ++ | | − |
| 196 | ++ | ++ | | + |
| 198 | ++ | ++ | | + |
| 200 | ++ | ++ | +++ | + |
| 204 | ++ | ++ | | + |
| 206 | ++ | ++ | +++ | + |
| 227 | +++ | +++ | +++ | |
| 228 | +++ | ++ | ++ | |
| 232 (8C) | +++ | +++ | +++ | +++ |
| 237 | | | ++ | |
| 250 | | | +++ | |
| 262 | | | ++ | |
| 322 | +++ | | + | |
| 386 | +++ | | ++ | |
| 441 | ++ | | +++ | |
| 443 | +++ | | + | |
| 446 | +++ | | + | |
| 448 | +++ | | + | |

+ = $pIC_{50}$ of 5.0–6.0;
++ = $pIC_{50}$ of 6.0–7.0;
+++ = $pIC_{50}$ of >7.0;
− = a negative or inconclusive result;
blank = not tested The compound of Example 276 was assayed using the TIE2-FP assay and gave an $IC_{50}$ of 0.0018 μM.

Structures of representative examples are presented in Table 2 through Table 9 following.

TABLE 2
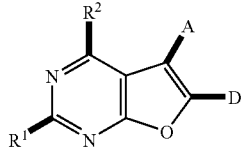
| Example No | R¹ | R² | A | D |
|---|---|---|---|---|
| Example 10 | H | NH$_2$ | 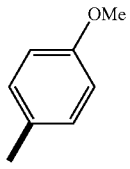 | 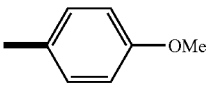 |
| Example 19 | H | NH$_2$ | 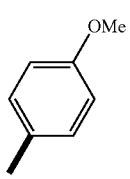 | 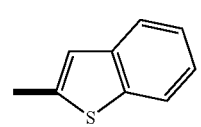 |
| Example 20 | H | NH$_2$ | 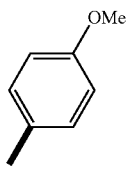 | 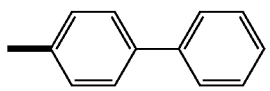 |
| Example 27 | H | NH$_2$ | 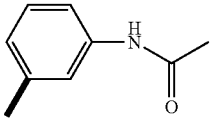 | 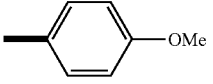 |
| Example 46 | H | NH$_2$ | 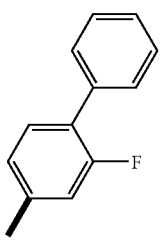 | 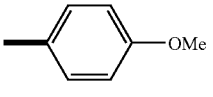 |
| Example 47 | H | NH$_2$ | 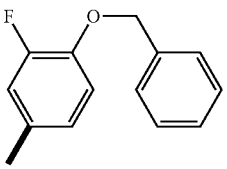 | 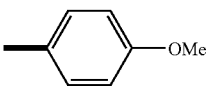 |
| Example 51 | H | NH$_2$ | 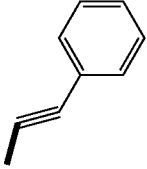 | 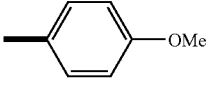 |

TABLE 2-continued
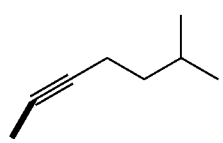
| Example No | R¹ | R² | A | D |
|---|---|---|---|---|
| Example 58 | H | NH₂ | 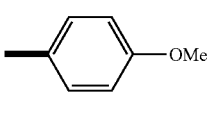 | 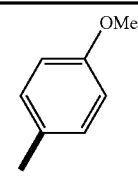 |
TABLE 3
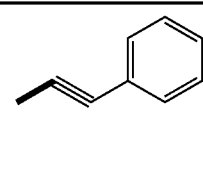
| Example No | R¹ | R² | A | D |
|---|---|---|---|---|
| Example 63 | H | NH₂ | 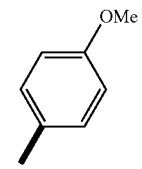 | 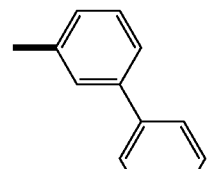 |
| Example 66 | H | NH₂ | 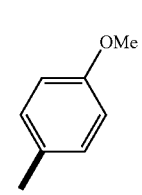 | 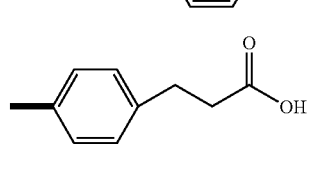 |
| Example 67 | H | NH₂ | 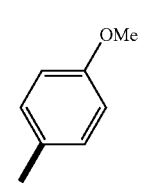 | 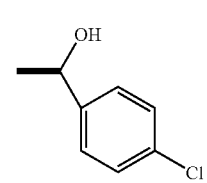 |
| Example 70 | H | NH₂ | | |
| Example 74 | H | 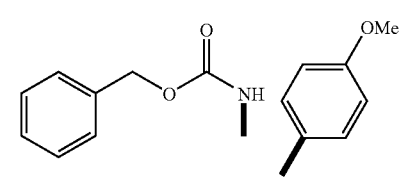 | | H |

TABLE 3-continued
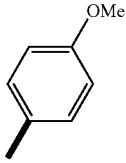
| Example No | R¹ | R² | A | D |
|---|---|---|---|---|
| Example 79 | H | NH₂ | 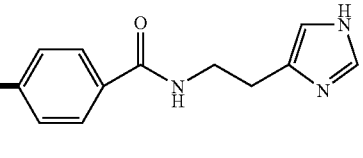 | 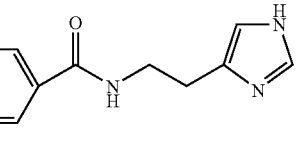 |
| Example 81 | H |  | 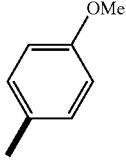 | 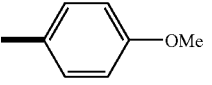 |
| Example 83 | H | NH₂ | 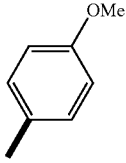 | 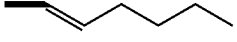 |
TABLE 4
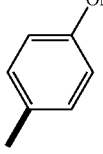
| Example No | R¹ | R² | A | D |
|---|---|---|---|---|
| Example 91 | H | NH₂ | 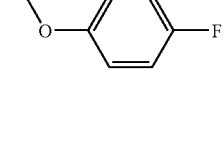 |  |
| Example 98 | H | NH₂ | 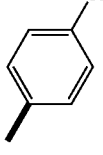 | 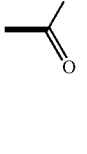 |
| Example 101 | H | NH₂ | 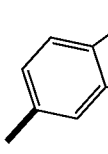 | 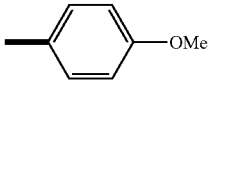 |

TABLE 4-continued

| Example No | R¹ | R² | A | D |
|---|---|---|---|---|
| Example 105 | H | NH₂ | 4-OMe-phenyl (via methyl) | 3-methylbenzamide-N-CH₂CH₂-N(Me)₂ |
| Example 117 | H | NH₂ | 4-OMe-phenyl (via methyl) | N-(1H-indazol-5-yl)acetamide (3-methyl) |
| Example 118 | H | NH₂ | 4-OMe-phenyl (via methyl) | N-ethyl-N'-(ethoxycarbonyl)hydrazinecarboxylate ethyl ester |
| Example 148 | H | NH₂ | 4-OMe-phenyl (via methyl) | N-phenyl-N-acetyl-glycinamide |
| Example 154 | H | NH₂ | 4-OMe-phenyl (via methyl) | 2-methyl-4,5-dihydroimidazole |

TABLE 5

| Example No | R¹ | R² | A | D |
|---|---|---|---|---|
| Example 163 | H | NH₂ | 4-OMe-phenyl (via methyl) | N-phenyl-2-methylthiazole-4-carboxamide |

TABLE 5-continued
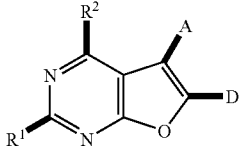
| Example No | R¹ | R² | A | D |
|---|---|---|---|---|
| Example 168 | H | NH₂ | 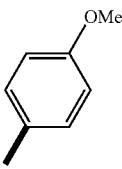 | 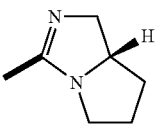 |
| Example 169 | H | NH₂ | 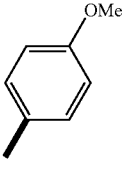 | 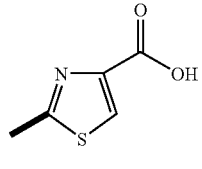 |
| Example 175 | H | NH₂ | 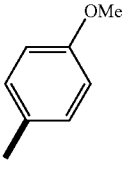 | 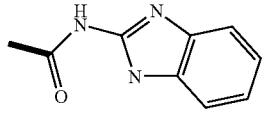 |
| Example 180 | H | NH₂ | 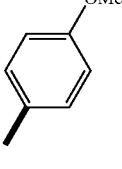 | 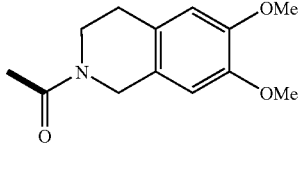 |
| Example 182 | H | NH₂ | 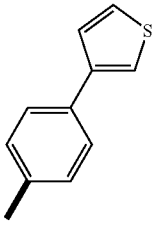 | 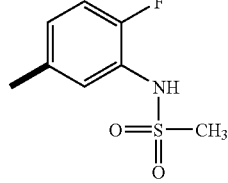 |
| Example 187 | H | NH₂ | 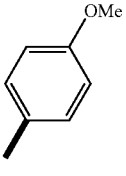 | 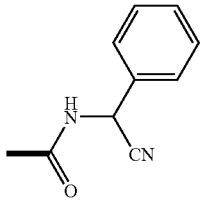 |

TABLE 5-continued
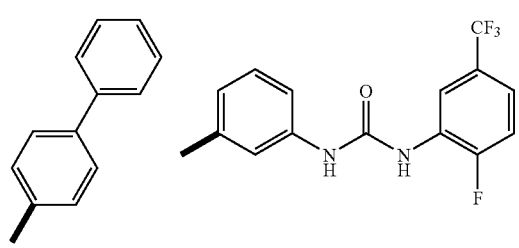
| Example No | R¹ | R² | A | D |
|---|---|---|---|---|
| Example 190 | H | NH₂ | 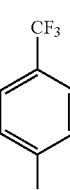 | 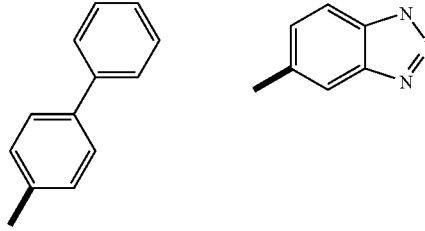 |
TABLE 6
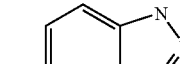
| Example No | R¹ | R² | A | D |
|---|---|---|---|---|
| Example 196 | H | NH₂ | 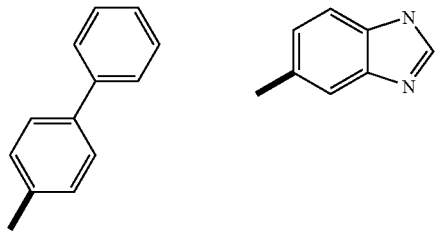 | 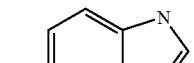 |
| Example 198 | H | NH₂ | 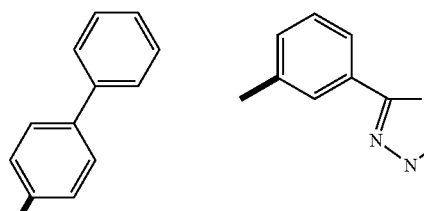 | 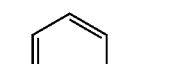 |
| Example 210 | H | NH₂ | | |

TABLE 6-continued

| Example No | R¹ | R² | A | D |
|---|---|---|---|---|
| Example 213 | ethyl acetate (–CH₂OC(O)CH₃) | NH₂ | 4-methoxy-3-methylphenyl | 4-methoxyphenyl |
| Example 215 | H | NH₂ | 2-fluoro-4'-methyl-[1,1':4',1''-terphenyl] | 3-sulfamoylphenyl |
| Example 222 | H₃C– | NH₂ | 4-methoxy-3-methylphenyl | 4-methoxyphenyl |
| Example 230 | H | NH₂ | 4-methoxy-3-methylphenyl | 4-methoxyphenyl |
| Example 231 | H | NH₂ | 2-fluoro-5-(trifluoromethyl)phenyl with N'-(4-methylbenzyl)urea | 4-methoxyphenyl |

TABLE 7

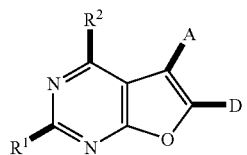

| Example No | R¹ | R² | A | D |
|---|---|---|---|---|
| Example 235 | H | NH₂ | 4-[3-(4-methylphenyl)ureido]-2-fluoro-5-(trifluoromethyl)phenyl | 3-sulfamoylphenyl |
| Example 237 | H | NH₂ | 4-methylphenyl-NH-C(=S)-NH-phenyl | H |
| Example 238 | H | PhNH– | 4-nitrophenyl | H |
| Example 240 | H | CH₃NH– | 4-aminophenyl | H |
| Example 243 | H | (CH₃)₂N– | 4-nitrophenyl | H |
| Example 248 | CH₃S– | H | 4-[3-(4-methylphenyl)ureido]-2-fluoro-5-(trifluoromethyl)phenyl | H |
| Example 263 | (CH₃)₂NCH₂CH₂N(CH₃)– | H | 4-[3-(4-methylphenyl)ureido]-2-fluoro-5-(trifluoromethyl)phenyl | H |

TABLE 7-continued
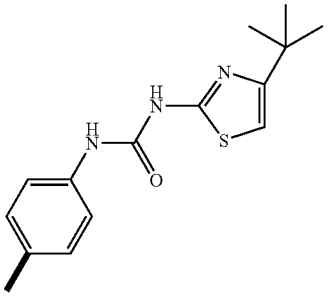
| Example No | R¹ | R² | A | D |
|---|---|---|---|---|
| Example 273 | H | NH₂ | 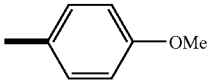 | 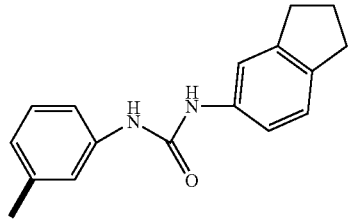 |
TABLE 8
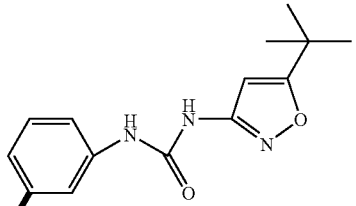
| Example No | R¹ | R² | A | D |
|---|---|---|---|---|
| Example 306 | H | NH₂ | 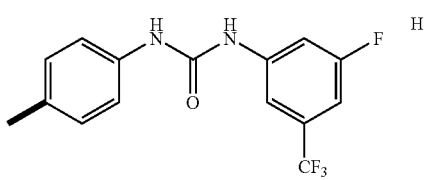 | H |
| Example 307 | H | NH₂ | | H |
| Example 311 | H | NH₂ | | H |

TABLE 8-continued

| Example No | R¹ | R² | A | D |
|---|---|---|---|---|
| Example 317 | H | NH₂ | (4-methylphenyl)-NH-C(=O)-CH₂-(3,5-bis(trifluoromethyl)phenyl) | H |
| Example 319 | H | NH₂ | (4-methylphenyl)-NH-SO₂-(2,3-dichlorophenyl) | H |
| Example 329 | H | NH₂ | (4-methylphenyl)-NH-SO₂-(4,5-dichlorothiophen-2-yl) | H |
| Example 370 | H | NH₂ | (4-methylphenyl)-NH-SO₂-(5-(pyridin-2-yl)thiophen-2-yl) | H |
| Example 386 | H | NH₂ | (4-methylphenyl)-NH-SO₂-(5-(2-methylthiazol-4-yl)thiophen-2-yl) | H |

TABLE 9

| Example No | R¹ | R² | A | D |
|---|---|---|---|---|
| Example 429 | H | NH₂ | 4-methylphenyl-NH-C(O)-NH-(2-fluoro-5-trifluoromethylphenyl) | H |
| Example 440 | H | NH₂ | 4-methylphenyl-NH-C(O)-(trans-2-phenylcyclopropyl) | H |
| Example 446 | H | NH₂ | 4-methylphenyl-NH-C(O)-CH₂-(3,5-bis(trifluoromethyl)phenyl) | H |
| Example 453 | H | NH₂ | 4-methylphenyl-NH-C(O)-(1-phenylcyclopentyl) | H |
| Example 455 | H | NH₂ | 4-methylphenyl-NH-C(O)-CH₂-(2-fluoro-5-trifluoromethylphenyl) | H |
| Example 457 | H | NH₂ | 4-methylphenyl-NH-C(O)-(bicyclo[4.2.0]octa-1,3,5-trien-7-yl) | H |
| Example 468 | H | NH₂ | 4-methylphenyl-N(CH₃)-C(O)-NH-(3-ethylphenyl) | H |

TABLE 9-continued

| Example No | R¹ | R² | A | D |
|---|---|---|---|---|
| Example 470 | H | NH₂ | (structure: N-(4-methylphenyl)-1-(2,5-difluorophenyl)cyclopropanecarboxamide) | H |

What is claimed is:
1. A compound selected from the group consisting of:
4-Amino-3-(4-((2-fluoro-5-(trifluoromethyl)phenyl)-aminocarbonylamino)phenyl)thieno[2,3-d]pyrimidine;
4-Amino-3-(4-((2-chloro-5-(trifluoromethyl)phenyl)-aminocarbonylamino)phenyl)thieno[2,3-d]pyrimidine;
4-Amino-3-(4-(((S)-2-amino-2-phenylacetyl)amino)phenyl)-thieno[2,3-d]pyrimidine;
4-Amino-3-(4-(((1S,2S)-2-phenyl-cyclopropanecarbonyl)amino)-phenyl)thieno[2,3-d]pyrimidine;
4-Amino-3-(4-(((R)-2-amino-2-phenylacetyl)amino)phenyl)-thieno[2,3-d]pyrimidine;
4-Amino-3-(4-(((1R,2R)-2-phenyl-cyclopropanecarbonyl)amino)-phenyl)thieno[2,3-d]pyrimidine;
4-Amino-3-(4-((1-phenylcyclopentanecarbonyl)amino)-phenyl)thieno[2,3-d]pyrimidine;
4-Amino-3-(4-((2-phenylisobutyryl)amino)phenyl)thieno[2,3-d]pyrimidine;
4-Amino-3-(4-(((bicyclo[4.2.0]octa-1(6),2,4-trien-7-yl)carbonyl)-amino)phenyl)thieno[2,3-d]pyrimidine;
4-Amino-3-(4-((2-phenylbutyryl)amino)phenyl)thieno[2,3-d]pyrimidine;
4-Amino-3-(4-(((5-methyl-[1,3,4]thiadiazol-2-yl)carbonyl)amino)phenyl)thieno[2,3-d]pyrimidine;
4-Amino-3-(4-(((5-tert-butyl-2-methyl-2H-pyrazol-3-yl)carbonyl)amino)phenyl)thieno[2,3-d]pyrimidine;
4-Amino-3-(4-((1-(3,4-dichlorophenyl)-cyclopropanecarbonyl)amino)phenyl)thieno[2,3-d]pyrimidine;
4-Amino-3-(4-((1-(2,5-difluorophenyl)-cyclopropanecarbonyl)amino)phenyl)thieno[2,3-d]pyrimidine;
4-Amino-3-(4-((1-(3,5-bis-(trifluoromethyl)phenyl)-cyclopropanecarbonyl)amino)phenyl)thieno[2,3-d]pyrimidine;
4-Amino-3-(4-((1-(3-chlorophenyl)cyclopropanecarbonyl)amino)-phenyl)thieno[2,3-d]pyrimidine; and
4-Amino-3-(4-((1-(3-(trifluoromethyl)phenyl)-cyclopropanecarbonyl)amino)phenyl)thieno[2,3-d]pyrimidine;
or a salt thereof.

2. A pharmaceutical composition, comprising a therapeutically effective amount of a compound as claimed in claim 1, or a salt thereof and one or more of pharmaceutically acceptable carriers, diluents and excipients.

* * * * *